(12) United States Patent
El-Khatib et al.

(10) Patent No.: US 11,154,656 B2
(45) Date of Patent: Oct. 26, 2021

(54) BLOOD GLUCOSE CONTROL SYSTEM WITH MEDICAMENT BOLUS RECOMMENDATION

(71) Applicant: Beta Bionics, Inc., Concord, MA (US)

(72) Inventors: Firas H. El-Khatib, Allston, MA (US); Edward R. Damiano, Acton, MA (US); Edward B. Raskin, Irvine, CA (US); David Chi-Wai Lim, Irvine, CA (US); Michael J. Rosinko, Anaheim, CA (US); John R. Costik, Livonia, NY (US)

(73) Assignee: Beta Bionics, Inc., Concord, MA (US)

( * ) Notice: Subject to any disclaimer, the term of this patent is extended or adjusted under 35 U.S.C. 154(b) by 0 days.

(21) Appl. No.: 17/062,436

(22) Filed: Oct. 2, 2020

(65) Prior Publication Data
US 2021/0085869 A1    Mar. 25, 2021

Related U.S. Application Data

(63) Continuation-in-part of application No. PCT/US2020/042195, filed on Jul. 15, 2020.
(Continued)

(51) Int. Cl.
*A61M 5/172* (2006.01)
*A61M 5/142* (2006.01)
(Continued)

(52) U.S. Cl.
CPC ............ *A61M 5/172* (2013.01); *A61M 5/142* (2013.01); *A61M 5/14244* (2013.01);
(Continued)

(58) Field of Classification Search
CPC .......... A61M 2005/1405; A61M 2005/14208; A61M 2205/18; A61M 5/142;
(Continued)

(56) References Cited

U.S. PATENT DOCUMENTS 4,280,494 A   7/1981  Cosgrove et al.
4,464,170 A   8/1984  Clemens et al.
(Continued)

FOREIGN PATENT DOCUMENTS

CN    1973768      6/2007
CN    201186082    1/2009
(Continued)

OTHER PUBLICATIONS

Aibisser et al., May 1974, An Artificial Endocrine Pancreas, Diabetes, 23(5):389-396.
(Continued)

*Primary Examiner* — Quynh-Nhu H. Vu
(74) *Attorney, Agent, or Firm* — Knobbe Martens Olson & Bear, LLP

(57) ABSTRACT

An automated blood glucose control system can provide automatic delivery of glucose control therapy to a subject and receive information about manual glucose control therapy provided to the subject. The automated blood glucose control system can indicate an amount of a bolus of medicament via a control algorithm configured to control blood glucose level in the subject. The automated blood glucose control system can indicate an amount of a manual bolus of medicament, which can be used to model a diminishment of the medicament in the subject over time based at least in part on the manual bolus of medicament.

25 Claims, 53 Drawing Sheets

Related U.S. Application Data

(60) Provisional application No. 62/874,934, filed on Jul. 16, 2019, provisional application No. 62/874,950, filed on Jul. 16, 2019, provisional application No. 62/874,968, filed on Jul. 16, 2019, provisional application No. 62/910,970, filed on Oct. 4, 2019, provisional application No. 62/911,017, filed on Oct. 4, 2019, provisional application No. 62/911,143, filed on Oct. 4, 2019, provisional application No. 62/987,842, filed on Mar. 10, 2020, provisional application No. 63/037,472, filed on Jun. 10, 2020.

(51) Int. Cl.

| | | |
|---|---|---|
| G16H 20/17 | (2018.01) | |
| G16H 40/40 | (2018.01) | |
| G06F 8/656 | (2018.01) | |
| H04W 76/10 | (2018.01) | |
| G06F 8/61 | (2018.01) | |
| H04L 29/08 | (2006.01) | |
| G16H 40/60 | (2018.01) | |
| G16H 80/00 | (2018.01) | |
| A61M 5/168 | (2006.01) | |
| G08B 21/04 | (2006.01) | |
| G08B 21/18 | (2006.01) | |
| G16H 40/67 | (2018.01) | |
| G06F 21/30 | (2013.01) | |
| G06F 21/31 | (2013.01) | |
| G06F 21/62 | (2013.01) | |
| G06F 21/84 | (2013.01) | |
| G16H 10/60 | (2018.01) | |
| G16H 50/30 | (2018.01) | |
| G06F 3/0488 | (2013.01) | |
| G06F 8/65 | (2018.01) | |
| H04L 29/06 | (2006.01) | |
| H04W 76/14 | (2018.01) | |
| H04L 9/08 | (2006.01) | |
| H04L 9/30 | (2006.01) | |
| G06F 3/0484 | (2013.01) | |
| G08B 25/00 | (2006.01) | |
| A61B 5/145 | (2006.01) | |
| G16H 40/00 | (2018.01) | |

(52) U.S. Cl.
CPC .... *A61M 5/14248* (2013.01); *A61M 5/16831* (2013.01); *G06F 3/04847* (2013.01); *G06F 3/04883* (2013.01); *G06F 8/61* (2013.01); *G06F 8/65* (2013.01); *G06F 8/656* (2018.02); *G06F 21/305* (2013.01); *G06F 21/31* (2013.01); *G06F 21/6245* (2013.01); *G06F 21/84* (2013.01); *G08B 21/0453* (2013.01); *G08B 21/18* (2013.01); *G16H 10/60* (2018.01); *G16H 20/17* (2018.01); *G16H 40/40* (2018.01); *G16H 40/60* (2018.01); *G16H 40/67* (2018.01); *G16H 50/30* (2018.01); *G16H 80/00* (2018.01); *H04L 9/088* (2013.01); *H04L 9/30* (2013.01); *H04L 63/101* (2013.01); *H04L 67/34* (2013.01); *H04W 76/10* (2018.02); *H04W 76/14* (2018.02); *A61B 5/14532* (2013.01); *A61M 5/1723* (2013.01); *A61M 2005/14208* (2013.01); *A61M 2005/1726* (2013.01); *A61M 2205/18* (2013.01); *A61M 2205/3327* (2013.01); *A61M 2205/3546* (2013.01); *A61M 2205/3553* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/609* (2013.01); *A61M 2230/201* (2013.01); *G08B 25/00* (2013.01); *G16H 40/00* (2018.01)

(58) Field of Classification Search
CPC .............. A61M 5/14244; A61M 5/172; A61M 5/1723; A61M 2205/35; A61M 2205/3507; G16H 20/17; G16H 20/13; G16H 20/10; G16H 40/60; G16H 40/63
See application file for complete search history.

(56) References Cited

U.S. PATENT DOCUMENTS

| | | |
|---|---|---|
| 5,665,065 A | 9/1997 | Colman |
| 5,876,370 A | 3/1999 | Blomquist |
| 6,164,921 A | 12/2000 | Moubayed |
| 6,544,212 B2 | 4/2003 | Galley et al. |
| 6,554,798 B1 | 4/2003 | Mann et al. |
| 6,572,542 B1 | 6/2003 | Houben |
| 6,744,350 B2 | 6/2004 | Blomquist |
| 6,852,104 B2 | 2/2005 | Blomquist |
| 7,347,836 B2 | 3/2008 | Peterson |
| 7,491,187 B2 | 2/2009 | Van Den Berghe et al. |
| 7,651,845 B2 | 1/2010 | Doyle, III et al. |
| 7,655,618 B2 | 2/2010 | Green et al. |
| 7,678,762 B2 | 3/2010 | Green et al. |
| 7,678,763 B2 | 3/2010 | Green et al. |
| 7,683,027 B2 | 3/2010 | Green et al. |
| 7,766,829 B2 | 8/2010 | Sloan et al. |
| 7,806,854 B2 | 10/2010 | Damiano et al. |
| 7,850,641 B2 | 12/2010 | Lebel et al. |
| 8,273,052 B2 | 9/2012 | Damiano et al. |
| 8,348,842 B1 | 1/2013 | Osorio |
| 8,377,031 B2 | 2/2013 | Hayter et al. |
| 8,454,510 B2 | 6/2013 | Yodfat et al. |
| 8,457,901 B2 | 6/2013 | Beshan |
| 8,478,557 B2 | 7/2013 | Hayter |
| 8,562,587 B2 | 10/2013 | Kovatchev et al. |
| 8,622,988 B2 | 1/2014 | Hayter |
| 8,679,016 B2 | 3/2014 | Mastrototaro et al. |
| 8,690,820 B2 | 4/2014 | Cinar |
| 8,823,528 B2 | 9/2014 | Blomquist |
| 8,840,582 B2 | 9/2014 | Blomquist et al. |
| 8,936,573 B2 | 1/2015 | Blomquist |
| 9,283,323 B2 | 3/2016 | Toumazou |
| 9,335,910 B2 | 5/2016 | Farnan et al. |
| 9,351,670 B2 | 5/2016 | Dunn |
| 9,398,869 B2 | 7/2016 | Kovatchev et al. |
| 9,445,757 B2 | 9/2016 | Desborough |
| 9,486,571 B2 | 11/2016 | Rosinko |
| 9,486,578 B2 | 11/2016 | Finan |
| 9,715,327 B2 | 7/2017 | Rosinko et al. |
| 9,750,438 B2 | 9/2017 | Kovatchev et al. |
| 9,801,997 B2 | 10/2017 | Estes et al. |
| 9,833,570 B2 | 12/2017 | El-Khatib et al. |
| 9,839,395 B2 | 12/2017 | Shariati |
| 9,901,677 B2 | 2/2018 | Estes |
| 9,907,909 B2 | 3/2018 | Finan |
| 9,940,441 B2 | 4/2018 | Walsh |
| 9,980,140 B1 | 5/2018 | Spencer et al. |
| 9,999,728 B2 | 6/2018 | Parikh |
| 10,117,993 B2 | 11/2018 | Estes |
| 10,188,793 B2 | 1/2019 | Mazlish |
| 10,188,795 B2 | 1/2019 | El-Khatib et al. |
| 10,213,547 B2 | 2/2019 | Rosinko |
| 10,272,200 B2 | 4/2019 | Shapley et al. |
| 10,341,866 B1 | 7/2019 | Spencer et al. |
| 10,357,607 B2 | 7/2019 | Blomquist et al. |
| 10,434,253 B2 | 10/2019 | DiPerna et al. |
| 10,448,885 B2 | 10/2019 | Schmid |
| 10,449,294 B1 | 10/2019 | Estes |
| 10,463,786 B2 | 11/2019 | Saint |

(56) References Cited

U.S. PATENT DOCUMENTS

| | | |
|---|---|---|
| 10,478,551 B2 | 11/2019 | Rosinko |
| 10,541,987 B2 | 1/2020 | Gillespie |
| 10,543,313 B2 | 1/2020 | Damiano et al. |
| 10,569,016 B2 | 2/2020 | Rosinko |
| 10,603,433 B2 | 3/2020 | Estes |
| 10,653,834 B2 | 5/2020 | Kruse et al. |
| 10,842,934 B2 | 11/2020 | El-Khatib et al. |
| 2003/0095648 A1 | 5/2003 | Kaib et al. |
| 2003/0114836 A1 | 6/2003 | Estes |
| 2003/0181852 A1 | 9/2003 | Mann et al. |
| 2004/0028707 A1 | 2/2004 | Pinkerton |
| 2004/0034295 A1 | 2/2004 | Salganicoff |
| 2004/0147872 A1 | 7/2004 | Thompson |
| 2004/0253736 A1 | 12/2004 | Stout et al. |
| 2005/0143864 A1 | 6/2005 | Blomquist |
| 2005/0182366 A1* | 8/2005 | Vogt ................... A61M 5/142 604/131 |
| 2005/0272640 A1 | 12/2005 | Doyle, III et al. |
| 2006/0229557 A1 | 10/2006 | Fathallah |
| 2006/0272652 A1 | 12/2006 | Stocker |
| 2006/0276771 A1 | 12/2006 | Galley |
| 2007/0255348 A1* | 11/2007 | Holtzclaw ............ G16H 20/17 607/60 |
| 2007/0282299 A1 | 12/2007 | Hellwig |
| 2008/0033360 A1 | 2/2008 | Evans et al. |
| 2008/0154187 A1 | 6/2008 | Krulevitch |
| 2008/0183060 A1 | 7/2008 | Steil et al. |
| 2008/0208113 A1 | 8/2008 | Damiano et al. |
| 2008/0269714 A1 | 10/2008 | Mastrototaro |
| 2008/0312512 A1 | 12/2008 | Brukalo |
| 2008/0312585 A1 | 12/2008 | Brukalo |
| 2008/0319384 A1 | 12/2008 | Yodfat et al. |
| 2009/0006061 A1* | 1/2009 | Thukral ............... G16H 20/10 703/11 |
| 2009/0036753 A1 | 2/2009 | King |
| 2009/0164239 A1 | 6/2009 | Hayter et al. |
| 2009/0177154 A1 | 7/2009 | Blomquist |
| 2010/0010646 A1 | 1/2010 | Drew |
| 2010/0057057 A1 | 3/2010 | Hayter et al. |
| 2010/0082167 A1 | 4/2010 | Haueter |
| 2010/0125241 A1 | 5/2010 | Prud'homme et al. |
| 2010/0137788 A1 | 6/2010 | Braithwaite et al. |
| 2010/0145262 A1 | 6/2010 | Bengtsson |
| 2010/0256466 A1 | 10/2010 | Shekalim |
| 2010/0262117 A1 | 10/2010 | Magni et al. |
| 2010/0292634 A1 | 11/2010 | Kircher, Jr. |
| 2011/0021898 A1 | 1/2011 | Wei et al. |
| 2011/0054391 A1 | 3/2011 | Ward et al. |
| 2011/0098638 A1 | 4/2011 | Chawla |
| 2011/0208155 A1 | 8/2011 | Palerm et al. |
| 2011/0208156 A1 | 8/2011 | Doyle, III et al. |
| 2011/0218489 A1 | 9/2011 | Mastrototaro et al. |
| 2012/0065894 A1 | 3/2012 | Tubb et al. |
| 2012/0078067 A1 | 3/2012 | Kovatchev et al. |
| 2012/0245556 A1 | 9/2012 | Kovatchev et al. |
| 2012/0246106 A1 | 9/2012 | Atlas et al. |
| 2012/0265126 A1 | 10/2012 | Estes |
| 2012/0265722 A1 | 10/2012 | Blomquist |
| 2012/0277723 A1 | 11/2012 | Skladnev |
| 2012/0283694 A1 | 11/2012 | Yodfat et al. |
| 2012/0330228 A1 | 12/2012 | Day |
| 2013/0079708 A1 | 3/2013 | Wimpenny |
| 2013/0102853 A1 | 4/2013 | Halvorson |
| 2013/0190583 A1 | 7/2013 | Grosman |
| 2013/0191513 A1 | 7/2013 | Kamen |
| 2013/0245604 A1 | 9/2013 | Kouyoumjian |
| 2013/0253465 A1 | 9/2013 | Holtwick |
| 2013/0297330 A1 | 11/2013 | Kamen |
| 2013/0317753 A1 | 11/2013 | Kamen |
| 2014/0005603 A1 | 1/2014 | Holtwick |
| 2014/0031786 A1 | 1/2014 | Kircher, Jr. et al. |
| 2014/0113553 A1 | 4/2014 | Brukalo |
| 2014/0276555 A1 | 9/2014 | Morales |
| 2015/0018633 A1 | 1/2015 | Kovachev et al. |
| 2015/0133886 A1 | 5/2015 | Morris |
| 2015/0150519 A1 | 6/2015 | Glenn |
| 2015/0151050 A1* | 6/2015 | Estes ................... A61M 5/172 604/500 |
| 2015/0165117 A1 | 6/2015 | Palerm |
| 2015/0217052 A1 | 8/2015 | Keenan et al. |
| 2015/0217053 A1 | 8/2015 | Booth |
| 2015/0343141 A1 | 12/2015 | Lindo |
| 2016/0030669 A1 | 2/2016 | Harris |
| 2016/0121047 A1 | 5/2016 | Kruse |
| 2016/0224751 A1* | 8/2016 | Bielawa ............... G16H 20/10 |
| 2016/0224756 A1 | 8/2016 | Berger |
| 2016/0331898 A1 | 11/2016 | Damiano |
| 2016/0350503 A1 | 12/2016 | Jun |
| 2017/0056590 A1 | 3/2017 | DiPerna |
| 2017/0068533 A1 | 3/2017 | Kiaie |
| 2017/0095612 A1 | 4/2017 | El-Khatib et al. |
| 2017/0102846 A1 | 4/2017 | Ebler et al. |
| 2017/0136198 A1 | 5/2017 | Delangre et al. |
| 2017/0161439 A1 | 6/2017 | Raduchel et al. |
| 2017/0182248 A1 | 6/2017 | Rosinko |
| 2017/0189614 A1 | 7/2017 | Mazlish et al. |
| 2017/0203038 A1 | 7/2017 | Desborough et al. |
| 2017/0296056 A1 | 10/2017 | Hresko |
| 2017/0316178 A1 | 11/2017 | Riedel |
| 2017/0345132 A1 | 11/2017 | Schluter |
| 2018/0021514 A1* | 1/2018 | Rosinko ............... G16H 50/30 604/503 |
| 2018/0060529 A1 | 3/2018 | Crothall |
| 2018/0103897 A1 | 4/2018 | Amirouche |
| 2018/0133398 A1* | 5/2018 | Blomquist ........... A61M 5/1723 |
| 2018/0169330 A1 | 6/2018 | Ludolph |
| 2018/0185587 A1 | 7/2018 | Brauker |
| 2018/0200434 A1 | 7/2018 | Mazlish et al. |
| 2018/0200440 A1 | 7/2018 | Mazlish et al. |
| 2018/0296757 A1 | 10/2018 | Finan |
| 2019/0019573 A1 | 1/2019 | Lake |
| 2019/0054236 A1 | 2/2019 | Estes et al. |
| 2019/0121524 A1 | 4/2019 | Hakansson et al. |
| 2019/0132801 A1 | 5/2019 | Kamath |
| 2019/0175823 A1 | 6/2019 | Rosinko |
| 2019/0180869 A1 | 6/2019 | Volpe |
| 2019/0206565 A1 | 7/2019 | Shelton, IV |
| 2019/0214124 A1 | 7/2019 | Mougiakakou |
| 2019/0247578 A1 | 8/2019 | Desborough |
| 2019/0336684 A1 | 11/2019 | O'Connor |
| 2020/0101223 A1 | 4/2020 | Lintereur et al. |
| 2020/0254240 A1 | 8/2020 | Windmiller |
| 2020/0342974 A1 | 10/2020 | Chen |
| 2020/0384190 A1 | 12/2020 | Jacobi |
| 2021/0016003 A1 | 1/2021 | El-Khatib |
| 2021/0016004 A1 | 1/2021 | El-Khatib |
| 2021/0016005 A1 | 1/2021 | El-Khatib |

FOREIGN PATENT DOCUMENTS

| | | |
|---|---|---|
| CN | 101795623 | 8/2010 |
| CN | 102667787 | 9/2012 |
| CN | 104667368 | 8/2017 |
| CN | 104667379 | 8/2017 |
| EP | 1 575 656 | 6/2009 |
| EP | 3 453 414 | 3/2019 |
| JP | 03-500129 | 3/1989 |
| JP | 2001-204817 | 7/2001 |
| JP | 2003-079723 | 3/2003 |
| JP | 2004-502474 | 1/2004 |
| JP | 2007-529241 | 10/2007 |
| JP | 2007-312923 | 12/2007 |
| JP | 2012-516735 | 7/2012 |
| JP | 2012-519018 | 8/2012 |
| WO | WO 00/28217 | 5/2000 |
| WO | WO 04/006982 | 1/2004 |
| WO | WO 04/084820 | 10/2004 |
| WO | WO 06/124716 | 11/2006 |
| WO | WO 08/057384 | 5/2008 |
| WO | WO 08/094249 | 8/2008 |
| WO | WO 08/114254 | 9/2008 |
| WO | Wo 08/157780 | 12/2008 |
| WO | WO 09/001349 | 12/2008 |
| WO | WO 12/058694 | 5/2012 |

(56) References Cited

FOREIGN PATENT DOCUMENTS

| WO | WO 14/100557 | 6/2014 |
|---|---|---|
| WO | WO 14/110541 | 7/2014 |
| WO | WO 15/021041 | 2/2015 |
| WO | WO 15/116524 | 8/2015 |
| WO | WO 19/125932 | 6/2019 |

OTHER PUBLICATIONS

Bellazzi et al., 1995, Adaptive Controllers for Intelligent Monitoring, Artif. Intell. Med., 7:515-540.

Bellomo et al., May 1982, Optimal Feedback Glycaemia Regulation in Diabetics, Med. & Biol. Eng. & Comp. 20:329-335.

Berian et al., 2019, A wearable closed-loop insulin delivery systme based on low-power SoCs, Electronics, 8:612.

Botz, May 1976, An Improved Control Algorithm for an Artificial .beta.-Cell, IEEE Trans. Biomed. Eng., BME-23(3):252-255.

Brunetti et al., 1993, A Simulation Study on a Self-Tuning Portable Controller of Blood Glucose, Int. J. Artif. Org., 16(1):51-57.

Candas et al., Feb. 1994, An Adaptive Plasma Glucose Controller Based on a Nonlinear Insulin/Glucose Model, IEEE Trans. Biomed. Eng. 41(2):116-124.

Clemens, 1979, Feedback Control Dynamics for Glucose Controlled Insulin Infusion Systems, Med. Prog. Technol. 6:91-98.

El-Khatib et al., Apr. 14, 2010, A Bihormonal Closed-Loop Artificial Pancreas for Type 1 Diabetes, Science.Trans. Med., 2(27):1-12.

El-Khatib et al., Jul. 2009, A Feasibility Study of Bihormonal Closed-Loop Blood-Glucose Control Using Dual Subcutaneous Infusion of Insulin and Glucagon in Ambulatory Diabetic Swine, Journal of Diabetes Science and Technology, 3(4):789-803.

El-Khatib, et al., Mar. 2007, Adaptive Closed-Loop Control Provides Blood-Glucose Regulation Using Dual Subcutaneous Insulin nd Glucagon Infusion in Diabetic Swine, Journal of Diabetes Science and Technology, 1(2):181-192.

El-Khatib, et al., May 2014, Autonomous and Continuous Adaptation of a Bihormonal Bionic Pancreas in Adults and Adolescents Nilh Type 1 Diabetes, Journal of Clinical Endocrin. Melab., 99(5):1701-1711.

Femat et al., Aug. 22-27, 1999, Blood Glucose Regulation: An Output Feedback Approach, Proc. IEEE Int. Conf. Control App. pp. 1290-1293.

Fischer et al., Aug. 1987, Does Physiological Blood Glucose Control Require an Adaptive Control Strategy?, IEEE Trans. Biomed. Eng., BME-34:575-582.

Fletcher et al., 2001, Feasibility of an Implanted, Closed-Loop, Blood-Giucose Control Device, Immunology 230, Stanford University, Spring 01, 31 pp.

Furler et al., Nov.-Dec. 1985, Blood Glucose Control by Intermittent Loop Closure in the Basal Mode: Computer Simulation Studies with a Diabetic Model, Diabetes Care, 8(6):553-561.

Kan et al., 2000, Novel Control System for Blood Glucose Using a Model Predictive Method. ASAIO Journal, 4:657-662.

Lal et al., Jul. 5, 2019, Realizing a closed-loop (artifical pancreas) system for the treatment of type 1 diabetes, Endocrine reviews, 40(6):1521-1546.

Lauritzen et al., May 1983 Pharmacokinetics of Continuous Subcutaneous Insulin Infusion, Diabetologia, 24(5):326-329.

Marliss et al., Jul. 1977, Normalization of Glycemia in Diabetics During Meals with Insulin and Glucagon Delivery by the Artificial Pancreas, Diabetes, 26:663-672.

Medtronic, 2020, Minimed™ 670G Insulin Pump System, product brochure, https://www.medtronicdiabetes.com/products/minimed-670g-insulin-pump-system, 7 pp.

Pagurek et al., 1972, Adaptive Control of the Human Glucose Regulatory System, Med. Biol. Eng., 10:752-761.

Panteleon et al., Jul. 2006, Evaluation of the effect of gain on the meal response of an automated closed-loop insulin delivery system, Diabetes, 55:1995-2000.

Parker et al., 1996, Model Predictive Control for Infusion Pump Insulin Delivery, Proceedings of the 18th Annual International Conference of the IEEE, 6:1822-1823.

Parker et al., Feb. 1999, A Model-Based Algorithm for Blood Glucose Control in Type I Diabetic Patients, IEEE Trans. Biomed. Eng. 46(2):148-157.

Parker et al., Jan.-Feb. 2001, The Intravenous Route to Blood Glucose Control, IEEE Eng. Med. & Biol., pp. 65-73.

Parrish et al., Jun. 1997, Control of an Artificial Human Pancreas Using the SDRE Method, Proc. American Control Conf., 2:1059-1060.

Russell et al., Nov. 2010, Efficacy Determinants of Subcutaneous Microdose Glucagon during Closed-Loop Control, Journal of Diabetes Science and Technology, 4(6):1288-1304.

Russell, et al., Jun. 15, 2014, Outpatient Glycemic Control with a Bionic Pancreas in Type 1 Diabetes, The New England Journal of Medicine, 371(4):313-325.

Russell, et al., Nov. 2012, Blood Glucose Control in Type 1 Diabetes With a Bihormonal Bionic Endocrine Pancreas, Diabetes Care, 35:2148-2155.

Sivaramakrishnan et al., 2017, Optimal model based control for blood glucose insulin system using continuous glucose monitoring, J. Pharm. Sci & Res., 9(4):465-469.

Steil et al., 2006, Metabolic modelling and the closed-loop insulin delivery problem, Diabetes Research and Clinical Practice, 74:S183-S186.

Steil et al., Dec. 2006, Feasibility of automating insulin delivery for the treatment of type 1 diabetes, Diabetes, 55:3344-3350.

Trajanoski et al., Sep. 1998, Neural Predictive Controller for Insulin Delivery Using the Subcutaneous Route, Biomedical Engineering, 45(9):1122-1134.

International Search Report and Written Opinion dated Nov. 2, 2020 in PCT/US2020/042195.

International Search Report and Written Opinion dated Dec. 24, 2020 in PCT/US2020/054025.

Admin, Aug. 25, 2016, "What's the latest with the bionic pancreas?", published on Aug. 25, 2016 to https://www.diabetes.co.uk/blog/2016/08/whats-the-latest-with-the-bionic-pancreas/.

Brown et al., Apr. 1, 2016, "Introducing Beta Bionics: Bringing the ilet Bionic Pancreas to Market", published on Apr. 1, 2016 to https://diatribe.org/introducing-beta-bionics-bringing-ilet-bionic-pancreas-market.

Close, Jun. 13, 2013, "The Bionic Pancreas", published on Jun. 13, 2013 to https://diatribe.org/bionic-pancreas.

Damiano, Feb. 17, 2017, The Long and Winding Road to the Bionic Pancreas, presented on Feb. 17, 2017, published to https://professional.diabetes .org/sites/professional.diabetes.org/files/media/damiano_the_long_and_winding_road_to_the_bionic_pancreas_final.pdf.

Faulkner, May 23, 2018, "Beta Bionics wins FDA nod for home-use trial of artificial pancreas tech", published on May 23, 2018 to https:// www.drugdeliverybusiness.com/beta-bionics-wins-fda-nod-for-home-use-trial-of-artificial-pancreas-tech/.

Gower, Jan. 24, 2018, "The Dawn of the Bionic Pancreas", published on Jan. 24, 2018 to protomag.com/articles/dawn-pancreas, retrieved on Jan. 27, 2021.

Harsch, May 3, 2016, "The Future of Diabetes: My 3 Weeks on a Bionic Pancreas", published on May 3, 2016 to https://onedrop.today/blogs/ blog/3-weeks-on-a-bionic-pancreas.

Melvin, May 25, 2018, "New iLet Bionic Pancreas System Begins Clinical Trial Testing", published on May 25, 2018 to https://beyondtype1.org/ new-iLet-bionic-pancreas-system-begins-clinical-trial-testing.

Smith, Mar. 10, 2017, "A BU Professor's Bionic Pancreas Could Change Diabetes Treatment", published on Mar. 10, 2017 to https://www.bostonmagazine.com/health/2017/03/10/bionic-pancreas-ilet/.

Stein, Jun. 16, 2014, "Father Devises a Bionic Pancreas to Help Son With Diabetes", published on Jun. 16, 2014 to https://www.npr.org/sections/health-shots/2014/06/16/320309856/father-devises-a-bionic-pancreas-to-help-son-with-diabetes.

Torgan, Jan. 10, 2017, "Bionic pancreas treats adults with type 1 diabetes", published on Jan. 10, 2017 to https://www.nih.gov/news-events/nih-research-matters/bionic-pancreas-treats-adults-type-1-diabetes.

U.S. Appl. No. 17/062,426, filed Oct. 2, 2020.

(56) References Cited

OTHER PUBLICATIONS

U.S. Appl. No. 17/062,399, filed Oct. 2, 2020.
U.S. Appl. No. 17/062,280, filed Oct. 2, 2020.
Clarke et al., 2009, Statistical Tools to Analyze Continuous Glucose Monitor Data, Diabetes Technology and Therapeutics, 11:S45-S54.
Hoskins, Oct. 2, 2018, iLet "Bionic Pancreas" making progress with gen 4 device, Healthline, https//www.healthline.com/diabetesmine/beta-bionics-ilet-update#1, 15 pp.
Idlebrook, Jul. 30, 2019, Beta Bionics secures funding for pivotal iLet bionic pancreas trials, https://t1dexchange.org/welcome-glu-users/articles/beta-bionics-secures-funding-for-pivotal-ilet-bionic-pancreas-trials, 4 pp.
Krugman, Aug. 25, 2018, iLet Bionic Pancreas Interface, sarakrugman.com/ilet-interface, 3 pp.
Sifferlin, Apr. 1, 2016, The bionic pancreas is getting closer to reality, time.com, https://time.com/4278068/bionic-pancreas-company, 5 pp.
University of California, San Francisco, Diabetes Education Online, Calculating Insulin Dose, https://dtc.ucsf.edu/types-of-diabetes/type2/treatment-of-type-2-diabetes/medications-and-therapies/type-2-insulin-rx/calculating-insulin-dose/, downloaded Apr. 9, 2021, 11 pp.

* cited by examiner

FIG. 33C

BLOOD GLUCOSE CONTROL SYSTEM WITH MEDICAMENT BOLUS RECOMMENDATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. In addition, this application hereby incorporates by reference in their entirety for all purposes and makes a part of this specification the following applications filed on the same date as this application:

| U.S. application No. | Title | Filing Date |
|---|---|---|
| 17/062,356 | AMBULATORY MEDICAL DEVICE UPDATE WITHOUT INTERRUPTION OF THERAPY DELIVERY | Oct. 2, 2020 |
| 17/062,361 | BLOOD GLUCOSE CONTROL SYSTEM SWITCHING WITHOUT INTERRUPTION OF THERAPY DELIVERY | Oct. 2, 2020 |
| 17/062,377 | SWITCHING BLOOD GLUCOSE CONTROL SYSTEM EXECUTION WITHOUT INTERRUPTION OF THERAPY DELIVERY | Oct. 2, 2020 |
| 17/062,353 | AMBULATORY MEDICAMENT DEVICE WITH ALARM STATUS INDICATION | Oct. 2, 2020 |
| 17/062,426 | AMBULATORY MEDICAMENT DEVICE WITH AUTOMATIC RESUMPTION OF MEDICAMENT DELIVERY | Oct. 2, 2020 |
| 17/062,167 | AMBULATORY MEDICAMENT DEVICE ALARM SYSTEM | Oct. 2, 2020 |
| 17/062,319 | AMBULATORY MEDICAL DEVICE DATA ACCESS MANAGEMENT VIA WIRELESS WIDE AREA NETWORK | Oct. 2, 2020 |
| 17/062,415 | AMBULATORY MEDICAL DEVICE WITH MALFUNCTION ALERT PRIORITIZATION | Oct. 2, 2020 |
| 17/062,399 | AMBULATORY MEDICAMENT DEVICE WITH SECURITY OVERRIDE PASSCODE | Oct. 2, 2020 |
| 17/062,217 | AMBULATORY MEDICAL DEVICE WITH THERAPY DATA SHARING VIA WIRELESS WIDE AREA NETWORK | Oct. 2, 2020 |
| 17/062,280 | AMBULATORY MEDICAMENT DEVICE WITH GESTURE-BASED CONTROL OF MEDICAMENT DELIVERY | Oct. 2, 2020 |

STATEMENT REGARDING FEDERALLY SPONSORED RESEARCH OR DEVELOPMENT

This invention was made with U.S. Government support under Contract No. DK120234, awarded by the National Institutes of Health. The Government has certain rights in the invention.

BACKGROUND

Technical Field

This disclosure relates to blood glucose control systems and to ambulatory medical devices that provide therapy to a subject.

Description of Related Art

Sustained delivery, pump driven medicament injection devices generally include a delivery cannula mounted in a subcutaneous manner through the skin of the subject at an infusion site. The pump draws medicine from a reservoir and delivers it to the subject via the cannula. The injection device typically includes a channel that transmits a medicament from an inlet port to the delivery cannula which results in delivery to the subcutaneous tissue layer where the delivery cannula terminates. Some infusion devices are configured to deliver one medicament to a subject while others are configured to deliver multiple medicaments to a subject.

SUMMARY

Blood glucose control systems and ambulatory medical devices that provide therapy to a subject, such as blood glucose control, are disclosed. Disclosed systems and devices can implement one or more features that improve the user experience, such as software update techniques that avoid interrupting delivery of therapy, gesture-based control of therapy delivery, automatic resumption of therapy after a user-initiated pause, improved alarm management, display of autonomously calculated dosing recommendations, wide area network connectivity, and security features.

BRIEF DESCRIPTION OF THE DRAWINGS

The systems, methods, and devices of this disclosure each have several innovative aspects, no single one of which is solely responsible for the all of the desirable attributes disclosed herein. Details of one or more implementations of the subject matter described in this specification are set forth in the accompanying drawings and the description below.

FIG. 33C is an illustration of a user interface user interface provided on a touch screen display for accessing the alarm notifications screen when the touch screen display is unlocked.

DETAILED DESCRIPTION

Figure 1A:
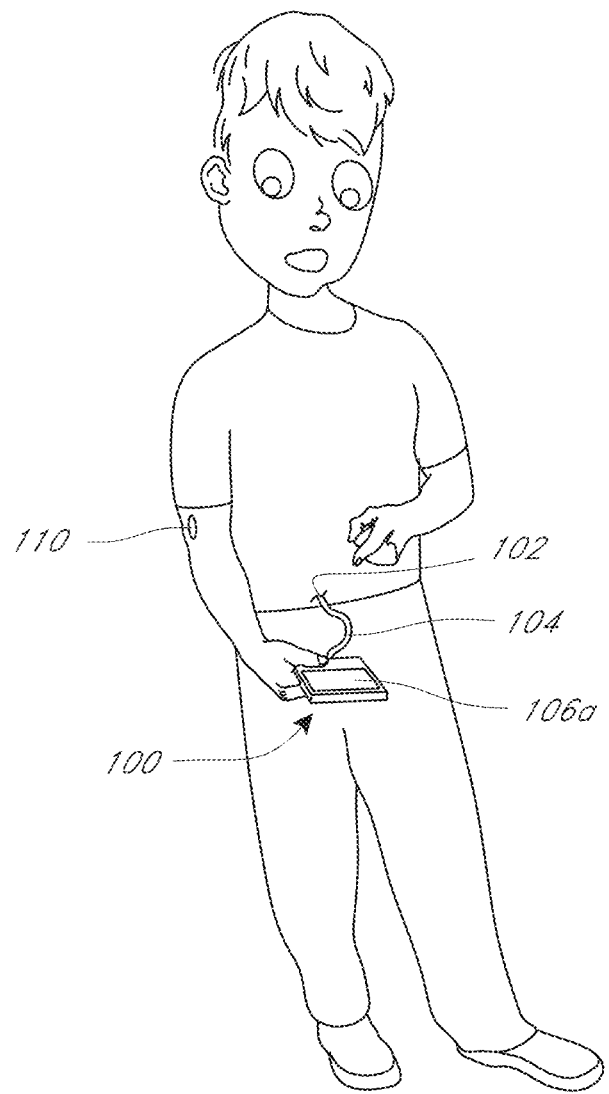
FIG. 1A illustrates an example blood glucose control system that provides blood glucose control via an ambulatory medicament pump.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a subject. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A blood glucose control system can operate in conjunction with an infusion system to infuse one or more medicaments, including at least one blood glucose control agent, into a subject. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Blood Glucose Control System Overview

A blood glucose control system (BGCS) is used to control blood glucose level in a subject. Blood glucose control systems can include a controller configured to generate dose control signals for one or more glucose control agents that can be infused into the subject. Glucose control agents include regulatory agents that tend to decrease blood glucose level, such as insulin and insulin analogs, and counter-regulatory agents that tend to increase blood glucose level, such as glucagon or dextrose. A blood glucose control system configured to be used with two or more glucose control agents can generate a dose control signal for each of the agents. In some embodiments, a blood glucose control system can generate a dose control signal for an agent even though the agent may not be available for dosing via a medicament pump connected to the subject.

Glucose control agents can be delivered to a subject via subcutaneous injection, via intravenous injection, or via another suitable delivery method. In the case of blood glucose control therapy via an ambulatory medicament pump, subcutaneous injection is most common. An ambulatory medicament pump 100 is a type of ambulatory medical device ("AMD"), which is sometimes referred to herein as an ambulatory device, an ambulatory medicament device, a mobile ambulatory device, or an AMD. Ambulatory medical devices include ambulatory medicament pumps and other devices configured to be carried by a subject and to deliver therapy to the subject. Multiple AMDs are described herein. It should be understood that one or more of the embodiments described herein with respect to one AMD may be applicable to one or more of the other AMDs described herein.

In some examples, the ambulatory medical device (AMD) is an electrical stimulation device, and therapy delivery includes providing electrical stimulation to a subject. An example of an electrical stimulation device is a cardiac pacemaker. A cardiac pacemaker generates electrical stimulation of the cardiac muscle to control heart rhythms. Another example of an electrical stimulation device is a deep brain stimulator to treat Parkinson's disease or movement disorders.

Figure 1B:
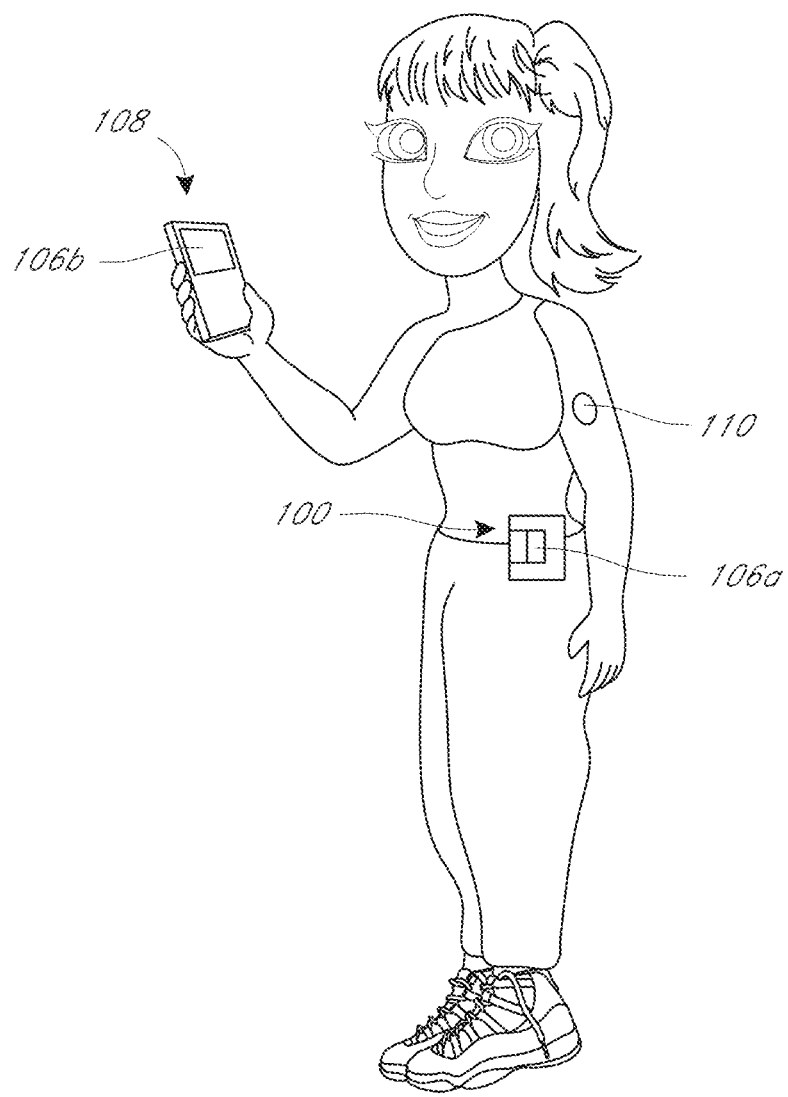
FIG. 1B illustrates another example blood glucose control system that provides blood glucose control via an ambulatory medicament pump.
Figure 1C:
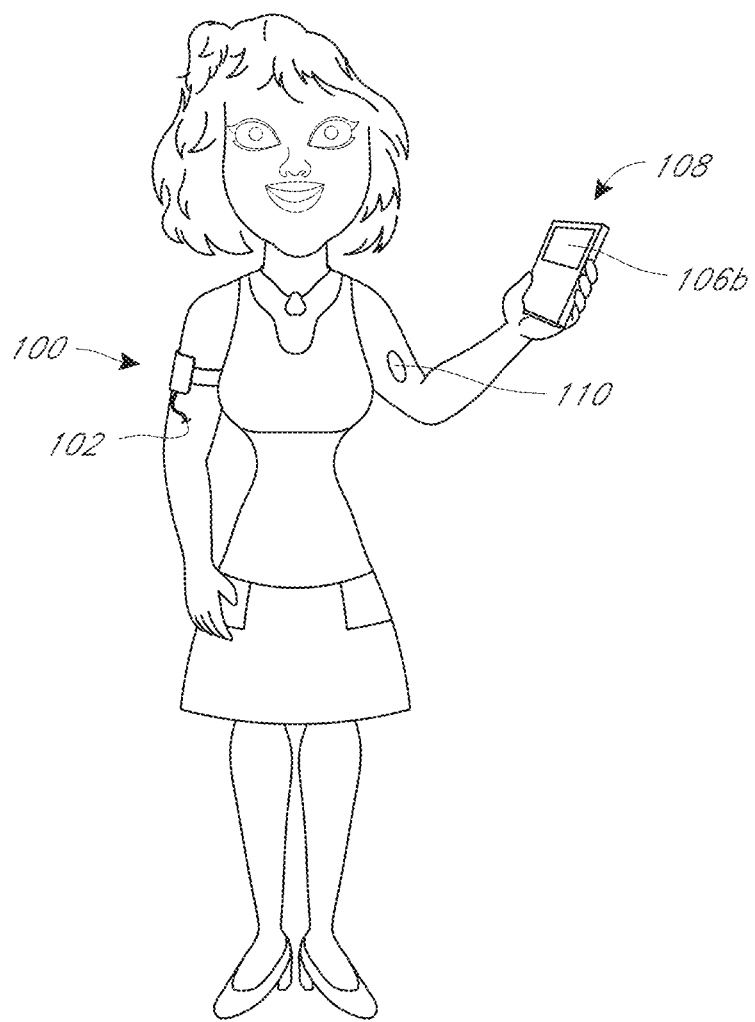
FIG. 1C illustrates a further example blood glucose control system that provides blood glucose control via an ambulatory medicament pump.

FIGS. 1A-1C show examples of blood glucose control systems that provide blood glucose control via an ambulatory medicament pump connected to a subject. In FIG. 1A, the medicament pump 100 is connected to an infusion site 102 using an infusion set 104. The medicament pump has integrated pump controls 106a that permit a user to view pump data and change therapy settings via user interaction with the pump controls 106a. A glucose level sensor 110 generates a glucose level signal that is received by the blood glucose control system.

In FIG. 1B, the medicament pump 100 communicates with an external electronic device 108 (such as, for example, a smartphone) via a wireless data connection. At least some of the pump controls 106a and 106b can be manipulated via user interaction with user interface elements of the external electronic device 108. The glucose level sensor 110 can also communicate with the medicament pump 100 via a wireless data connection.

In FIG. 1C, the medicament pump 100 includes an integrated cannula that inserts into the infusion site 102 without a separate infusion set. At least some of the pump controls 106b can be manipulated via user interaction with user interface elements of an external electronic device 108. In some instances, pump controls can be manipulated via user interaction with user interface elements generated by a remote computing environment (not shown), such as, for example, a cloud computing service, that connects to the medicament pump 100 via a direct or indirect electronic data connection.

Glucose control systems typically include a user interface configured to provide one or more of therapy information, glucose level information, and/or therapy control elements capable of changing therapy settings via user interaction with interface controls. For example, the user can provide an indication of the amount of the manual bolus of medicament from an electronic device remote from the medicament pump. The user interface can be implemented via an electronic device that includes a display and one or more buttons, switches, dials, capacitive touch interfaces, or touchscreen interfaces. In some embodiments, at least a portion of the user interface is integrated with an ambulatory medicament pump that can be tethered to a body of a subject via an infusion set configured to facilitate subcutaneous injection of one or more glucose control agents. In certain embodiments, at least a portion of the user interface is implemented via an electronic device separate from the ambulatory medicament pump, such as a smartphone.

Figure 2A:
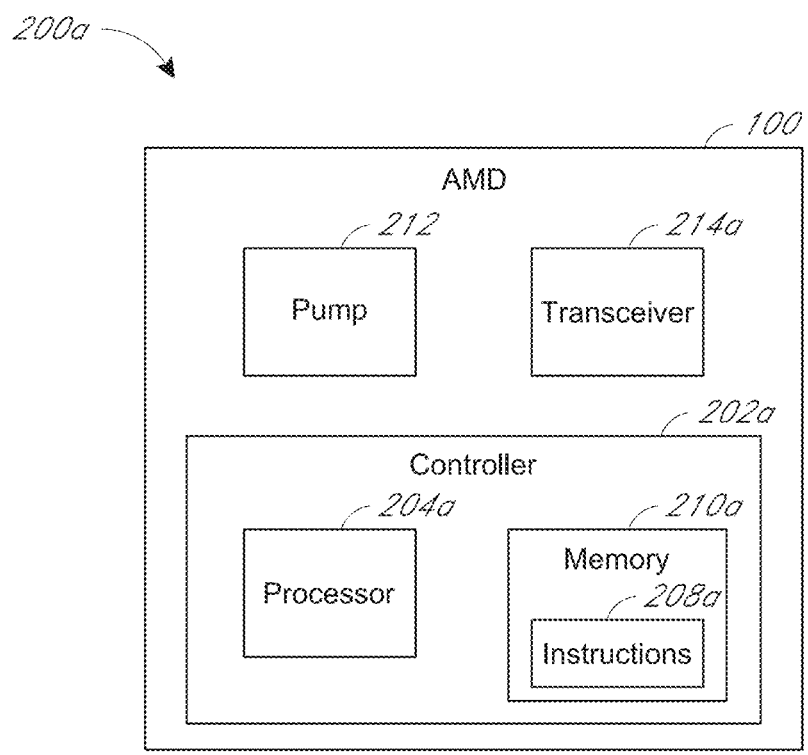
FIG. 2A shows a block diagram of an example blood glucose control system.

FIGS. 2A-2D illustrate block diagrams showing example configurations of a glucose control system 200a/200b/200c/200d. As shown in FIG. 2A, a glucose control system 200a can include a controller 202a having an electronic processor 204a and a memory 210a that stores instructions 208a executable by the processor 204a. The controller 202a and a pump 212 can be integrated into an ambulatory medical device (AMD) 100. The pump 212 can be a regulatory agent pump and/or counter-regulatory agent pump. The AMD 100 can have one or more pumps 212. The AMD 100 can include a transceiver or wireless electronic communications interface 214a for wireless digital data communications with external electronic devices. When the instructions 208a stored in memory 210a are executed by the electronic processor 204a, the controller 202a can implement at least a portion of a control algorithm that generates dose control signals for one or more glucose control agents based on time-varying glucose levels of the subject (e.g., received from a glucose level sensor 110 that is in communication with the medicament pump 100) and one or more control parameters. The dose control signals, when delivered to the pump 212, result in dosing operations that control the blood glucose of a subject.

Figure 2B:
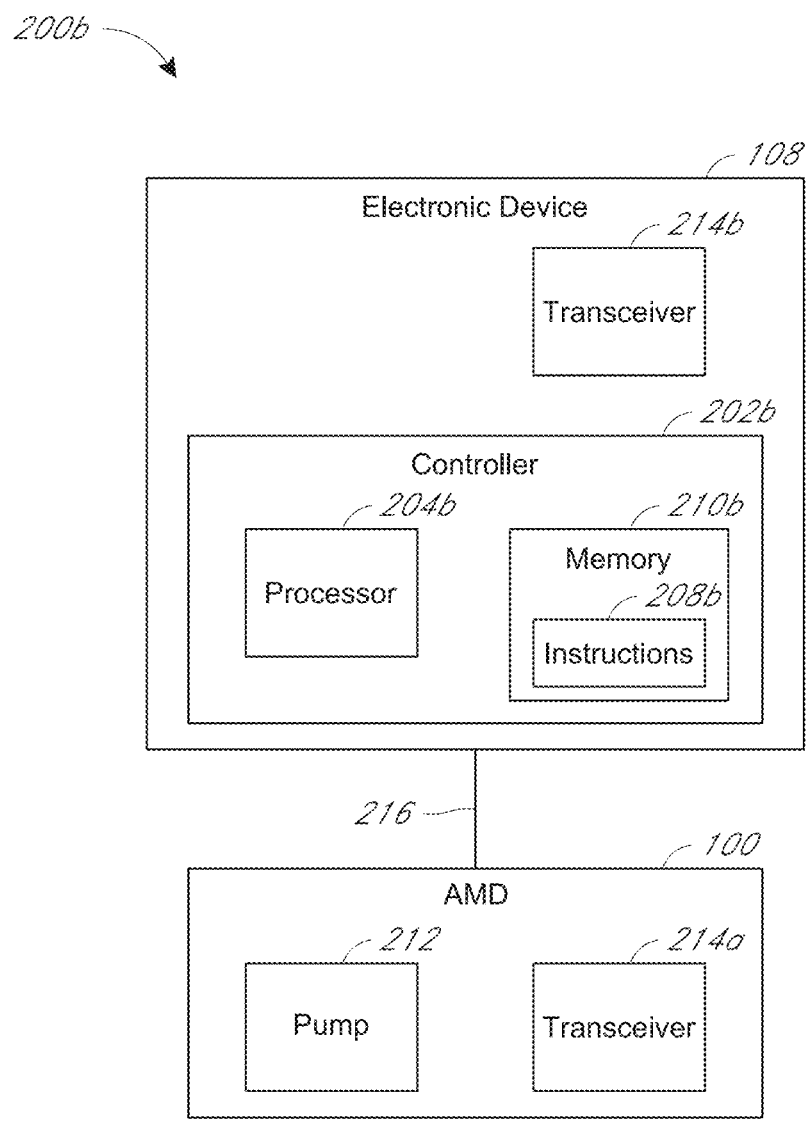
FIG. 2B shows a block diagram of another example blood glucose control system.

As shown in FIG. 2B, a glucose control system 200b can operate at least partially via execution of instructions 208b by an electronic processor 204b of an electronic device 108 separate from the ambulatory medical device 100. The electronic device 108 can include a transceiver 214b capable of establishing a wireless digital data connection to the AMD 100, and a controller 202b can implement at least a portion of a control algorithm via execution of instructions 208b stored in memory 210b. When the instructions 208b stored in memory 210b are executed by the electronic processor 204b, the controller 202b can implement at least a portion of a control algorithm that generates dose control signals for one or more glucose control agents based on time-varying glucose levels of the subject and one or more control parameters. The dose control signals, when delivered to the pump 212, result in dosing operations that control the blood glucose of a subject. In some embodiments, the dose control signals are transmitted from the device transceiver 214b to the AMD transceiver 214a over a short-range wireless data connection 216. The AMD 100 receives the dose control signals and passes them to the pump 212 for dosing operations.

Figure 2C:
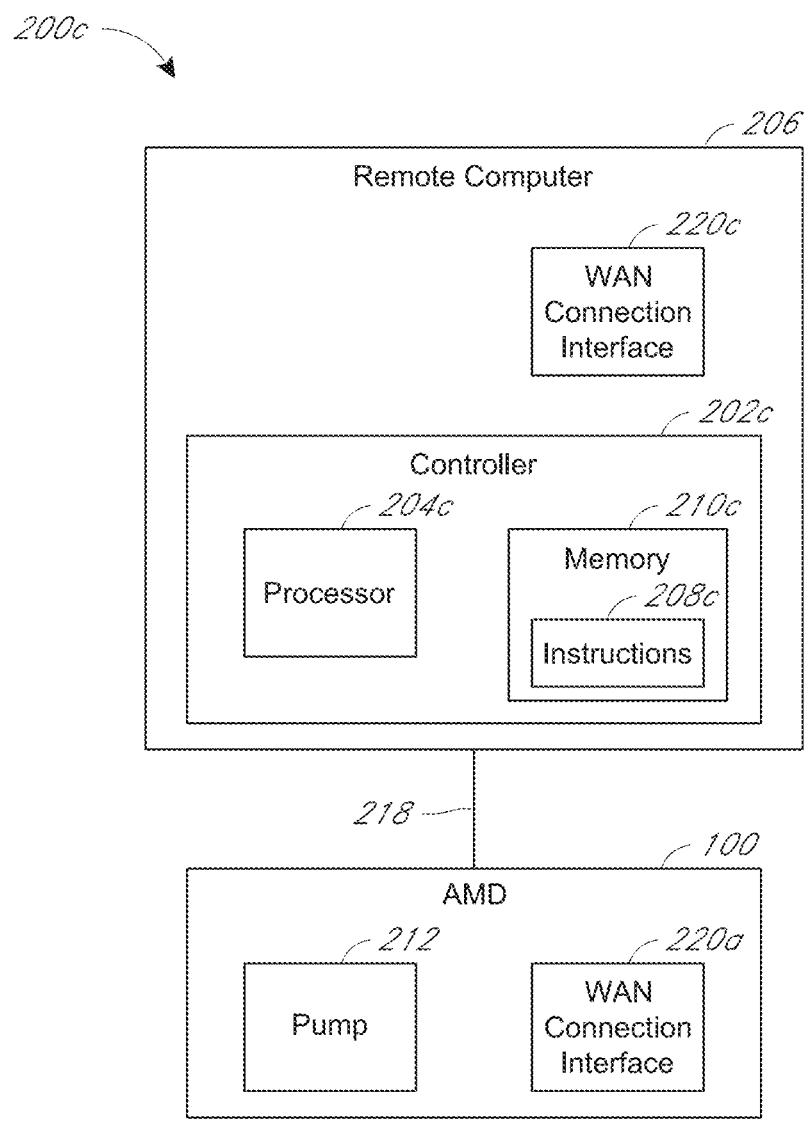
FIG. 2C shows a block diagram of another example blood glucose control system.

As shown in FIG. 2C, a glucose control system 200c can operate at least partially via execution of instructions 208c on an electronic processor 204c integrated with a remote computer 206, such as, for example, a cloud service. When the instructions 208c stored in memory 210c are executed by the electronic processor 204c, the controller 202c can implement at least a portion of a control algorithm that generates dose control signals for one or more glucose control agents based on time-varying glucose levels of the subject and one or more control parameters. The dose control signals, when delivered to the pump 212, result in dosing operations that control the blood glucose of a subject. In some embodiments, the dose control signals are transmitted from the remote computer WAN connection interface 220c to the AMD WAN connection interface 220a over an end-to-end wireless data connection 218. The AMD 100 receives the dose control signals and passes them to the pump 212 for dosing operations.

Figure 2D:
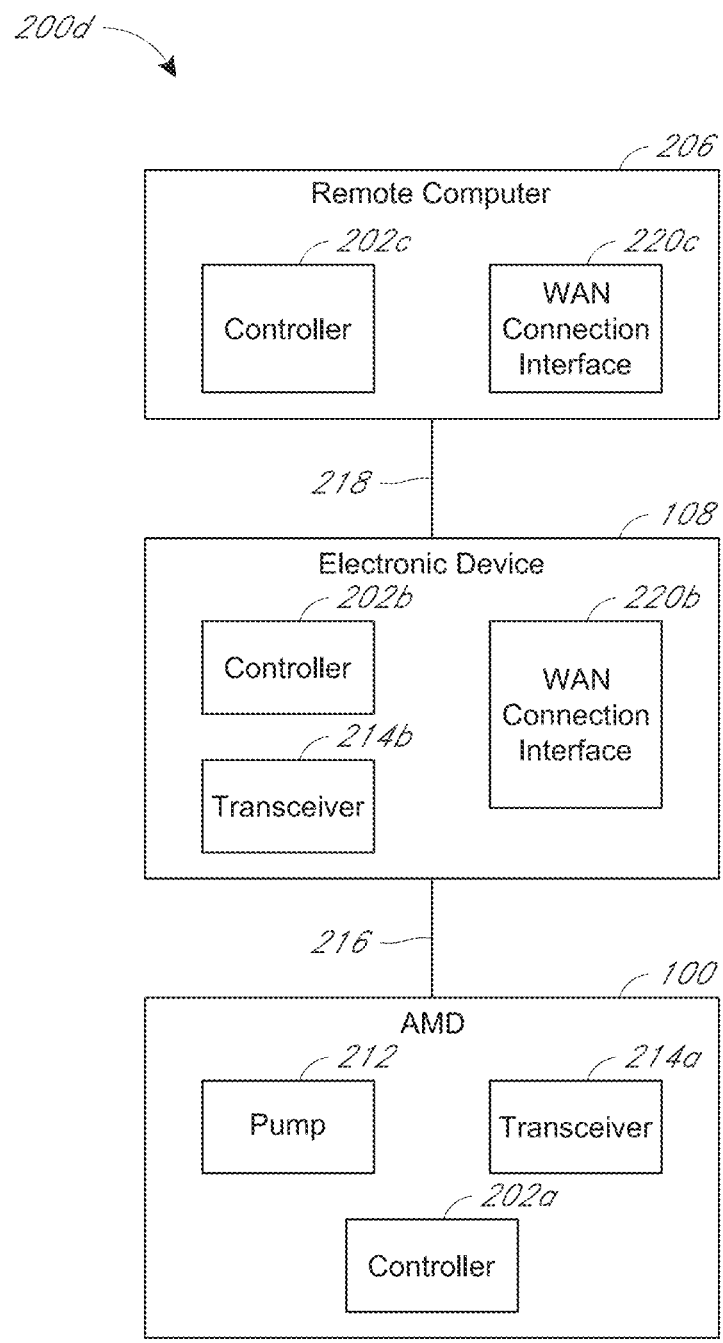
FIG. 2D shows a block diagram of another example blood glucose control system.

As shown in FIG. 2D, a glucose control system 200d can have two or more controllers 202a, 202b, 202c that cooperate to generate a dose control signal for dosing operations by the pump 212. A remote computer 206 can transmit or receive data or instructions passed through a WAN connection interface 220c via a WAN wireless data connection 218 to a WAN connection interface 220b of an electronic device 108. The electronic device 108 can transmit or receive data or instructions passed through a transceiver 214b via a short-range wireless data connection 216 to a transceiver 214a of an AMD 100. In some embodiments, the electronic device can be omitted, and the controllers 202a, 202c of the AMD 100 and the remote computer 206 cooperate to generate dose control signals that are passed to the pump 212. In such embodiments, the AMD 100 may have its own WAN connection interface 220a to support a direct end-to-end wireless data connection to the remote computer 206.

Figure 3:
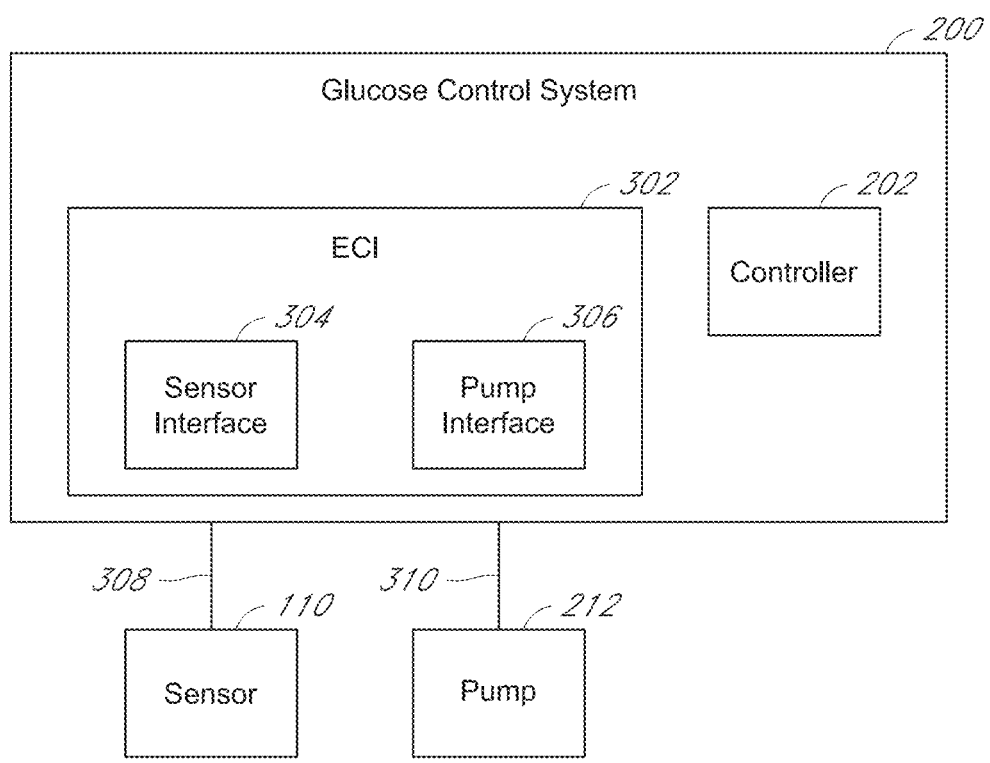
FIG. 3 is a schematic of an example glucose control system that includes an electronic communications interface.

As shown in FIG. 3, in some embodiments, the glucose control system 200 includes circuitry that implements an electronic communications interface (ECI) 302 configured to send and receive electronic data from one or more electronic devices. The ECI includes a sensor interface or glucose sensor interface 304 configured to receive a glucose level signal from a glucose level sensor 110 such as a continuous glucose monitor (CGM). Some CGMs generate the glucose level signal at fixed or periodic measurement intervals, such as five-minute intervals. The glucose level sensor 110 can be operatively connected to a subject in order to generate a glucose level signal that corresponds to a blood glucose estimate or measurement of the subject. The glucose level signal can be used by the controller 202 to generate a dose control signal. The dose control signal can be provided to a pump 212 via a pump interface or delivery device interface 306. In some embodiments, the sensor interface 304 connects to the sensor 110 via a short-range wireless connection 308. In some embodiments, the pump interface 306 connects to the pump 212 via a short-range wireless connection 310. In other embodiments, the pump interface 306 connects to the pump 212 via a local data bus, such as when the controller 202, the ECI 306, and the pump 212 are integrated into an AMD 100.

The controller can be configured to generate the dose control signal using a control algorithm that generates at least one of a basal dose, a correction dose, and/or a meal dose. Examples of control algorithms that can be used to generate these doses are disclosed in U.S. Patent Application Publication Nos. 2008/0208113, 2013/0245547, 2016/0331898, and 2018/0220942 (referenced herein as the "Controller Disclosures"), the entire contents of which are incorporated by reference herein and made a part of this specification. The correction dose can include regulatory or counter-regulatory agent and can be generated using a model-predictive control (MPC) algorithm such as the one disclosed in the Controller Disclosures. The basal dose can include regulatory agent and can be generated using a basal control algorithm such as disclosed in the Controller Disclosures. The meal dose can include regulatory agent and can be generated using a meal control algorithm such as disclosed in the Controller Disclosures. Additional aspects and improvements for at least some of these controllers are disclosed herein. The dose control signal can be transmitted to a pump interface 306 via the ECI 302 or can be transmitted to the pump interface 306 via an electrical conductor when the controller 202a is integrated in the same housing as the pump interface 306.

Figure 4A:
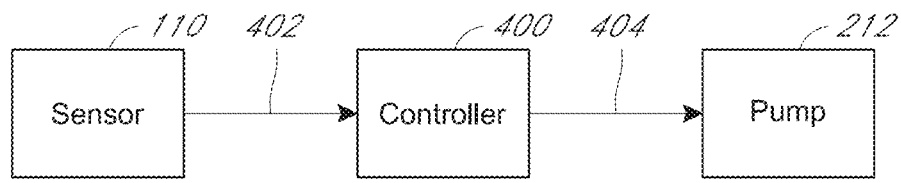
FIG. 4A shows a block diagram of an example blood glucose control system in online operation mode.

As shown in FIG. 4A, the controller 400 can be configured to operate in "online mode" during time periods when the controller receives a glucose level signal 402 from a glucose level sensor 110. In online mode, the control algorithm generates a dose control signal 404 that implements regular correction doses based on values of the glucose level signal 402 and control parameters of the control algorithm. The pump 212 is configured to deliver at least correction doses and basal doses to the subject without substantial user intervention while the controller 400 remains in online mode.

Figure 4B:
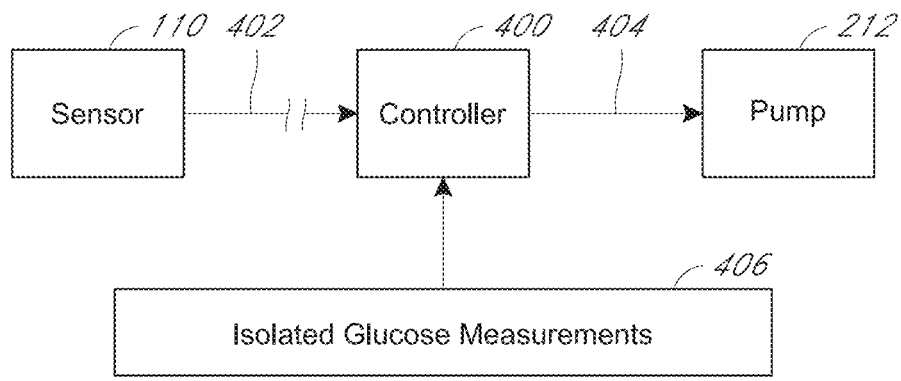
FIG. 4B shows a block diagram of an example blood glucose control system in offline operation mode.

As shown in FIG. 4B, the controller 400 can be configured to operate in "offline mode" during time periods when the controller does not receive a glucose level signal 402 from a sensor 110, at least during periods when the glucose level signal 402 is expected but not received. In offline mode, the control algorithm generates a dose control signal 404 that implements correction doses in response to isolated glucose measurements 406 (such as, for example, measurements obtained from the subject using glucose test strips) and based on control parameters of the control algorithm. The pump 212 is configured to deliver basal doses to the subject without substantial user intervention and can deliver correction doses to the subject in response to isolated glucose measurements 406 while the controller 400 remains in offline mode.

Example Ambulatory Medical Device

In some embodiments, the ambulatory medical device (AMD) can be a portable or wearable device (e.g., an insulin or bi-hormonal medicament pump) that provides life-saving treatment to a subject by delivering one or more medicaments (e.g., insulin and/or glucagon) to a subject. Some AMDs may continuously monitor the health condition of a subject (e.g., blood glucose level) using a sensor (e.g., a blood glucose level sensor that can measure values corresponding to the blood glucose level) and deliver therapy (e.g., one or more medicaments) to the subject based on the condition of the subject. Certain ambulatory medicament devices may be worn by subjects constantly (e.g., all day), or for a large portion of the day (e.g., during waking hours, during sleep hours, when not swimming, etc.) to enable continuous monitoring of the health condition of the subject and to deliver medicament as necessary. In some embodiments, an AMD may be an ambulatory medicament device such as a medicament delivery pump. In some examples, an AMD may be a device that provides therapy in the form of electrical stimulation based on a health condition of a subject (e.g., heart rhythm or brain activity) determined using signals received from one or more sensors (e.g., heart beat monitor or electrodes monitoring activity of the brain).

Figure 5A:
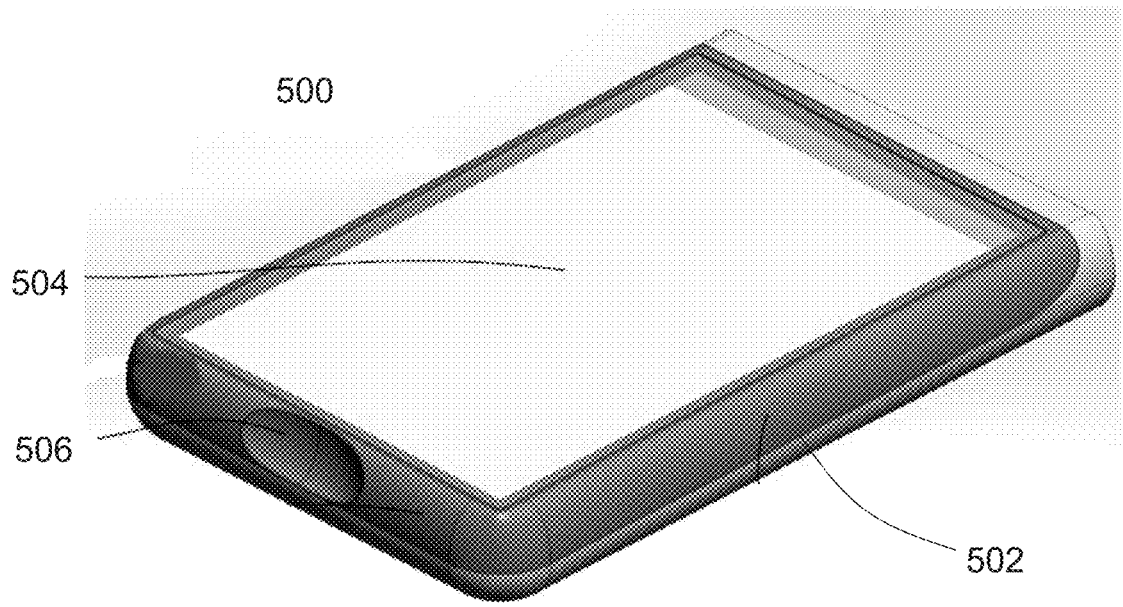
FIG. 5A illustrates a perspective view of an example ambulatory medical device.
Figure 5B:
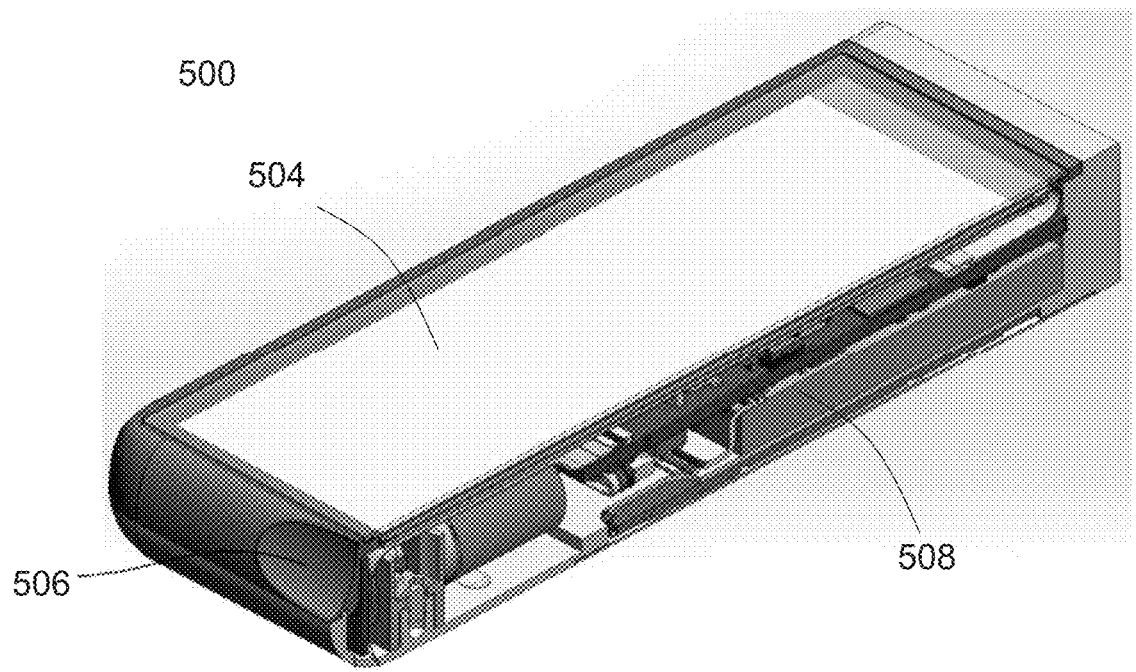
FIG. 5B illustrates a cross sectional view of the ambulatory medical device shown in FIG. 5A.

FIG. 5A illustrates a three-dimensional (3D) view of an example ambulatory medical device (e.g., an ambulatory medicament delivery pump such as an insulin pump) 500 comprising a housing 502 with a wake button 506 and a touchscreen display 504. FIG. 5B is an illustration of a cross sectional view of the AMD 500 shown in FIG. 5A. In this example, all the electronic systems 508 are included inside the housing 502, for example, as a single integrated electronic board. The wake button 506 may be any type of button (e.g., capacitive, inductive, resistive, mechanical, etc.) that registers an input generated by user interaction with the wake button 506 to generate a wake signal. In some embodiments, the wake signal is generated by a sensor (e.g., a biometric sensor such as a fingerprint reader or a retinal scanner, an optical or RF proximity sensor, and the like). In various embodiments, the wake signal may be generated by user interaction with the touch screen display 504 or with an alphanumeric pad (not shown). In some examples, a wake signal may be generated based on facial recognition or other biometric indicia. In some examples, the wake signal may be generated by a wireless signal such as a signal generated by an RFID system or Bluetooth signals received from an electronic device or by detection of movement using one or more motion sensors such as an accelerometer. The wake button 506, if touched, pressed, or held for a certain period of time, may generate a wake signal that activates the touchscreen display 504. In some examples, touches on the touchscreen display 504 are not registered until the wake button activates the touchscreen display. In some such examples, the AMD remains locked from accepting at least certain types of user interaction or settings modification until a gesture (such as, for example, any of the gesture interactions described with reference to any of the embodiments disclosed herein) is received after the touchscreen display 504 is activated by the wake button 506. In some examples, after the touchscreen display 504 has been activated by the wake signal, a passcode may be required to unlock the touchscreen display.

Figure 6:
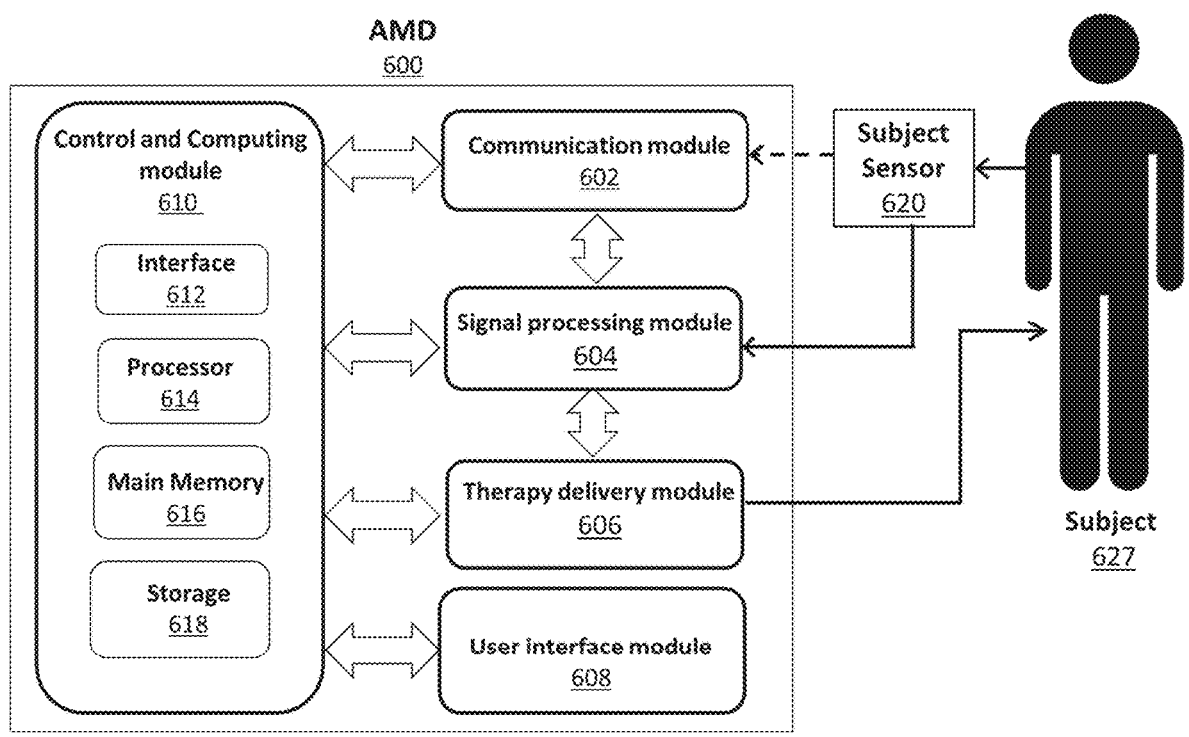
FIG. 6 illustrates different modules that may be included in an example ambulatory medical device (AMD).

FIG. 6 illustrates different modules that may be included in an example AMD 500 (e.g., a glucose control system). As mentioned above, in some examples, the AMD may comprise a complete glucose control system (e.g., AMD 100 and glucose control system 200a). In some implementations, the AMD may include one or more systems that can facilitate monitoring a subject's blood glucose level, maintaining the subject's diabetes, tracking a condition of the AMD, and/or communicating with one or more computing systems. For example, the AMD may include a mono-hormonal or bi-hormonal medicament pump configured to administer one or more types of insulin and, in some cases, counter-regulatory agent (e.g., Glucagon or other medicament that can reduce or address hypoglycemia). As another example, the AMD may include one or more alarm generators, transceivers, touchscreen controllers, display controllers, encryption modules, etc. In some examples, two or more of the modules or systems may be integrated together inside a single housing 502 (as shown in FIGS. 5A and 5B). In some examples, one or more modules may be individual modules contained in separate housings that communicate with other modules and/or the main unit via a wired or wireless communication link (e.g., Bluetooth). The modules included in the AMD may include a communication module 602, signal processing module 604, a therapy delivery module 606, a user interface module 608, and a control and computing module 610. In some embodiments, one or more modules may comprise one or more single purpose or multipurpose electronic systems. In some such examples, one or more electronic systems may perform procedures associated with different features of the AMD. In some other embodiments, one or more modules may comprise a non-transitory memory that stores machine readable instructions and a processor that executes instructions stored in the memory. The memory may be a non-volatile memory, such as flash memory, a hard disk, or any other type of non-volatile memory. In some such examples, a module may include several procedures each implemented based on different sets of instructions.

The control and computing module 610 may include one or more processors 614, a main memory 616, a storage 618 that may comprise one or more non-transitory and/or non-volatile memories and an interface 612 that enables data and signal communication among systems within the control and computing module 610 as well as communication between the control and computing module and all other modules of the AMD. The main memory 616 and the storage 618 each may be divided into two or more memory locations or segments. The main memory 616 may communicate with the other components of the control and computing module 610 as well as other modules via the interface 612. Instructions may be transmitted to the main memory (e.g., from the storage) and the processor 614 may execute instructions that are communicated to the processor through the main memory 616. The storage 618 may store data while the control and computing system 610 is powered or unpowered. The storage 618 may exchange data with the main memory directly or through the interface 612. The main memory 616 can be any type of memory that can store instructions and communicate them to the processor 614 and receive executed instructions from the processor 614. Types of main memory include but are not limited to random access memory ("RAM") and read-only memory ("ROM"). The processor 614 may be any type of general-purpose central processing unit ("CPU"). In some embodiments, the control and computing module may include more than one processor of any type including, but not limited to complex programmable logic devices ("CPLDs"), field programmable gate arrays ("FPGAs"), application-specific integrated circuits ("ASICs") or the like. The storage 618 can be any type of computer storage that can receive data, store data, and transmit data to the main memory 616 and possibly other modules of AMD 600. Types of storage 618 that can be used in the control and computing system 610 include, but are not limited to, magnetic disk memory, optical disk memory, flash memory and the like. The interface 612 may include data transfer buses and electronic circuits configured to support data exchange among different components within the control and computing system 610. In some examples, the interface 612 may also support data and signal exchange among other modules as well as data exchange between any of the modules and the control and computing module 610.

The signal processing module 604 may include a plurality of interconnected electronic modules for signal conditioning and signal conversion (e.g., A-to-D or ADC conversion and D-to-A conversion or DAC conversion) configured to support communication and data exchange between different modules. For example, the signal processing module 604 may convert an analog signal received from the communication module 602 and convert it to a digital signal that can be transmitted to the control and computing module 610 (e.g., via the interface 612). As another example, the signal processing module may receive a digital control signal from the control and computing module 610 and convert it to an analog signal that can be transmitted to the therapy delivery module 606, for example, to control one or more infusion pumps included in the therapy delivery module 606.

In some embodiments, the therapy delivery module 606 may comprise one or more infusion pumps configured to deliver one or more medicaments (e.g., insulin or glucagon) to a subject 627. In some examples, the medicaments may be stored in one or more medicament cartridges housed in the therapy module 606. In some examples, the therapy delivery module 606 may include electronic and mechanical components configured to control the infusion pumps based on the signals received from control and computing module 610 (e.g., via the signal processing module 604).

The user interface module 608 may include a display to show various information about the AMD 600, for example, medicament type and delivery schedule, software status, and the like. The display may show graphical images and text using any display technology including, but not limited to OLED, LCD, or e-ink. In some embodiments, the AMD 600, may include a user interface (e.g., an alphanumeric pad) that lets a user enter information or interact with the AMD 600 to modify the settings of the AMD 600, respond to request for certain actions (e.g., installing a software) and the like. The alphanumeric pad may include a multitude of keys with numerical, alphabetical, and symbol characters. In different embodiments, the keys of the alphanumeric pad may be capacitive or mechanical. The user may be a subject 627 receiving medicament or therapy, or may be another user, such as a clinician or healthcare provider, or a parent or guardian of the subject 627. In some other embodiments, the AMD 600 may include a touchscreen display that produces output and also accepts input enabling a two-way interaction between the user and the AMD 600. The touchscreen display may be any input surface that shows graphic images and text and also registers the position of touches on the input surface. The touchscreen display may accept input via capacitive touch, resistive touch, or other touch technology. The input surface of the touchscreen display can register the position of touches on the surface. In some examples, the touchscreen display can register multiple touches at once. In some embodiments, the keypad may be a display of a keypad. For example, an alphanumeric pad comprising user-selectable letters, numbers, and symbols may be displayed on the touchscreen display. In some examples, the touchscreen may present one or more user-interface screens to a user enabling the user to modify one or more therapy settings of the ambulatory medicament device. In some examples, a user-interface screen may comprise one or more parameter control elements. Further, a user-interface screen may include one or more user input elements displayed on the screen that enable a user to interact with the AMD 600.

In some embodiments, the communication module 602, may include one or more wireless transceivers, one or more antennas, and one or more electronic systems (e.g., front end modules, antenna switch modules, digital signal processors, power amplifier modules, etc.) that support communication over one or more communication networks. In some examples, each transceiver may be configured to receive or transmit different types of signals based on different wireless standards via the antenna (e.g., an antenna chip). The transceiver may support communication using a low power wide area network (LPWAN) communication standard. In some examples, the transceiver may support communication with wide area networks (WANs) such as a cellular network transceiver that enables 3G, 4G, 4G-LTE, or 5G. Further, the transceiver may support communication via a Narrowband Long-Term Evolution (NB-LTE), a Narrowband Internet-of-Things (NB-IoT), or a Long-Term Evolution Machine Type Communication (LTE-MTC) communication connection with the wireless wide area network. In some cases, the transceiver may support Wi-Fi® communication. In some examples, the transceiver may be capable of down-converting and up-converting a baseband or data signal from and to a wireless carrier signal. In some examples, the communication module may wirelessly exchange data between other components of the AMD 600 (e.g., a blood glucose level sensor), a mobile device (e.g., smart phone, a laptop and the like), a Wi-Fi network, WLAN, a wireless router, a cellular tower, a Bluetooth device and the like. The antenna may be capable of sending and receiving various types of wireless signals including, but not limited to, Bluetooth, LTE, or 3G. In some examples, the communication module 602 may support direct end-to-end communication between the AMD 600 and a server or a cloud network. In some examples the AMD may communicate with an intermediary device (e.g., a smart phone or other mobile devices, a personal computer, a notebook, and the like). In some embodiments, the AMD may include an eSIM card that stores information that may be used to identify and authenticate a mobile subscriber. The eSIM card may enable the AMD to function as an IoT device that can communicate over a network that supports communication with IoT devices. In other embodiments, the AMD may be configured to transmit data using a narrowband communication protocol such as 2G or EDGE. Using the cellular connection, the AMD 600 may be paired with a mobile device at inception and permit real-time data access to the AMD 600 by a healthcare provider. In certain implementations, the AMD 600 may include a geolocation receiver or transceiver, such as a global positioning system (GPS) receiver. As previously stated, each of the AMDs described herein may include one or more of the embodiments described with respect to the other AMDs unless specifically stated otherwise.

Example Operation of the AMD

In some embodiments, the AMD 600 (or AMD 100) may continuously, periodically, or intermittently receive information about one or more parameters that are correlated with a health condition of the subject 627 (e.g., blood glucose level, blood glucose trend, heart rate, body movement indicia, etc.). This information may be encoded to a signal provided to AMD 600 by a glucose level sensor hereinafter referred to as "subject sensor" 620 (e.g., a wearable biomedical sensor that measures an analyte in the interstitial fluid) that is connected to the AMD 600 via a wired or wireless link (e.g., Bluetooth). In some examples, the signal sent by the subject sensor 620 may be received by the communication module 602 and transmitted to a signal processing module 604 that converts the signal to a machine-readable signal (e.g., a digital signal). In some examples, a second communication module may be included in the AMD 600 to communicate with the subject sensor 620. In some examples, the signal processed by the signal processor module 604 may be transmitted to the control and computing module 610 where the signal may be analyzed to determine whether medicament should be delivered to the subject 627. If it is determined that medicament should be administered to the subject, the control and computing module may determine the dosage and type of medicament to administer based on the information received from the subject sensor 620 and send a dose signal to the therapy delivery module 606 (e.g., directly or via the signal processing module 604) to initiate the medicament delivery to the subject (e.g., using an infusion pump of the therapy delivery module 606).

In some embodiments, one or more procedures within the control and processing module 610 may be executed by the processor 614 (or a plurality of processors) based on instructions provided by one or more software applications installed in one of the memories (e.g., the main memory 616) of control and computing module 610. These procedures include, but are not limited to, determining the need for delivering medicament, determining the type of medicament and the required dose, determining the rate of delivery during a therapy session, providing information (e.g., device status, next delivery time, level of certain analytes in the subject's blood and the like) via the user interface module 608, processing the information received from a subject sensor 620 via the user interface 608, and the like. In some embodiments, a first software application may control the AMD 600 and may be installed on the main memory 616 while a second software application (e.g., different version) may be stored in the storage 618. In some examples, the first and second software applications may be both installed in the main memory 616 but in different locations or segments. In some such examples, if needed, the control of the device can be switched from the first software application to the second software application.

In some embodiments, the AMD 600 may deliver multiple types of therapies that are selectable by a user or the control and computing module 610. For example, the AMD 600 may deliver the therapy of infusing insulin into a user and may also deliver the therapy of infusing glucagon into the user. In some examples, the user interface may include an option for the user to select an infusion of insulin, glucagon, or both insulin and glucagon. In other embodiments, other hormones, liquids or therapies may be delivered. In some examples, the software application executed by the control and computing module 610, may determine the type of hormone that needs to be delivered, at least in part based on the information received from the subject sensor 620.

Communication and Networking

Figure 7:
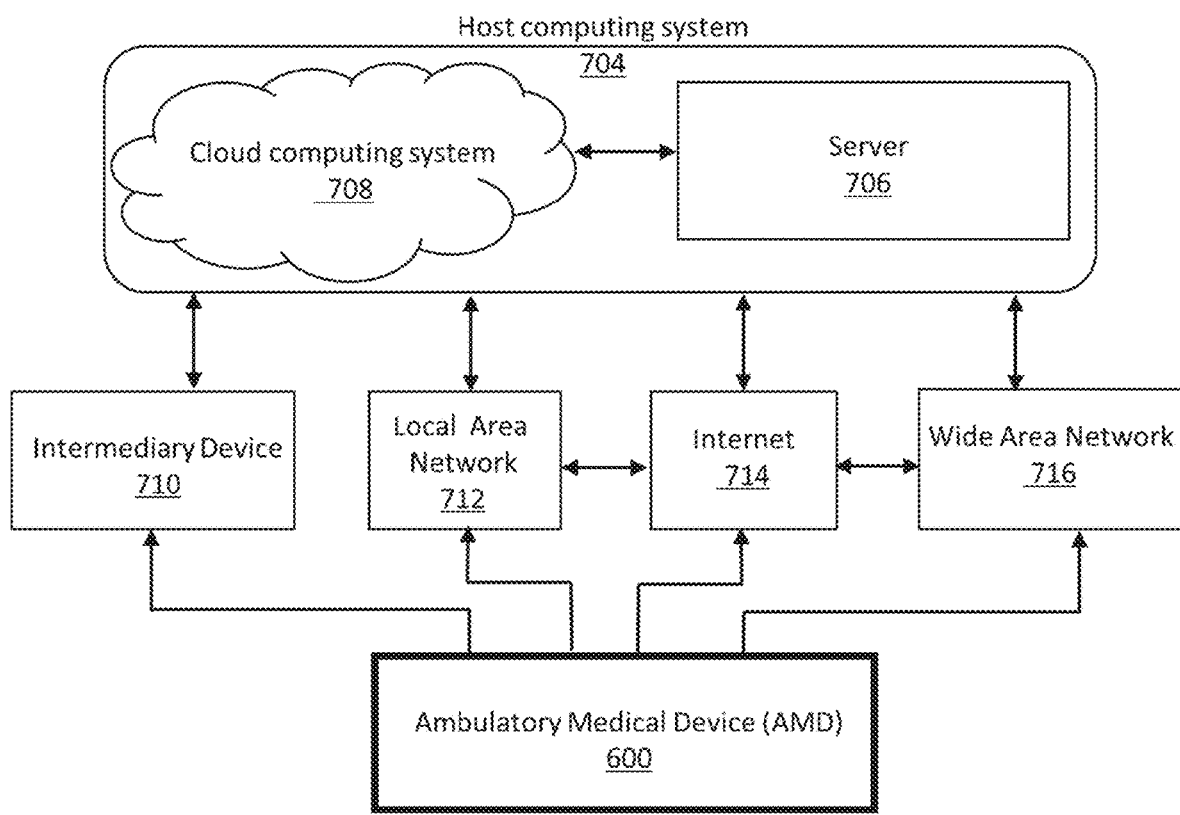
FIG. 7 illustrates various methods and links that AMD may use to establish a communication connection with a host computing system.

FIG. 7 illustrates various methods and links or communication paths that an AMD 702 may use to communicate (e.g., by establishing a connection) with a host computing system 704, for example, to obtain an application update, send and/or receive therapy reports, receive passcodes, receive control parameters and the like. In some examples, the host computing system 704 may be a server 706 or a computing system within a cloud computing network 708, or other networked computing environments, that provide networking computing services (e.g., network storage, application hosting, and/or network processing services). In some examples, the host computing system 704 may be part of a data center (e.g., the data center of a healthcare provider).

In some embodiments, the AMD 600 may establish a connection (e.g., using the communication module 602) with the host computing system 704 through an intermediary device 710 (e.g., a smart phone or other mobile devices, a personal computer a notebook or the like). In some such examples, the AMD 600 may receive an application update from a local device 710 of a user (e.g., a clinical computer, a subject's home computer, a smartphone, etc.) that has obtained a copy of the application update from the host computing system directly or via internet 714. In some examples, the AMD 600 may communicate with the host computing system 704 through a local area network (LAN) and/or through a Wi-Fi connection. Alternatively, or in addition, the AMD 600 may establish a communication connection to the host computing system 704 via a wide area network (WAN) 716. In some examples, the communication between the AMD 600 medical device and the cloud computing service may be encrypted.

In some embodiments, the AMD 600 may establish a direct end-to-end communication connection over a wide area network (WAN) 716 (e.g., a cellular network) with the host computing system 704. In some cases, a direct-end-to-end communication connection may be a connection that does not involve a local device, a device that is accessible by the user or the subject (besides the AMD 600), a Wi-Fi network, a short range wireless link (e.g., Bluetooth), or the like. In some such cases, the direct end-to-end communication may pass through one or more wireless systems (e.g., receivers, transmitters or antenna) of a WAN. In some examples, the host computing system 704 may establish the end-to-end connection by receiving a public key from the AMD 600. In some examples, the public key and a private key stored in the host computing system 704 can be used to permit the host computing system 704 to decrypt data communications transmitted by the AMD 600. In some implementations, the host computing system 704 may establish a direct end-to-end data connection with the AMD 600 based on receiving a device identifier associated with the AMD 600. The device identifier may be a unique identifier specific to the AMD. In some other implementations, establishing the direct end-to-end data connection may include determining that the AMD 600 is permitted to communicate with the host computing system 704 based at least in part on the device identifier. In some examples, the device identifier may be initially provided to the networked-computing environment prior to provisioning of the AMD 600 to the subject. For example, the device identifier may be initially provided to the networked-computing environment as part of a manufacturing process for manufacturing the AMD 600. In some examples, the device identifier may include or may be based on one or more of an Internet Protocol (IP) address, a Media Access Control (MAC) address, a serial number, or a subject identifier of a subject that receives therapy from the AMD 600. In some cases, the subject or a user may establish or initiate establishing the direct end-to-end data connection with the host computing system 704. In some cases, the direct end-to-end data connection may be initiated or established without any action by the subject or the user. For example, the direct end-to-end data connection may be established automatically at particular times and/or when the AMD 600 is in a particular location. In some such cases, this automatic connection may occur using information supplied to the AMD 600 at a time of manufacture, shipment, sale, or prescription to the subject. Alternatively, or in addition, a subject or other user may configure the AMD 600 to automatically connect to the host computing system 704 at particular times and/or locations. In some cases, the wide area network may include, or may communicate with, the Internet 714.

In some embodiments, the AMD 600 may be configured to communicate via the wide area network during manufacture or prior to being provisioned to the subject. For example, a manufacturer can register the AMD 600 with a wireless wide-area network provider (e.g., T-Mobile or Verizon) and provide an International Mobile Equipment Identity (IMEI) number or serial number for the AMD 600 to the network provider. Moreover, fees can be negotiated between the manufacturer and the network provider or between the subject's health insurance and the network provider. Similarly, fees may be paid by the manufacturer or health insurance provider, or other entity, without subject involvement. Thus, the subject's AMD 600 may be configured to communicate via the network of the network provider without any action by the subject or the user. In some cases, the subject may be responsible for obtaining wireless service to connect the AMD 600 to a wide area network 716 (e.g., a cellular network).

In some examples, the AMD 600 may be pre-registered or authenticated with a computing network of the cloud services provider as part of the manufacturing process or before AMD 600 is provided to the subject. This enables the AMD 600 to communicate over the wide area network with the computing system of the cloud services provider from day one without any or with minimal configuration by the subject. In some cases, a user, such as a healthcare provider may register or associate the AMD 600 with the subject at the computing network of the cloud services provider.

In some embodiments, the AMD 600 may use a whitelist, or approved list, that identifies via a unique identifier (e.g., via an IP address, a MAC address, or a URL) one or more permitted cloud servers or computing systems of the cloud computing system 708 that the AMD 600 is permitted to access. By restricting access to an approved set of computing systems, the risk of malicious actors accessing the AMD 600 is reduced. Moreover, in some cases, the AMD 600 may include a blacklist, or restricted list, that identifies systems the AMD 600 is not permitted to access. The blacklist may be updated as more restricted or unsafe websites, network accessible systems, or computing systems are identified. Similarly, the whitelist may be updated over time if approved systems are added or removed.

Further, the cloud computing service may have a whitelist, or approved list, that uses unique identifiers to specify AMD 600 and/or other computing systems (e.g., remote display systems) that are permitted to communicate with the cloud computing system 708. Moreover, as with the AMD 600, the cloud computing service may have a blacklist or restricted list that identifies AMDs, or other computing devices, that are not permitted to access the cloud computing services. An AMD may be added to the restricted list if it is decommissioned, damaged, or is no longer in possession of the subject. It may be desirable to remove an AMD's access to the cloud computing service to help protect private or personal data of a subject. Advantageously, establishing a connection based on a whitelist may enhance the security of the communication link established between AMD 600 and the cloud computing system 708 or other computing systems. In addition to the identifiers that identify permitted computing systems for access by the AMD and/or permitted AMDs for access by a cloud or networked computing service, the whitelist may include any information that may facilitate access to the systems identified on the whitelist. For example, the whitelist may include access information (e.g., usernames, passwords, access codes, account identifiers, port identifiers, a shared secret, public keys, etc.). It should be understood that the whitelist may include different information depending on whether the whitelist is publicly accessible, accessible by only the AMD, accessible by authorized users or devices, etc. For example, a publicly accessible whitelist or a whitelist accessible by more than one authorized system or user may not include passwords or access codes.

In some cases, the AMD 600 may use a whitelist that identifies via, for example, a unique identifier (e.g., via an IP address, a MAC address, or a URL) permitted cloud servers or computing systems of the cloud computing system 708. In some examples, the cloud computing system may have a whitelist that uses unique identifiers to specify AMD 600 and/or other computing systems (e.g., remote display systems) that are permitted to communicate with the cloud computing system 708. The whitelist may be stored in a memory of AMD 600 and/or in a memory of a trusted computing device that is accessible by the AMD 600. The trusted computing device can include any computing device that a manufacturer of the AMD has identified as trusted. Alternatively, or in addition, the trusted computing device can include any computing device that a subject or user that helps caste for the subject (e.g., parent, guardian, healthcare provider) has identified as a trusted computing device that is designated to store the whitelist. In some examples, the whitelist may be configured during manufacture of the AMD 600. For example, the whitelist may be configured with connection information to establish communication with one or more computing systems of a networked-computing environment. In some examples, the AMD 600 may be configured to execute the specific computer-executable instructions to at least obtain an address of a computing system from the whitelist and to establish a direct end-to-end data connection to the computing (e.g., a computing system in the networked-computing environment), via a wireless wide area network using the address. In some embodiments, the AMD 600 may be configured to execute the specific computer-executable instructions to at least receive a public key from the computing system of the networked-computing environment.

Application Update of Ambulatory Medical Device

It is often the case that a computer or software application is updated after it is released. Similarly, it is possible in some cases to update software or an application used to control or provide features for a medical device (e.g., an automated blood glucose control system or other AMD). In some cases, the application is updated to patch bugs or vulnerabilities. In some cases, the application is updated or replaced with a new version to introduce new features or improve existing features, or to provide access to newly purchased, licensed, or otherwise obtained features. Regardless of the reason, it is often the case that an application is shutdown or is not executing while the application is updated. For most applications, there is minimal to no harm in shutting down or not executing an application while it is updated or otherwise replaced. For example, it is inconsequential that a video game, word processing, or edutainment application is not executing while it is updated.

However, it can be inconvenient, harmful, or, in some cases, life-threatening to cause an application on an ambulatory medical device (AMD) to cease executing while it is updated or replaced by a new version of the application. If a subject that is receiving therapy from the ambulatory medical device enters a state where therapy is desired or needed while an application or control software of the AMD is being updated or replaced, harm may occur to the subject. For example, suppose the AMD is an insulin pump, such as those that may be used by a type-1 diabetic. If the insulin pump becomes inoperative due to an application update process occurring at a time when a subject's blood glucose level exceeds a set-point or target range, the user may not receive a necessary insulin bolus from the AMD. Thus, it is desirable to reduce or eliminate disruption to subject care or therapy when updating applications, such as control software, of an ambulatory medical device.

In some embodiments, an AMD includes a computer-implemented method of updating an application executing on the AMD without interrupting, or while causing minimal interruption, to therapy provided by the AMD to a subject or subject. The method may generally be performed by a hardware processor, (e.g., a controller, and the like), included in an AMD and based on a set of instructions that may be stored, for example, in a non-transitory memory of the AMD. The application update may include a binary executable file that may be executed by various processors of the AMD. The application update may be a new version of the application, a replacement or substitute application, or an application patch. Further, the application update may add or remove features to the version of the application installed on the AMD. In some examples, the application update may be an older version of the application that has been used by instances of the AMD for more than a threshold period of time and has experienced less than a threshold number of faults. The application to be updated on the AMD may be currently executing on the ambulatory medical device or may be executed in future. In some examples, The application update may be stored in one or more host computing systems. In some cases, the application update may be pushed to the host computing systems by a company that manages or manufactures the ambulatory medical device or other software company that is authorized by the manufacturer or licensee of the device. In some cases, the host computing system comprises a server computing device, a cloud computing device, a computing device of a healthcare provider, a computing device of a manufacturer of the AMD, an application server, or other network accessible computing device or system. In some cases, the application update may be stored in a local computing device, for example, a local computing device of the subject (e.g., a smartphone, a laptop or a personal computer).

Figure 8:
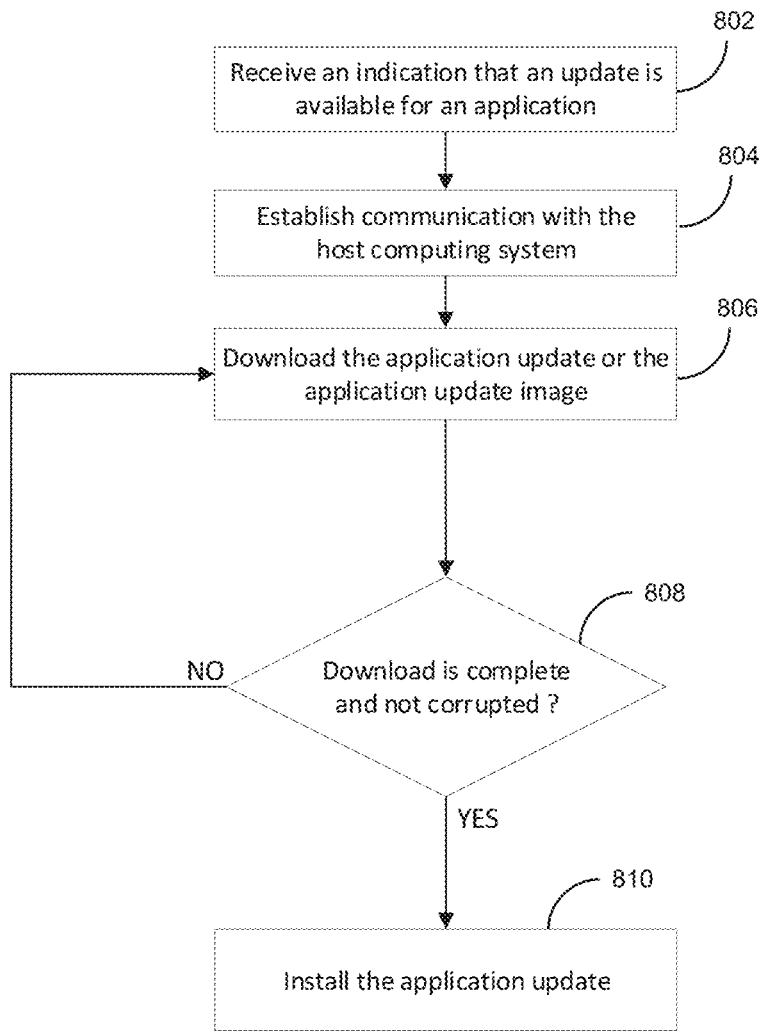
FIG. 8 is a flow diagram showing an example of a computer-implemented method that may be used by an AMD in order to detect and download an application update.

FIG. 8 is a flow diagram showing an example of a computer-implemented method that may be used by the AMD 600 in order to detect and download an application update from a host computing system or other computer readable media in which a copy of the application update may be stored. In some examples, the AMD 600 may directly communicate with the host computing system. In some cases, the AMD 600 may communicate with a proxy or other system to determine the availability of an application update or to acquire the application update. In some cases, the application update may be obtained from a content delivery network (CDN) or cache server.

At block 802 the AMD 600, such as a medicament delivery device or a medicament pump may receive an indication that an update is available for an application, such as control software or other software that controls or facilitates the operation of the AMD 600. In some embodiments, the indication may be a determination made by a software or hardware module included in the AMD 600. For example, the AMD 600 may access a particular host computing system (e.g., using its communication module) to determine whether an update is available, based on a set of update trigger conditions stored in a memory of AMD 600. The set of update trigger conditions may include any type of trigger condition that may cause the AMD 600 to determine if a software update is available and/or to update an application executing on the AMD 600. In some cases, the set of update trigger conditions may be defined/changed by a user and/or received by AMD 600 from a host computing system. For example, an update trigger condition may push the AMD 600 to periodically search for an update at time intervals set by the user or received from a host computing system. In other words, an application update availability check may be triggered by the AMD 600. The application update availability check may be performed in response to a time trigger or any other type of trigger. For example, an update availability check trigger can be a user command, the replacement of medicament within the ambulatory medical device, connecting to a particular network (e.g., connecting to a Wi-Fi network using a wireless transceiver, or the like), a scheduled time being reached, an occurrence of a fault, an occurrence of a particular condition in the AMD, or any other type of trigger. In some examples, the indication that the application update is available comprises an indicator of whether the application update corresponds to a first application version or a second application version of the application. In some examples, the AMD 600 may access an update server to determine whether the application update exists, and in response to accessing the update server, receive the indication that the application update is available. In some cases, a trigger to connect to an update server to determine the availability of an application update may include a detection of a fault with the currently executing application or an indication of a change in permitted features that a user or subject is permitted to access with the AMD 600.

In some examples, the host computing system may query or access the AMD 600 to determine an installed software version of the application and/or a hardware configuration to determine the eligibility of the ambulatory medical device for a software upgrade. In some cases, the eligibility for the software upgrade may be based at least in part on a license or warranty. The serial number, the model number, and/or the software version may be used to determine application update (e.g., a software upgrade) eligibility. In some embodiments, the eligibility for an application update may be determined based on the geoposition of the device and/or whether the device is connected to a local area network (e.g., a Wi-Fi network) or a wide area network (e.g., a cellular network). In various embodiments, the ambulatory medical device may have a transceiver and an antenna that provides the device with GPS, text or picture messaging, telephone calling, and data transfer capabilities. In some cases, the application update may be provided on a limited release, such as to test groups of varying size, e.g., 1-100, 1-1000, or 1-10000 users. Further, there may be a phased rollout of the application updates to different groups of users. In some embodiments, the AMD 600 may respond to an upgrade eligibility request by transmitting an identity of a version of the application or a model identification information of the AMD 600 or a manufacturing date of the AMD 600 to the host computing system.

If at block 802 the AMD 600 determines that an update is available for an application (e.g., an application that may be executing on the AMD 600), at block 804 the AMD 600 may establish a communication connection to a host computing system that hosts the update to the application. Such connection may be established, for example, via one or more links or methods discussed above with reference to FIG. 7. For example, the AMD 600 may communicate with a cloud 708 or a server 706 using a local area network 712, Internet 714, or wide area network 716. In some examples, a healthcare provider system may push the update to the AMD 600. In some examples, a communication connection via wide area network 716, may be a direct end-to-end communication connection. In some examples, the communication connection with the host computing system may be established via an intermediate device 710 (e.g., a personal computing device of the user or the subject).

In some examples, the AMD 600 may establish a direct end-to-end data connection to a host computing system via a wireless wide area network (WAN). The direct end-to-end data connection may comprise a narrow band long-term evolution (NB-LTE) connection, an NB Internet-of-Things (NB-IoT) connection, a cellular IoT connection, a 4G LTE connection, or a 5G connection. The direct end-to-end data connection may be a connection that is directly between the AMD 600 and the host computing system allowing without an intermediary system or computing device within a local area network of the AMD 600 being involved in the communication. A direct end-to-end data connection may include routing data or the connection through networking hardware, base stations, or other devices included in a wide area network, such as the Internet. However, other computing devices within a local area network that includes the AMD 600 may be omitted. Thus, for example, the AMD 600 does not communicate with a smartphone, laptop, smart appliance, or other device within a local area network of a user or subject that uses the AMD 600. In some cases, the AMD 600 may communicate with an intermediary system to obtain the application update. For example, the application update may be downloaded to a local system (e.g., a laptop or smartphone of the user), and then provided to the AMD 600 via a local area network, a USB connection, a near-field communication technology (e.g., Bluetooth, ZigBee, LoRa, etc.).

Once a communication connection is established at block 804, at block 806 the AMD 600 may download the application update from the host computing system over the communication connection. In some examples, the AMD 600 may download an image of the application update from the host computing system. While the application update is being downloaded, an existing version of the application on the ambulatory medical device may continue to execute. Thus, there may be little or no interruption to therapy provided by the AMD 600 while the application update is being obtained by the AMD 600.

In some examples, the AMD 600 may be linked to an intermediary device 710 (e.g. a mobile device) via a communication link (e.g., Bluetooth, WiFi, NFC or other wireless or wired means of communications). In some examples, the AMD 600 may include a SIM card or an electronic SIM (eSIM) card that stores information for identifying and authenticating a mobile intermediary device. The eSIM card enables the AMD 600 to function as an IoT device that can communicate or transmit data over a network that supports communication with IoT devices. Further, the ambulatory medical device may be configured to transmit data in a narrowband communication protocol such as 2G or EDGE, NB-LTE, 5G, etc. The intermediary device 710 may also communicate with a cloud 708, a server 706. In some such examples, the software update may be initially downloaded by the intermediary device that communicates with the AMD 600 periodically or at pairing. The intermediary device may determine if the AMD 600 is eligible for the software update based at least partially on the serial number, manufacturing date, current software version, model number, and most recent software image on the cloud 708 or the server 706, and the like. If AMD 600 is eligible for the software upgrade, the intermediary device may download the target image and transfer the image to the AMD 600.

In some examples, the application or the application comprises one of a first application version comprising a first feature set or a second application version comprising a second feature set. In some cases, both application versions may have the same feature set, but the feature set may include an improved or modified version of at least one of the features. For example, one of the application versions may have a user interface that is less cluttered compared to the other application version. As another example, one of the application versions may support a meal controller while the other application version may not. In some examples, the AMD 600 may download the first application update corresponding to the first application version or a second application update corresponding to the second application version. In some examples, the AMD 600 may download the first application update or the second application based at least in part on the application version of the application.

Once the application update is obtained, at the decision block 808 the AMD 600 may perform one or more operations to confirm that the downloaded copy of the application update is complete and/or is not corrupted (e.g., using its control and computing module 610). To determine that the downloaded application update is complete and/or not corrupted, the AMD 600 may calculate a hash or checksum value from the downloaded application update and may compare the calculated hash or checksum value with a received hash or checksum value received from the application host system. If the calculated hash or checksum value matches the received hash or checksum value, then it may be determined that the download is complete and/or not corrupted. Further, the AMD 600 may use the checksum, a tag, a payload size, or any other method to confirm that the download of the application update is complete and not corrupt. If it is determined that the download is corrupt and/or did not download completely, the AMD 600 may discard the corrupted or incomplete copy of the update. The AMD 600 may attempt to download another copy of the update and/or alert a user to the failed attempt to download the application update or to update the application. If it is determined that the download is complete and not corrupt, the AMD 600 may proceed to the installation step 810 where the application update may be installed on the AMD 600 without interrupting the ongoing or upcoming therapy sessions.

Figure 9:
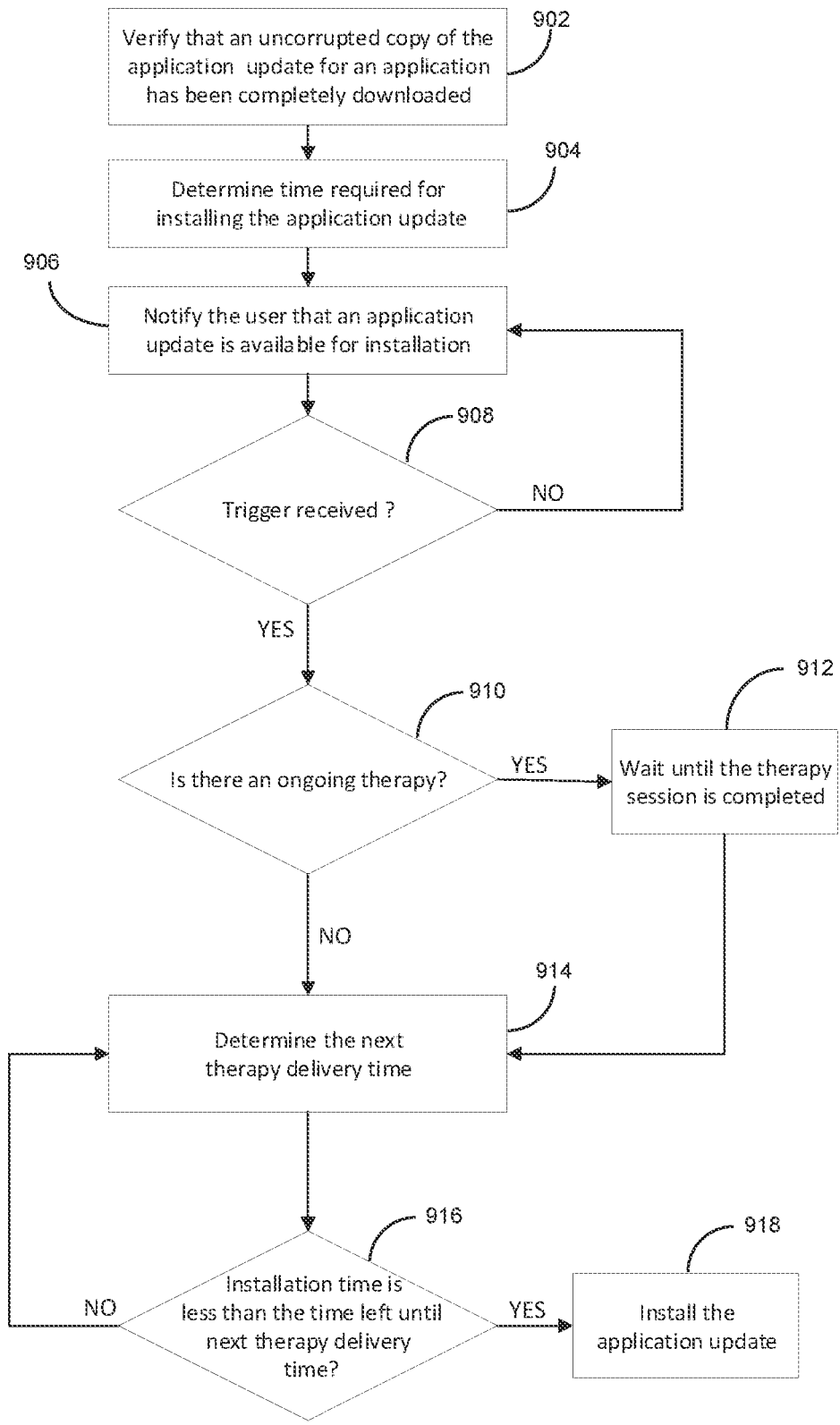
FIG. 9 is a flow diagram showing an example of a computer-implemented method that may be used by an AMD to install a downloaded application update without interrupting the therapy provided to a subject.
Figure 10:
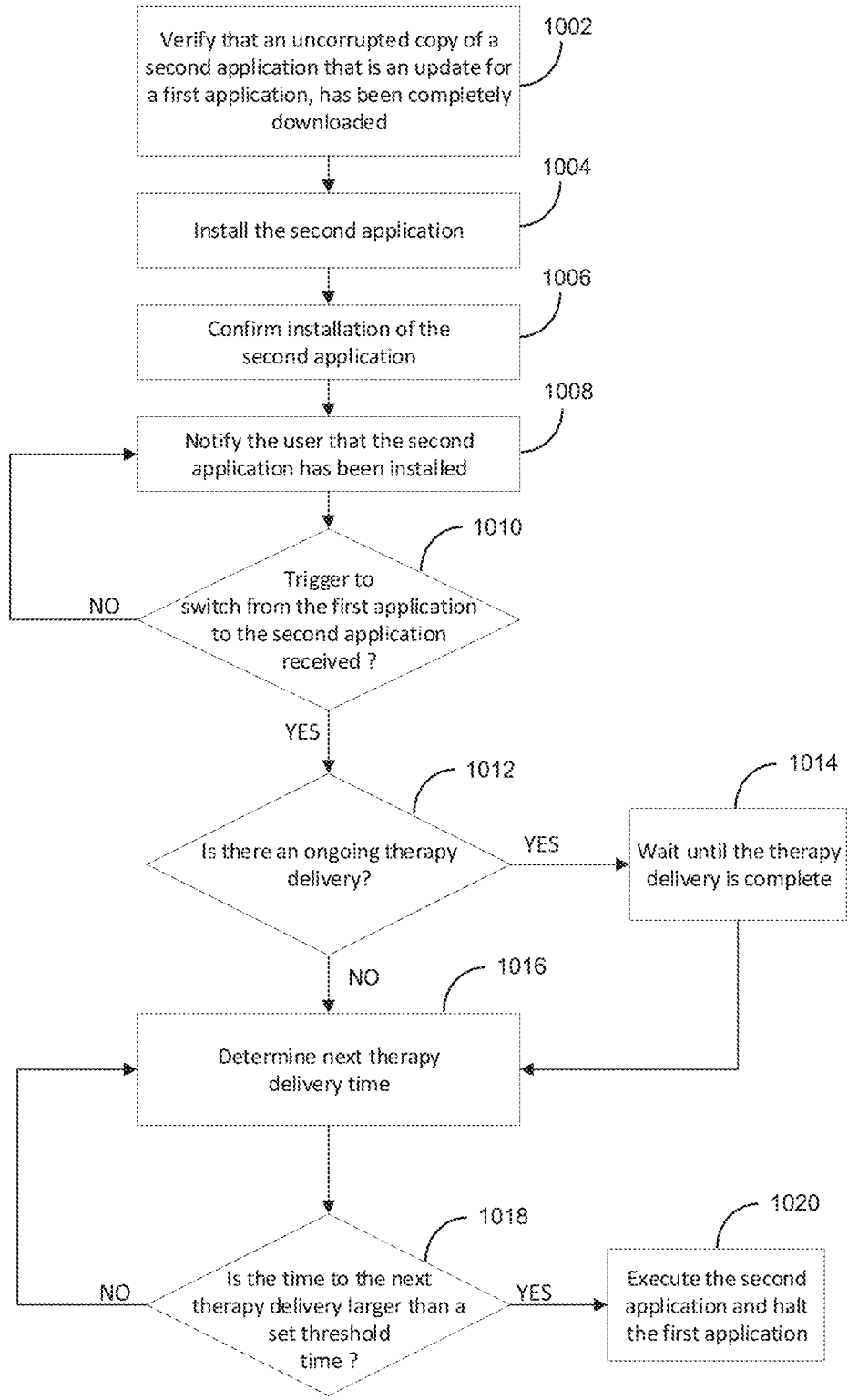
FIG. 10 is a flow diagram showing an example of a computer-implemented method that may be used by an AMD to install a second update downloaded from a host computing system and switch control of the AMD from a first application to the second application without interrupting the therapy provided to a subject.
Figure 11:
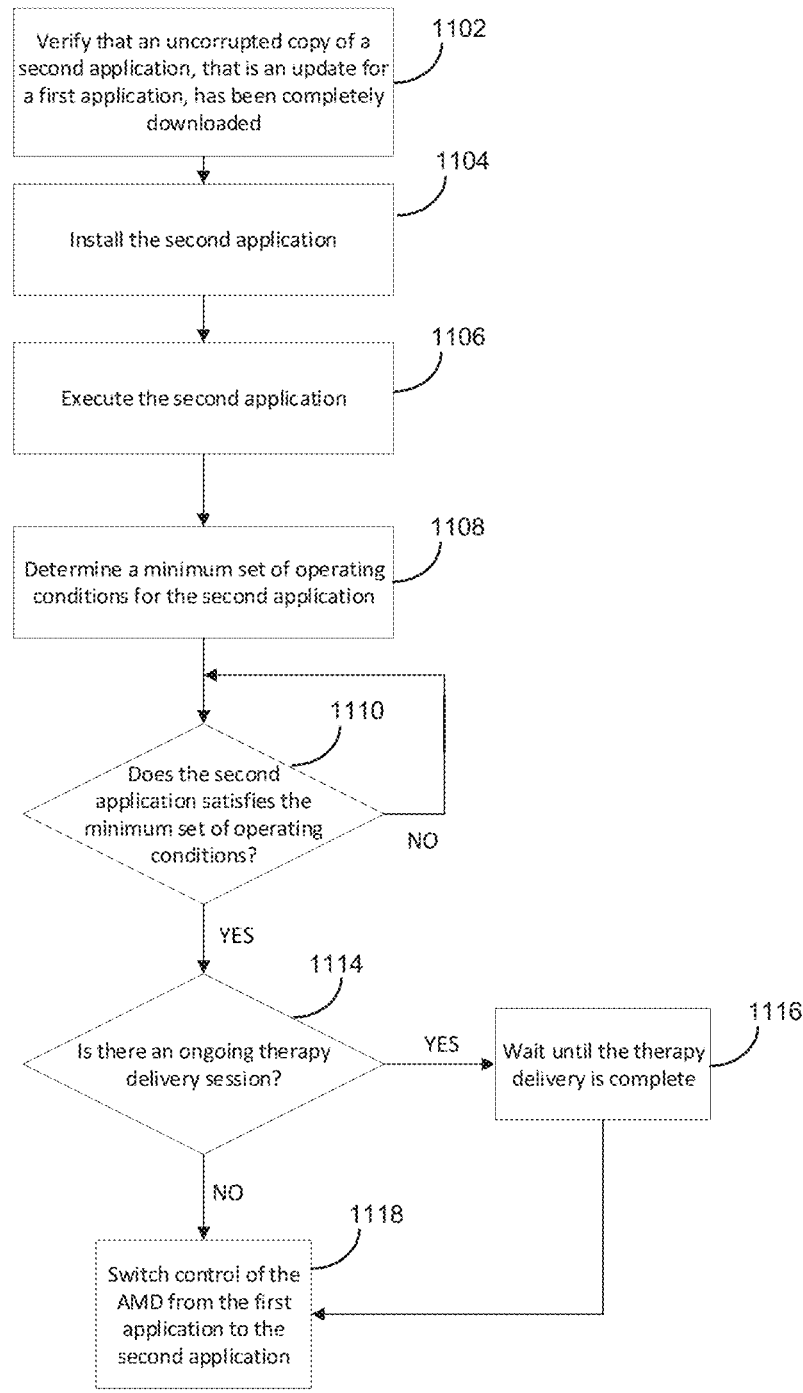
FIG. 11 is a flow diagram showing an example of a computer-implemented method that may be used by an AMD to install a second application downloaded from a host computing system, verify and switch control of the AMD from a first application to the second application without interrupting the therapy provided to a subject, only if the second application satisfies a minimum set of operation conditions.

FIG. 9-11 are flow diagrams illustrating examples of computer-implemented methods that may be used by the AMD 600 to install a downloaded application update without disrupting the therapy provided to a subject.

In the example method illustrated in FIG. 9, at block 902 the AMD 600 verifies that an uncorrupted copy of the update for an application is successfully downloaded (e.g., using the procedure described above with reference to FIG. 8). At block 904, AMD 600 (e.g., the control and computing module (CCM) 610 of the AMD 600) may determine an amount of time required to install the application update. In some examples, the installation time may be an execution time for executing a process to install the downloaded copy of the application update. Alternatively, or in addition, the installation time may be an amount of time to perform the installation process. In some cases, the time determined at the block 904 is an estimated install time. A general-purpose computing system may execute any number or type of applications, and it is unknown what applications a particular user may decide to execute. However, an AMD typically is special purpose and it is generally known what applications it executes. Often the only application executing may be control software or user interface software. Thus, usually, the estimate of installation time will be close to the actual installation time. However, differences in manufacture of electronic elements or natural deterioration of components (e.g., memory) over time may lead to some small changes in installation time application. Accordingly, the install time for the application may, in some cases be buffered or padded to ensure that the estimated or determined install time is not shorter than the actual install time for the application update.

The installation time may be determined by the CCM 610 based on the data or metadata included in the downloaded application update. For example, the application update may include a file (e.g., a text file or configuration file) that includes the install time or an estimate thereof. The installation time may be determined by the manufacturer of the ambulatory medical device or the publisher of the application update. For example, the developer of the software update may average the install time across several test devices to determine the install time metadata that is provided with the software update. General purpose computers have a wide variety of configurations and the performance of a general-purpose computer may vary depending on the applications executing at a particular time. Thus, the determination of install time for an application based on the measurement of install time on a test device is typically unreliable. However, as an AMD 600 is often a special-purpose device that is designed to perform a specific function (e.g., provide insulin to a subject), an install time determined during testing by a manufacturer may, in many cases, be a reliable determination of install time on an ambulatory medical device of a subject. Alternatively, or in addition, the install time of an application update may be determined or estimated based on a size of the application update (e.g., by the manufacturer or the CCM 610 of the AMD 600). In some cases, the provided or estimated install time may include a buffer. In other words, an additional amount of time may be added to the install time to account for variances in operating condition of the ambulatory medical device or inaccuracies in the estimated install time.

At block 906 the AMD may notify the user that an application update is available for installation and wait for a trigger signal to initiate the installation process. In some examples, the AMD 600 may notify the user through a user interface (e.g., a touchscreen display), that an update downloaded and is ready for installation. The notification may include the installation time and information about the update, such as what features are modified or added, or what bugs are patched or fixed.

At decision block 908 the AMD 600 may determine whether an installation trigger is received or not. If the installation trigger is not received, AMD 600 may send one or more notifications to the user indicating that a new update is ready for installation. In some examples, the installation trigger may be the confirmation that the application was successfully downloaded. In other words, once it is confirmed that the application is successfully downloaded, the application may be automatically installed. Alternatively, or in addition, the installation trigger may be an installation command received based on an interaction of a user or subject with a user interface that is part of or that communicates with the ambulatory medical device. In some such examples, the AMD 600 may provide an option to the user to select a time at which the application will be installed and/or may permit the user to request a reminder to install the application update at a later time. In some examples, the installation trigger may comprise a determination that the downloaded copy of the application update is complete, a determination that the downloaded copy of the application update is not corrupted, or a detection of a fault during execution of an application currently running on or controlling the AMD.

At block 910, the AMD 600 determines if therapy is currently being administered to the subject. If the AMD 600 determines that no therapy is currently being administered, the process proceeds to block 914, If the AMD 600 determines that therapy is currently being administered, the system proceeds to block 912 and waits until the therapy session is completed delaying the installation of the application or application update at least until the therapy session or the administering of the therapy is complete. In some cases, the AMD 600 may continue to check whether there is ongoing therapy occurring. Ongoing therapy may at least include administering a medicament. However, other actions may be included as part of the ongoing therapy, such as performing one or more physiological parameter measurements. Once the current therapy session is complete or is determined to be complete, the process may proceed to block 914.

At block 914 the AMD 600 may determine an amount of time or a time remaining until a scheduled or anticipated next therapy delivery time (e.g., during which medicament, such as insulin is delivered to a subject). In some cases, the determination of the next time that therapy is to be delivered may be an estimate based on historical delivery of therapy, a present condition of the subject (e.g., when a glucose level is of a subject is at the center of a desired range, the next therapy delivery time may be estimated to be further off than when the glucose level is at the edge of the desired range), and/or an indication provided by a user or subject (e.g., an indication that the user is planning to have a meal, to exercise, or to go to sleep). Alternatively, or in addition, the determination of the next time that therapy is to be delivered (e.g., next scheduled dosage period) may be based on a scheduled delivery of therapy (e.g., every 5 minutes or every hour, etc.). Further, in some cases, the determination of the next therapy delivery time period may be determined by querying a user (e.g., the subject). In some examples, a dose control signal can be generated at a next scheduled dosage period after determining that a resumption condition has occurred as discussed herein. In some examples, a dose control signal can be generated immediately after, or shortly after, determining that the resumption condition has occurred.

As previously described, it is desirable to prevent disruption to therapy during the application update process. Thus, after the next therapy time is determined at block 914, at the decision block 916 the AMD 600 may compare the estimated installation time to the determined or estimated next therapy delivery time to determine whether the installation of the application update can be completed before the next therapy delivery to the subject. If the AMD 600 determines that the time left until the next therapy session is sufficiently longer (e.g., the length of installation time, or the estimated installation time and a minimum additional time buffer) than the determined time for completing the installation, the process may proceed to block 918 where installation of the application update may be initiated. In some examples, the determined time to the next therapy session may be required to be longer than the determined installation time by a threshold value before installation may be permitted to commence. The threshold value may vary for different application updates and/or the type of therapy to be administered during the next scheduled or anticipated therapy session. If at the decision block 916 it is determined that the application installation cannot be completed before the next therapy delivery (or the time left until the next therapy is not larger than that estimated installation time by a threshold value), the installation of the application may be delayed, regardless of receipt of the trigger. In this case, the process may return to block 914 where the AMD 600 waits for the next therapy to be completed and then determines a new therapy time. This process may be repeated until AMD 600 determines that the update can be installed without interrupting an expected or scheduled therapy delivery by the AMD. In some examples, a new determination may be made before completion of the next therapy, to determine whether installation may be completed prior to a subsequent therapy time after the next therapy time. In some cases, if at the decision block 916 the AMD determines that the installation process will not complete prior to the next therapy time, the AMD may cause an alert to be output for display to a user.

In some cases, a time when the application can be installed without interrupting therapy may not be identified. In some such cases, a user (e.g., a clinician or other medical provider, or a subject) may be provided with an alert that an application update is available and/or that the application update cannot be installed without interrupting therapy. The user may be provided with an option as to whether to permit the update and/or when to install the application update. The option may include presenting the user with the estimated install time enabling the user to schedule the application update at a time when interruptions to therapy may be minimal or when an alternative source of therapy (e.g., injection therapy) can be utilized.

FIG. 10 is a flow diagram illustrating an example of a computer-implemented method that may be used by the AMD 600 in order to install a second application that is an update to a first application executing on the AMD 600, without disrupting the therapy provided to a subject. The AMD may identify and download the second application update using the process described with reference to FIG. 8. In some cases, the second application update may be a new version of the application, a patch to the application, an older version of the second application, or a replacement application for the application. In some examples, the second application may be a version of the first application that has been determined to operate without fault with a threshold degree of certainty.

At block 1002, the AMD 600 verifies that an uncorrupted copy of the second application is successfully downloaded. In some embodiments, block 1002 may include one or more of the embodiments previously described with respect to block 808 in FIG. 8 and/or block 902 in FIG. 9. At block 1004 the AMD 600 may initiate the installation process of the second application without interrupting the execution of the first application. In some examples, the application update may be installed in a different memory location or separate area of the volatile memory than the memory location or area of the volatile memory where the original application (or current version of the application) is installed and executed. In some embodiments, the second application may be executed in a second execution space that is separate from the first execution space. The separate execution spaces may be in separate areas of a volatile and/or non-volatile memory. For example, the first and second application may be stored in separate areas of the non-volatile memory. Further, the first and second application may each be allocated separate areas of a volatile memory for execution. The separate areas of the volatile memory may serve as separate sandboxes preventing interference between the execution of the first application and the second application. In some embodiments, the first application may be executed by a first controller and the second application may be executed by a second controller.

At block 1006 the AMD 600 may confirm the successful installation of the second application and wait for a trigger signal. At block 1008 the AMD 600 may send a notification to the user via a user interface of the AMD (e.g., a touchscreen display) and request a trigger to execute the second application and switch control of the AMD 600 from the first application to the second application. At the decision block 1010 the AMD 600 may determine whether a trigger is received or not. In some examples, the AMD 600 may determine the amount of time required for switching the control of AMD from the first application to the second application. In some such examples, the notification may include information about the update and the time required for switching between the applications. In some examples, the trigger may be a user command received based on an interaction by a user or subject with a user interface that is part of or that communicates with the AMD. In some examples, the trigger may be a confirmation of successful installation of the second application or a detection of a fault during execution of the first application by the AMD 600. In some examples, the trigger may be an indication of an availability of the second application or a detection of an application fault associated with execution of the first application. As with the process described in FIG. 9, the trigger may be based at least in part on whether therapy is currently being administered and/or the timing of a subsequent therapy to be delivered.

If at the decision block 1010 the AMD 600 determines that a trigger is not received, the process may return to block 1008 where the AMD 600 may send one or more notifications to the user indicating that a new update is ready for installation. If at decision block 1010 it is determined that a trigger is received, at block 1012 the AMD 600 may check whether a therapy session is ongoing or not. If the AMD 600 determines that therapy is currently being administered, the process proceeds to block 1014 and the AMD 600 waits until the therapy delivery is complete. Once the current therapy session is complete, the process proceeds to block 1016. If at decision block 1012 the AMD 600 determines that therapy is not currently being administered, the process proceeds to block 1016. The block 1012 may include one or more of the embodiments previously described with respect to the block 910.

At block 1016 the AMD 600 determines an amount of time until or a time remaining until the next therapy session. In some cases, the AMD 600 may determine a condition of the subject based at least in part on a measurement of a physiological parameter of the subject and determine the next therapy delivery time based at least in part on the condition of the subject. In some cases, the AMD 600 may determine the next therapy delivery time based at least in part on a therapy delivery schedule stored at the AMD 600. The block 1016 may include one or more of the embodiments previously described with respect to the block 914.

At decision block 1018 the AMD 600 determines whether the time left until the next therapy delivery session is longer than a set threshold time or threshold time period. The decision block 1018 may include one or more of the embodiments described with respect to the block 916. If at decision block 1018 it is determined that the time left until the next therapy delivery session is longer than the set threshold time or threshold time period, the process moves to block 1020 where the execution of the second application will be initiated and the execution of the first application will be halted. At block 1020 the AMD 600 may switch the control of the AMD 600 to the second application. In some examples, at block 1020 the AMD 600 may switch control of one or more features of the AMD 600 from the first application to the second application. In some such examples, one or more features of AMD 600 may remain under control of the first application. In some examples, at least the control of the therapy delivery module 606 of the AMD 600 may be switched to the second application.

If at decision block 1018 it is determined that the time left until the next therapy delivery session is shorter than the set threshold time, the process returns to block 1016 where the AMD 600 determines the next therapy delivery time. In some examples, the set threshold time may be determined by the CCM at least partly based on the time required to execute the second application and halt the first application. In some examples, the set threshold time may be received from a host computing system. In some examples, the estimated next therapy delivery time may be compared to a set threshold time to determine whether the switching from the first application to the second application can be performed without interfering with the next therapy delivery session.

In some embodiments, the AMD 600 may receive an indication that a third application is available for download. In some such examples the AMD 600 may download the third application using the steps and procedures described with respect to the flow diagram in FIG. 8 and switch the control of the AMD from the second application to the third application using the steps and procedures described with respect to the flow diagram in FIG. 10, starting from block 1002. In some examples, the third application may be an update to the first application that addresses an application-fault of the first or second application.

In some examples, once it is verified that an uncorrupted copy of the update for an application is successfully downloaded at block 902 or 1002, the AMD 600 may notify the user (e.g., via a user interface) and wait for a trigger signal. Once the trigger has been received, the AMD 600 initiates the installation process of the downloaded copy of the application update without interrupting therapy provided by the ambulatory AMD 600. In some examples, once a new application is installed, approval of the subject or user may be required to upgrade an application. In these examples, once the approval is received the application update may be transferred to the main memory where it is executed and take control of the AMD 600 or a subset of operations in the AMD 600. In some cases, before an application update is installed or before the control of the AMD 600 is switched to a newly installed application update, the current configuration of the AMD 600 may be stored in a memory of the AMD 600.

In some embodiments, the performance of an application update may be tested before switching control of the AMD 600 to the application update. FIG. 11 illustrates an example method that may be used for one or more such embodiments. The AMD may identify and download a second application that is an update for a first application and that has been downloaded using the process described with reference to FIG. 8. In some embodiments, the second application may be a new version of the first application, a patch to the first application, or a set of one or more additional features for the first application. In some cases, the first application can be a first version of the first application having a first feature set or a second version of the first application having a second feature set. In some examples, the first feature set may be different from the second feature set, but may include at least one feature included in the second feature set. In some examples, the AMD 600 may download a particular version of the second application that corresponds to a particular version of the first application. For example, there may be two versions of the first application. A first version of the first application may be for a mono-hormonal pump that can administer insulin. A second version of the first application may be for a bi-hormonal pump that can administer insulin and a counter-regulatory agent. When the AMD 600 is configured as a mono-hormonal medicament pump, the AMD 600 may download and/or install a first version of the second application that corresponds to the first version of the first application. On the other hand, when the AMD 600 is configured as a bi-hormonal medicament pump, the AMD 600 may download and/or install a second version of the second application that corresponds to the second version of the first application. Thus, depending on which version of the first application is installed on the AMD 600, the AMD 600 may download and/or install a first version of the second application corresponding to the first version of the first application or a second version of the second application corresponding to the second version of the first application. Although described as two versions, it should be understood that more versions of the application may exist, and that the AMD 600 may install an update based on the installed version of the application. Moreover, in some cases, the AMD 600 may install a different version of an application to enable or unlock new features (or in some cases to remove a feature, such as if a fault is discovered with a particular feature).

At block 1102 the AMD 600 verifies that an uncorrupted copy of the second application is successfully downloaded. In some embodiments, block 1102 may include one or more of the embodiments previously described with respect to block 808 in FIG. 8 and/or block 902 in FIG. 9. Next, at block 1104, the AMD 600 may install the downloaded copy of the second application without interrupting therapy provided by the AMD 600 to the subject. In some cases, the second application may be installed in a separate memory space of a memory of the AMD 600 than a location of the first application within the memory.

At block 1106 the AMD 600 executes the installed second application without interrupting the execution of the first application and therefore, the therapy that may be provided by the ambulatory medical device to the subject using the first application. In some examples, the second application update may be installed to a separate portion of a storage space (e.g., a separate execution space or separate memory) from the portion where the first application is installed and is being executed. In some examples, the AMD 600 may execute the second application using a separate processor than a processor executing the first application. In some examples, the AMD 600 may execute the second application in a separate execution space than an execution space used to execute the first application. In some examples, the first application may be executed by a first controller and the second application is executed by a second controller.

At block 1108, the AMD 600 may determine that a minimum set of operating conditions are satisfied by the second application. In some embodiments, the minimum set of operating conditions may relate to maintaining therapy provided by the ambulatory medical device to the subject. In some embodiments examples, determining a minimum set of operating condition are satisfied may comprise determining that the AMD 600 is not currently administering a medicament or has less than a threshold probability of administering a medicament within a threshold period of time, or has recently administered a medicament within a threshold period of time.

At the decision block 1110, the AMD 600 determines whether the second application satisfies the minimum set of operating parameters. If it is determined that the minimum set of operating conditions are not satisfied by the second application, the AMD 600 may wait a period of time and then repeat the process associated with the decision block 1110. In some cases, if the second application fails to satisfy the minimum set of operating conditions, the AMD 600 may proceed to block 1112 where it waits for an indication that a third application is available and repeats the procedure described above to evaluate the performance of the third application. If at decision block 1110 the AMD 600 determines that the minimum set of operating conditions are satisfied by the second application, at decision block 1114 the AMD may check whether therapy is being delivered to the subject (e.g., a medicament is being administered to the subject). If it is determined that currently no therapy is delivered to a subject, at block 1118, the AMD 600 may switch the control of the AMD from the first application to the second application. If at block 1114 it is determined that therapy is currently being provided to the subject, the process proceeds to block 1116 where the AMD 600 waits until the therapy delivery session is completed and then process proceeds to block 1118 where the AMD 600 switches the control of the AMD 600 from the first application to the second application. In some embodiments, the AMD 600 may switch the control of the AMD 600 from the first application to the second application by generating a dose control signal using the second application. In some examples, using the second application, the AMD 600 may determine doses of a medicament to be infused into the subject for the purpose of controlling blood glucose of the subject based at least in part on a glucose level signal obtained from a blood glucose sensor. The doses of the medicament may be determined automatically and/or autonomously. Subsequently, the AMD 600 may provide a dose control signal that is generated using the second application to a medicament delivery interface (e.g., medicament delivery interface of the therapy delivery module 606) that infuses the medicament into the subject.

In some cases, the AMD may be updated (or downgraded) to add (or remove) features from the ambulatory medical device. For example, the ambulatory medical device may be or may be configured as a mono-hormonal medicament pump that provides a single medicament, such as providing only insulin therapy. At some point in time, the ambulatory medical device may be upgraded to include bi-hormonal control (e.g., to provide both insulin therapy and counter-regulatory agent (e.g., Glucagon) therapy). The upgrade may be based on newly available features and/or based on a decision by a user to purchase or otherwise obtain additional features. Similarly, a user may opt to downgrade therapy from bi-hormonal to insulin-only therapy. Alternatively, the upgrade or downgrade may be made based on the availability of medicament. In some examples, a first update can be a first application version comprising a first feature set (e.g., providing Insulin therapy) and a second update can be a second application version comprising a second feature set (e.g., provide both Insulin therapy and Glucagon therapy). In some such examples, the first feature set may comprise a subset of the second feature set. In some examples, the first feature set may comprise a partially overlapping set of features with the second feature set.

In some examples, a computer-implemented method may be used by the AMD 600 in order to detect, download and install an update to an application executing on the AMD 600 that comprises one of a first application version comprising a first feature set or a second application version comprising a second feature set. In some examples, the first feature set may comprise a partially overlapping set of features with the second feature set. The AMD 600 may receive an indication of availability of the application update, download the application update and verify that an uncorrupted image of the application update is successfully downloaded (e.g., using the procedure described above with reference to FIG. 8). Next, the AMD 600 may initiate the installation process of the application update image without interrupting the execution of the application. In some examples, the indication received by the AMD 600 (block 802 in FIG. 8), may include information about an application update being an update to the first application version or to the second application version. In some such examples, the AMD 600 may determine the version of the application update and download the application update image based on the determined version.

In some embodiments, any downloaded application update may be installed to a separate portion of a storage space (e.g., a separate execution space or separate memory) from a currently executing version of the application. Once installation of the application is complete and the application is verified as being successfully installed, the active version of the application can be switched. For example, control of AMD 600 can be provided to the updated application, the previously executing application can be ceased or halted. The old application can then be removed or kept as backup. Determining when to switch with the active version of the application may follow a similar process as previously described for identifying a next therapy delivery time and selecting a time to switch active versions of the application when there will not be an interruption to the therapy provided by the AMD 600.

In some embodiments, the AMD 600 may be configured to store multiple instances of an application (e.g., AMD control software or a control application for the ambulatory medical device). For example, the AMD 600 may have a current, or first, version of the application that is installed in a first memory location (e.g., in the main memory 616) and is executing to, for example, control therapy provided to a subject. Further, the ambulatory medical device may include an updated, or second version of the application installed in a second memory location (e.g., in the main memory 616). The update of the second version may have been downloaded and installed (e.g., in a prior to detection of the fault). In such embodiments, when a fault is detected during execution of the first version of the application, AMD 600 may initiate the execution of the second version of the application and then switch control of the AMD 600 to the second version of the application to maintain therapy to the subject.

In some examples, a second application update or a second version of the application installed on the AMD 600 may be older than the first application or the first version of the application. In some cases, the second or older version of the application may be a version of the application that has a track record of stability and reliability. In contrast, the first application, or newer application, may have been released too recently to determine whether it will be reliable or function as desired. In some such examples, the AMD 600 may revert to the second version of the application if a fault is detected in the first version of the application.

Figure 12:
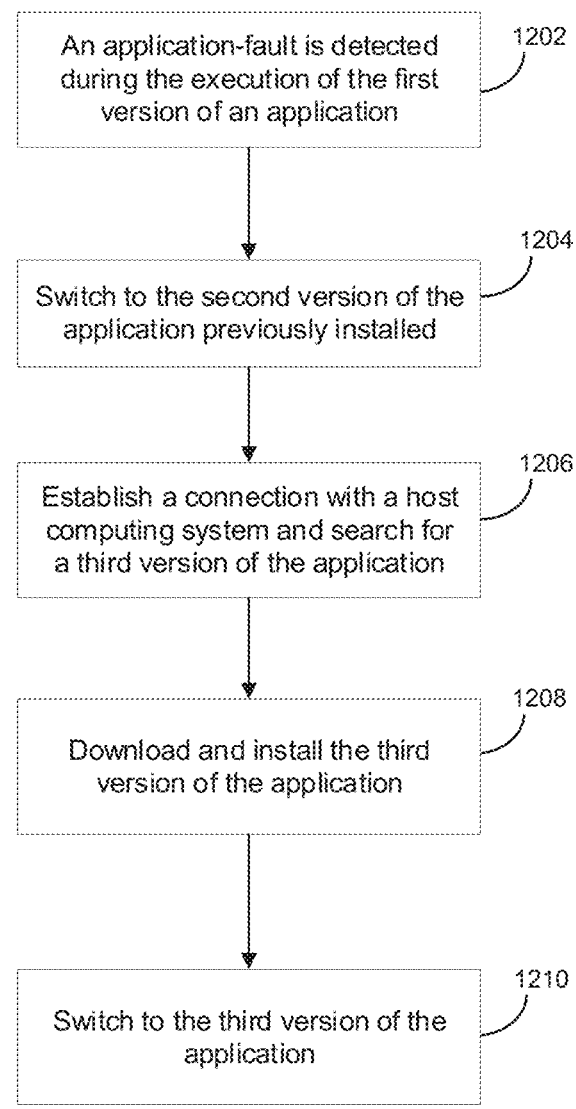
FIG. 12 is a flow diagram showing an example of a computer-implemented method that may be used to respond to detection of an application fault during the execution of a first version of an application and switching control of the AMD to a second version of the application installed on the AMD.

In some cases, the AMD 600 may revert to an older stable version of the application until a third version of the application that corrects the application fault in the first version of the application is available. FIG. 12 presents a flowchart related to an embodiment of a process of switching from an application with a fault to a known reliable version of the application until the application fault in the original application can be patched in an application update (e.g., a third version of the application). At block 1202, the AMD 600 detects an application-fault while executing the first version of the application. In some examples, the AMD 600 may transmit an indication of the application-fault to a computing device of a manufacturer or a maintenance service of the ambulatory medical device. In some examples, the AMD 600 may send an alert to a user indicating that an application-fault has occurred. Sending the alert to the user may include outputting an alert on a display, transmitting an alert to an account or device of the user, generating an audio alert or a visual alert, or any other type of alert.

At block 1204, the AMD 600 may switch the control of the AMD 600 to a second version of the application. This second version of the application may be downloaded from a host computing system. Alternatively, or in addition, the second version of the application may be a standby or backup version of the application that is stored at the AMD 600. This standby or backup version of the application may be an older version of the application that has been determined to be stable and/or fault free or associated with less than a threshold percentage of faults based on a history of use and/or testing. At block 1206 the AMD 600 may establish a communication connection with a host computing system configured to host a third application update and download the third application update (block 1208). The third version of the application update may be a new version, a version prior to the first version, an update to the first application that addresses the detected application-fault or an older version that satisfies the conditions to be classified as a "safe version" (e.g., less than a threshold number or rate of faults over a minimum period of time). The second version (installed in the device) may control the AMD while the third version is being downloaded and installed 1208 without interrupting the therapy. Once the AMD verifies that the third version has been downloaded and the downloaded copy is uncorrupted, the AMD 600 may initiate the installation process of the downloaded copy of the third application and switch control of the AMD 600 form the second version of the application to the third version of the application (block 1210) without interrupting therapy delivery to the subject by the AMD. In various embodiments the operation and processes described with respect to FIG. 12 may be performed by the control computing module (CMM) 610 of the AMD 600.

In yet other embodiments, a "safe version" of the application may have been installed on the AMD 600 prior to detection of a fault. The safe version, or safe copy, of the application may include a version of the application that has been used by instances of the ambulatory medical device for more than a threshold period of time and has experienced less than a threshold number of faults. For example, the safe version of the application may be a two-year old version of the application that has demonstrably had less than a threshold number of faults occur over the period of two years. This safe version of the application may have less features than the first or second version of the application. However, when a fault is detected during execution of the first or second version of the application, the AMD 600 may switch control of the device to the safe version of the application to maintain therapy to the subject.

In some cases, if a fault is detected during the installation or execution of an updated version of the application, the AMD 600 may revert to the current version or a safe version installed on the AMD 600.

In some embodiments, the AMD 600 may be triggered to establish a communication connection with the host computing system and search for the second version of an application once a fault is detected during execution of the first version of the application. In these examples, the AMD may revert to the safe version (installed in the device) while downloading and installing the second version without interrupting the therapy.

Figure 13:
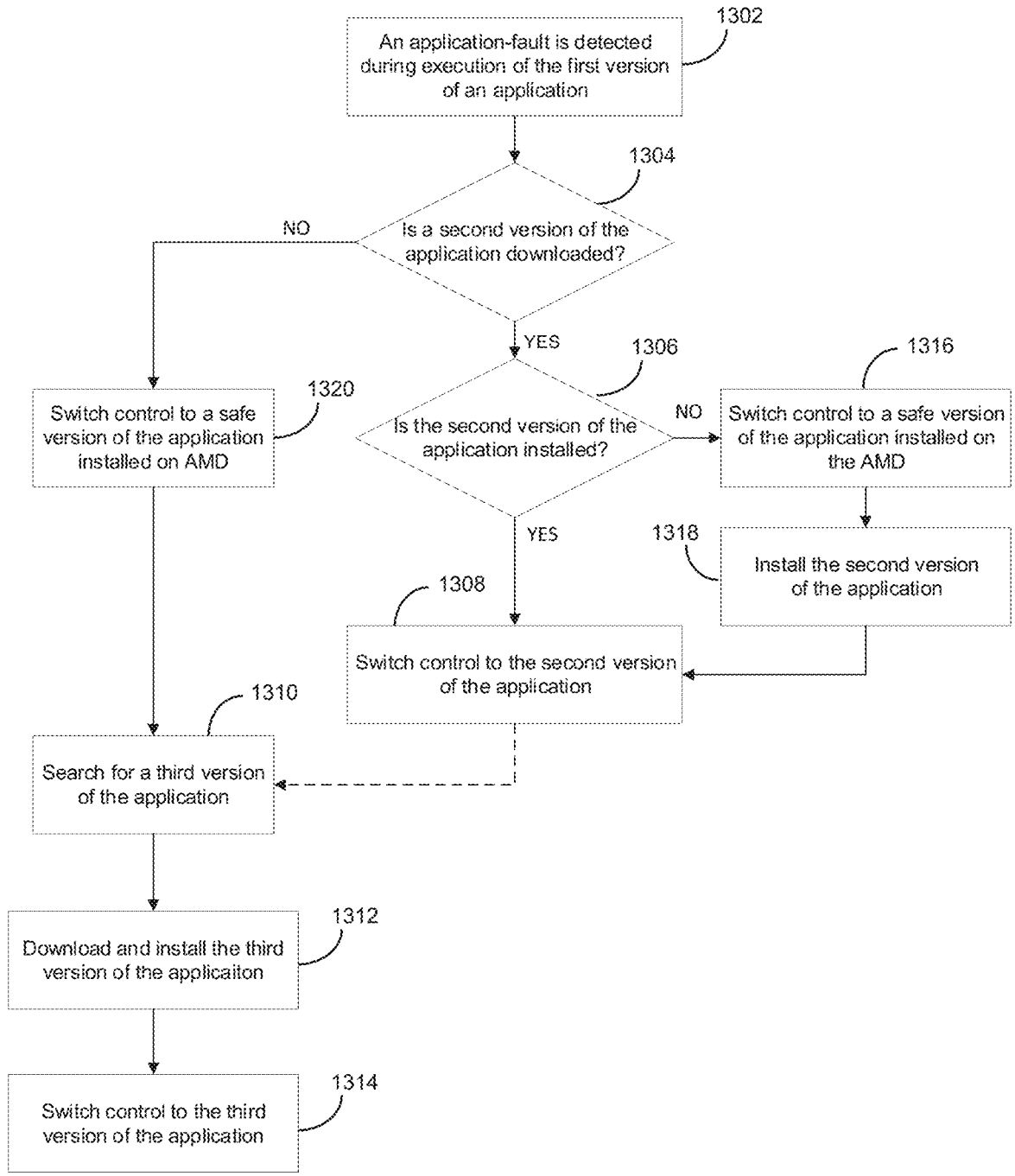
FIG. 13 is a flow diagram showing an example of a computer-implemented method that may be used to respond to detection of an application fault during the execution of a first version of an application and switching control of the AMD to a second version an application installed on the AMD and/or downloading a third version of the application.

FIG. 13 is a flow diagram illustrating yet another example of a method of responding to a fault detection by the AMD 600. In this example, once an application-fault is detected during execution of the first version of an application at block 1302, at block 1304 the AMD 600 may access a second version of the application in the main memory 616 or the storage of the AMD 600. If it is determined that the second version has already been downloaded, at block 1306 the AMD 600 may determine whether the second version of the application is installed in a memory location and whether it is ready to be executed. If at block 1306 it is determined that the second version of the application is installed, at block 1308 the AMD 600 may switch the control of the AMD 600 to the second version of the application. If at block 1306, the AMD 600 determines that the second version exists in the memory but it is not installed, the process proceeds to block 1316 where the control of the AMD 600 is switched to a safe version 1316 that may be already installed. At block 1318, eth AMD 600 may initiate the installation of the second version. Once the installation of the second version is complete, the process may proceed to block 1308 where the AMD 600 may switch control of the AMD 600 from the safe version of the application to the second version of the application. In some embodiments, after the control of the AMD 600 is switched to the second version of the application (at block 1308), at block 1310 the AMD 600 may search for a third version of the application that may be an update to the previously downloaded second version. If a third version is found, at block 1312 the AMD 600 may download and install the third version of the application and switch the control of the AMD 600 to the third version (block 1314). If at block 1304, if the AMD 600 cannot find a second version of the application in a memory or storage location, it will switch the control of the AMD 600 to a safe version of the application (block 1320) that may be installed in a memory location (e.g., in the main memory or in the storage) and search for a third version of the application (block 1310). If a third version is found, the system may download and install the third version of the application (block 1312) and switch the control of the device to the third version (block 1314).

In some embodiments, when an application-fault of an application executing on the AMD 600 is detected, the AMD 600 may transmit an indication of the application-fault to the host computing system of a manufacturer or maintenance service of the ambulatory medical device. In some other embodiments, the AMD 600 may notify the user when an application-fault occurs through a user interface of the AMD 600 or user interface communicating with the AMD 600.

In some of the examples mentioned above, once a software update has been installed, the AMD 600 may offer the option to save the user's configuration or profile data. For example, the software update should not change the patient state data (patient weight, CGMid, meal size equals volume of meal).

In various examples, the application update may be pushed to a dedicated memory location in CCM 610 of the AMD 600 prior to transfer to executable memory location (e.g., the main memory) for security checks. In some examples, a healthcare provider system or the AMD may check the version of application update against the current version. In some such examples, an alert may be sent to the user or the subject with information regarding the difference between the current application and the application update.

Direct Network-Connected Medical Device Communication and Remote Viewing

An ambulatory medical device (AMD), such as an ambulatory medicament device (e.g., blood glucose control system, an insulin pump (e.g., a mono-hormonal pump), or a bi-hormonal pump that includes insulin and a counter-regulatory agent), a pacemaker, or any type of medical device that may be connected to a subject to provide therapy to the subject, can generate a significant amount of data related to therapy provided to a subject (therapy data). This therapy data may be useful for the subject, a healthcare provider, or other users (e.g., parent or guardian) to actively manage the subject's health condition. For example, the therapy data may be useful to determine whether a modification to therapy may be desirable or to confirm that intended therapy is being delivered at the right time. In some cases, the therapy data may be used to generate alerts about the health condition of the subject when therapy data indicates that immediate or urgent attention is needed with regards to the subject's health condition.

Various aspects of accessing the therapy data or other types of data stored in a memory of the AMD needs proper management in order to provide uninterrupted, secure and easy access to authorized users. As described above, the procedures and tasks performed by an AMD, including those associated with data transfer management, may be associated with certain computer-executable instructions stored in and executed by the control and computing module (CCM) 610 of the AMD 600. As such, different AMD configurations used for various data transfer management tasks, may be different instructions executed by the CCM 610 of the AMD 600.

Accessing the data from the AMD can be problematic in some cases. For example, accessing the data may require a user to connect the AMD to a computer to upload the data. This places a burden on the user to remember to connect the AMD. Further, during the period when the device is connected to the computer, the subject may not be receiving therapy from the ambulatory medical device. In some cases, the subject may not be capable of connecting the device to the computer (e.g., when the AMD is not within range of the local device) and may not have someone available to assist the subject. Thus, a direct end-to-end connection to a computing system that (e.g., computing system of a healthcare provider) can safely share data (e.g., therapy data) with authorized users may facilitate data management and access.

Figure 14:
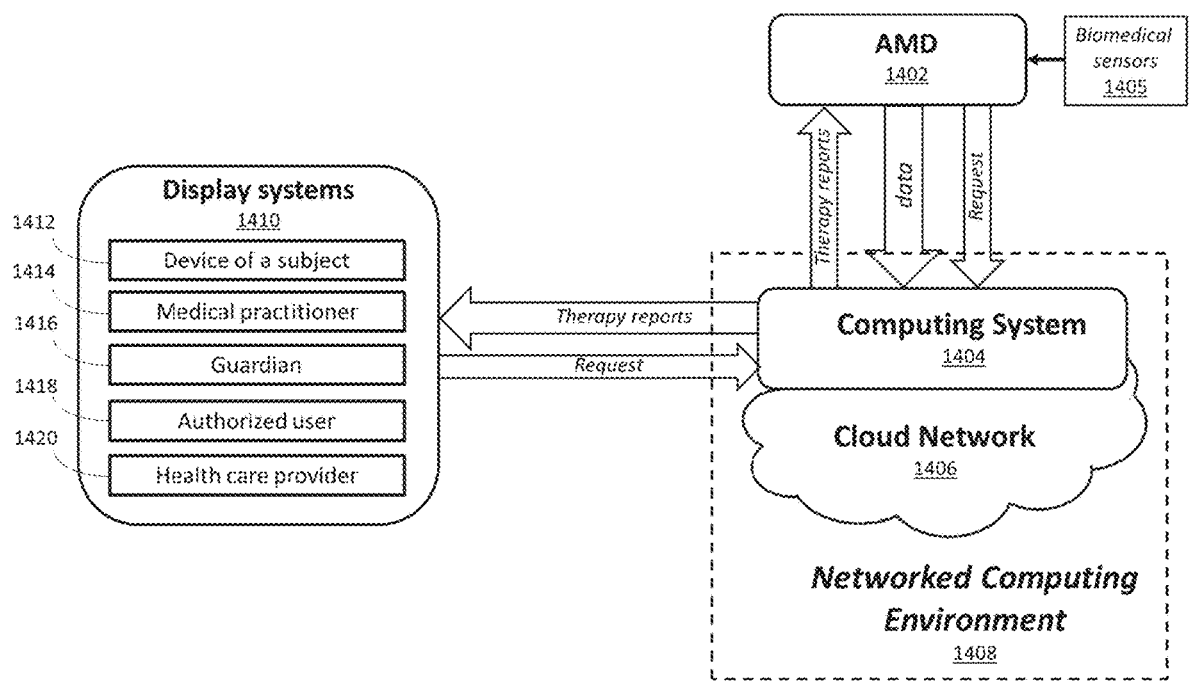
FIG. 14. is a block diagram, illustrating an example network configuration wherein the AMD is directly connected to a computing system and the computing system shares the therapy reports with one or more display systems and the AMD.

FIG. 14 is a block diagram illustrating an example network configuration wherein the AMD 1402 is directly connected to a computing system 1404. The computing system 1404 may be part of a networked computing environment 1408 (e.g., a data center), or a cloud computing system (e.g., a cloud server) of a cloud service provider. The computing system 1404 may include one or more non-transitional memories and one or more hardware processors configured to execute the computer-executable instructions stored in one or more non-transitory memories. In some such examples, the procedures performed by the computing system 1404 may be associated with the execution of certain computer-executable instructions stored in a memory of the computing system 1404 by a hardware processor of the computing system 1404.

In some examples, the direct end-to-end data connection may be supported by one or more transceivers (e.g., wireless transceivers) in AMD's communication module 602. For example, a direct connection may be established between the AMD 1402 and the computing system 1404 over a wide area network (e.g., a cellular network) without using an intermediary system. The connection may use one or more wireless standards and technologies (e.g., 4G, 5G and the like). In some examples, a transceiver of the AMD may support communication via communication standards, including but not limited to, low power wide area network (LPWAN), Narrowband Long-Term Evolution (NB-LTE), Narrowband Internet-of-Things (NB-IoT), Long-Term Evolution Machine Type Communication (LTE-MTC) and the like. In some cases, the transceiver is always on, and in some cases, the transceiver may be activated when a data transfer is scheduled, requested or activated. In some cases, the capability of the AMD 1402 to communicate with the computing system 1404 may be activated during manufacture or before providing the device to a subject.

In some cases, the subject or a user establishes or initiates the direct end-to-end data connection with the computing system 1404. For example, the subject may interact with a user interface to cause the AMD 1402 to communicate with the cloud computing system. In some cases, the direct end-to-end data connection may be initiated or established without action by the subject or the user. For example, the direct end-to-end data connection may occur automatically at particular times or when the AMD 1402 is in particular locations. This automatic connection may occur using information supplied to the AMD 1402 at a time of manufacture, shipment, sale, or prescription to the subject. Further, in some cases, the AMD 1402 can communicate with the computing system 1404 without having access to a WiFi network or a local area network (LAN). For example, the AMD 1402 may communicate using a cellular or other wide area network. Further, in some cases, the interaction by the user with the AMD 1402 may be relatively minimal or simple compared to traditional network communication. For example, a user may push a single button (e.g., an "upload" button) to trigger establishing of a connection with the cloud computing system 1404 and causing data to be provided from the AMD 1402 to the cloud computing system 1404.

In some cases, the AMD 1402 may be turned on and paired with the wireless wide area network (e.g., a cellular network) at the time of manufacture, or prior to being provided to a subject. Further, the AMD 1402 may be authenticated with the networked-computing environment as part of the manufacturing process Further, establishing the direct end-to-end data connection may include determining that the AMD 1402 is permitted to communicate with the computing system 1404 based at least in part on the device identifier.

In some implementations, establishing the direct end-to-end data connection may include determining that the AMD 1402 is permitted to communicate with the computing system 1404 based at least in part on a device identifier associated with the AMD 1402. The device identifier may be a unique identifier specific to the AMD 1402. The device identifier may include or may be based on one or more of an Internet Protocol (IP) address, a Media Access Control (MAC) address, a serial number, or a subject identifier of a subject that receives therapy from the ambulatory medical device.

Further, establishing the direct end-to-end data connection may include determining that the AMD 1402 is permitted to communicate with the computing system 1404 based at least in part on the device identifier. The device identifier may be initially provided to the networked-computing environment prior to provisioning of the AMD 1402 to the subject. For example, the device identifier may be initially provided to the computing system 1404 or the networked-computing environment as part of a manufacturing process for manufacturing the AMD 1402.

The AMD 1402 may be configured to at least identify a computing system (or a cloud server) 1404 of a networked-computing environment 1408 (e.g., a cloud network, a data storage services provider, or an application services provider, etc.) based on a whitelist, or approved list, of one or more approved computing systems. The whitelist may be stored in a memory of the AMD 1402 (e.g., a memory in the control and computing module of the AMD). Further, the whitelist may be configured during manufacture of the AMD 1402. For example, the whitelist may be configured with connection information to establish communication with one or more computing systems of a networked-computing environment. Further, the AMD 1402 may be configured to at least obtain an address of the computing system 1404 from the whitelist and to establish a direct end-to-end data connection to the computing system 1404 of the networked-computing environment via a wireless wide area network using the address. The whitelist may include unique identifiers, such as MAC addresses or static IP addresses that are associated with computing system 1404s of the cloud services provider. The whitelist may include one or more of the embodiments previously described above with respect to FIG. 7.

To enhance security, the AMD 1402 may use a whitelist that identifies via a unique identifier (e.g., via an IP address, a MAC address, or a URL), permitted cloud servers or computing systems in the networked computing environment. Further, the cloud computing systems (or cloud servers) 1404 may have a whitelist that uses unique identifiers to specify AMD 1402 and/or other computing systems (e.g., remote display systems) that are permitted to communicate with the computing systems 1404 of the networked computing system.

When a device communicates data over a network, there is generally a risk of a data breach. To reduce or prevent a data breach, the AMD 1402 may communicate with a computing system, such as a computing node in a networked computing environment or a cloud network, based on a secure data transmission method. For example, the AMD 1402 may encrypt all data using an asymmetric key pair. In some cases, the AMD 1402 may establish a shared secret with the computing system as described below.

In some cases, the therapy data may be encrypted before being transferred to the computing system 1404. To enable encryption, the AMD 1402 may have a public key and a private key stored in memory permitting the AMD 1402 to encrypt data transmitted by the AMD 1402 to the computing system 1404. In some cases, the AMD 1402 may generate the public key based at least in part on the private key. The encryption key(s) may be stored in a protected area of memory or in separate memory that is separate from the application memory. In some cases, the AMD 1402 may transmit a public key to the computing system 1404. Using the public key, the computing system 1404 can encrypt data to transmit to the AMD 1402. The AMD 1402 can use its private key to decrypt the data, such as an analysis of therapy data generated by the computing system 1404 in response to received therapy data from the AMD 1402. Similarly, the computing system 1404 may provide a public key to the AMD 1402. Using the public key, the AMD 1402 can encrypt therapy data (and/or device data) to be transmitted to the computing system 1404 for storage, analysis, presentation to a user, reordering medicament, determining a status of the AMD 1402 and/or subject, or any other purpose or process that can be performed responsive to the therapy data. The computing system 1404 may use its private key to decrypt the encrypted data to obtain access to the therapy data (and/or device data).

In some cases, the public key may timeout and a new public key may be obtained from the AMD 1402 (or from the computing system 1404) to facilitate encrypting and/or decrypting subsequent communications from the AMD 1402. In some cases, the public key may be associated with a time-to-live (TTL) value. In some such cases, the public key may timeout and a new public key may be obtained from the AMD 1402 to facilitate encrypting and/or decrypting subsequent communications from the AMD 1402.

Moreover, the secure data transmission may include generating a shared secret based at least in part on a public or common piece of data and a private key. In some cases, the public or shared piece of data can be a public key. In some such cases, therapy or device data may be encrypted or decrypted using the shared secret. In some examples, the shared secret may be established using a public key exchange algorithm (e.g., Diffie-Hellman key exchange algorithm).

In some cases, the computing system 1404 may be configured to transfer, or receive, the data after receiving a request to transfer data (e.g., therapy data or device status data) stored on the AMD 1402 to the computing system 1404 over the direct end-to-end data connection, for example, via the wireless wide area network. The request may include a device identifier associated with the AMD 1402. Responsive to receiving the request to transfer data stored on the AMD 1402 to the computing system 1404, the computing system 1404 may be configured to receive the data, via the direct end-to-end data connection. In some cases, the computing system 1404 may open or provide a port to the AMD 1402 enabling the AMD 1402 to connect to the identified port and transfer data to the computing system 1404 via the identified port. Further, transferring data may include the computing system 1404 sending an acknowledgement packet that the transfer request is approved or permitted. The AMD 1402 may transfer the data in response to approval by the computing system 1404 to transfer the data. In some cases, the approval may be based on the computing system 1404 confirming user account information (e.g., such as a username and/or password).

In some examples, once a connection is established and the therapy data is transferred to the computing system 1404, the computing system 1404 may analyze the therapy data received from the AMD 1402 and generate a therapy report. The therapy report may include data relating to the subject's disease, treatment by the AMD 1402, anonymized comparisons with other subjects, statistical data relating to the subject's treatment, statistical data relating to other subjects' disease or disease management, and the like. For example, the therapy report may determine whether the subject is maintaining blood glucose levels on average or whether control parameter settings for the AMD 1402 are similar to an average subject with similar physiological characteristics as the subject associated with the AMD 1402. Further, the computing system 1404 may detect an alarm condition, based on therapy data analysis, and generate an alarm that may be provided to the subject, authorized user (e.g., healthcare provider). In some cases, the therapy data may trigger an automatic response by the computing system 1404. For example, the AMD 1402 may determine that a medicament or another disposable is running low based on the received data and may automatically reorder the medicament or the disposable.

In some cases, the computing system 1404 may periodically receive data (e.g., therapy data) from the AMD 1402 based on a regular schedule. Alternatively, or in addition, the data may be received in response to a command or when the ambulatory medical device determines it is within a certain location. For example, when the AMD 1402 determines it is within a subject's home or at a healthcare provider's office, the AMD 1402 may transmit the data to the computing system 1404. The AMD 1402 may determine its location based at least in part on a connection to a local area network connection or a geolocation signal, such as from a global positioning system (GPS). In some implementations, additional encrypted data is received from the AMD 1402 on an intermittent basis. Alternatively, or in addition, additional encrypted data may be received from the AMD 1402 basis for at least a time period. The AMD 1402 may be configured to transmit data as it is generated, or shortly thereafter, (e.g., in real or near real-time (e.g., within a few millisecond, seconds, or minutes of the data being generated)), or in bulk at specified periods of time. Transmitting the data in bulk at particular time periods may extend battery life, but may provide for less up-to-date analysis. In cases where bulk transfer of data occurs at particular time periods, a user may request a data transfer at an unscheduled time, such as when the user is attending a doctor's appointment or the subject is being attended to by emergency services personnel during an emergency. Data can be made available on-demand by keeping the transceiver always on, which may consume more power compared to keeping the transceiver in sleep mode when not in use. Alternatively, the transceiver may be activated when a data transfer operation is requested. Thus, the scheduling of data transfer may be balanced based with other considerations, such as: (1) power consumption and/or (2) a need or desire to share information with authorized users or systems.

In some cases, the computing system 1404 may be used as a backup for the AMD 1402. For example, the AMD 1402 can backup data to the computing system 1404 every night, when it is charging, or when it is in proximity to home or a physician's office (e.g., when the subject is in the waiting room at the physician's office, the device may upload data that the physician can access to treat the subject's disease). Moreover, if the AMD 1402 is replaced (e.g., for a new model or to replace a damaged device), the device can automatically synchronize with the computing system 1404 to obtain subject-specific configuration or therapy control data.

Therapy Data and Therapy Report

In some examples, the therapy data comprises dose or dosage data corresponding to one or more doses of medicament provided by the AMD 1402 to the subject. Further, the therapy data may comprise subject data corresponding to a medical or physiological state of the subject as determined by the AMD 1402 device (e.g., using one or more biomedical sensors 1405).

In some examples, the data provided to computing system 1404 may include any type of data that may be measured or obtained by the AMD 1402 and may include a record of therapy provided by the AMD 1402. For example, the data may include a time that therapy was provided, an amount of medicament provided as part of the therapy, a measure of one or more vital signs of the subject, a measure of blood glucose levels (e.g., measured blood glucose level) at different times for the subject, a location of the subject, and the like.

In some cases, the therapy data may be used to track the use of disposables, such as insulin or other medicament, or insulin injection site kits. In some cases, the computing system 1404 may automatically order or reorder disposables at a particular time based on tracking the use of the disposable. Alternatively, or in addition, the reordering of the disposables may be initiated or performed from the AMD 1402 (e.g., via a wireless wide area network or via a local connection through a separate electronic device).

In some cases, the data transferred to the computing systems may comprise operation data corresponding to operation of the AMD 1402. Alternatively, or in addition, the data may further comprise error data corresponding to an error in operation of the AMD 1402.

In some examples, the data, therapy data, and/or the therapy report may be stored in a memory of the computing system 1404 and/or at a storage of the networked-computing environment.

In some cases, the method may include converting the therapy data from one format to another format. For example, the method may include converting the therapy data from a format used to store and/or present data on AMD 1402 to a format that can be stored or processed on the computing system 1404. In some cases, the therapy data is converted from a machine-readable format to a human-readable format. The data may be stored in a more easily interpreted format that can be understood by different types of users. For example, the data may be presented in one format for a healthcare provider (e.g., sensor readings), a simplified format for a subject or parent of a subject, or other data formats for displaying data to different types of users. In some cases, the data may be presented in different formats depending on the maturity of the subject. For example, simplified data may be presented to a pre-teen child, while more detailed data may be presented to a teenager, and yet more detailed information may be presented to an adult.

In some examples, the therapy data collected from different AMDs associated with a plurality of subjects may be aggregated for a group of subjects. The aggregation may be based on any factor or commonality among the plurality of subjects. For example, the therapy data may be aggregated based on an association with an institution or organization (e.g., a clinic, an insurance company, and the like), age, gender, nationality, ethnicity, job, stress factors, recency of being diagnosed with or acquiring the disease, location, diet (e.g., vegetarian, vegan, omnivore, etc.), or any other factor that may link subjects. Advantageously, aggregating data based on particular demographics and/or physiological characteristics may be useful for determining how to best care for a particular subject within a group, how to improve care for a set of subjects, to learn more about how diabetes affects certain types of subjects, and the like.

In some examples, a therapy report based at least in part on the therapy data may be generated by the computing system 1404. The therapy report may comprise time-series therapy data relating to the therapy delivered by the ambulatory medical device over a particular time period.

In some examples, the therapy report may be sent to the AMD 1402. In cases where the AMD 1402 includes a display, such as, but not limited to, a touchscreen display, the subject or other user may review the therapy report via the display of the AMD 1402. Alternatively, or in addition, a user may view the therapy report on the display of another electronic device that is in communication with the computing system 1404 and is authorized to access the therapy report.

In some cases, the ambulatory device data and/or data generated by the computing system 1404 based on the ambulatory device data can be viewed on a secondary display system from the computing system 1404. For example, a clinician or parent can access the data from their personal device. The communication between the computing systems and the viewing device may be encrypted. Moreover, permission for sharing of end user data with a 'follower' (e.g., family member) or clinician may be granted or controlled by the end user (e.g., the subject or a guardian).

An association between a subject, a clinic, and/or an ambulatory medical device may be performed by association of a device serial number of the ambulatory medical device with the subject and/or clinic. Further, a user (e.g., a subject, clinician, or parent) can access therapeutic recommendations through the cloud in case either the ambulatory medical device (e.g., an insulin pump) or the CGM sensor fails to function.

In some cases, the computing system 1404 may be configured to at least receive a request from one or more display systems 1410 that are separate from the networked computing environment to access the therapy report, therapy data or other data received by or stored in the AMD. In some cases, the display system may be a computing system of a medical practitioner 1414 (e.g., such as a doctor, nurse, physician's assistant, etc.), a guardian of the subject 1416 (e.g., subject's parents), an authorized user 1418 (e.g., a user authorized by the subject such as spouse, relative, friend, and the like), a healthcare provider 1420, or a device of the subject 1412 (e.g., cell phone, personal computer, tablet and the like). In some cases, the display system 1410 can be the AMD.

In some examples, the display system can be a therapy data management system that analyses therapy data associated with a specific type of health problem (e.g., data associated with managing diabetes) and provides information derived from the therapy data to the subject or an authorized user to monitor and manage the corresponding ailment.

In some examples, the request to access the therapy data, therapy report, or other data may comprise an account identifier associated with a user that generated the request. In some examples, the account identifier may comprise a unique identifier associated with the subject. Alternatively, or in addition, the account identifier comprises a unique identifier associated with a user that is authorized to access the therapy report. The user may or may not be the subject. In some aspects of the present disclosure, the method may further include associating the therapy data with the account identifier at a storage of the networked-computing environment. Further, the computing system 1404 may be configured to determine whether an account associated with the account identifier is permitted to view the therapy report. In some examples, account permissions may be granted and/or modified by the subject. For example, the subject can access an account at a networked computing environment 1408, for example, a cloud network provided by a cloud service provider associated with the subject, and provide one or more identifiers associated with one or more other users to give them permission to access the subject's therapy data or report stored on the computing system 1404.

Responsive to determining that the account is permitted to view the therapy report, the computing system 1404 may transmit the therapy report to the display system over an encrypted communication channel. As previously explained, the encrypted communication channel may be created by using asymmetric key pairs to encrypt the data transmitted. Thus, the computing system 1404 may obtain a public key from the target system (e.g., the display system, AMD 1402, or other computing system that is to receive the therapy report). The computing system 1404 may encrypt the therapy report with the received public key and transmit it to the target system, which may use its private key corresponding to the public key to decrypt the therapy report. Alternatively, or in addition, a shared secret may be determined for the commuting system 1404 and the target system. The shared secret may be used to encrypt the therapy report.

In some cases, the method may include receiving an identity or identification information of one or more users that are authorized to access therapy data stored at the networked-computing environment. For example, a user or subject may authorize a clinician or other healthcare provider, a parent or guardian, or other users that the subject desires to have access to the therapy data. The identity information of the one or more users may include any type of information that may identify the user or enable the user to be authenticated. For example, the identity information may include a name, unique identifier (e.g., social security number), an email, an address, a phone number, account information for the user at the networked-computing environment, or any other identifying information.

Figure 15A:
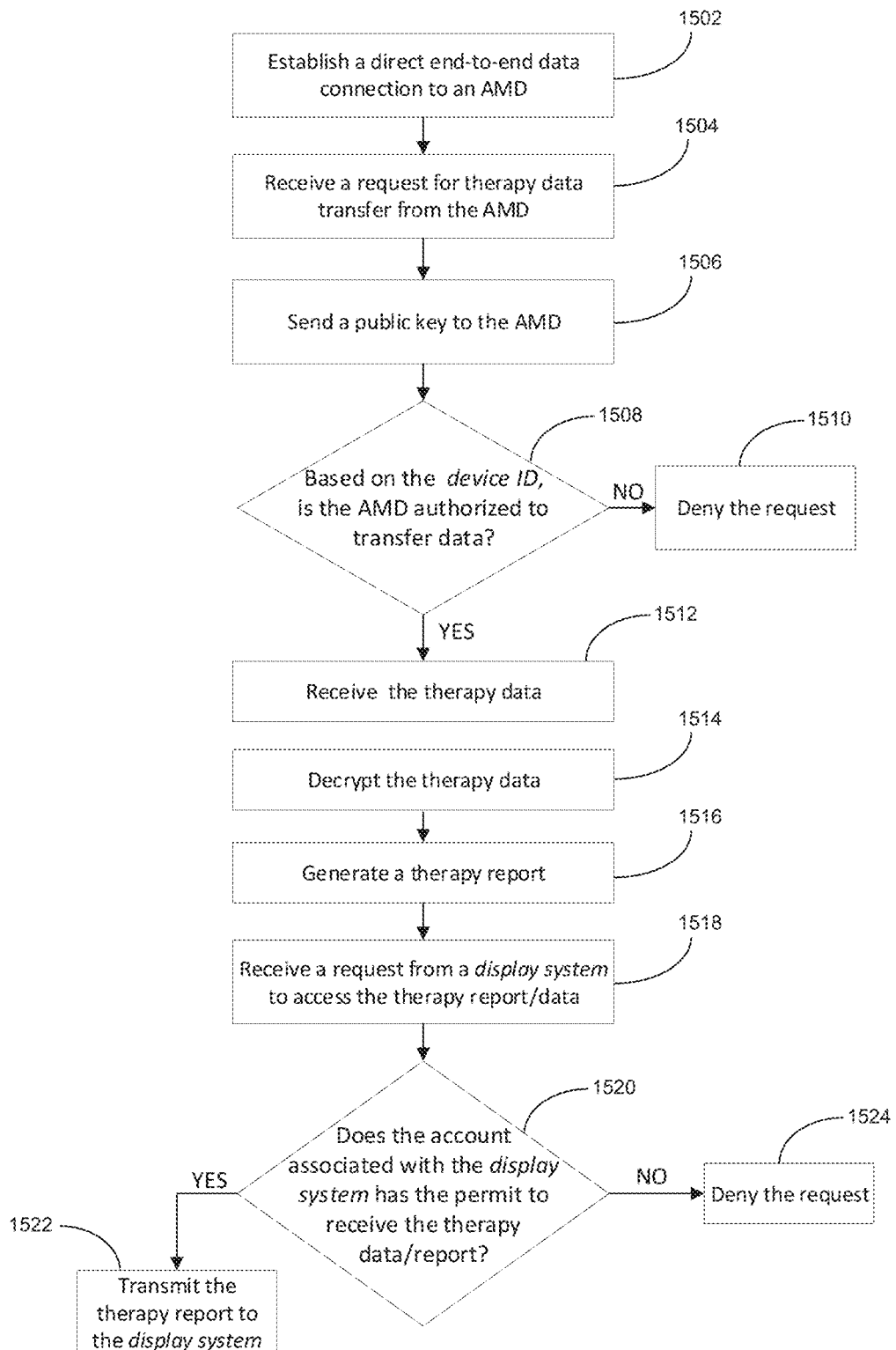
FIG. 15A is a flow diagram illustrating an example method that may be used by a computing system, to generate and share a therapy report based on encrypted therapy data received from an AMD.

FIG. 15A is a flow diagram that illustrates an example method that may be used by computing system 1404, to generate and share a therapy report based on therapy data received from an AMD 1402. In some examples, the AMD 1402 may encrypt the therapy data using a public key and/or a shared secret. The encrypted therapy data may be provided to another computing system, such as a computing system of a clinician or a computing system of a networked computing environment (e.g., a computing system at a data center of a cloud computing network).

At block 1502, the computing system 1404 may establish a direct end-to-end data connection to the AMD 1402, for example, via a wireless wide area network (WAN) using a Narrowband Long-Term Evolution (NB-LTE) transceiver included in the AMD 1402. The direct end-to-end data connection may be initiated by the computing system 1404 or by the AMD 1402. The direct end-to-end connection may be a connection between the AMD 1402 and the computing system 1404 that omits an intermediary computing system (e.g., a local computing system such as a laptop or smartphone). However, the direct end-to-end connection may, in some cases, include intermediary connection hardware, such as a router, base station, or switch.

Once a direct end-to-end data connection between the AMD 1402 and the computing system 1404 is established, at block 1504 the computing system 1404 may receive a request from the AMD 1402 to transfer data (e.g., therapy data) stored on the AMD 1402 to the computing system 1404 over the direct end-to-end data connection. Alternatively, the computing system 1404 may request the data (e.g., therapy data) from the AMD 1402. Regardless of whether the AMD 1402 or the computing system 1404 requests the data transfer, the data transfer may be requested as part of the processes of establishing the direct end-to-end data connection or may be requested after the direct end-to-end data connection is established.

At block 1506, the computing system 1404 and the AMD 1402 may exchange public keys. In some cases, the public key exchange may occur as part of establishing the direct end-to-end data connection so as to establish a secure or encrypted channel. In some cases, the public key exchange may occur after establishing the connection to create a secure data channel. In some cases, one of the computing systems 1404 or the AMD 1402 may provide a public key, while the other device may not. In some such cases, only one of the devices may provide the public key as data transfer may be unidirectional. In some examples, the AMD 1402 may use the public key received from the computing system 1404 to encrypt therapy data to be transmitted to the computing system 1404. Alternatively, or in addition, the computing system 1404 may use the public key received from the AMD 1402 to encrypt a therapy report based on the therapy data, or other data obtained by the computing system 1404, to be transmitted to the AMD 1402.

At block 1508, the computing system 1404 may determine whether the AMD 1402 is authorized to transmit data (e.g., therapy data) to the computing system 1404. The computing system 1404 may determine whether the AMD 1402 is authorized to transmit the data based on a device identifier associated with the AMD 1402, an account identifier associated with the AMD 1402 or a subject, or any other information that may be used to determine whether an operation is authorized. In some cases, the computing system 1404 may use a whitelist to confirm that the AMD 1402 is authorized to communicate with or transfer data to the computing system 1404.

If it is determined that the AMD 1402 is authorized to transfer data to the computing system 1404, the computing system 1404 may receive the data from the AMD 1402 at block 1512. The data may be encrypted therapy data associated with therapy provided by the AMD 1402 to the subject. In some embodiments the computing system 1404 may store the therapy data at one or more of a storage of the computing system 1404 or a storage of the networked-computing environment 1408. In some examples, the encrypted data may include at least one of operation data corresponding to operation of the AMD 1402 or error data corresponding to an error in the operation of the AMD 1402. In some embodiments additional encrypted data may be received from the AMD 1402 on an intermittent basis, a periodic basis, a scheduled basis, or on a continuous basis for at least a time period.

If at block 1508, the computing system 1404 determines that the AMD 1402 is not authorized to transfer data to the computing system 1404, the process may proceed to block 1510 where the request is denied. In some cases, denying the request may include sending an indication to the AMD 1402 that the request is denied. Further, the computing system 1404 may provide a reason why the request is denied, such as incorrect password or unrecognized device identifier.

At block 1514, the computing system 1404 may decrypt the encrypted therapy data received from the AMD 1402. The computing system 1404 may use a private key (e.g., stored in a memory of the computing system 1404) that corresponds to the public key provided by the computing system 1404 to the AMD 1402. Alternatively, or in addition, the computing system 1404 may use a shared secret generated between the computing system 1404 and the AMD 1402 to decrypt the encrypted therapy data.

At block 1516, the computing system 1404, may use the therapy data received from eth AMD 1402, to generate a therapy report. In some examples, the decrypted therapy data and/or therapy report may be stored in a memory of the computing system 1404. The therapy report may include any type of statistics or data that can be extrapolated from the therapy data, or from a series of therapy data received over time from the AMD 1404 and/or from a plurality of AMD associated with a plurality of subjects.

At block 1518, the computing system may receive a request from a display system 1410 that is separate from the networked computing environment, to access the therapy report generated at block 1516. The request may comprise an account identifier associated with a user that caused the request for the therapy report to be generated. Alternatively, or in addition, the request may include an identifier associated with the display system 1410 requesting the therapy report. Further, the request to access the therapy report may include account information and password for the display system 1410 and/or for a user associated with the display system 1410. In some cases, the display system 1410 may be the AMD 1402. In some such cases, the AMD 1402 may not need to authenticate to receive the therapy report as authentication may occur as part of the block 1502. In some cases, such as when the therapy report is generated at a different time than receipt of the therapy data, the AMD 1402 may authenticate with the computing system 1404 before receiving the therapy report.

At block 1520, the computing system 1404 may use an account identifier, a device identifier, or other authentication information received at the block 1518 as part of the request to access the therapy report to determine whether the account associated with the account identifier is authorized or permitted to view the therapy report. In some cases, the display system 1410, or user, is authenticated prior to the receipt of the request to access the therapy report.

If the display system 1410 or the account associated with the request to access the therapy report (or therapy data) is not successfully authenticated and/or is determined to not be authorized to access the therapy report (or therapy data), the computing system 1404 may deny the request at the block 1524. The operations associated with the block 1524 may include one or more of the embodiments associated with the block 1510.

If at block 1520 the computing system 1404 determines that the account is permitted to view the therapy report, the computing system 1404, at block 1522, may transmit the therapy report to the display system 1522. The therapy report may be transmitted over a direct connection to the display system 1410 or over a computing network, which may include the Internet. Further, the computing system 1404 may use an encrypted communication channel to communicate the therapy report (or therapy data). In some cases, upon the computing system 1404 receiving the request to provide access to or to transmit the therapy report (e.g., as part of the block 1518), the computing system 1404 may request a public key from the display system 1410 and can encrypt the therapy report using the received public key. In some such examples, the display device 1410 may use a private key to decrypt the encrypted therapy report received from the computing system 1404. This private key may correspond to the public key provided by the display system to the computing system 1404. In some examples, the display system can be the AMD 1402. In some such examples, the subject or an authorized user may be able to view the therapy report received from the computing system 1404, on a user interface (e.g., a touchscreen display) of the AMD 1402.

In certain implementations, the computing system 1404 may determine that the therapy data or other data received from the AMD 1402 satisfies an alert threshold condition based at least in part on physiological information of the subject obtained from the AMD 1402. In some such implementations, if the computing system 1404 determines that the therapy data or other data received from the AMD 1402 satisfies an alert threshold condition, the computing system 1404 may send an alert to one or more display systems 1410 designated to receive alerts from the computing system 1404. In some cases, the alert may be sent to a user device of the subject, a user device of another user (e.g., a parent, guardian, or medical practitioner), a user device of an emergency services provider, or a user device of any other authorized user associated with the subject.

In some examples, the alert threshold condition may be associated with the health condition of the subject. For example, the alert threshold condition may include the subject's blood glucose level being above (hyperglycemia) or below (hypoglycemia) a set value or setpoint range. In some examples, the alert threshold condition may be associated with the operation of the AMD. For example, the alert threshold condition may include the rate of therapy (e.g., the rate at which insulin is provided to a subject) being above or below a set value. As another example, the alert threshold condition may relate to a quantity of medicament remaining in a medicament cartridge.

In some examples, alert threshold condition may be associated with the temporal behavior of therapy data over a period of time. For example, the alert threshold condition may relate to fluctuations or variations of the subject's blood glucose level being outside of a particular range.

In some cases, the one or more alert threshold conditions may be defined or specified by a healthcare provider. In some such examples, the healthcare provider may change one or more alert threshold conditions based at least in part on physiological parameters or characteristics of the subject.

Figure 15B:
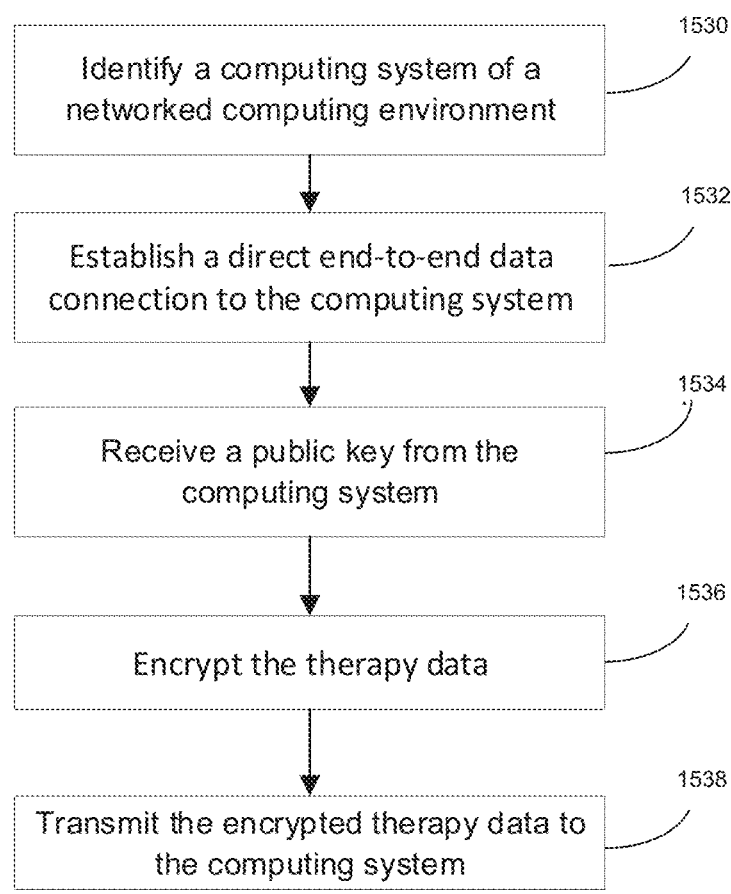
FIG. 15B is a flow diagram illustrating an example method that may be used by an AMD to transmit therapy to a computing system in a networked computing environment.

FIG. 15B is a flow diagram that illustrates an example method that may be used by AMD 1402 to transmit therapy data to the computing system 1404 over a direct end-to-end connection. The process illustrated in FIG. 15B may include one or more of the embodiments previously described with respect to the FIG. 15A.

At block 1530, the AMD 1402 may identify a computing system 1404 of a networked computing environment 1408 based at least in part on a whitelist of one or more approved computing systems stored in the memory of AMD 1402. In some examples, the whitelist may be stored in a memory of AMD 1402 during manufacture of the ambulatory medical device. In some cases, the AMD 1402 may accept data packets from and/or communicate exclusively with computing systems identified on the whitelist. Further, in some cases, the AMD 1402 may confirm, for example, by accessing a packet header, that received packets are received from a computing system on the whitelist. Data packets received from computing systems that are not on the whitelist may be ignored or discarded. In some cases, a user may be able to add a computing system to the whitelist, such as a laptop or smartphone of the subject or a guardian of the subject.

At block 1532, the AMD 1402 may establish a direct end-to-end data connection to the computing system 1404 using an address of the computing system 1404 obtained from the whitelist. In some examples, the address may be a network address (e.g., a network address of the networked computing environment 1408). In some such examples, the network address can be an Internet Protocol (IP) address, a Uniform Resource Locator (URL), a Uniform Resource Identifier (URI), or a Uniform Resource Name (URN). In some embodiments the direct end-to-end data connection may be established via a wireless wide area network (WAN) using a transceiver of the AMD 1402 configured to support communication over one or more communication standards such as a low power wide area network (LPWAN) communication standard, a Narrowband Long-Term Evolution (NB-LTE) standard, a Narrowband Internet-of-Things (NB-IoT) standard, or a Long-Term Evolution Machine Type Communication (LTE-MTC) standard. In some such embodiments, the transceiver may be configured to communicate via the wireless wide area network using the address. In some examples, the direct end-to-end data connection to the computing system 1404 may be established by transmitting a connection request to the computing system 1404. In some such examples, the connection request may include a device identifier of the AMD 1402.

At block 1534, the AMD 1402 may receive a public key from the computing system 1404. At block 1536, the AMD 1402 may encrypt therapy data related to therapy delivered by the AMD 1402, based at least in part on the public key received from the computing system. In some embodiments, the AMD 1402 may encrypt the therapy data based at least in part on a shared secret generated based on an asymmetric key pair (e.g., a public key and a private key) of the AMD 1402 and an asymmetric key pair of the computing system 1404. For example, the shared secret may be generated using a Diffie-Hellman key exchange.

At block 1538, the AMD 1402 may transmit the encrypted therapy data to the computing system 1404 over the direct end-to-end connection. In some embodiments, the AMD 1402 may obtain additional therapy data that may be obtained at a different time period than the transmitted therapy data. The AMD 1402 may encrypt the additional therapy data using the same key or shared secret used to encrypt the therapy data at the block 1536. Alternatively, a different key or shared secret may be obtained and used to encrypt the additional therapy data. For example, at the time that the additional therapy data is obtained, a new secure channel may be established using a new asymmetric key pair. The additional encrypted therapy data may be transmitted to the computing system over the direct end-to-end connection. In some embodiments the computing system may decrypt the received encrypted therapy data using the public key sent to the AMD 1402 and a private key stored in a memory of the computing system. In some cases, in addition to the therapy data, AMD 1402 may transmit status information of the AMD 1402 to the computing system 1404. The status information of the AMD 1402 may include one or more of operation data or error data, wherein the operation data corresponds to operation of the ambulatory medical device, and wherein the error data corresponds to an error in operation of the AMD 1402.

In various embodiments, the computing system 1404 that performs the steps described with respect to FIGS. 15A and 15B can be a computing system in a networked computing environment 1408/1608, a data center, a computing system of a hosted services environment, or a cloud network 1406/1606.

In some embodiments, the AMD 1402 may receive an account identifier associated with a user authorized to access data associated with the subject at the networked computing environment 1408 and transmit the account identifier to the computing system 1404. In these embodiments, the computing system 1404 may allow the authorized user to access the therapy data received from the AMD 1402. In some embodiments, the AMD 1402 may also transmit a set of permissions to the computing system 1404 that may authorize the user to access the therapy data associated with a subject.

Figure 16:
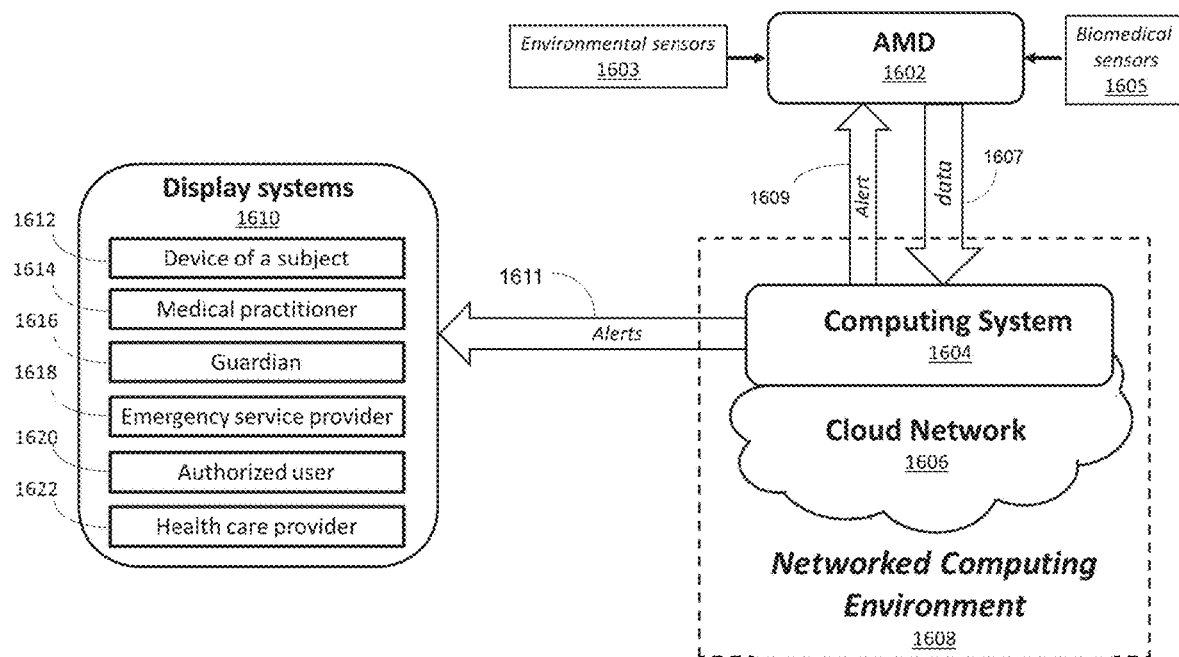
FIG. 16. is a block diagram, illustrating an example network and data flow configuration wherein the AMD is directly connected to a computing system and the computing system generates and sends alerts to one or more display systems and the AMD.

FIG. 16 is a block diagram, illustrating an example network and data flow configuration where an AMD 1602, which is directly connected to a computing system 1604 (e.g., computing system within a cloud network 1606), may generate and send alerts 1611 to various display systems 1610 (e.g., alert messages, alert signals and the like) upon determining that data received from the AMD 1602 satisfies a threshold condition. The computing system 1604 may be part of a networked computing environment 1608 (e.g., a data center, networked computing system), or a cloud network 1606 or cloud computing system of a cloud service provider. The computing system may include one or more non-transitory memories and one or more hardware processors configured to execute the computer-executable instructions stored in one or more non-transitory memories. The AMD may receive data from one or more biomedical sensors 1605 (e.g., blood glucose level sensor, analyte sensor, temperature sensor, heart beat sensor, and the like) and/or one or more environmental sensors 1603 (e.g., geolocation receiver, motions sensor, accelerometer, and the like). These sensors may be included in the AMD unit or may be connected to the AMD via a wired or wireless link.

In some cases, the one or more display systems 1610 receiving the alert 1611, may be display systems that have previously received therapy reports from the computing system 1604. In some examples, the one or more display systems may be selected and/or authorized by the subject who is receiving therapy from the AMD 1602 to receive alerts 1611. The display systems 1610 may receive alerts 1611 from the AMD 1602 may include: a medical practitioner 1614 (e.g., a doctor, a nurse, etc.), a guardian of the subject 1616 (e.g., subject's parents), an emergency service provider 1618, an authorized user 1620 (e.g., a user authorized by the subject such as spouse, relative, friend, and the like), a healthcare provider 1622, or a device of the subject 1612 (e.g., a mobile device, cell phone, personal computer, tablet, and the like). In some examples, when it is determined that received data from the AMD 1602 satisfies a threshold condition, an alert may be sent to one or more display systems 1610 (e.g., alert 1611) and/or the AMD 1602 (e.g., alert 1609).

In some examples, the AMD 1602 may be configured to establish a connection to support continuous data transfer to the computing system 1604 for a given period of time (e.g., provided to the AMD by the subject), in order to capture data that is generated over the given period of period and/or that satisfies an alert threshold condition. For example, the subject may request a continuous connection between AMD and the computing system when going for a hike alone to make sure that if his/her health condition deteriorates during the hike, an alert is sent to one or more authorized display systems.

In some examples, a geolocation sensor (e.g., a Global Positioning System (GPS) receiver) and/or a proximity sensor can be used to enable location-activated features, such as automatic upload of data at certain locations.

In some cases, the AMD 1602 may include, communicate with, or otherwise connect or interface with a motion sensor, an accelerometer, or a geolocation system. In some examples, the aforementioned sensors may be used to determine or detect the velocity of the AMD and/or the subject. In some such examples, using the data 1607 obtained from the AMD 1602, such as the location and/or velocity information, can be used to provide intelligent alerts. For example, if the AMD 1602 (or a computing system 1604 receiving data from the AMD 1602) determines from the location and/or motion data that a user is travelling at a high rate of speed (e.g., likely in a car) and the user's blood glucose level is low (e.g., below 55 mg/dl), the AMD 1602 (or the computing system 1604) may automatically alert an emergency service provider 1618 that a subject is at risk of hypoglycemia and may be driving. Further, the AMD 1602 and/or the computing system 1604 can provide a location of the subject to the emergency service provider 1618. In some cases, the determined velocity of the AMD may be used to generate driving alerts to inform the subject to pull over immediately or as soon as it is safe due to a risk of a hypoglycemic event. In some examples, if it is determined that the subject is moving at 6-7 mph, exercise alerts may be generated, for example, to alert the subject to pause exercising if the subject's blood sugar level drops below a certain level. In some examples, if the subject hasn't moved for 3 hours and has low blood sugar, the system can enable automatic notification to emergency services. Further, the determined activity level of the subject can be sensed and used to modify the therapy delivery. For example, a determination of the subject's motion can be used to automatically adjust the rate of therapy delivery (e.g., raise the blood sugar level that triggers the therapy delivery).

In some examples, the computing system 1604 may generate alerts based on a trend of the aggregated therapy data or based on therapy data that is an outlier to the aggregate therapy data or an outlier to a time-based average of the therapy data.

Additionally, the computing system 1604 can send a text message, call, or generate any other type of alert that may be automatically provided to a device (e.g., smartphone, laptop, etc.) of a follower, healthcare provider, or other user associated with the subject when the therapy data satisfies an alert threshold. These messages or alerts may be provided from the computing system to a third-party device in cases where roaming or disabling of the data plan on the AMD occurs (e.g., no TCP/IP available). Further, the computing system 1604 may send a text message or call 911 in case of a detected emergency. The computing system 1604 can track, for example, via GPS, the end user's most recent location and share that information with a follower and/or emergency personnel. Moreover, the computing system 1604 may enable an end user to order and re-order medical supplies directly from the viewing device.

In some examples, the computing system 1604 can generate notifications regarding potential medical risks (e.g., generate a message when there is a risk of hypoglycemia). Further, more detailed processing in the computing system can result in improved recommendations (e.g., trigger levels for therapy delivery, or other control parameters)

Figure 17:
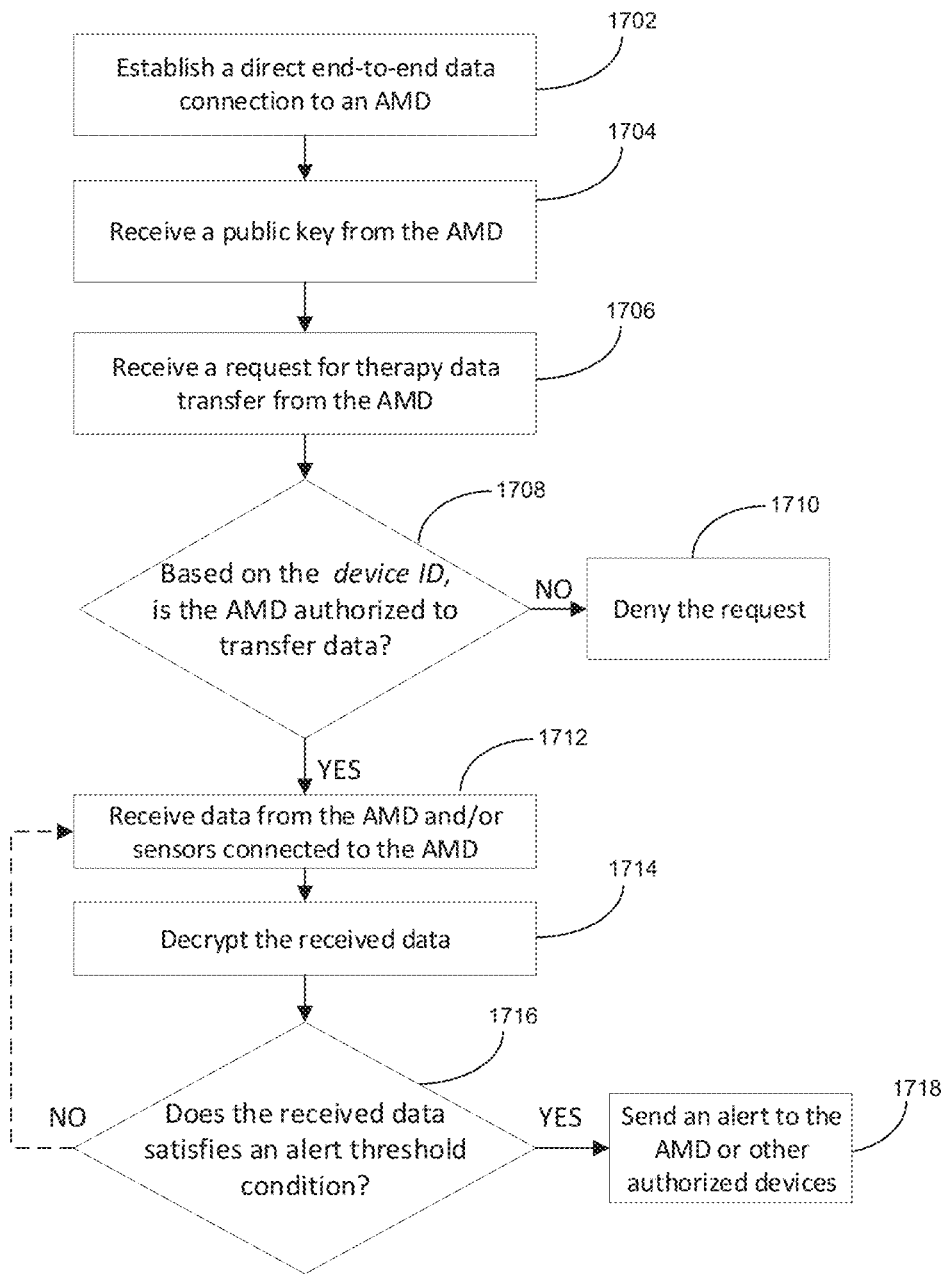
FIG. 17 is a flow diagram illustrating an example method that may be used by a computing system, to generate and send an alert to one or more authorized devices.

FIG. 17 is a flow diagram illustrating an example method that may be used by computing system 1604 to generate and send alerts (e.g., alert messages, alert signals and the like) to one or more authorized devices and to the AMD. At block 1702, the computing system 1604 may establish a direct end-to-end data connection to an AMD 1602, for example, via a wireless wide area network (WAN) using a Narrowband Long-Term Evolution (NB-LTE) transceiver included in the AMD 1602. In some examples, the direct end-to-end connection may be established for a given period of time set by the subject or an authorized user (e.g., a guardian of the subject). The block 1702 may include one or more of the embodiments described with respect to the block 1502.

Once a direct end-to-end data connection between the AMD 1602 and the computing system 1604 is established, at block 1704 the computing system 1604 may receive a public key, from the AMD 1602 over the established connection. As previously described, in some cases, the key exchange may be part of the process of establishing the data connection. Further, the block 1704 may include one or more of the embodiments described with respect to the block 1504.

At block 1706 the computing system may receive a request from the AMD 1602 to transfer data (e.g., therapy data, medical sensor data or environmental sensor data) generated by the AMD 1602 to the computing system 1604 over the direct end-to-end data connection. In some cases, the request to transfer data may be the data itself. In other words, in some cases, there may not be a formal request to transfer the data, but instead data may be transmitted by the AMD 1602 to the computing system 1604 upon establishing the data connection. The block 1706 may include one or more of the embodiments described with respect to the block 1506.

In some cases, the request may include a time period during which AMD 1602 continuously transmits data generated by the AMD 1602 or obtained from one or more sensors (e.g., medical sensors 1603 or environmental sensors 1605), to the computing system 1604. In some such cases, the time period for continuous data transfer from the AMD 1602 to the computing system 1604, may be provided by the subject or a guardian of the subject to the AMD.

At block 1708, the computing system 1604 may determine whether the AMD 1602 is authorized to transfer data to the computing system 1604. In some cases, the determination may be based at least in part on the device ID associated with the AMD 1602. The block 1708 may include one or more of the embodiments described with respect to the block 1508.

If it is determined that the AMD 1602 is not authorized to transfer data to the computing system, the request received at block 1706 may be denied at block 1710. The block 1710 may include one or more of the embodiments described with respect to the block 1510.

If the computing system 1604 determines that the AMD 1602 is authorized to transfer data to the computing system 1604, at block 1712 the computing system 1604 may permit the AMD 1602 to provide the encrypted therapy data to the computing system 1604. In other words, the computing system 1604 may receive the therapy data, which may be encrypted therapy data, from the AMD 1602. The block 1712 may include one or more of the embodiments described with respect to the block 1512.

At block 1714, the computing system 1604 may decrypt the received data using a private key. The private key may correspond to a public key of the computing system 1604 provided to the AMD 1602 to encrypt the therapy data. This private key may be stored in a memory of the computing system 1604. The block 1714 may include one or more of the embodiments described with respect to the block 1514.

At block 1716, the computing system 1604 may determine whether the received data (e.g., therapy data, medical sensor data or the environmental sensor data), satisfies a threshold condition. In some examples, the computing system 1404 may determine that the therapy data or other data received from the AMD 1402 satisfies an alert threshold condition based at least in part on physiological information or physiological measurements of the subject obtained from the AMD 1402. In some cases, the physiological measurements may be obtained from one or more physiological sensors (e.g., glucose monitors, heart rate monitors, blood pressure monitors, etc.) that provide physiological measurements to the AMD 1402. In some cases, the threshold condition may be provided to the AMD 1602 by the subject or an authorized user (e.g., a guardian of the subject). In some examples, the threshold condition may be provided by a healthcare provider. In some such examples, the threshold condition may be stored in a memory of the AMD 1602.

If the computing system 1604, determines that the therapy data satisfies a threshold condition, the computing system may generate and transmit an alert to one or more display systems 1610 that are authorized (e.g., by the subject or a guardian of the subject) to receive alerts at block 1718. In some examples, the subject, or other authorized user, may authorize one or more display systems 1610 to receive alerts by, for example, providing the account IDs of the one or more display systems to the computing system 1604 or the networked computing environment 1608. If at block 1716, the computing system 1604, determines that the therapy data does not satisfy a threshold condition, the process may return to block 1712 where the computing system 1604 continues receiving therapy data from the AMD 1602.

Preventing Inadvertent Therapy Changes

As described above, the ambulatory medical device (AMD) may include a user interface (e.g., touchscreen interface or a non-touchscreen interface) that may present one or more user-interface screens to a user enabling the user to modify one or more therapy settings of the AMD, such as a quantity of medicament delivered when a condition is met or the condition that triggers the delivery of medicament to a subject. In some cases, the AMD can be an ambulatory medicament device. The user may be a subject who is receiving medicament or therapy, a clinician or healthcare provider, a parent or guardian, or any other user who may be permitted to modify settings of the ambulatory medicament device. For AMD that include a user interface, there is a risk that a setting is accidentally modified or is modified (intentionally or unintentionally) by a user that does not fully comprehend his or her action (e.g., a child or a user with a reduced mental capacity). Further, AMD may accidentally have settings modified by inadvertent interactions with a user interface, such as may occur when an AMD is worn against the body of a subject.

An ambulatory medicament device (AMD) may be configured to prevent an inadvertent modification to a control parameter and/or to medicament delivery, for example, in the event of a setting of the AMD being accidentally modified by a user or inadvertent interactions with a user interface of the AMD.

As mentioned above, in some embodiments the user may modify the control or configuration of the AMD using a user interface. There is a possibility that the control or configuration of the AMD is accidentally modified through the user interface. For example, as the user may transport the AMD, there is a danger that the user will inadvertently activate input in the AMD that initiates a therapy change input (e.g., by applying pressure on the AMD that may be placed in the jacket pocket of the user).

Figure 18:
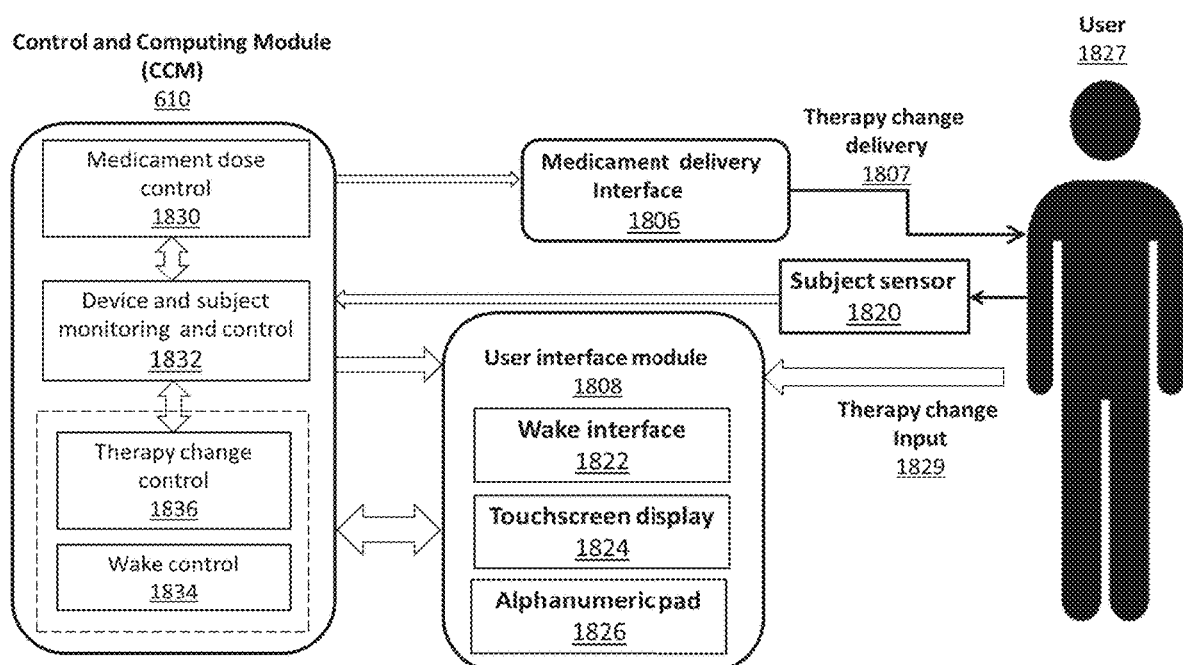
FIG. 18 illustrates the interconnection among modules and procedures in AMD involved in receiving, accepting and/or canceling therapy change request.

With reference to FIG. 18, in some embodiments, the control and computing module (CCM) 610 of the AMD may include a set of therapy change procedures implemented to prevent therapy change inputs 1829 that are inadvertent. The therapy change procedures implemented by the CCM 610 may be implemented as instructions stored in a memory of CCM (e.g., the main memory 616) and executed by the processor 614. The CCM 610 may verify the therapy change input 1829, received from a user 1827, using one or more therapy change procedures before the AMD 600 administers therapy based on the received therapy change input 1829. In some cases, the therapy change inputs 1829 may be received in response to a user interaction with a user interface module 1808. The therapy change inputs 1829 may control or relate to one or more therapy change procedures performed by the control and computing module (CCM) 610 or one or more of the controllers (e.g., the controllers 1830-1836) implemented by the CCM 610.

The user interface module 1808 may include any type of user interface controller for providing a user interface. The user interface may be provided on a display of the AMD 600, or may be transmitted to a display of an electronic device in communication with the AMD 600. In some cases, the user interface controller may be a touchscreen controller that is configured to output display signals configured to generate one or more user interface screens on a touchscreen. Further, the touchscreen controller may be configured to receive user input signals corresponding to user interaction with the touchscreen.

In certain embodiments, the user 1827 may wake the AMD from a sleep state or unlock the AMD by interacting with a wake interface 1822. When the AMD is in a sleep state, the touchscreen controller may not receive user input or user input signals corresponding to user input. Waking the AMD 600 may include activating a touchscreen interface or presenting a lock screen to a user. Further, waking the AMD may include waking the touchscreen controller such that it can receive user input or user input signals corresponding to user input. The wake interface 1822 can include one or more of the additional user interfaces mentioned above that are configured to generate and provide a wake input (or wake signal) to the CCM when detecting a pre-set user interaction. Alternatively, or in addition, the wake interface 1822 can be any type of wake interface element of the AMD that a user can interact with to wake at least a feature (e.g., a touchscreen interface) of the AMD. For example, the wake interface element can be a physical button (e.g., a push button, a slide button, etc.), a capacitive element, a resistive element, or an inductive element. In some cases, the wake interface element can be or can include a biometric element, such as a fingerprint reader, an iris scanner, a face detection scanner, etc. In some cases, the AMD may wake in response to detection of a particular movement or motion. For example, a determination that the ambulatory medicament device is being moved with a particular motion or within a line of sight or a visual range of a user may cause the AMD to awaken or cause the AMD to awake the touchscreen interface of the AMD. The AMD may determine that the AMD is being moved within a line of sight of the user based on the type of motion and/or the detection of a user's eyes via, for example, an iris scanner or a camera.

In some examples, the therapy change input 1829 can be an input provided by the user 1827 to change a therapy that is currently being delivered to the user 1827. For example, the therapy change input 1829 may cause the insulin or glucagon infusion pump to start infusing an amount of insulin or glucagon into the user 1827. In some examples, the therapy change input 1829 provided by the user 1827, may affect the therapy delivery at future time. In some examples, the therapy change input 1829 may modify the rate of insulin or glucagon infusion into the user 1827. The therapy change input 1829 may also cancel insulin or glucagon infusion into the user 1827 from the insulin or glucagon infusion pump. In some cases, the therapy change input 1829 is a request to change a control parameter. The control parameter may be changed in response to the request. Alternatively, or in addition, a confirmation action (e.g., a swipe gesture or an interaction with a physical or digital button on the touchscreen) confirming the requested control parameter change may be required before the control parameter is changed.

In some cases, when a wake action is detected by the wake interface 1822, a wake input is sent to the control and computing module 610, which may imitate or perform a wake control procedure to wake/unlock the user interface (e.g., a touchscreen display). In some cases, the CCM 610 may use the wake controller 1834 to perform the wake procedure.

When in the wake and/or unlocked state, a user may interact with the touchscreen 1824, alphanumeric pad 1826 or other types of user interfaces that may be included in the user interface module 1808, to obtain access to therapy change user interface.

The therapy change user interface may be activated by a first user interaction with the user interface (e.g., touchscreen display 1824). When the first user interaction is detected, the user interface module 1808 may send an input signal to the control and computing module 610 to determine if the first user interaction relates to a therapy change request or a control parameter change request. In some cases, the CCM 610 may use the therapy change controller 1836 to determine whether the first user interaction corresponds to a request to change a control parameter, or a request to access a control parameter change interface. If it is determined that the first user interaction satisfies a set of predefined conditions, the therapy change controller 1836 sends a signal to the user interface module 1808 to activate the therapy change user interface.

In some embodiments, the type of therapy change user interface and/or the available therapy change selections included in the user interface may depend on the user interaction. For example, in response to one of two user interactions, the therapy change control procedure 1836 may send one of two signals to the user interface module 1808. The therapy change user interface, or the therapy change controller 1836, may unlock one of two different therapy change user interfaces that result in different options of therapy change selections for the user 1827. In an implementation of this example, a therapy change selection to make a significant therapy change, such as dramatically (e.g., more than a magnitude, or more than 3 change increments) increase the rate of insulin or glucagon infusion rate, may require a user interaction that is different from the user interaction that may be required for an insulin or glucagon infusion at a normal or prescribed rate, or a smaller change to the control parameter. In some examples, the user interaction may be a simple interaction (e.g., a simple gesture or unlock gesture interaction) that unlocks a therapy change user interface with therapy change selections that are limited. Another user interaction may be a complicated interaction (e.g., a series of complex gestures) that unlocks a therapy change user interface with therapy change selections that have no limits. An example of this implementation may be useful for child users. The child user may perform the first or simpler gesture that is made up of a series of simple inputs to unlock therapy change selections that are limited. An adult user may perform the second or more complex gesture that is made up of a series of complex inputs to unlock the therapy change user interface with therapy change selections that have no limits.

Once activated, the therapy change user interface generated by the user interface module 1808 may provide one or more therapy control elements that enable the user to modify the one or more settings of the AMD 600. In some examples, the therapy control element may include any type of user interface screen on the touchscreen, or other type of user interface in the non-touchscreen context, that enables or permits a user to change a configuration of the AMD 600. This change in configuration of the AMD 600 may relate to a change in the therapy provided or in the detection of a triggering event that causes therapy (e.g., medicament delivery) to be provided to a subject. For example, the change in configuration may include a selection between one or more hormones that regulate blood sugar level (e.g., insulin or glucagon) of a user, an amount of the one or more hormones that regulate blood sugar level of the user, a rate of delivery of the one or more hormones, a threshold for determining when to deliver the one or more hormones, a change in an estimated blood absorption rate of the one or more hormones, and the like. In some examples, the therapy control element may include any type of user interface screen on the touchscreen, or other type of user interface in the non-touchscreen context, that enables or permits a user to change one or more control parameters of the AMD 600 that control the therapy delivery.

In some cases, a change to the setting (e.g., control parameters or configuration of the AMD) of the AMD is automatically and/or instantly recognized or implemented by the AMD, and/or transmitted to the AMD. In some cases, a confirmation of the change may be required before the setting change is implemented by or transmitted to the AMD.

This confirmation may be entered based on a second user interaction with a user interface (e.g., touchscreen display 1824). When the second user interaction is detected, the user interface module 1808 sends an input signal to the control and computing module 610 wherein it is analyzed by a therapy change control procedure 1836. If it is determined that the second user interaction satisfies a set of predefined conditions, the therapy change control procedure 1836 implements the change to the configuration of the AMD.

The first and/or second user interactions may include the selection of an icon, a series of taps or inputs, one or more gestures (e.g., a linear swipe, an arcuate swipe, a circular swipe, or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. Gesture interactions can be guided by visual indicia displayed or printed on the AMD. In some embodiments, the visual indication can include animations that suggest or guide user interactions with a touchscreen. For example, the first user interaction can include an arcuate swipe around at least a portion of a generally circular icon or logo. In some examples, the first and/or second user interactions may include a predetermined sequence of numerical and/or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds.

Further, one or more of the interactions may include interacting with a sensor as an optical sensor (e.g., visible light or IR sensor), biometric sensor (e.g., a fingerprint or retinal scanner), a proximity sensor, a gyroscope, or a combination of accelerometer and gyroscope, and the like. Also, in some cases, the second user interaction may be received through a wireless signal such as RFID or Bluetooth. In some embodiments, the second user interaction may include receiving a selection of an indicator box that correspond to either insulin or glucagon and receiving a predetermined sequence of numerical inputs in order to deliver the therapy change selection.

The type of user interaction that unlocks the touchscreen, provides access to a configuration screen, and/or confirms a change to the configuration of the AMD may be the same or may differ.

In some examples, the system may have a time-out such that if no interaction occurs for a set period of time, the user interface will turn off and the therapy change request process has to start again. In one implementation of the time-out, if no interaction occurs for more than 30 seconds after the system is waked/unlocked before the second user interaction is received by the user interface, the user interface will be deactivated.

In some implementations, once a change or modification to the therapy setting (e.g., a change in control parameters or configuration of the AMD) is confirmed, implemented, or transmitted, the AMD may begin operating based on the modified setting selected and/or provided by the user.

In some cases, this operation may include triggering therapy delivery based on the new setting or providing therapy based on the new setting. For example, the AMD may generate a dose control signal based at least in part on the modified configuration or control parameter or may detect a trigger based at least in part on the modified configuration or control parameter that leads to the provisioning of therapy.

With reference to FIG. 18, in some embodiments, the changes made through the therapy change user interface are sent to CCM wherein the therapy control change procedure 1836 in CCM transfers the changes to the device and subject monitoring and control procedures 1832. The device and subject monitoring and control procedures 1832 may be implemented in the CCM 610 to monitor and control one or more modules or systems of the AMD (e.g., therapy delivery configuration) as well as the health condition of the subject 1827 using the subject sensor (e.g., CGM sensor). For example, the device and subject monitoring and control procedures 1832 may receive information about a therapy change requested by a user 1827 through a user interface (a touchscreen display 1824 or alphanumeric pad 1826) or information about glucose level in subject's blood from the subject sensor 1820. Subsequently, the device and subject monitoring procedure and control procedures 1832 may transmit the information pertaining a health condition of the subject and/or the AMD configuration, to the medicament dose control procedure 1830. In some examples, the parameters in the medicament dose control procedure 1830 may be adjusted based on the changes and/or information captured by the device and subject monitoring and control procedures 1832. The medicament dose control procedure 1830, may control and activate the medicament delivery interface 1806 by providing a medicament dose signal. In some examples, the medicament does control may be generated at least partially based on detected conditions or physiological characteristics of the subject (e.g., provided by the readings of the subject sensor 1820) and according to parameter values received from the therapy change control procedures 1836. The medicament delivery interface 1806 may provide a therapy change delivery to the user according to the information received by device and subject monitoring procedure 1832.

In some examples, the dose control signals may be produced based on time (e.g., medicament may be delivered on a periodic basis), one or more user commands, indication that the subject is planning to engage or is engaging in a particular activity (e.g., eating a meal, exercising, sleeping, fasting, etc.), or any other factor that may relate to or cause the triggering of therapy (e.g., medicament delivery).

Figure 19:
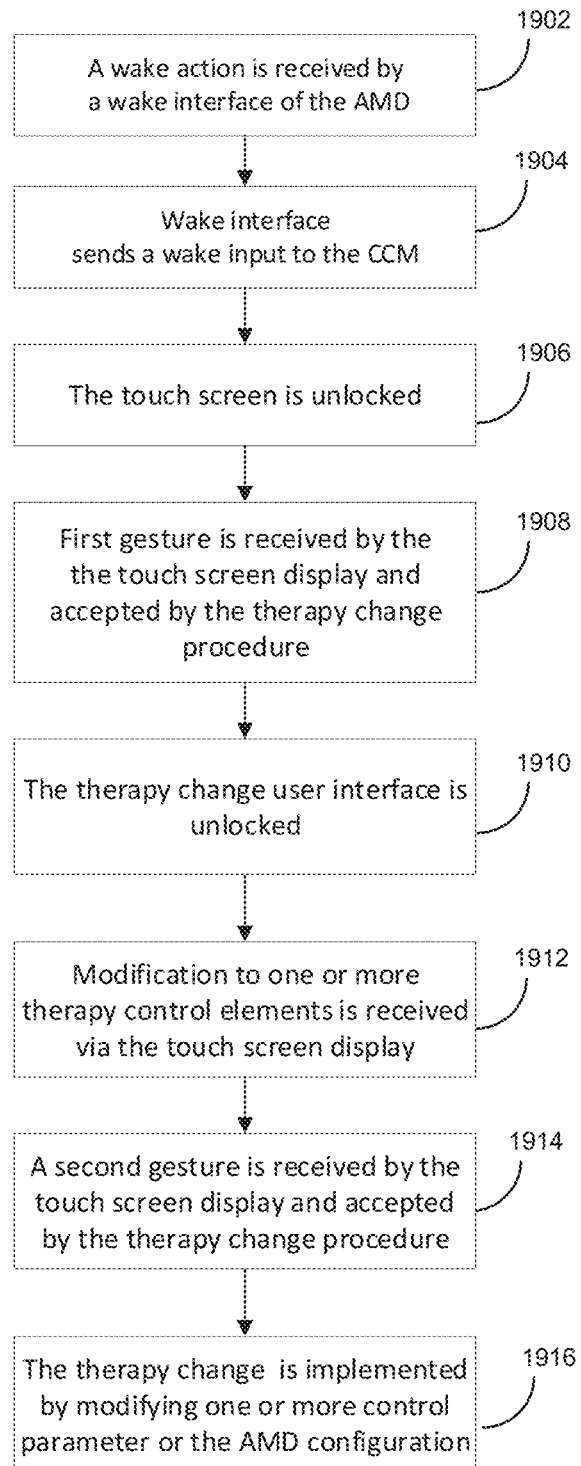
FIG. 19 is a flow diagram illustrating an example method that may be used by an AMD to allow a user to change the configuration of the ambulatory medicament device using a touch screen user interface.

FIG. 19 is a flow diagram illustrating an example method that may be used by an AMD to allow a user to change the configuration of the AMD using a touch screen user interface. The user may initiate the configuration change process by waking/unlocking the touch screen using a wake action. At block 1902 a wake action is received by the wake interface 1822 of the AMD. At block 1904 the wake interface 1822 sends a wake signal to the CCM module 610 of the AMD. Within CCM 610, the wake procedure generates, activates, or unlocks the touch screen display 1824 (at block 1906). At block 1908 the AMD receives a response or a first gesture from the user. A block 1908, a therapy change user interface is unlocked. At block 1912, the user may modify or change one or more therapy settings (e.g., control parameter or configurations) of the AMD, using one or more therapy control elements provided in the corresponding therapy change user interface. At block 1914 the user may confirm the changes made, by providing a second gesture on the touchscreen display 1824. Once the confirmation is received, at block 1916 the requested therapy changes or therapy modification are implemented, and the AMD may begin operating according to a modified configuration or modified set of control parameters. In some examples, once the user confirms the changes made, the medicament dose control module 1830 may be sent a dose control signal to the medicament delivery interface 1806 to trigger a therapy delivery to the subject based on the modified therapy settings.

In some cases, AMD, or a control device that enables a user to modify a configuration of the AMD, may have a timeout feature. The timeout feature may cause the AMD or the control device to enter a sleep or locked state after a period of time of inactivity by the user. In some cases, the timeout feature may cause the AMD or the control device to enter a sleep or locked state after a particular period of time regardless of whether the user is interacting with the ambulatory medicament device or control device. In some cases, the timeout feature may cause the user interface (e.g., a touchscreen display) to become inactive or enter a lock state. Thus, a user may have a limited period of time to modify the configuration of the AMD.

In some examples, the therapy change made by a user may trigger the delivery of a medicament according to the therapy change received and confirmed by a user. This therapy change delivery may occur after a set time from period from receiving the confirmation.

In some embodiments of the AMD, an alarm status indicator may be presented to the user via the user interface. The alarm status indicator can be an alert message or an alert symbol. The alarm status indicator may be related to a configuration change made by a user, a change in the status of the AMD not related to a user input, or the condition of the subject (e.g., detected by the subject sensor).

Figure 20A:
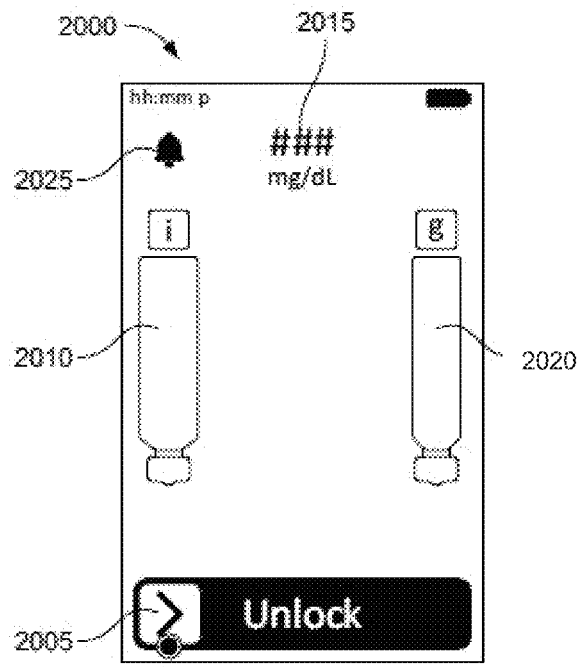
FIG. 20A is an illustration of the touchscreen display of an example AMD after the touch screen is waked/unlocked by a wake action of a user and before the first user gesture is received.

FIG. 20A is an illustration of the touchscreen display 2000 of an example AMD after the touch screen is waked/unlocked by a wake action of a user and before the first user gesture is received. Even while the touchscreen display is locked, the touchscreen display 2000 may display any images, animations, text, or other graphics. The first gesture prompt 2005 displays to the user 1827 the input required to unlock the therapy change user interface. Here, the first gesture prompt 2005 shows the user 1827 that a touch movement that begins at the greater-than symbol (>) and moves right across the "Unlock" text is the acceptable first gesture. In addition to the first gesture prompt, the refill status of the AMD 600 is shown in a graphic representation 2010. Here, the graphic representation 2010 shows that the insulin cartridge in the AMD device 600 is almost full. A current blood sugar level 2015 is shown at the top of the touchscreen display 2000, which can inform the user 1827 of the need for a hormone that regulates blood sugar levels. The touchscreen display 2000 also shows a graphic representation 2020 of a cartridge of glucagon. The graphic representation of an alarm 2025 in the touchscreen display 2000 shows that an alert is set on the AMD 600.

Figure 20B:
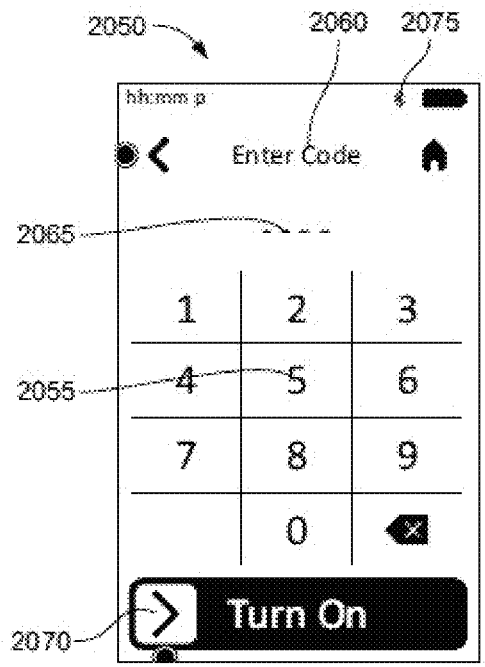
FIG. 20B is an illustration of an example touchscreen display that may prompt the user to enter a predetermined series of inputs for the first gesture or second gesture.

FIG. 20B is an illustration of an example touchscreen display 2050 that may prompt the user to enter a predetermined series of inputs for the first gesture or second gesture. In various embodiments, such as the embodiment shown in FIG. 20B, the touchscreen display 2050 may display touchable number keys 2055. In various embodiments, the touchscreen display 2050 prompts the user 1827 to enter the series of inputs that complete the first gesture or second gesture. The text "Enter Code" 2060 prompts the user 1827 to enter a predetermined or preselected numerical sequence as part of the first gesture or second gesture. The numerical sequence being typed by the user 1827 is displayed in field 2065 as it is entered as an aid to the user 1827. The input 2070 of the touchscreen display 2050 shows that a touch movement of a swipe right across the bottom of the screen is required to complete the predetermined series of inputs for the first gesture or second gesture. A Bluetooth connection symbol 2075 shows that the AMD 600 is paired or can be paired to another electronic device.

Figure 20C:
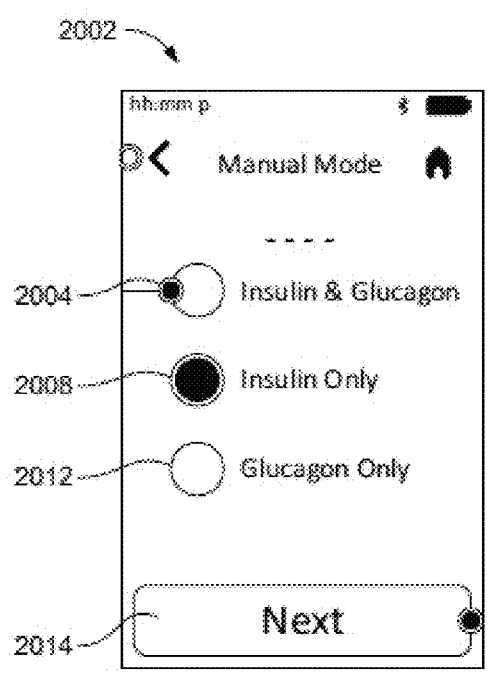
FIG. 20C is an illustration of an example therapy change user interface.

FIG. 20C is an illustration of an example therapy change user interface (in this case a touchscreen display 2002). The example screen shown here may prompt the user 1827 to select one or more hormones for regulating the blood sugar level of the subject. The touchscreen display 2002 presents the user 1827 with an option to select between two hormones (e.g., insulin and glucagon), or select both hormones. In the screen shown in FIG. 20C, the selected option by the user is "insulin only" 2008. The user 1827 is also given the options of selecting the "glucagon only" button 2012 or both "insulin & glucagon" button 2004. Once the user 1827 selects one of the options provided on the touchscreen display, the "Next" button 2014 may be selected to complete the therapy change selection. In some examples, selecting the "Next" button may provide the user with more options. For example, selecting the "Next" bottom may prompt the user 1827 to select an amount of the one or more hormones selected by the user 1827. In some implementations, a therapy change user interface may prompt the user 1827 to select a target blood sugar level and the AMD device may automatically select a hormone (or a combination of hormones) and determine the amount of the one or more selected hormones that should be delivered during a therapy session to maintain the blood sugar level at the target level or within a margin of the target level.

Figure 20D:
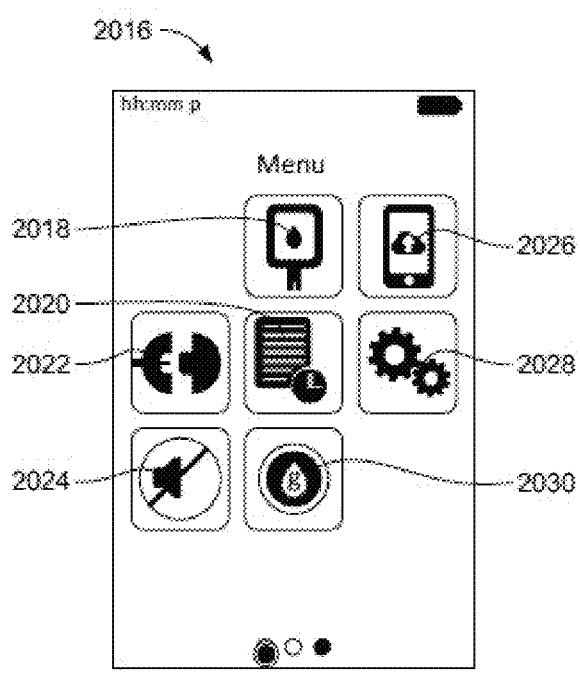
FIG. 20D is an illustration of another therapy change user interface on a touchscreen display.

FIG. 20D is an illustration of another example of user interface on a touchscreen display 2016 that supports therapy change by the user 1827. Here, the user 1827 is given a multitude of options. One or more options in the therapy change user interface allow the user 1827 to make a therapy change selection. Other options are related to other AMD functions (e.g., generating a therapy report, replacing a cartridge, and the like). A "Deliver Hormone" button 2030 allows the user 1827 to select a therapy change that delivers a hormone that regulates blood sugar to the user 1827. A "Test Blood Sugar" button 2018 allows the user 1827 to test the blood sugar level of the user 1827. A "Generate Report" button 2020 generates a document that reports the therapy changes that have been delivered to the user 1827. A "Refill Cartridge" button 2022 allows the user 1827 to fill a cartridge in the AMD device 600 with medicament. An "Upload to Cloud" button 2026 allows the user 1827 to transmit therapy change information to a cloud-based server. A "Sound Control" button 2024 allows the user 1827 to control the sounds emitted by the AMD 600. A "Settings" button 2028 allows the user 1827 to manipulate one or more other settings of the AMD 600.

As mentioned above, in some embodiments of the AMD, an alarm status indicator may be presented to the user via the user interface to alert the user about a change made or occurred in the AMD configuration.

For example, with reference to FIG. 18, the user 1827 may make a therapy change 1829 using the user interface 1808 and based on the procedure illustrated in FIG. 19. Once therapy change procedure 1836 implements the therapy change, the AMD may alert the user that a therapy change is implemented. The alert message or symbol may be presented on a user interface (e.g., touchscreen display 1824) before and/or during the therapy change delivery 1807. For example, an alarm indicator may inform the user 1827 that a therapy change is about to occur. Any number of details of the therapy change may be displayed as part of the alert message or symbol. In some examples, the alarm status indicator may appear after the user unlocks or wakes the user interface using a wake action. In some examples, the alarm status indicator may be shown on the user interface when the user interface is inactive or locked.

Figure 21:
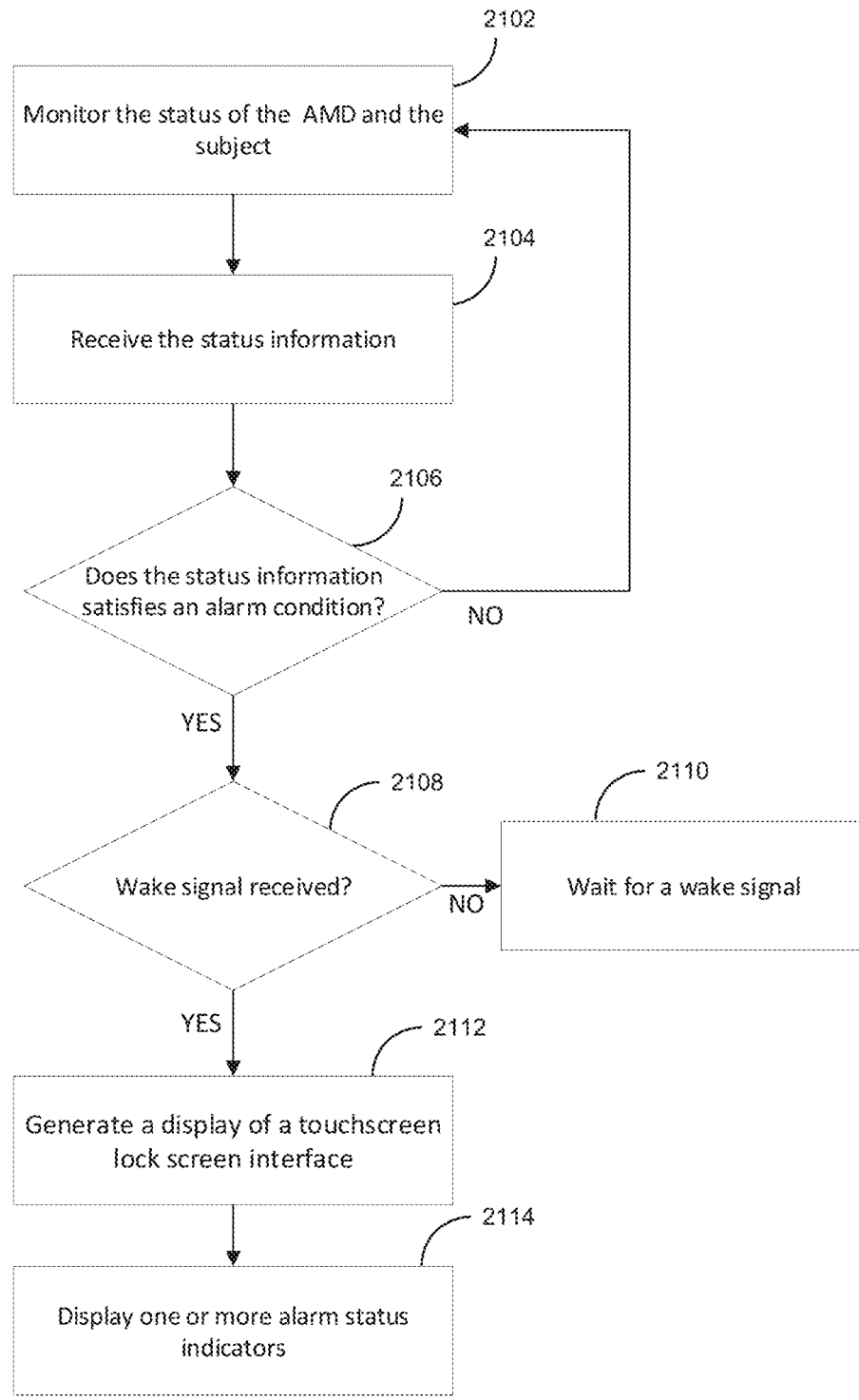
FIG. 21 is a flow diagram illustrating an example method that may be used by an AMD to generate an alarm status indicator.

FIG. 21 is a flow diagram illustrating an example method that may be used by an AMD to generate an alarm status indicator. In some embodiments, the device and subject monitoring procedures may continuously monitor the status of the AMD 2102 (e.g., the user interface, different modules of the AMD and the like) as well as the health condition of a subject (e.g., using various subject sensors such as analyte sensors). AMD Once a set of status information is received at the block 2104, the device and subject monitoring procedure may determine whether the received status information satisfies an alarm condition at decision block 2106. If the received status information does not satisfy an alarm condition, no action will be taken and device and subject monitoring procedure continuous monitoring the AMD and the subject. If it is determined that the received status information satisfies an alarm condition, the system may determine if a wake signal is received at decision block 2108. If no wake signal is detected, the system waits for a wake signal to be received at block 2110. Once a wake signal is received via one or more user interfaces or sensors, the CCM 610 (e.g., using the wake control 1834 and therapy change control 1836) may generate a display of a touchscreen lock screen interface at block 2112 and display one or more alarm status indicators at block 2114, corresponding to the detected alarm condition, on the lock screen. Alternatively, in some cases, the alarm status indication may be generated and included in one or more user interface screens, such as a touchscreen lock screen interface regardless of the sleep or wake condition of the AMD. However, in some cases, the alarm status indicator may not be presented to a user until a user performs wake interaction to awaken the AMD and cause a user interface screen to be presented.

In some cases, additional status information may be received by an AMD at some point in time after the previous status information that satisfies an alarm condition was received. If the AMD determines that the additional status information satisfies the alarm condition for the AMD or for the subject, the AMD may modify one or more alarm status indicators based at least in part on the additional status information. For example, the alarm indicator may indicate an increased severity of the alarm condition via a different status indicator or a modifying of a color or text associated with the status indicator. If the additional status information satisfies a different alarm condition, an additional alarm indicator may be displayed on the touchscreen lock screen interface of the AMD. On the other hand, if the additional status information indicates that the alarm condition has been resolved, the alarm indicator may be removed or modified to indicate resolution of the alarm condition.

Figure 22:
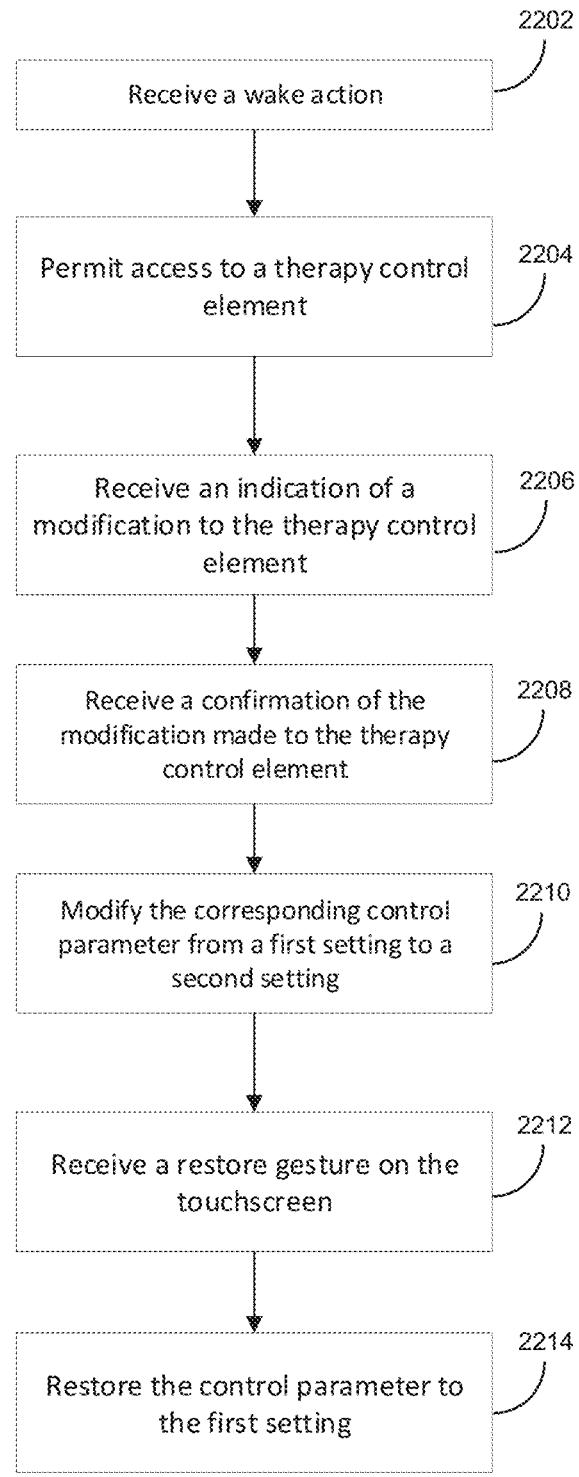
FIG. 22 is a flow diagram illustrating an example method that may be used to cancel a therapy change using a touchscreen interface.

In some embodiments, the AMD may allow the user to provide a therapy change and then cancel the therapy change. The user may provide the therapy change by modifying one or more control parameters of the AMD. FIG. 22 is a flow diagram illustrating an example method that may be used to cancel a therapy change using a touchscreen interface. The user may unlock the touchscreen display 2202 using a wake action and get access to a therapy change user interface 2204 (e.g., using a first gesture), where one or more therapy control elements may be displayed. Next, an indication of a modification to a therapy control element may be received 2206 by the user interface followed by a confirmation of the modification made 2208 (e.g., a second gesture). In response to receiving an indication and confirmation of a modification to a therapy control element, the corresponding control parameter may be changed from a first setting to a second setting 2210. In some examples, once the change is implemented 2210, the user may decide to cancel it, for example, after realizing that requested change is erroneous. In these examples, the user may provide a third gesture 2212 on the touch screen. In response to receiving the third gesture from the user interface, the therapy change procedure may restore the modified control parameter to the first setting 2214. In some examples, the third gesture may be a restore gesture. In some cases, the restore gesture may be a swipe gesture. In some examples the swipe gesture may be performed near or in a region of the therapy change user interface that is occupied by the therapy control element (or a particular portion thereof). An example of a restore swipe gesture may be a gesture performed from a starting swipe position to an ending swipe position located closer to a left edge of the touchscreen than the starting swipe position. For instance, a user may position a finger at a point on the touchscreen and drag the finger across at least a portion of the touchscreen towards a left edge (e.g., reminiscent of a back arrow). It should be understood that other gestures are possible to indicate a restore gesture. In some cases, a user can define the gesture to be used as a restore gesture. In some embodiments, the restore gesture is received on a different user interface screen than a therapy change user interface wherein one or more therapy control element are provided. In various examples, the restore gesture is performed in the opposite direction from a therapy change confirmation gesture that confirms the modification to the therapy control element.

In some examples, in order to cancel a therapy change request, the restore gesture has to be provided within a set time period after the confirmation gesture is received by the user interface. In some such examples, during the set time period one or more dose control signals may be provided to the medicament delivery interface resulting in one or more therapy change deliveries. In some cases, the restore gesture can be received at any time after the confirmation gesture or therapy change. In some cases, the restore gesture restores the control parameter modified during a therapy change to an immediately preceding value. In some cases, the restore gesture restores the control parameter to a value designated as a restore value (e.g., a default value or other designated restore value) or to a most recent value that maintained the subject's blood glucose level with a target setpoint range. The designated restore value may be specific to a subject or AMD or may be determined based on clinical data for a set of subjects. The set of subjects may be subjects that share certain characteristics with the subject using the AMD. For example, the set of subjects may be of the same gender, similar age range, similar severity of diabetes, etc.

In some cases, the system may allow the user to modify a therapy change before confirmation. In these cases, the user may modify a therapy control element for a second time to change the corresponding control parameter from a second setting to a third setting.

In some examples, the third setting may be the same as the first setting. In some cases, the first setting or the third setting may be a default setting. In some cases, the first setting or the third setting may be a restore setting.

Figure 23A:
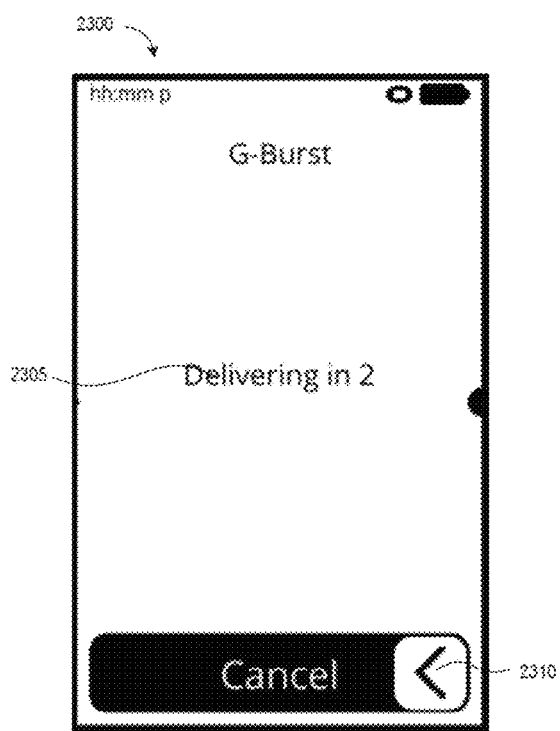
FIG. 23A is an illustration of a touchscreen display alerting the user that the delivery of one or more medicaments will occur.

In some examples, the user may be able to cancel a therapy change delivery after confirming the therapy change and before a therapy delivery based on new settings. In some such examples, an alert may notify the user that a therapy delivery based on new settings will occur shortly. FIG. 23A is an illustration of a touchscreen display 2300 alerting the user that the delivery of one or more medicaments will occur. The alert may be accompanied by sound or vibration effects. Here, the alert informs the user 1827 a delivery of medicament will occur in 2 seconds 2305. The touchscreen display 2300 is further allowing the user 1827 to perform a gesture to cancel the therapy delivery. The gesture to cancel the delivery is a touch movement that starts at the less-than symbol 2310 and swipes left across the "Cancel" text. In the embodiment shown in FIG. 23A, a single gesture by the user 1827 may cancel the therapy change. In some cases, input of the wake signal, the first gesture, the therapy change selection, and the second gesture are all required to cancel a therapy that is being delivered.

In some examples, the user may be able to cancel a therapy change delivery triggered based on therapy change made by the user. In these examples, the user may get access to the user interface using a wake action and provide a gesture to cancel the ongoing therapy delivery based on a therapy change delivery.

Figure 23B:
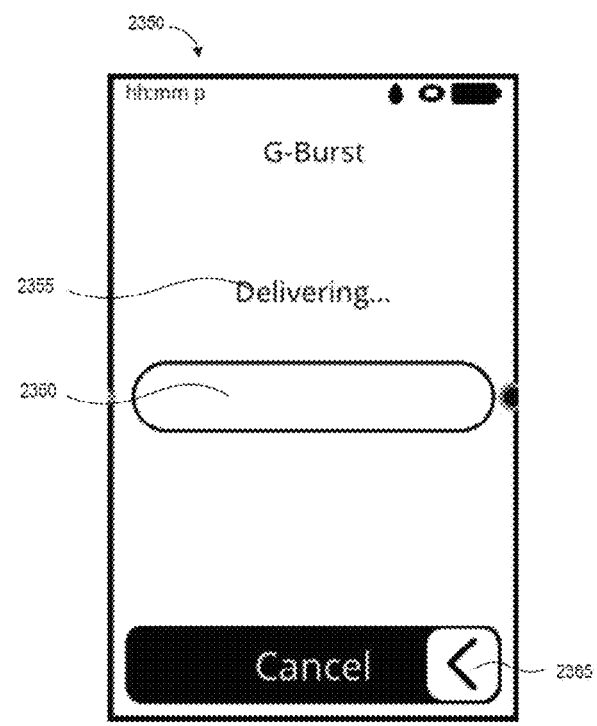
FIG. 23B is an illustration of a touchscreen display showing that a medicament is being delivered to the user.

FIG. 23B is an illustration of a touchscreen display 2350 showing that a medicament is being delivered to the user 1827. The text "Delivering" 2355 informs the user 1827 that a medicament is currently being delivered to the user 1827. The progress bar 2360 is a graphic representation of the progress of the delivery. As shown in FIG. 23B, the delivery is only starting, and zero progress has been completed. The touchscreen display 2350 is allowing the user 1827 to perform a gesture to cancel the delivery, which includes interrupting and discontinuing the delivery if it had already begun but has not yet been completed. The gesture to cancel the delivery is a touch movement that starts at the less-than symbol 2365 and swipes left across the "Cancel" text. In some examples, a therapy change delivery 1807 may be canceled by an input by a user input comprising a wake action followed by a series of touch inputs (e.g., gestures, alphanumeric inputs and the like).

Additional embodiments relating to interacting with an ambulatory medicament device that can be combined with one or more embodiments of the present disclosure are described in U.S. Provisional Application No. 62/874,950, which was filed on Jul. 16, 2019 and is titled "PREVENTING INADVERTENT THERAPY CHANGES ON AN AMBULATORY MEDICAL DEVICE," the disclosure of which is hereby incorporated by reference in its entirety herein for all purposes, and in U.S. Provisional Application No. 62/874,954, which was filed on Jul. 16, 2019 and is titled "CAPACITIVE TOUCH WAKE BUTTON FOR AN AMBULATORY MEDICAL DEVICE," the disclosure of which is hereby incorporated by reference in its entirety herein for all purposes.

Automatic Resumption of Medicament Delivery Following Manual Suspension

In some cases, it may be desirable to suspend operation of the ambulatory medicament device (AMD) or to suspend at least the delivery of one or more medicaments by the AMD to a subject for a period of time. For example, it may be desirable to suspend an operation associated with the delivery of medicament when the medicament reservoir or cartridge in the AMD is empty or needs to be replaced. As another example, it may be desirable to suspend delivery of medicament when the ambulatory medicament device is removed or is being moved to another site on the subject. In yet another example, it may be desirable to suspend delivery of the medicament when the subject is taking or ingesting another medicament that may produce a contraindication with the medicament provided by the AMD. In some cases, when a subject suspends the treatment delivered by an AMD, the subject may forget to resume the treatment delivered by the AMD. In some cases, the health condition of the subject may deteriorate during the suspension period requiring therapy delivery to resume prior to the end of the suspension period. As such, there is a need for AMDs that allow subjects to safely suspend treatment for temporary amounts of time (e.g., temporary suspension period) and are capable of automatically resuming the medicament delivery if necessary. Suspending delivery of the medicament can include the processor of the AMD not generating a dose control signal during the temporary suspension period.

In some embodiments, the AMD may support a therapy suspension and resumption procedure allowing a user (e.g., the subject, a parent or guardian) to suspend all therapies or a subset of therapies for a period of time defined by the user as well as automatic resumption of one or more therapies at the end of the requested suspension period (e.g., temporary suspension period) or when a threshold condition is met (e.g., a threshold condition associated with the health condition of the subject). In some such embodiments, the AMD can be a mono-hormonal insulin pump. In some other embodiments, the AMD can be a bi-hormonal pump capable of administering insulin and a counter-regulatory agent (e.g., glucagon).

In AMDs that support therapy suspension, inadvertent activation and/or resumption of therapy delivery can be dangerous (e.g., when the AMD is an insulin and/or glucagon infusion device). In some examples to mitigate this risk, the AMD may be configured to avoid inadvertent suspension or resumption of therapies. For example, inadvertent activations of suspensions of medicament delivery may be prevented by requiring a user to perform gestures (e.g., on a touchscreen display or other types of user interface), to suspend and/or resume therapy delivery by the AMD. In some examples, the gestures may be entered at a particular prompt provided on a user interface to activate or resume a therapy suspension.

One particular application of the therapy suspension with automatic resumption feature in an AMD can be in the field of diabetes drug delivery. For example, the subject may need the ability to suspend delivery of insulin during situations such as exercise, which has a blood glucose lowering effect. Suspension of insulin delivery can prevent a subject from entering a hypoglycemic state (extreme low blood glucose), which carries severe complications. Once the therapy is suspended the user may be at the risk of entering a hyperglycemic state (high blood glucose that may result in complications such as diabetic ketoacidosis or neurovascular complications), if the user forgets to reactivate the drug delivery after exercise. Further, the subject's blood glucose level may raise above or below a dangerous level during the period of exercise. In these situations, the automatic medicament delivery resumption may improve the health of the subject.

In certain cases, the AMD may suspend one or more therapy deliveries when the AMD receives an indication that therapy (e.g., delivery of medicament) is to be suspended. The indication that therapy is to be suspended may be a command from a user. Often the user is the subject, but the user may also include other users that may have a say or interest in the care of the subject. For example, the user may be a clinician or other healthcare provider, or a parent or guardian.

In some examples, the indication that the therapy or medicament delivery is to be suspended may be a command received via a user interface of the AMD or from another device that provides the user with an interface to request that medicament delivery be suspended. For example, the device may be a smartwatch, smartphone, laptop or desktop, or other control device that can communicate via a wired or wireless connection with the AMD.

In some cases, the indication that the therapy or medicament delivery is to be suspended may be received from the AMD itself. In some such embodiments, the AMD may suspend therapy or medicament delivery responsive to determining that one or more components or modules of the AMD do not satisfy a minimum requirement for operation. For example, if the quantity of medicament available to the AMD device drops below a threshold (e.g., the cartridge or reservoir is empty or below a minimum dosage amount), a signal may be generated to suspend medicament delivery. In some embodiments, suspension of therapy occurs based on a loss of a sensor signal, such as the loss of a glucose level signal.

Figure 24:
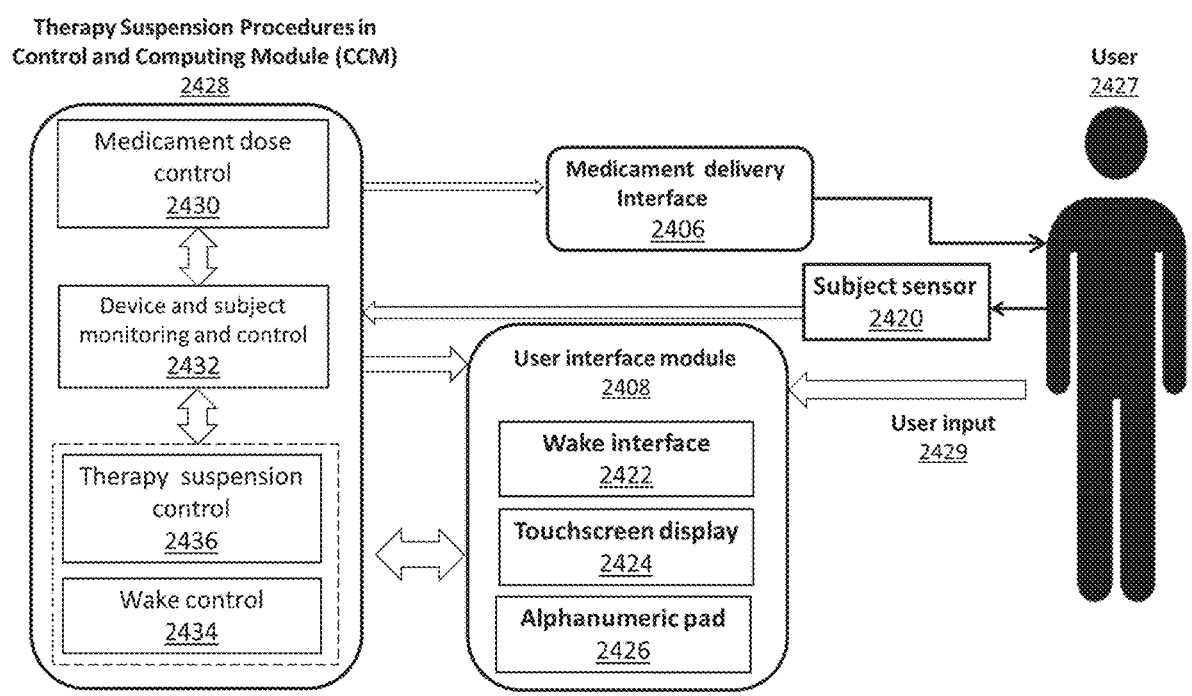
FIG. 24 is a block diagram illustrating the interconnection among modules and procedures in AMD involved in receiving, accepting and/or canceling a therapy suspension request.

FIG. 24 illustrates the interconnection among modules and procedures involved in receiving, accepting and/or canceling a therapy suspension request, in an example AMD. In some examples, these procedures may be implemented in the CCM 2428 (and/or 610) of the AMD. In some embodiments, a request for suspending one or more therapies (e.g., delivery of one or more medicament to the subject) can be made by a user 2427 by providing an input 2429 (e.g., the start and stop time for therapy suspension, selecting the type of therapy that should be suspended, and the like), through a therapy suspension user interface provided by the user interface module 2408 having, for example, a wake interface 2422, touchscreen display 2424, and/or alphanumeric pad 2426. The therapy suspension user interface may send a suspension request along with the corresponding information to CCM wherein the suspension control procedures 2436, implemented in CCM, process and send a therapy suspension signal to the device and subject monitoring and control procedures 2432. In some examples, the AMD can generate an alert prior to suspending delivery of the medicament to the subject. The alert can indicate a suspension start time at which the delivery of the medicament will be suspended. In some examples, in order to prevent therapy suspension request inputs 2429 that are inadvertent, the therapy suspension control procedures 2436 may include a therapy suspension request verification procedure to verify the therapy suspension requests received from the user interface module 2408 or other devices that may communicate with the AMD via wired or wireless links (e.g., smartwatch, smartphone, laptop or desktop).

In some examples, when the subject monitoring and control procedures 2432 receives the request for therapy suspension from the therapy control procedures 2436, it may send a signal to the medicament dose control procedures 2430 indicating that no dose control signal should be send to the medicament delivery interface 2406 during the period requested by the user 2427.

In some cases, after receiving a request for suspending the medicament delivery, the AMD may delay the medicament delivery suspension responsive to determine that a medical condition of the subject satisfies a threshold medical condition. For example, the device and subject monitoring and control procedures 2432 may receive a signal from the subject sensor (e.g., a CGM sensor) indicating that blood glucose level of the subject is above a threshold level and therefore do not suspend the medicament (e.g., insulin)

delivery at a time request by the user. In some such examples, the AMD may suspend the therapy once it determines that medical condition of the subject is improved and does not satisfy a threshold medical condition anymore.

In some cases, if during the suspension period, certain pre-set or resumption conditions (e.g., one or more medical conditions of the subject) are satisfied, the device and subject monitoring and control procedures 2432 automatically resume the therapy delivery by sending a signal to the medicament dose control procedures 2430 that generates and provides a dose signal to the medicament delivery interface 2406. In some examples, a dose control signal can be generated at a next scheduled dosage period after determining that a resumption condition has occurred as discussed herein. In some examples, a dose control signal can be generated immediately after determining that the resumption condition has occurred. In some examples, the AMD can generate an alert responsive to determining that a resumption condition has occurred. The alert can indicate that a medical condition of the subject satisfies a threshold medical condition. In some examples, if during the suspension period, the AMD determines that the level of one or more analytes in subject's blood and/or interstitial fluid above or below a set threshold (e.g., based on the signal received from a subject sensor 2420), it may resume the medicament delivery to the subject 2427 by a sending a dose control signal to the medicament delivery interface 2406. For example, if the signal received from a glucose sensor (e.g., CGM sensor) indicates that the blood glucose level of a subject is above a certain threshold level, it may resume the delivery of insulin to the subject to reduce the level of glucose in subject's blood. In some cases, if the signal received from a glucose sensor (e.g., CGM sensor) indicates that the blood glucose level of a subject is below a certain threshold level, it may resume the delivery of insulin to the subject to reduce the level of glucose in subject's blood. In some examples, when if during the suspension period, if a medical condition of the subject satisfies a threshold medical condition, the AMD may generate an alert indicating that the medical condition has satisfies a threshold medical condition. In some such examples, the AMD may display the alert on a user interface of the AMD and/or a user interface of another device connected to the AMD (e.g., a local or remote electronic device that is wirelessly connected to the AMD).

In order to prevent inadvertent activation of a suspension, the user may initiate a therapy suspension request starting with a wake action (e.g., received by the wake interface 2422 and processed by the wake control procedure 2434), that activates the user interface module 2408. Using a first interaction with a user interface (e.g., a touchscreen display) the user may unlock a therapy suspension user interface where the information pertaining therapy suspension is provided. Next, the user may confirm the requested therapy suspension using a second interaction with the user interface. In some examples, the system may allow access to the therapy suspension user interface and accept the suspension request, only if the first and second interaction with the user interface are both verified by the therapy suspension control procedure 2436.

In some examples, the therapy suspension control procedure 2436 may receive the request for suspension and suspension information from another local or remote device connected (e.g., wirelessly) to AMD. For example, a user may use a smart watch or smart phone to send a therapy suspension request to the AMD.

The suspension information provided by the user may include a set of parameters needed for a suspension. For example, the suspension information may include the dates and/or times for starting and ending the therapy suspension, threshold values needed to define a threshold condition that may trigger an early resumption of the therapy delivery, and the like. In some examples, suspension information may indicate that the suspension of therapy should happen at a particular time (e.g., suspension start time) or after a particular event (e.g., after the next dose of medicament is delivered or after the condition of the subject reaches a particular state, such as the middle of a desired blood glucose range). In some examples, the threshold values may be associated with input provided by the subject sensor 2420 or other types of sensors that may be used to monitor one or more parameters associated with the health condition of the user 2427.

The parameters for a suspension may include the start and stop conditions for a suspension. The start condition for a suspension may be a condition that, when met, activates a suspension. In some such examples, the start condition is met when a timer runs out. Similarly, the stop condition is a condition that, when met, ends the suspension. In one example, the stop condition is met when a timer runs out (e.g., temporary suspension period). In another example, the stop condition is met when a threshold is met. A threshold may be related to a measurement taken by AMD (e.g., by a subject sensor 2420), such as a measured blood glucose level of the subject 2427. The threshold may be met if the blood glucose level goes above, goes below, or matches a set blood glucose level. In some examples, multiple conditions may be included in the suspension information received from the user. For example, a time condition and a threshold condition may be set simultaneously. In such examples, the suspension may end sooner than the set time, for example, if the glucose concentration of the user meets a threshold.

In some cases, the request to suspend therapy may include an indefinite suspension period. In other words, the request may not include a time period specified by a user or an identity of a resumption condition (e.g., without or no user action to trigger the resumption condition). In some cases, the indication may include a request to temporarily suspend delivery of therapy for a defined period of time (e.g., temporary suspension period) or until a further interaction or event occurs. Thus, the resumption condition can include an expiration of time (e.g., expiration of a temporary suspension period) or an active event (e.g., a command or a determined condition of a subject). Further, the therapy to be suspended may include any type of therapy. For example, the therapy to be suspended may be the suspension of the delivery of medicament, which may include insulin, counter-regulatory agent (e.g., Glucagon), or both insulin and a counter-regulatory agent. In some cases, the AMD may be capable of and/or configured to administer multiple medicaments (e.g., both insulin and a counter-regulatory agent). In some such cases, the request to suspend therapy may include a request to suspend one (e.g., insulin or the counter-regulatory agent) or both of the medicaments.

In some examples, the interactions with the user interface may include the selection of an icon, a series of taps or inputs, one or more gestures (e.g., a swipe or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. In some examples, the first and/or second user interactions may include a predetermined sequence of numerical or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds. In some cases, a visual guide may assist the user in generating the user interaction. For example, one or more arrows or images may be presented to the user to guide the user in providing the command to suspend the delivery of therapy.

Further, one or more of the interactions may include interacting with a sensor as an optical sensor (e.g., visible light or IR sensor), biometric sensor (e.g., a fingerprint or retinal scanner), a proximity sensor, a gyroscope, or a combination of accelerometer and gyroscope, and the like. Also, in an exemplary embodiment, the second user interaction may be made through a wireless signal such as RFID or Bluetooth. In some embodiments, the second user interaction may include receiving a selection of an indicator box that correspond to either insulin or glucagon and receiving a predetermined sequence of numerical inputs in order to deliver the therapy change selection.

The type of user interaction that unlocks the touchscreen, provides access to a therapy suspension user interface or confirms a suspension request may be the same or may differ.

In an exemplary embodiment, the system may have a time-out such that if no interaction occurs for a set period of time at each step during the therapy suspension request process, the user interface will turn off and the therapy suspension request process has to start again. In one implementation of the time-out, if no interaction occurs for more than 30 seconds after the system is waked/unlocked before the second user interaction is received by the user interface, the user interface will be deactivated.

Figure 25:
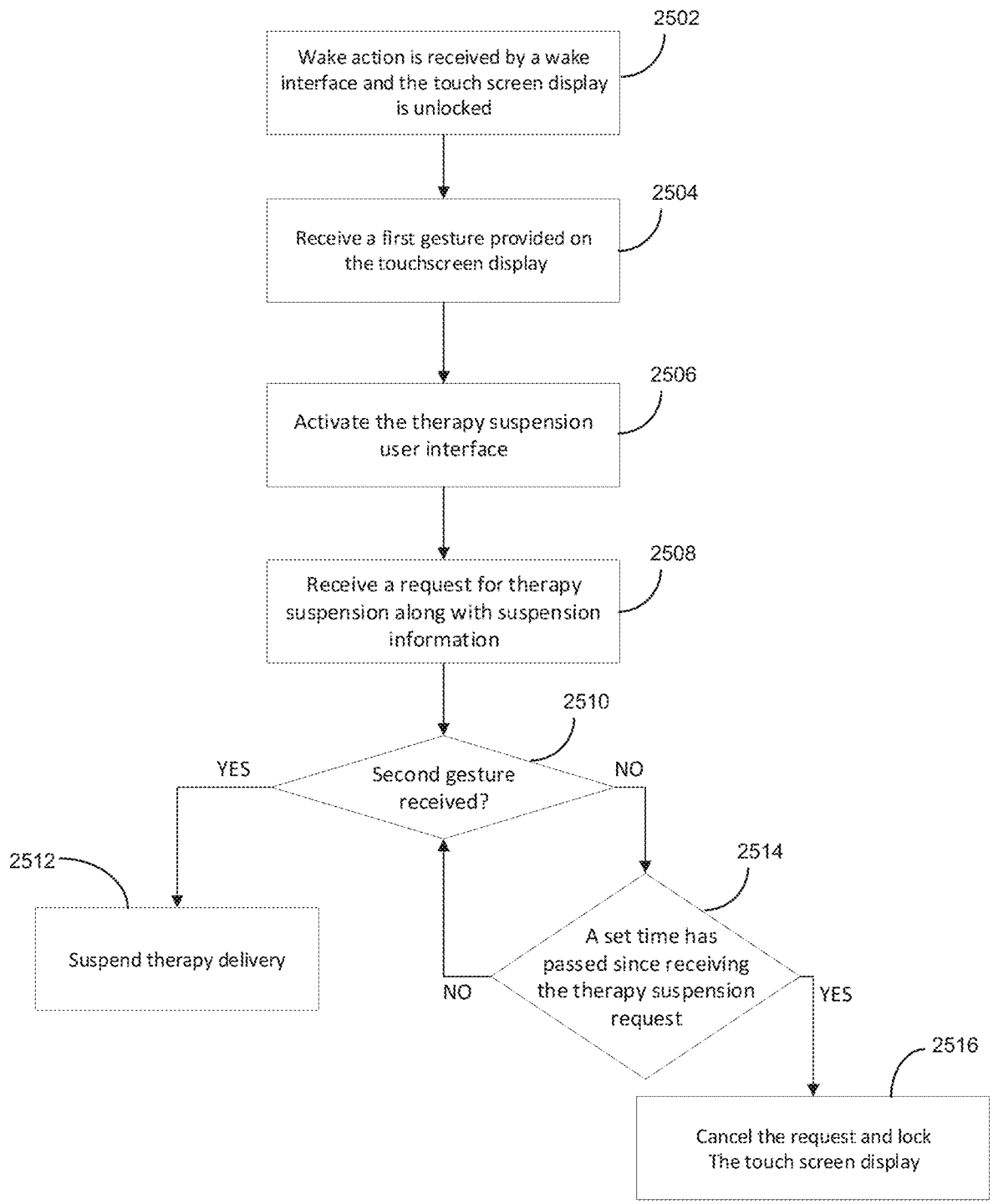
FIG. 25 is a flow diagram illustrating an example method for receiving and implementing a suspension request, which may be implemented by an AMD

FIG. 25 is a flow diagram illustrating an example method for receiving and implementing a suspension request, which may be implemented by an AMD. In this example the user may use a touchscreen interface to request and confirm a therapy suspension. Once the user activates the touchscreen using a wake action 2502, the AMD may wait for a first gesture on the touchscreen. After the user provides the first gesture and the gesture is verified by the therapy suspension control procedures 2436, a therapy user interface may be activated 2506 where the user can request a therapy suspension and provide 2508 the suspension information (e.g., a start day/time (e.g., suspension start time) and stop day/time (or suspension period) and/or a resumption condition). Next, the AMD may wait for second gesture on the user interface 2510. If the second gesture is received and verified by the therapy suspension control procedure 2436, the therapy delivery will be suspended 2512. If the second gesture is not received or not verified by the therapy suspension control procedure 2436, the therapy suspension control procedure 2436, may determine if a set time has passed since receiving the therapy suspension request 2514. If it is determined that a set time has passed since receiving the therapy suspension request, the request will be canceled, and the touch screen will be locked 2516. If it is determined that time from receiving the therapy suspension is less than a set time the AMD may wait for the second gesture to be received.

In some examples, once a wake action is received 2502, the AMD may automatically activate a therapy suspension user interface 2506, without the need for a first gesture 2504. In these examples, once the request for therapy suspension is received 2508, a gesture (e.g., a first gesture) may be required to verify the request. In some such examples, once the therapy delivery is suspended, a second gesture may stop a suspension before any of the conditions of the stop parameter are met. This allows the user the versatility of being able to modify a suspension that has been activated.

Figure 26:
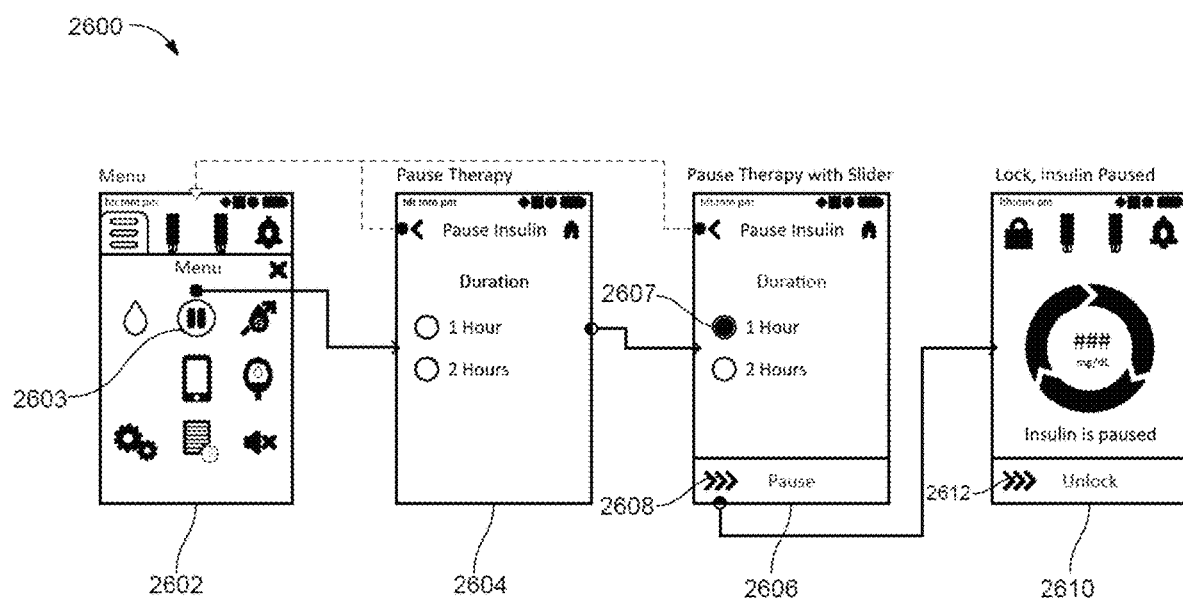
FIG. 26 illustrates a plurality of screens that the ambulatory medical device may display when a user pauses therapy.

FIG. 26 is an illustration 2600 of a plurality of example screens that may be displayed on the touchscreen display 2424 of an AMD when a user activates a therapy suspension user interface. Screen 2602 shows a screen an AMD may display to a user 2427 once the user provides a wake action. The therapy suspension system 600 is not limited to the displays shown in FIG. 26. Various other screens may communicate, to the user 2427, the same information shown in FIG. 26. The screen 2602 allows the user 2427 to select various functions. The pause button 2603, shown on screen 2602 is a function that suspends the delivery of a medicament to the user 2427. When the pause button 2603 is selected, the pause screen 2604, may appear on the touchscreen display. The pause screen 2604 allows the user 2427 to select a duration of the medicament suspension (e.g., suspension period or temporary suspension period). The AMD 600 may display various interfaces to allow the user 2427 to select a duration of the medicament suspension. The example pause screen 2604 shows a simple interface, giving the user 2427 one of two duration options (e.g., 1 hour and 2 hours).

When the user 2427 makes a duration selection on the pause screen 2604, the pause screen 2606 shows the duration 2607 that the user 2427 selected (e.g., in the figure the user 2427 selected 1 hour. Thus, the medicament delivery is suspended for 1 hour after the suspension begins). The pause screen 2606 has a prompt 2608 for the user to make a gesture to confirm the requested suspension before the medicament suspension begins. As shown by the prompt 2608, the user 2427 is being prompted to swipe right across the bottom of the screen. Once the user 2427 performs the gesture to begin the medicament suspension, the suspension screen 2610 is displayed on the touchscreen. The suspension screen 2610 informs the user 2427 that the medicament is paused. On the suspension screen 2610, the user 2427 has the option of performing another gesture to unlock 2612 the AMD in the event that the user wants to end the suspension and/or access to other functions of the AMD 600.

Suspending the medicament delivery may occur by not generating a dose control signal to deliver a dose of medicament during the suspension period. Alternatively, or in addition, suspending the medicament delivery may occur by sending a signal to the medicament delivery interface, to cease providing therapy or medicament to the subject.

In some cases, the AMD may not immediately suspend therapy upon receiving a command to suspend therapy. For example, if the AMD is in the process of delivering medicament or determines that a condition of the subject indicates that medicament may soon be required to maintain the subject's condition (e.g., blood glucose) within a particular state (e.g., within a desired blood glucose range), the suspension of therapy may be delayed until at least such time that medicament is not being delivered, is predicted to not be required during the suspension period, or the next therapy has been delivered. In some such cases, the AMD may inform that user that the suspension of therapy is being delayed. Further, the AMD may indicate the reason for the delay. In some cases, the user may be able to override the delay and request immediate suspension of therapy. For example, if the user is replacing the medicament cartridge, the user may override an indication that the suspension of therapy should be delayed to, for example, a suspension start time. In some cases, the requested start time may be overridden by a determined condition of the subject. The AMD can delay the suspension of medicament delivery responsive to determining that a medical condition of the subject satisfies a threshold medical condition.

The suspension of therapy or the suspension of the delivery of medicament may continue until a resumption condition occurs. In certain cases, when a resumption condition is met, the suspension period may automatically end without action by the user or subject.

The resumption condition may include the expiration of a time period (e.g., temporary suspension period), a command from a user (e.g., the subject), detection that the AMD devise satisfies a condition (e.g., that medicament has been refilled), that the condition of the subject meets certain criteria (e.g., the subject's blood glucose level drops below a threshold range or rises above a threshold range), or any other condition that may satisfy the reason for suspension of therapy or that overrides the request for suspension of therapy. For example, the drug delivery device may be configured to automatically resume drug delivery when a glucose threshold is reached or exceeded. This threshold could be set to 300 mg/dl for example. The resumption condition may include detection of an impending risk of hypoglycemia or hyperglycemia, or a hypoglycemia or hyperglycemia event. Further, the resumption condition may include a meal announcement, or an "exercise concluded announcement," a motion sensing event, a pause of other administered medicament, a conclusion of an undefined suspension length (e.g., during cartridge change), a speed-based resumption event, a location-based resumption, a remote resumption in case of an emergency (e.g., commanded from caregiver admin software or clinician), or any other type of resumption event. In some cases, the resumption condition can include a combination of criteria.

In some cases, automatically resuming therapy may include discontinuing the suspension of therapy before the expiration of the suspension period. For example, if a condition that caused therapy to be suspended is resolved prior to the expiration of the suspension period, therapy may be resumed.

In some cases, when a resumption condition (provided by the user) is met, the AMD may confirm that one or more additional condition of the ambulatory medicament device are satisfied before therapy is resumed. For example, if the AMD determines that medicament has not been refilled or if there is a problem with the refill (e.g., cartridge is incorrectly installed), the AMD may continue to maintain the suspension of therapy despite the trigger to resume therapy.

Figure 27:
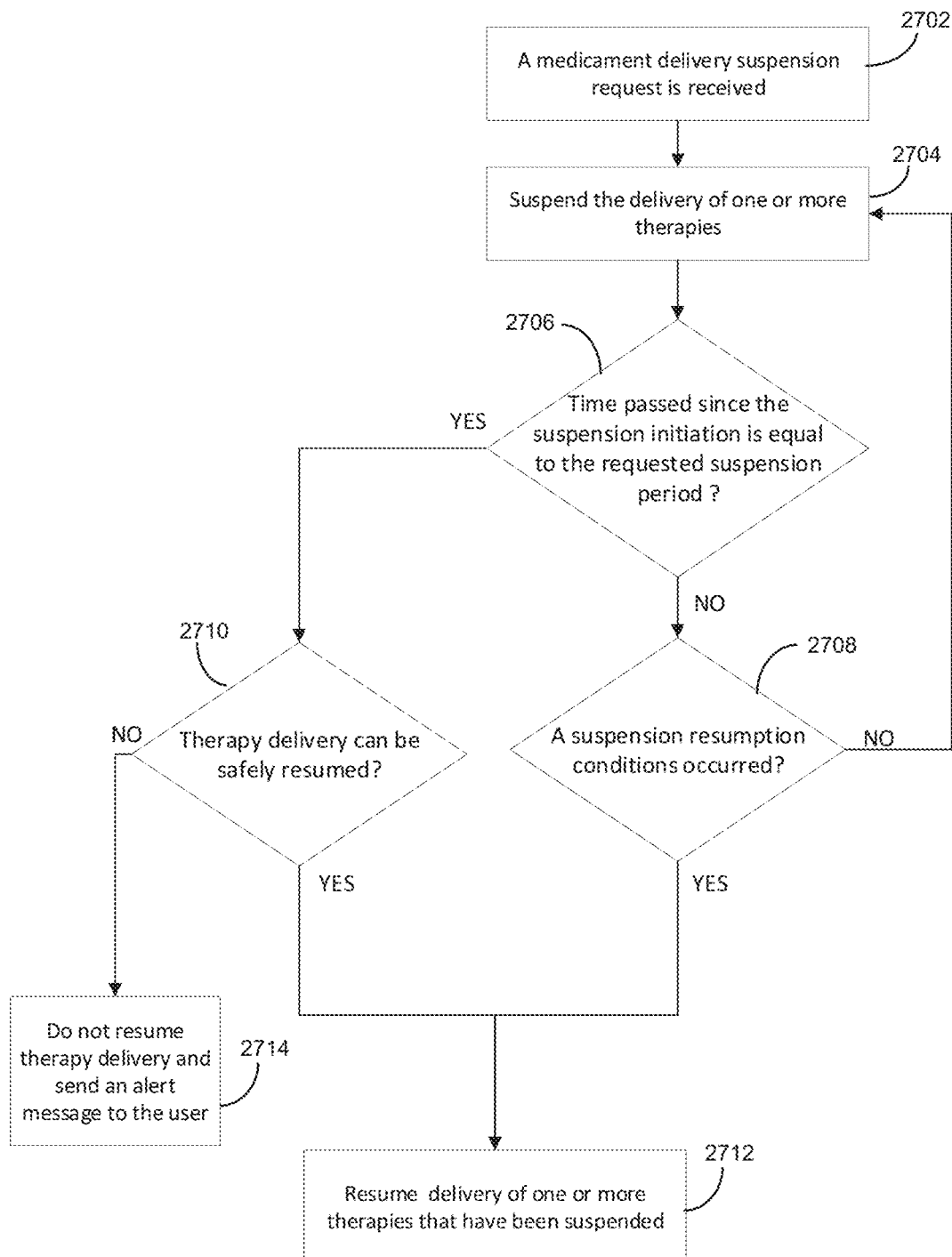
FIG. 27 is a flow diagram illustrating an example method of resuming a suspended therapy that may be implemented by an AMD.

FIG. 27 is a flow diagram illustrating an example method for automatic resumption of a suspended therapy that may be implemented by an AMD. Once a therapy suspension has been requested and confirmed by a user (e.g., using the procedure illustrated in FIG. 24) 2702, the AMD suspends the delivery of one or more therapies 2704 selected for suspension at suspension initiation time received as part of the suspension information. For example, therapy suspension control procedures 2436 may deactivate the medicament dose control procedures 2430 using the device and subject monitoring and control procedures 2432. During the suspension period, the therapy suspension control procedures 2436 may continuously monitor the system clock and the subject and device condition (e.g., using medicament dose control procedure 2430).

If the therapy suspension control procedures 2436 determine that the time passed since the suspension initiation is less than the requested suspension time period 2706 and none of the conditions for resumption has been met 2708, the therapy suspension may continue. If a suspension resumption condition occurs, the one or more suspended therapies will be resumed 2712.

If the therapy suspension control procedures 2436 determine that the time passed since the suspension initiation is equal to the requested suspension time period 2706, or one or more resumption conditions have been met 2708, it may check other AMD or subject conditions (not included in the therapy suspension information), in order to determine whether the therapy delivery can be safely resumed 2710. If it is determined that the therapy delivery cannot be safely resumed, an alert message may be sent to the user interface to inform the user about the reason for such determination 2714. If it is determined that the therapy delivery can be safely resumed, the one or more suspended therapies will be resumed 2712.

In some examples, a therapy suspension may be ended before the one or more conditions to end the suspension are met if a third interaction with a user interface (e.g., a gesture) is detected. The third user interface interaction may be detected by the user interface module 2408 and sent to the therapy suspension procedures 2436. If the therapy suspension procedures 2436 verify that the third interaction with the user interface is a predetermined third user interface interaction, the device and subject monitoring and control procedures 2432 may activate them medicament dose procedures 2430. This allows the user the versatility of being able to end a suspension that has been activated, during the suspension period set by the user before the confirmation (second interface with the user interface). In some cases, a user may decide to end a therapy suspension to modify one or more suspension conditions set prior to activation of the current therapy suspension. In some examples, user may decide to end a therapy suspension due to change in user's health condition not included in one or more therapy resumption conditions provided before activating the current therapy suspension. In some examples, the user may need to provide a fourth gesture to end the suspension before the one or more conditions to end the suspension are met. Like the first and second gestures, the third and fourth gestures may be simple or complex.

Figure 28:
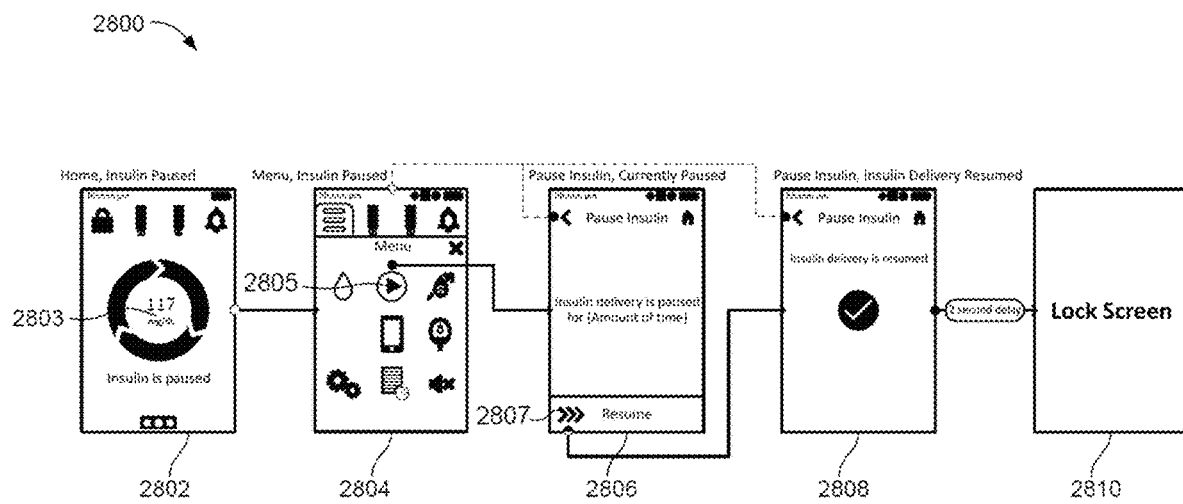
FIG. 28 illustrates a plurality of screens that the ambulatory medical device may display when a user resumes therapy.

FIG. 28 is an illustration 2800 of a plurality of example screens that may be displayed on the touchscreen display 2424 of an AMD when a user 2427 resumes a suspended therapy. Screen 2802 informs the user that the delivery of medicament is currently in a suspended mode. The screen 2803 also shows the user 2427, the current glucose concentration in user's blood. In some examples, various vital measurements that are useful to the user 2427, may be displayed on the screen 2802 that may be displayed during therapy suspension period. In one implementation, the therapy suspension ends if the glucose concentration of the blood of the user meets or passes a threshold.

The screen 2804, which may be activated by a user interaction (e.g., a gesture on the touchscreen display), allows the user 2427 to select and execute various functions on the AMD 600. For example, the resume button 2805 may be used to end a therapy suspension. When the resume button 2805 is selected by the user, a resume screen 2806 may appear on the touchscreen display. The resume screen 2806 has a prompt 2807 that prompts the user 2427 to perform a gesture. In the examples shown, the user 2427 is being prompted in the resume screen 2807 to swipe right across the bottom of the resume screen 2806. The requirement to perform the gesture to resume medicament delivery prevents the user 2427 from inadvertently resuming medicament delivery by the AMD.

Once the user 2427 performs the gesture to resume medicament delivery, the therapy suspension ends and a resumption screen 2808 appears on the display indicating that the regular medicament delivery has been resumed. Once the resumption screen 2808 has been displayed to the user 2427 for a sufficient amount of time (to inform the user 2427 that the suspension has been ended), a lock screen 2810 may be displayed. The lock screen 2810 prevents the user 2427 from inadvertently executing more functions on the AMD device 600 after resuming the medicament delivery.

With reference to FIG. 24, in some examples, if the therapy suspension procedures 2436 determine a resumption condition has been satisfied or receive a user input 2429 from the user interface module 2408 indicating that therapy suspension should be ended, they may activate the medicament dose procedures 2430 using the device and subject monitoring and control procedures 2432. Subsequently, if the medicament dose control procedures 2430 determine that a dose of medicament should be supplied to the user (at least in part based on the information received from one or more subject sensors 2420), it may provide a dose control signal to the medicament delivery interface 2406. In some examples, a dose control signal can be generated at a next scheduled dosage period after determining that a resumption condition has occurred as discussed herein. In some examples, a dose control signal can be generated immediately after determining that the resumption condition has occurred.

In some cases, the AMD device may alert the user and/or the subject that therapy is being resumed. This alert may occur before generating a dose control signal and/or after or upon a resumption condition is satisfied (e.g., a suspension time expires).

Additional embodiments relating to suspending medicament delivery to a subject that can be combined with one or more embodiments of the present disclosure are described in U.S. Provisional Application No. 62/910,970, which was filed on Oct. 4, 2019 and is titled "METHOD FOR SUSPENDING DELIVERY OF A DRUG INFUSION DEVICE WITH AUTOMATIC RESUMPTION OF DELIVERY," the disclosure of which is hereby incorporated by reference in its entirety herein for all purposes.

AMD with Security Functionality

An ambulatory medical device (AMD), such as, but not limited to, an ambulatory medicament device (e.g., an insulin pump), that provides life-saving treatment to subjects, for example, based on the condition of the subject, may include a user interface (e.g., a touchscreen display) that lets a user to modify the settings of the AMD. The setting may include, but not limited to, a condition that triggers the delivery of medicament to a subject, the quantity of medicament delivered when a condition is met, type of the medicament and the like. The setting may also include features of the AMD that may not be directly related to the medicament delivery (e.g., the screen brightness, an alarm sound, and the like). In some examples, it is desirable to manage access to various settings of AMD in order to avoid inadvertent changes while enabling changes that may be necessary for uninterrupted and proper operation of the AMD. For example, it may be desirable to limit the access to some settings to certain authorized users (e.g., a healthcare provider) while enabling access to some other settings to other authorized users (e.g., the subject, a guardian or parent of the subject).

In many cases, a healthcare provider can modify the settings of the AMD. However, it is often desirable that a non-healthcare provider modify at least some settings of the AMD. For example, when the AMD runs out of or has below a threshold amount of medicament, it is often desirable that a user be able to refill or change a medicament cartridge without visiting a healthcare provider. In some cases, changing the medicament cartridge may include interacting with a user interface and/or one or more settings of the AMD. Another example of when it is desirable for a non-healthcare user (e.g., a subject, parent, or guardian) to modify settings of the AMD is when the initial settings of the AMD are not providing the desired effect (e.g., sufficient medicament, too much medicament, providing the medicament too slowly or too fast, etc.). In some cases, normal maintenance of the AMD and/or subject may require interaction with the AMD settings and/or controls. For example, negative consequences may begin to occur when an AMD remains connected to a subject at the same site for more than a threshold period of time (e.g., for more than 2-3 days, more than 5 days, more than a week, etc.). Thus, the AMD may need to be periodically moved from one site on the subject to another site on the subject (e.g., from left-side to right-side, from arm to leg, from stomach to back, etc.). The change in site location may require interaction with settings of the AMD (e.g., pausing operation until the site change is completed).

Although, as explained above, there are a number of reasons it is desirable to enable a user other than a healthcare provider (e.g., the subject receiving therapy, a parent, or a guardian) to have access to at least some user settings of an AMD, it is also desirable to regulate access to at least some of the AMD settings. For example, it is generally undesirable that a child (subject or otherwise), or a user below a particular age, have access to AMD settings that could cause harm to the subject if modified. Further, it may be undesirable for certain subjects who have diminished mental capacity regardless of age to have access to at least some AMD settings.

The user may be a subject receiving medicament or therapy, or may be another user, such as a clinician or healthcare provider, or a parent or guardian of the subject.

One solution to regulating access to settings of the AMD is to implement a lock feature to require that a user provide a passcode, password, or other information before the user is permitted to modify a setting of the AMD, such as a control parameter. To simplify the discussion, the disclosure will describe using a passcode. However, it should be understood that the passcode can be substituted for a password or any other type of secret or semi-secret information. The user may enter a security code into the AMD or an intermediary device that the AMD and/or the intermediary device may validate or verify matches the passcode to access certain functions of the AMD as discussed herein. If the security code cannot be validated after a predetermined number of security code entry attempts, further security code entry attempts can be denied for a period of time. In some examples, when the AMD is in the locked state, it may continue delivering therapy to the subject at the same rate as unlocked state.

The lock feature may be activated by default or may be activated by a user. In some examples, the lock feature can be enabled through a setting in a control menu of the AMD device provided on a user interface (e.g., touchscreen display). The setting may include an on/off toggle (via, for example, a software interface element or a hardware interface element) so when the toggle is on, a passcode (e.g., 4 to 8 numeric digits) may be required. In some cases, if the lock feature is on, the passcode (e.g., a 4 to 8 numeric digit code) may be required to turn the lock feature off. When the lock feature is activated, the user may program the AMD with a user passcode selected by the user. Alternatively, or in addition, the user passcode may be set in response to a passcode change request. In some cases, a user passcode may expire. In such cases, a user may be required to generate a new passcode after the previous passcode expires or before the previous passcode is permitted to expire. In some cases, the AMD may periodically generate a new passcode (e.g., an override passcode), or may generate the new passcode at a time when a user supplies the passcode.

In some cases, the user interface element used for accessing a user interface that enables changing one or more settings of the AMD may differ from a user interface for modifying the control parameters associated with that setting. For example, a keypad may be used to enter a passcode for unlocking a user interface for changing a control parameter and a touchscreen may be used to modify the control parameter.

In some examples, when the lock feature is enabled, the user interface screen may look and function the same as if the lock feature were not enabled. In these examples, if the lock feature is enabled, when a visual guide for unlocking the device (such as, for example, a linear unlock slider, an arcuate unlock slider, or another unlock user interface element) is activated, a passcode entry interface (e.g., a keypad user interface element) may be displayed. If either the user passcode or another passcode (e.g., a global override passcode) is entered, the user interface may proceed as normal. Otherwise, the user interface may revert back to the original lock screen.

In some examples, the user action that permits a user to change one or more settings of the AMD may be different from the wake action that activates a user interface. For example, a wake action may be used to activate a touchscreen display that may display a plurality of user selectable elements some of which may be accessible without a passcode. In such examples, a subset of the user selectable elements, for example those allowing the user to change therapy control parameters, parameter control elements, or user parameter control elements, may require a passcode. In some cases, access to each user parameter control element may require a different passcode. In some examples, providing a passcode to an AMD in locked state may directly enable access to a subset of parameter control elements. In some examples, after the user interface (e.g., a touchscreen display) is activated, a first gesture may be required before a plurality of user selectable elements are presented.

To help recall the passcode, the passcode may be set by the user enabling the user to select a passcode the user is more likely to remember. However, regardless of who sets the passcode, there is a risk that the user will not remember the passcode. Due to the nature of the device (e.g., a device that may provide life-saving treatment), it is desirable that certain user's not be restricted from accessing particular settings of the AMD, and be able to quickly (e.g., within seconds, minutes, prior to a next therapy event, or before harm may occur to the subject) obtain access to the particular settings when required. Thus, while some non-medical devices may implement lockout periods or other restrictions to prevent a malicious user from trying to brute-force determine a passcode for a device, such features may be generally undesirable for an ambulatory medicament device. Accordingly, embodiments disclosed herein include an AMD that includes an override passcode that enables access to the AMD (or control settings thereof) regardless of whether the user passcode is provided.

In some examples, the passcode or the override passcode can be a series of taps, series of inputs, a complex or a simple gesture (e.g., a swipe or other movement across the touchscreen). The series of inputs may be any combination of touch movements, touch points, numerical characters, alphabetical characters, and other symbols. In some examples, the time that the series of inputs are entered may also be a part of the range of parameters. For example, a series of inputs may need to be entered in no less than 3 seconds or more than 3 seconds, and no more than 15 seconds or less than 15 seconds. One example of the complex gesture is a swipe.

In some examples the passcode or the override passcode may comprise performing a pattern or sequence on the touchscreen (e.g., drawing an image), a multi-touch interaction or any other type of interaction with a touchscreen, or portion thereof. Another example of a complex gesture is entering a predetermined sequence of touches. In some cases, the passcode may include a quiz or set of questions.

In some examples, the AMD may be configured to receive therapy settings or modifications to therapy settings from an intermediary device via a communication connection. For example, the intermediary device may be a laptop or desktop computer, a smartwatch, a smartphone, or a hardware control device that may be configured to interact with the AMD. In some cases, this feature may be supported in addition to providing the user with options of modifying one or more settings with a user interface of the AMD. The communication connection between the intermediary device and the AMD may be a direct connection via, for example, Bluetooth®, or a connection via a network, such as over a local area network or a wide area network. In some such cases, the AMD may include a wireless transceiver, such as an NB-LTE transceiver, a Wi-Fi transceiver, or a Bluetooth transceiver. The intermediary device, that provides the user with a user interface to modify settings of the AMD, include any type of device (e.g., a computing device) that can communicate with an AMD. In some cases, access to the user interface of the intermediary device that allows modifying AMD settings may require a passcode. In some examples, the passcode required for changing one or more settings via an intermediary device may be different from the passcode required for changing the same settings directly using the AMD's user interface.

In some such cases, a user may provide a user-generated passcode or an override passcode via an interface of the intermediary device. The intermediary device may then provide the user-generated passcode or the override passcode to the AMD via the network connection between the devices.

In some examples, even if the AMD is in locked state, certain intermediary devices may have access to user interfaces that may be used to change one or more settings (e.g., therapy settings) of the AMD. For example, the smart phone of a guardian or a parent of the subject may be used to change one or more settings of the AMD while the AMD is in the locked state.

Embodiments disclosed herein are applicable regardless of whether the user interface for modifying therapy settings or the configuration of the AMD device is generated or presented by the AMD to the user or via another device.

In some examples, the AMD may be configured to receive a passcode from or via a computing system (e.g., a cloud computing system). In these examples, the AMD may receive passcode through a direct end-to-end connection (e.g., a wireless connection over a wide area network) established with the computing system. In some such examples, another computing device (e.g., a smartphone, a laptop, a personal computer, and the like) connected to the computing system, may send a passcode to the AMD and be able to change one or more settings of the AMD if the passcode is validated by the AMD.

In cases where the user cannot recall the user passcode, the user can obtain access to the user interface that permits modification of the control parameter by supplying an override passcode. In some examples, the override passcode may be a universal fixed passcode (e.g., an 8-digit override passcode) that can be used instead of the user set passcode. The override passcode can be stored in the AMD at the time of manufacture and may be shared among multiple AMDs (e.g., a global override passcode), or may be unique to a particular AMD. The override passcode may be managed by the manufacturer or by a third-party service. To obtain the override passcode, the user may contact the manufacturer or passcode managing service. Generally, enabling the passcode may exist to prevent a user with a diminished mental capacity (e.g., a child) from modifying settings of the AMD. Thus, security may be less of a concern and any user can contact the manufacturer or passcode managing service to obtain the override passcode. In some such cases, a single global override may be used for all devices produced by the manufacturer. However, in some cases, a level of security may be desired. In some such cases, it may be necessary for the user to authenticate him or herself. Further, the user may be required to provide a serial number of the AMD. In some cases, each model or each unit of the AMD may have a different override passcode. The user may provide authorization information and a serial number of the ambulatory medicament device to the manufacturer or passcode managing service to obtain the override passcode.

In some examples, the AMD may periodically generate a new override passcode or may generate an override passcode at a time when a user supplies the passcode. In these examples, the AMD may use the same parametric values to generate the override passcode as another device may use thereby ensuring a match between the override passcodes. Advantageously, in some cases, by using an algorithm to generate the override passcode, the override passcode can be obtained regardless of whether a user is able to contact a manufacturer or other passcode managing service. In some cases, the user may generate the override passcode without access to a network or phone using, for example, using a computing device that can access a common parameter value as the AMD.

In some cases, the override passcode may change over time or be a rotating passcode. For example, in some cases, the override passcode may change at periodic intervals every thirty seconds, every minute, every hour, etc. In some such cases, the override passcode may be determined from an algorithm executed by an application. The AMD may store a copy of the algorithm in a memory of the AMD and may execute the algorithm to determine the override passcode that is currently valid. A copy of the algorithm may be executed by another computing device accessible by the user. The output of the algorithm may be based on a value that is commonly accessible by the AMD and the copy of the algorithm accessible by the computing device. For example, the output of the algorithm may be generated based on a time, a user identifier, a provided value, or any other factor that may be used to repeatedly generate the same output. In some cases, the override passcode may be calculated based on a combination of factors. For example, the override passcode may be calculated based on a portion of a serial number or model number for the AMD and the time. The determination of the override passcode may be calculated by the AMD, a computer server, and/or an application on a user device.

In some cases, the override passcode can be automatically received by the AMD (e.g., after a user requests an override passcode). Thus, a user may not need to see or enter the override passcode. In some cases, the override passcode may be transmitted to another device of the user (e.g., a smartphone or laptop). For example, the override passcode can be texted to a user's smartphone, for example, for the user to then enter the override passcode on the AMD. In some cases, the override passcode may be received in a coded manner that may not be understandable by a child or user with diminished mental capacity.

In some cases, the override passcode may be linked to a location. For example, the override passcode may only be enterable at a healthcare provider's office or at the subject's place of residence. The determination of the location of the AMD be based on a geolocation system (e.g., a Global positioning System (GPS)) available to the AMD.

In some examples, at least for a subset of therapy settings, the passcode may provide a second level of security in addition to other interactions with the user interface (e.g., a first and a second gesture on a touchscreen display) that may be used to change the therapy settings and/or accept the change made to a therapy setting. In some examples, at least for a subset of settings, the passcode may be used instead of other interactions with the user interface (described above).

As mentioned above, interacting with the user interface may cause the AMD, or other devices that can modify a control of the AMD, to present a passcode input screen to the user. The user may enter the passcode to unlock additional user interface features including, for example, a user interface that enables the user to modify at least one control parameter of the AMD. The control parameter can be modified based on an interaction with a parameter control element of the user interface. Further, modification of the control parameter may cause modification of the generation of a dose control signal that is generated by a control algorithm based at least in part on the control parameter.

In some embodiments, the AMD may have an advanced therapy screen, or other user interface, that permits a healthcare provider, or other user, to obtain additional details or advanced settings relating to therapy provided by the AMD. Although the advanced therapy screen or state may generally be intended for a knowledgeable user, such as a clinician, in some cases, any user may obtain access to the advanced therapy screen or state. The advanced therapy screen (displaying, for example, advanced settings of the AMD) may permit the healthcare provider to modify control parameters (e.g., advanced control parameters via one or more advanced parameter control elements) that may not be modifiable by other users. For example, the healthcare provider may be able to control parameters that relate to the calculation of a rate of insulin accumulation, the rate the insulin diminishes within the blood of the subject, the setting of a glucose setpoint, an aggression level or factor of therapy relating to an amount of insulin provided when the subject's glucose level is outside the setpoint range, or when the insulin reaches a point of maximum concentration within the blood of the subject (e.g., $T_{max}$).

Access to the advanced therapy screen may be limited by requirement of a passcode or advanced settings passcode via, for example, a user entering a security code or an advanced settings security code (using for example one or more advanced settings parameter control elements) that can be validated or verified to match the passcode or advanced settings passcode. The passcode or advanced settings passcode may be referred to as a clinician passcode to distinguish it from the user-generated passcode and/or the override passcode. This clinician passcode may or may not be user generated. However, the clinician passcode may be a separate passcode from the user-generated passcode that permits access to the non-advanced therapy screen interface. Further, the clinician passcode may be separate from the override passcode that permits a user to override the user-generated passcode to obtain access to the non-advanced therapy screen interface. In some cases, the clinician passcode may be used as an override passcode. In some examples, the clinician passcode can be valid for a period of time (e.g., set by a subject or another authorized user such as the guardian or apparent of the subject). The clinician passcode may expire after a predetermined period. For example, the clinician passcode may be valid for a day, a week, or a month (expiring at least once per day, per week, or per month). In some examples, the AMD may allow certain authorized users to terminate the clinician access at any time.

In some cases, access to the advanced therapy screen or state may be limited to a particular period of time. After the time period expires, the AMD may automatically restrict access to the advanced therapy screen or state. In some cases, the window of access may be extended. For example, if the healthcare provider is continuing to interact with the advanced therapy screen or state, the screen or state may remain accessible.

In some cases, the advanced therapy screen may provide additional features. For example, while a user may be able to indicate that an amount of insulin provided for a meal or as a correction factor should be higher or lower, the healthcare provider may be able to specifically adjust the amount of insulin. Moreover, while a user's direction may or may not be followed depending, for example, if the request exceeds a threshold or may cause blood glucose to not satisfy a setpoint range, an indication provided via the advanced therapy screen may be followed regardless, or may have a wider range or different threshold that may control whether the instruction is followed. Further, the advanced therapy screen may be used to temporarily pause therapy and/or may prevent subject access.

In some cases, the manufacturer of the AMD may provide a remote unlock signal that can be used to unlock access to the ambulatory medicament device and/or to an advanced therapy screen or state of the AMD.

As described above, the passcode may be desired to prevent particular users from inadvertently changing certain control parameters of the AMD device. However, features of the AMD that do not affect therapy may remain accessible to a user when the AMD is in a locked state. For example, a user may be able to access therapy history, screen brightness settings or colors, or any other feature that is unlikely to harm a subject if modified in a particular manner. Further, as the passcode feature is generally to prevent control parameter changes, the AMD may provide therapy and continue to provide therapy at the same rate and under the same condition, whether or not the AMD is locked or unlocked.

When the AMD receives the user passcode or the override passcode, the AMD may validate the passcode. The passcode may be validated by comparing the received passcode to a passcode stored in a memory of the AMD or generated by the AMD. If the passcode received from the user is successfully validated, the user may be granted access to a user interface to modify one or more control parameters. In some cases, the user may be requested to re-enter a passcode to confirm a change to a control parameter. In some examples, the user may be requested to provide a gesture on a touchscreen to confirm a change to a control parameter.

If the passcode is not validated, the AMD, or other control device that can provide access to control parameters of the AMD, may prevent access to the user interface to modify the one or more control parameters. In some cases, the user interface that presents the user with the ability to enter the passcode may permit the user a particular number of tries or a particular number of tries within a particular time period to enter the user passcode. If the correct user passcode is not entered within the provided number of tries or within the particular time period, the user interface may enter a lock state (e.g., the screen will be turned off) and prevent further attempts to enter a passcode for at least a period of time. In some cases, the user passcode option may be indefinitely locked or blocked. In some such cases, the control parameters of the AMD may only be accessible if the override passcode is provided. Alternatively, or in addition, a user passcode of a different user may be used to provide access to the control parameters of the AMD. In some examples, if the correct override passcode is not entered within the provided number of tries or within the particular time period, the user interface may block any attempt to change the override passcode for at least a period of time.

In some cases, once the passcode is successfully entered or validated, a user may deactivate the passcode feature of the AMD. Deactivating the passcode feature may require use of a separate passcode or the override passcode in addition to the user passcode.

In some cases, the passcode may be optional or omitted based on the computing device connected to the AMD. For example, if the end-to-end connection is established between a smartphone registered to a particular user (e.g., a parent of the subject), the ambulatory medicament device may unlock automatically without requiring a passcode. In some cases, the smartphone, or other computing device, may automatically provide the user-generated passcode or the override passcode to the AMD upon establishing a connection. In some cases, the AMD may automatically be unlocked when connected to a charger or when in a particular geographic area. For example, a geo-fence may be configured in one or more locations, such as the subject's house or the clinician's office. When the AMD determines it is within the geo-fence, the AMD may automatically be unlocked. Similarly, when the AMD determines that it is not within the geo-fenced region, it may automatically be locked. The determination of the location of the AMD may be made based on a geo-location system, such as the Global Positioning System (GPS).

Figure 29:
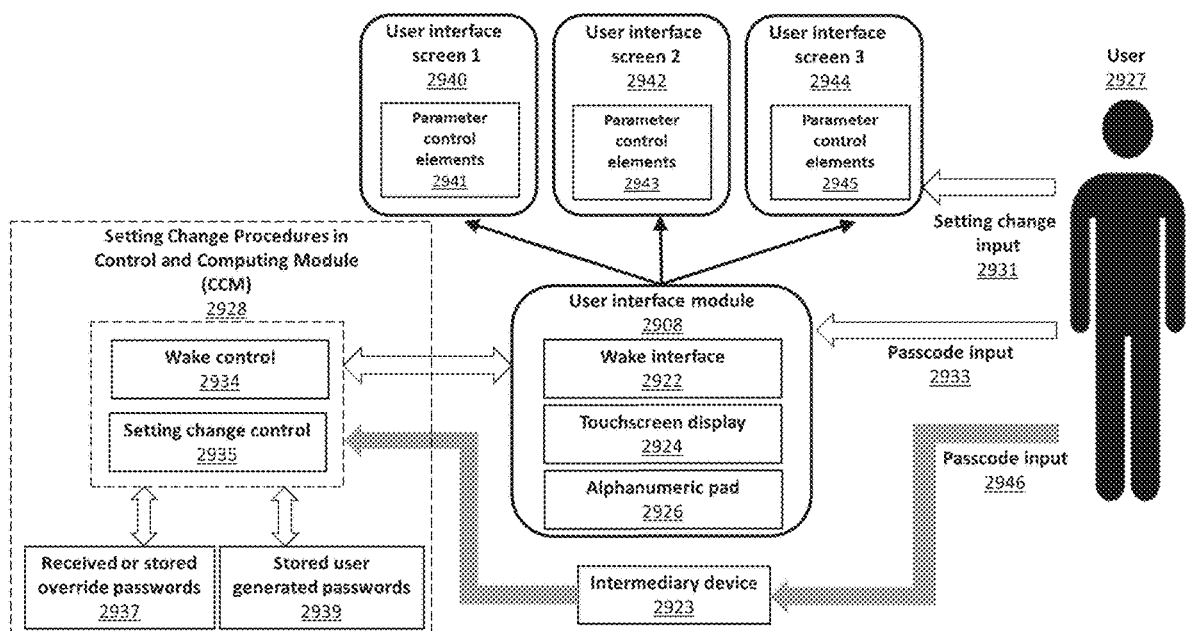
FIG. 29 is a block diagram illustrating the interconnection among modules and procedures in AMD involved in changing the settings of the AMD.

In some cases, after a certain number of unsuccessful passcodes are entered (e.g., after 5 tries), the user interface screen may be turned off or may accept only the global override passcode Example AMD with Passcodes FIG. 29 is a block diagram illustrating an example of the interconnection among modules and procedures in AMD involved in changing the settings of the AMD. In some cases, one or more settings of the AMD may be changed using one or more parameter control elements 2941/2943/ 2945 presented on one or more setting control screens 2940/2942/2944 provided by the user interface module 2908. In some examples, when the lock feature is activated, access to one or more setting control screens 2940/2942/ 2944 and/or one or more parameter control elements 2941/ 2943/2945, may be protected by a passcode. In order to access one or more control parameter 2941/2943/2945, the user may provide a security code for a passcode input 2933 (e.g., a security code for a user generated passcode or an override passcode), via the user interface module 2908 (e.g., using a touchscreen display 2924 or alphanumeric pad 2926). Alternatively or in addition the user 2927 may provide a security code for a passcode input 2946 using an intermediary device 2923 (e.g., a laptop, a smart phone, and/or the like) that is connected to the AMD (e.g., via a wired or wireless link). In some examples, once a security code or an override security code is received (e.g., from an intermediary device 2923 or the interface module 2908), the security code may be transmitted to the control and computing unit of the AMD where a set of setting change control procedures 2935 determines the validity of or verifies the security code by comparing security code to the one or more user generated passcodes or passwords 2939 or override passcodes or passwords 2937 stored in a memory of the CCM.

In some examples, the access to one or more setting control screens 2940/2942/2944 and/or parameter control elements 2941/2943/2945 may be managed by the setting change procedures 2928. In some examples, the setting change procedures 2928 may be changed and may be considered the advanced settings as discussed herein, requiring a different passcode for access from the passcode to access, for example, the one or more setting control screens 2940/2942/2944 and/or parameter control elements 2941/ 2943/2945. Setting change procedures can be machine readable instructions stored in the AMD and executed by one or more hardware processors.

In some examples, the option to provide a security code corresponding to a passcode may become available, when the user 2927 performs a wake action on a wake interface 2923, which can include a user input element associated with recognizing the wake action or some other user interaction. In these examples if the wake control module 2934 of the CCM determines that a valid wake action is performed (and enters a valid security code), it may present selectable elements associated with the setting control screens 2940/ 2942/2944, for example, on a touchscreen display. In some examples, the first screen presented on the touchscreen display, may provide other selectable elements including an element to change the settings of the AMD. In such examples, selecting the element associated with settings change may activate a second screen that presents selectable elements associated with the setting control screens 2940/ 2942/2944.

When the lock feature is activated, access to one or more of the setting control screens 2940/2942/2944 and/or parameter control elements 2941/2943/2945 may require a passcode. In some examples, each one of the control screens 2940/2942/2944 and/or parameter control elements 2941/ 2943/2945 may require a different passcode. In some examples, one or more control screens 2940/2942/2944 and/or parameter control elements 2941/2943/2945 may not require a passcode. For example, access to the first screen 2940 may require a first passcode, the access to the second screen 2942 may require a second passcode and the access to the third screen 2944 may not need a passcode. In some examples, all the control screens 2940/2942/2944 may be presented without the requirement a passcode, but access to the one or more control elements in a control screen may require a passcode. For example, the user may select the second screen 2942 without entering a security code, but in order to select one or more parameter control elements 2943 on that screen, the user may need to enter one or more security codes matching one or more passcodes. In some cases, after the user provides a security code matching a passcode to access a parameter control element 2941/2943/ 2945, the user may interact with the parameter control element to provide a setting change input 2931 that changes the corresponding control parameter.

Figure 30:
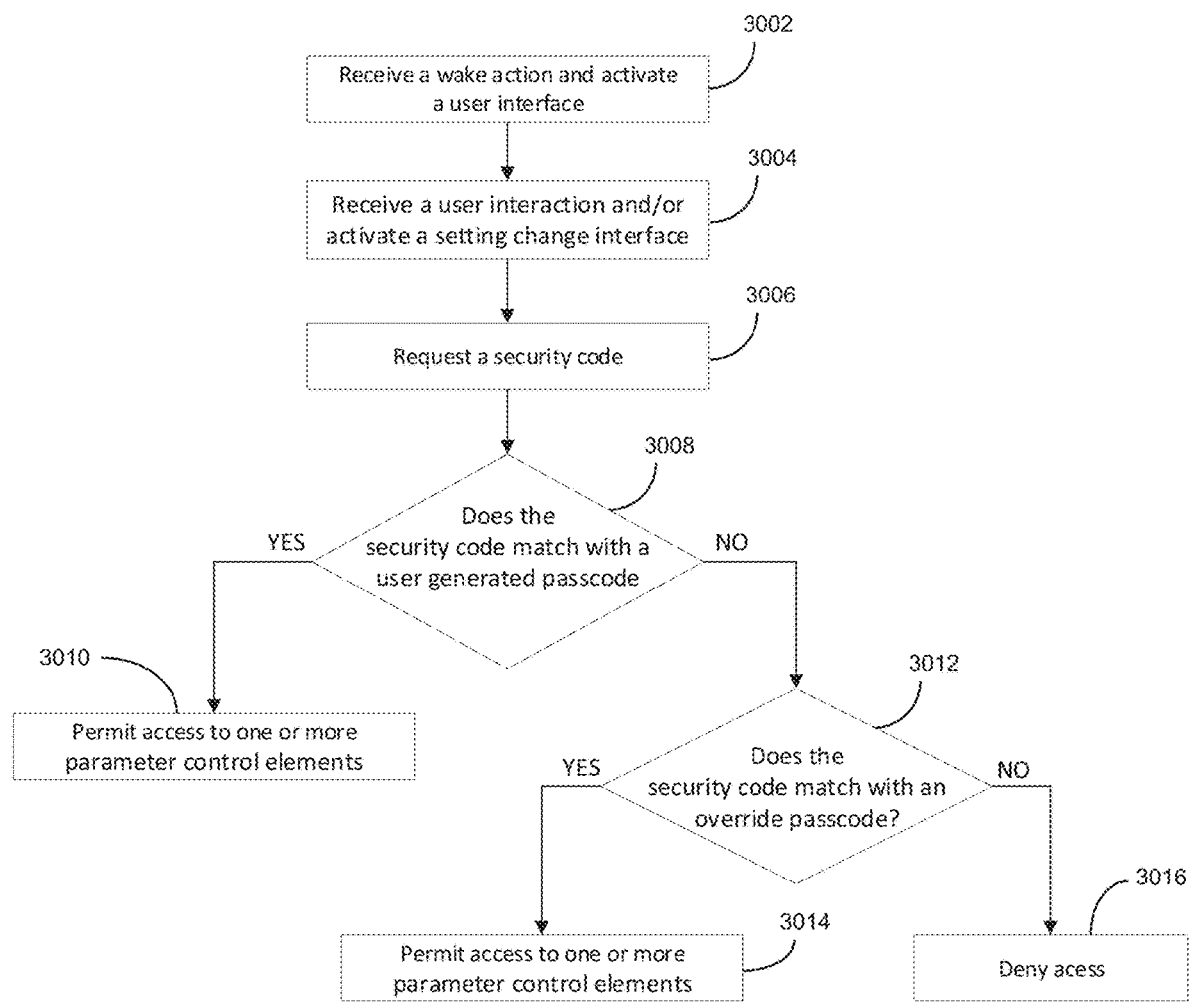
FIG. 30 is a flow diagram illustrating an example method that may be used by an AMD to allow a user to change a setting of the AMD using a user generated passcode or an override passcode.

FIG. 30 is a flow diagram illustrating an example method that may be used by an AMD and/or intermediary device to allow a user to change a setting of the AMD and/or intermediary device using a user generated passcode or an override passcode. Once the AMD and/or intermediary device 2923 receives a valid wake action 3002, a user interface may be activated (e.g., a user interface on the touchscreen display 2924). In some examples, the wake action may be received by the wake interface 2922 of the AMD). In some examples, the wake action may directly activate a setting change interface 3004 (e.g., a setting change screen presented on a touchscreen display with one or more parameter control elements). In some examples, a first gesture may be required after the wake action to activate a setting change interface. In some examples, a specific wake action may activate the setting change interface.

In some cases, in for example the setting change interface or another user interface, the AMD and/or intermediary device (e.g., the setting change procedure in the CCM) may request a security code 3006 (e.g., by presenting a window to enter a security code such as a passcode display of a keypad). Once a security code is received, the AMD (e.g., the setting change procedure in the CCM) and/or intermediary device may determine whether the security code matches a user generated passcode 3008. If it is determined the security code matches with a user generated passcode, the AMD and/or intermediary device may provide access 3010 to one or more control parameter elements associated with the validated passcode. If the received security code does not match with any of the stored user generated passcodes, the AMD and/or intermediary device may determine whether the security code matches with an override passcode 3012. If it is determined the security code matches an override passcode stored in a memory of AMD and/or intermediary device (or a memory of an authorized computing device), the AMD and/or intermediary device may provide access 3014 to one or more control parameter elements associated with the validated override passcode. If it is determined the security code does not match an override passcode, the AMD and/or intermediary device denies access to one or more passcode protected parameter control elements 3016.

Figure 31:
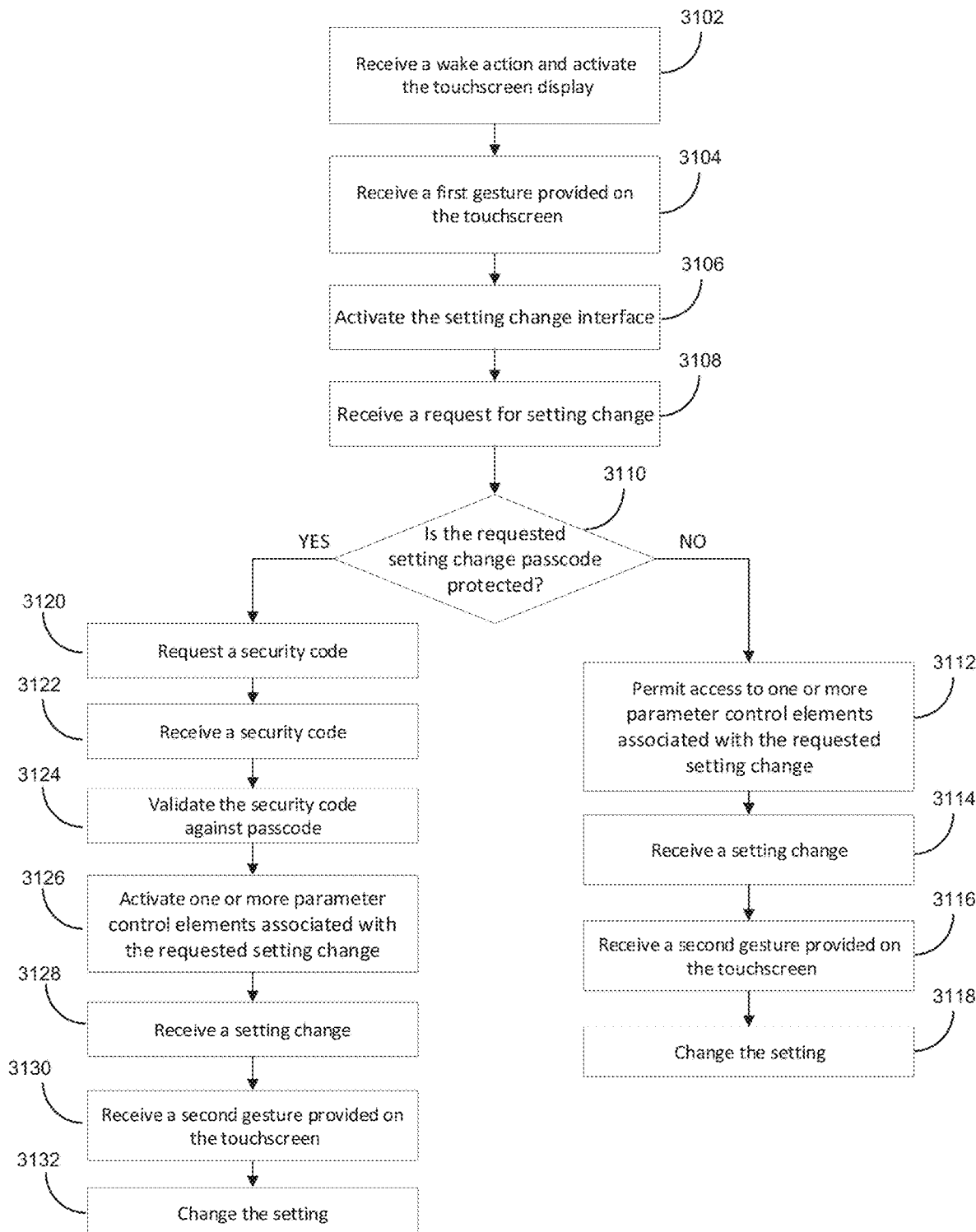
FIG. 31 is a flow diagram illustrating an example method that may be used by an AMD to allow a user to change a setting of the AMD using a user generated passcode or an override passcode.

FIG. 31 is a flow diagram illustrating another example method that may be used by an AMD and/or intermediary device to allow a user to change a setting of the AMD using a user generated passcode or an override passcode. Once the AMD (e.g., the wake action procedure in the CCM) and/or intermediary device receives a wake action 3102, the AMD and/or intermediary device may provide a user interface (e.g., a touchscreen display) on which the user can provide a first gesture to activate a setting change interface or screen. When a first gesture is received from a user or subject 3104, the AMD and/or intermediary device may activate 3106 a setting change interface (e.g., a setting change screen on a touchscreen display). In some examples, the setting change interface may include one or more parameter control elements associated with one or more AMD settings. In some examples, the setting change interface or a screen may include one or more selectable elements each associated with a setting change screen (e.g., a screen provided on a touchscreen display) that may include one or more control parameters. When a request for setting change is received 3108, for example by a user interaction with one or more parameter control elements, the AMD and/or intermediary device may determine whether the requested setting change is passcode protected 3110. In some examples, the request for setting change may include selecting a list of parameter control elements (e.g., included in a separate screen provided on a touchscreen display).

If the AMD and/or intermediary device determines that the requested setting change is not protected by a passcode, it may permit access to one or more parameter control elements associated with the requested setting change 3112. In some examples, once the changes are received via parameter control elements 3114, the user may need to provide a second gesture on the user interface (e.g., touchscreen display) to confirm the changes made. In response to receiving the second gesture 3116, the AMD and/or intermediary device may change one or more settings 3118 according to the requested and confirmed changes.

If the AMD and/or intermediary device determines that the requested setting change is protected by a passcode, it may request security code 3120 via a passcode display (e.g., provided on a touchscreen display). In some examples, the request for the security code may be presented on a display but the security code may be received via a physical keypad. Once a security code is received 3122 from the user or subject, the AMD and/or intermediary device may validate the security code against a passcode 3124 by comparing it with one or more user generated passcodes or an override passcode (e.g., does the entered security code match the passcode). If it is determined that the security code matches with a user generated passcode or an override passcode, the AMD and/or intermediary device may activate 3126 one or more parameter control elements associated with the requested setting change. Subsequently, the AMD and/or intermediary device may receive a setting change via the selected control parameter element 3128. In some examples, the user may need to provide a second gesture on the user interface (e.g., touchscreen display) to confirm the changes made. In response to receiving the second gesture 3130, the AMD and/or intermediary device may change one or more settings according to the requested and confirmed changes 3132.

AMD with Alarm System

In some cases, a condition may occur that impacts the operation of the ambulatory medicament device. This condition may be associated with the ability of the ambulatory medicament device (AMD) to operate as intended by the manufacturer, a subject receiving therapy from the ambulatory medicament device, and/or user (e.g., healthcare provider, parent, or guardian of the subject). In some cases, the AMD may be operating as intended, but the condition of the subject may not satisfy a desired level of health. In either case, it is generally desirable to generate an alarm to inform the subject and/or one or more users of the condition of the AMD and/or the subject. Moreover, it is desirable to track the alarm until the condition that caused the alarm is resolved. Further, it is desirable to issue different types of alarms for different conditions to enable a subject or user to easily distinguish the severity of the condition that triggered the alarm. The user may be a subject receiving medicament or therapy, or may be another user, such as a clinician or healthcare provider, or a parent or guardian.

This section of the disclosure relates to an ambulatory medicament device (AMD), such as an insulin pump or a combined insulin and counter-regulatory agent (e.g., Glucagon) pump, configured to generate a dose control signal configured to cause a medicament pump to infuse medicament into a subject. Moreover, the present disclosure relates to an ambulatory medicament device configured to detect a condition of the ambulatory medicament device and/or the subject, and to generate an alarm when it is determined that the detected condition satisfies an alarm condition.

As mentioned above, an ambulatory medicament device may include an alarm system configured to monitor the ambulatory medicament device and/or the subject, and to generate an alarm when it is determined that a condition has been detected that satisfies an alarm condition. In some examples, the alarm system that may organize a list of alarms, notifying a user of these alarms, and allowing the user to acknowledge alarms.

In some embodiments, the alarm system may comprise a plurality of sensors that monitor the AMD or the subject, a monitoring system interface that receives the data from sensors, and alarm annunciation and control system that process the received data and generate alarms if an alarm condition is met. In some examples, the monitoring system interface and the alarm annunciation and control module are implemented using one or more hardware processors and machine readable instructions. In some examples, the monitoring system interface and the alarm generation module are separate hardware modules.

Figure 32:
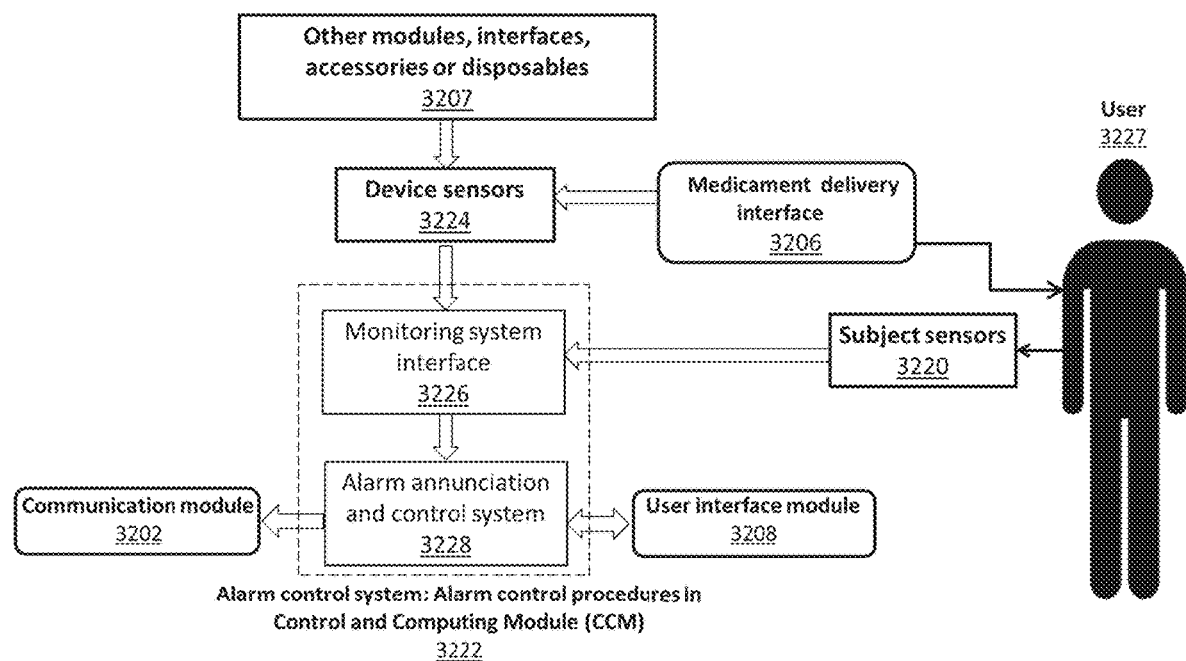
FIG. 32 is a schematic diagram illustrating the interconnection among modules and procedures in AMD involved in monitoring the status of the AMD and/or the subject and generate alarms when an alarm condition is met.

With reference to FIG. 32, in some embodiments, an alarm system 3222 implements alarm control procedures in the control and computing module 610 (CCM) of the AMD. The alarm system 3222 can be implemented as instructions stored in a memory of the CCM (e.g., the main memory 616) and executed by a hardware processor 614 to generate an alarm upon detection of a condition of the ambulatory medicament device and/or the subject. In some cases, the hardware processor of the monitoring system is a hardware processor of the ambulatory medicament device that controls medicament delivery. In some cases, the hardware processor of the monitoring system may be a separate hardware processor.

In some examples, the alarm system 3222 includes a monitoring system interface 3226 and an alarm annunciation and control system 3228. The alarm annunciation and control system 3228 may include sub-systems for determining the severity of an alarm condition, user notification processing and receiving alarm control commands from the user interface module 3208. The user interface module 3208 may include one or more of the embodiments described with respect to the user interface module 1808. The monitoring system interface 3226 may monitor the condition or status of the AMD and/or the subject at least partially based on signals or status values received from a set of device sensors 3224 and a set of subject sensors 3220. In some examples, the device sensors 3224 may be configured to track the status of the components or the elements of the AMD, and the subject sensors 3220 can be configured to obtain measurements of one or more physiological characteristics of the subject In some examples, a device sensor 3224 is a sensor that generates a signal or status value associated with the condition of modules, interfaces, accessories, disposables of the AMD. In some examples, a device sensor 3224 may generate a signal that corresponds to a parameter associated with a component in a module or interface. For example, one device sensor may record the voltage of a battery and another device sensor may record the follow rate of a pump the medicament delivery interface 3206.

In some examples, a subject sensor 3220 may be any sensor that generates a signal or status value associated with one or more physiological indicators (or parameters) of a subject (e.g., heart rate, blood pressure, body temperature, level of blood sugar, serum levels of various hormones or other analytes). In some such examples, the subject sensor can be a continuous glucose monitoring sensor (CGS). The device and subject monitoring system interface 3226 may continuously receive and analyze signals from device sensors 3224 and subject sensors 3220 to determine the condition of the AMD, the subject, a sensor, and/or other accessories.

In some cases, a single sensor may be used to monitor both the condition of the subject and the ambulatory medicament device or accessories and sensors connected to AMD. For example, a continuous glucose monitoring CGM sensor may be used to monitor the condition of the subject, and may also be monitored to determine whether the condition of the CGM satisfies an alarm condition (e.g., to alarm a user that the CGM should be replaced).

Although described as sensors of the AMD, one or more of the sensors may be accessories that may or may not be part of the AMD, but that may communicate with the AMD.

In some examples, the alarm system 3222 implements procedures for allowing a user or the subject to change the alarm settings and/or acknowledging an alarm annunciation via the user interface 3208. In some examples, the user may be able to see one or more alarms annunciated on a user interface (e.g., as a list of alarms), even if the AMD is in locked state. In these examples, the user may not be able to acknowledge or respond to alarm when the AMD is in locked state.

In some such examples, a user or the subject may get access to an alarm setting screen or acknowledge an alarm annunciation by providing a wake action or a wake action followed by a first gesture on, for example, a touchscreen display. In some cases, the first gesture may be created by entering predetermined or particular characters on the alphanumeric pad. In some such examples, the alarm system 3222 distinguishes inadvertent alarm control inputs from intentional alarm control inputs. An inadvertent alarm control input is an alarm acknowledgment input that was made without the intent of the user 3227 to acknowledge the alarm that the ambulatory medical device 600 is delivering to the user. An example of an inadvertent alarm acknowledgment is one that was accidentally executed by the user 3227 by putting pressure on the ambulatory medical device 600 in the jacket pocket of the user 3227.

In some examples, the alarm system 3222 implements processes for determination and categorization of an alarm condition based on its severity level (e.g., a severity level between 0 and 5), according to the information received through the monitoring system interface 3226. In some examples, once an alarm condition is detected, the alarm annunciation and control system 3228 may place it in the appropriate queue, for example, based on severity or category. In one or more embodiments, a list of alarms may be generated wherein alarms may be sorted numerically in descending order with the highest priority fault displayed at the top.

In some examples, the alarm system 3222 implements procedures for controlling the annunciation of alarm conditions via the user interface module 3208, at least partially, based on their severity level. In some such examples, a user interface (e.g., a touchscreen display) may be configured to allow the user to navigate directly to the issue or fault for which an alarm is being delivered and to address the fault causing the alarm so that it could be corrected thereby stopping the alarm.

Alarm Conditions

In some examples, the device and subject monitoring system interface 3226 may provide a status information received from the device 3224 and/or subject sensors 3220 to the alarm annunciation and control system 3228. In some examples, the status information may comprise one or more status values. In some examples, the status information may comprise device information pertaining to a condition of the ambulatory medicament device or subject information pertaining to a condition of the subject. In some such examples, the alarm annunciation and control system 3228 is configured to determine based at least in part on the status information received from the monitoring system 3226, whether an alarm condition is satisfied.

Determining whether the alarm condition is satisfied may include comparing one or more status values associated with the ambulatory medicament device and/or the subject to one or more alarm thresholds or alarm conditions. In some cases, each alarm threshold or alarm condition may be associated with an alarm profile. In some such cases, determining whether the alarm condition is satisfied may include comparing the status information to one or more alarm thresholds or alarm conditions included in one or more alarm profiles. In some examples, the alarm profile may be stored in the storage 618 of the CCM 610. In some such examples, at least some of the alarm profiles may be provided to the CCM by an authorized user or the subject via a user interface or directly transferred from another device to the storage (e.g., from USB drive, a laptop, smart phone, PC and the like). In some examples, at least some of the alarm profiles may be stored in the storage 618 at the time of manufacture, Each of the alarm profiles may indicate the characteristics or status of the AMD and/or subject that triggers an alarm corresponding to the alarm profile. For example, at least some alarm profiles may indicate the threshold status values below or above which an alarm should be triggered. For example, one alarm profile may indicate that when a blood glucose level of the subject exceeds a particular threshold, a particular alarm is to be generated and/or annunciated. As another example, an alarm profile may indicate that when an available amount of medicament is below a particular threshold, a particular alarm is to be generated and/or annunciated. The type of alarm and/or the alarm frequency or intensity associated with the medicament level may differ from the alarm triggered based on the blood glucose level. Although the previous examples described a single condition associated with a single alarm profile, it should be understood that multiple conditions may be associated with an alarm profile. For example, a blood glucose level that exceeds an upper threshold or is below a lower threshold may be associated with different alarm profiles or the same alarm profile. As another example, a blood glucose level that is above an upper threshold or a medicament pump that is unable to supply insulin may be associated with the same alarm profile. On the other hand, a medicament pump that is unable to supply insulin due to an empty insulin cartridge may be associated with a different alarm profile than if the medicament pump is unable to supply insulin due to damage to the medicament pump.

Some non-limiting examples of conditions of the AMD or of the subject that may be associated with an alarm profile include conditions relating to a battery capacity (e.g., below a threshold charge capacity or below a capacity associated with a particular amount of operating time (e.g., one day)), a battery condition (e.g., high temperature or low voltage), a medicament or drug delivery condition (e.g., medicament is empty or below a threshold, motor is stalled, catheter is occluded, etc.), subject sensor condition (e.g., blood glucose sensor is expiring, or signal was not received from sensor), calibration failure, high or low glucose levels, network (e.g., Bluetooth® or BN-LTE) communication errors, haptic interface errors (e.g., motor non-responsive), speaker errors (e.g., noise or low volume), medicament cartridge errors (e.g., empty cartridge, cartridge detection error, etc.), and the like. As explained below, each of these errors or conditions may be associated with different severity levels that cause the annunciation of different alarms.

In some cases, each alarm profile may be associated with a severity level of the alarm. The severity level may be associated with how urgently the condition that triggered the alarm should be addressed or resolved. Further, the severity level may be associated with an amount of harm that may be caused to a subject if the condition that triggered the alarm is not resolved or is not resolved within a particular time period. The number of severity levels may vary based on the type of ambulatory medicament device. Generally, there is no limit to the number of severity levels. However, there may be a point of diminishing returns as the number of severity levels exceeds a particular number because, for example, it may be difficult for a user to distinguish between the different numbers of severity levels or to identify with which severity level a particular alarm is associated. Thus, the number of severity levels may be limited to a particular number, such as 3, 5, 6, 9, or some number in between. However, it is possible for there to be more than 9 severity levels.

There may be multiple alarm profiles associated with a severity level. Or each condition of the AMD and/or subject that is associated with the same severity level may be associated with the same alarm profile.

The AMD may determine a severity of an alarm condition based on the condition of the ambulatory medicament device and/or the subject that triggered the alarm condition. In some cases, the ambulatory medicament device may determine the severity of the alarm condition based at least in part on an alarm profile associated with the alarm condition.

Generally, if the alarm condition does not prevent the AMD from providing therapy, the AMD may continue to provide therapy. However, in some examples, if the alarm condition interferes with the delivery of therapy, operation of the AMD may be suspended or partially suspended. Generally, alarm conditions that interfere with the provisioning of therapy may be associated with a higher severity level. However, some alarm conditions that interfere with the provisioning of therapy may be associated with lower severity levels. For example, a determination that the AMD cannot supply insulin may normally be associated with a highest severity alarm. But if a user indicates that the site location is currently in process of being changed, the alarm condition may be associated with a lower severity level (e.g., an informational alarm reminding the user that insulin cannot be delivered during site change). In some examples, in response to determining that the severity level of the alarm condition matches an unsafe operation (e.g., a condition that may cause the AMD to provide doses of the medicament that are above or below certain values, or to unreliably determine the subject's condition), the AMD may suspend delivery of the medicament to the subject. Once the condition is resolved, the AMD may resume delivery of medicament to the subject. If on the other hand it is determined that the alarm condition matches a safe operation severity level, the AMD may be configured to maintain delivery of medicament to the subject.

Alarm Annunciation

When an alarm condition is satisfied, the alarm annunciation and control system 3228 can implement an annunciation pattern selected based at least in part on the status information generated by and/or received from the monitoring system 3226. The annunciation pattern may be selected from a plurality of annunciation patterns based at least in part on the alarm condition and/or the status information. The annunciation pattern may include one or more different text patterns or text information, audible alarms, visual alarms, or haptic alarms. Determining whether the alarm condition is satisfied may include comparing one or more status values associated with the ambulatory medicament device and/or the subject to one or more alarm thresholds or alarm conditions associated with an alarm profile.

Upon verifying that an alarm condition associated with an alarm profile or alarm condition is satisfied, the alarm annunciation and control system 3228 annunciates the alarm condition. In some cases, at least some of the alarm conditions may be associated with a unique annunciation pattern. Advantageously, by having unique annunciation patterns for at least certain alarm conditions, a user can instantly know the stated of the AMD and/or subject based on the annunciation pattern for the alarm.

In some cases, the AMD may have a wireless electronic communications interface that can be used to transmit an alarm signal, status information, alarm condition data, and/or an annunciation pattern to a remote electronic device. In some such cases, the remote electronic device may annunciate an alarm if an alarm condition is met. The remote electronic device may include any device that can receive alarm information or status information from the AMD. For example, the remote electronic device may be a smartphone, smartwatch, smart glasses, a laptop, a tablet, or any other computing device.

In some examples, the alarm system may generate a list of pending alarm conditions and store it in a memory of the AMD (e.g., storage 618 in CCM 610). In these examples, any time an alarm condition associated with an alarm profile is satisfied, the alarm system may update the list of pending alarm condition by adding the new alarm condition to the list of pending alarm conditions. In some examples, the list of pending alarm conditions may comprise a list of elements (e.g., icons, text, and the like) each indicating an alarm condition (e.g., an alarm condition that has been annunciated). In some examples, the AMD may display an alarm state icon comprising a visual indication of a count of alarm conditions on the list of pending alarm conditions.

In some examples, the list of pending alarm conditions may be sorted according to the severity level associated with the alarm conditions.

In some examples, the alarm system may annunciate the alarm conditions via the user interface module 3208 of the AMD 600. For example, the alarm condition may be annunciated via one or more user interfaces (e.g., a display, a touchscreen display, a speaker, and the like). In some such examples, an alarm may comprise an audio alarm, a text message, a graphical message, a text or graphical message with audio, vibrations, flashing light and any combination of these.

In some examples, the alarm conditions may be transmitted to other devices, via the communication module 3202 of the AMD where, for example, an authorized user (e.g., guardians or parents of the subject), the subject or an emergency provider can view the alarm condition. In some examples, the alarm annunciation and control system 3228, may establish a direct end-to-end connection with a computing system (e.g., a cloud computing system) using the communication module 3202 and send the alarm condition to the computing system through the end-to-end connection.

Based on the severity of the alarm condition and/or the alarm profile corresponding to the alarm condition, an alarm may be generated and/or annunciated that is associated with the severity of the alarm condition and/or the type of alarm condition. Different alarm conditions and/or alarm profiles may result in different types of alarms or different annunciations of the alarm. For example, an alarm associated with the highest severity level may include an audible alarm with a loudness that exceeds a particular decibel level (e.g., above 70 or 80 decibels), a visible alarm (e.g., a flashing or steady light) with a luminance above a particular luminance value (e.g., a luminance between $10^5$ or $10^6$ candelas per square meter), and/or a vibrational alarm. Further, the alarm associated with the highest severity level may not be snoozed or dismissed. Alternatively, the alarm associated with the highest severity level may be snoozed for a shorter time period than alarms of lower severity levels (e.g., for 5 minutes, for 10 minutes, etc.). An alarm associated with a different severity level than the highest severity level may include a different combination of audible, visible, and vibrational alarms. Not only may the existence of audible, visible, and vibrational alarms differ for different severity levels, but so may the characteristics of each of the alarm types. For example, audible alarms may have different sound patterns, loudness, frequencies, etc. Visible alarm may be of different intensity, color, pattern, etc. Vibrational alarms may be of different pattern, intensity, etc. Further, an alarm with a different severity level than the highest severity level may be permitted to be snoozed or dismisses or snoozed for a longer period of time. In some examples, the severity of the alarm condition may determine the type of type of the alarm generated (e.g., audio, text, graphical, or any combination of these).

Further, the display of alarm conditions on the user interface may include an icon for each type of alarm condition. The user interface may display the number of alarm conditions and/or the number of alarm conditions of a particular type or severity level. In some cases, a duplicate alarm may be omitted from the list of alarms. In some cases, a count of the occurrence of alarms may be increased to reflect the duplicate alarm. In some cases, a duplicate alarm may result in the annunciation of the duplicate alarm. In some cases, the duplicate alarm is ignored. In some cases, the occurrence of a duplicate alarm may cause an escalation of the existing alarm. For example, if an alarm condition that causes an annunciation of an alarm with a first severity level is detected as occurring a second time, the alarm may be annunciated with a second severity level that indicates a greater degree of severity than the first severity level. It should be understood that an alarm occurring after an alarm condition is resolved may not be considered a duplicate alarm, but instead may be a reoccurrence of the alarm condition and/or an indicator that the resolution for the alarm condition failed (e.g., an insulin cartridge replacement is faulty or is empty)

In some cases, the list of alarms may be observed via a user interface (e.g., a touchscreen display) when the user interface is locked. In some such cases, further, details about the alarms may be accessible when the user interface is locked. In some cases, in order to access more details about the alarms and/or resolve the alarms, it may be necessary to unlock the user interface unlocked (e.g., by a wake action and/or a gesture).

Each of the alarm conditions, or information associated therewith, may be added to an indicator or user interface (e.g., a list, or other data structure or user interface element) that may be accessed by a user. This user interface may maintain the alarm condition on the user interface until the alarm condition is resolved. Further, the alarm conditions may be sorted or ranked based on the severity level of the alarm condition, the time that the alarm condition occurred, whether the alarm condition relates to the subject or the ambulatory medicament device, any combination of the foregoing, or any other factor for sorting or ranking the alarm conditions.

In some cases wherein the alarm is presented on a display, the displayed information may include details about what caused the alarm, the severity of the alarm, how to respond to or address the alarm, or any other information that may be informative regarding why the alarm was generated and/or how to respond to the alarm. In some cases, the information may provide a workflow or instructions on how to respond to the alarm. The instructions may include a link to a workflow provided by a manufacturer of the ambulatory medicament device or of another entity, such as an entity that provides medicament or site changing kits.

In some cases, different views of an alarm or different information associated with the alarm may be provided based on an identity of the user, or a role of the user, viewing the alarm. For example, a child may be instructed to contact a parent to address an alarm. But a parent may be provided with information to resolve the alarm. The parent may receive simplified information (e.g., blood glucose level is high) about what caused the alarm, but a healthcare provider may receive more detailed information regarding the alarm (e.g., internal control parameter values, insulin flow rates, curvature of insulin diminishment predictions, etc.) that facilitates the healthcare provider caring for the subject.

The alarm conditions may be displayed on a display of the AMD. Alternatively, or in addition, the alarm conditions may be displayed on a remote display that is separate from the ambulatory medicament device. The remote display may be a display that is authenticated or associated with a computing device that is authenticated to access data, such as alarm conditions, from the AMD. In some cases, the list of alarms may be presented on a mobile device (e.g., a smartwatch or smartphone) or on a computing device (e.g., a laptop or desktop) that can obtain data directly or indirectly from the AMD.

In some cases, annunciating the alarm may include contacting a manufacturer and/or user (e.g., a healthcare worker, a parent or guardian, or other registered user). Further, the alarm may include instructions on repairing the ambulatory medicament device and/or on addressing the alarm condition. For example, the alarm may provide a user with instructions to replace the insulin cartridge and how to replace the insulin cartridge. As another example, the alarm may provide instructions on how to change the battery of the device or on how to change a site where the insulin pump connects to the subject. In some cases, the alarm may include one or more operations associated with the alarm. For example, the alarm may trigger reordering of insulin or may request that the user confirm a reorder request to reorder insulin.

Resolving an Alarm

Certain alarms, such as informational alarms, may be dismissible. However, generally the alarm may remain on the alarm list until the condition that caused the alarm is resolved.

A user may be able to acknowledge and/or snooze alarms via a user interface. In some examples, in order to acknowledge and/or snooze alarms, the user may first need to activate the user interface (e.g., by providing a wake action) and then provide a gesture to unlock the user interface. For example, the user may use the wake button to activate a touchscreen display and then provide a gesture on the screen to unlock display. In some example, the touchscreen display may be configured to allow the user or subject to navigate directly to the issue or fault for which an alarm is being delivered. This capability provides the user with access to address the fault causing the alarm so that it could be corrected thereby stopping the alarm.

Resolving the alarm may include any action that addresses the condition that caused the alarm to be generated. For example, resolving the alarm may include replacing an insulin cartridge, changing a site where the ambulatory medicament device is connected to the subject, charging a battery of the ambulatory medicament device, providing insulin or a counter-regulatory agent to the subject and/or the ambulatory medicament device, or any other action that may be performed to address an alarm condition. In some cases, the resolution action may be acknowledging the alarm. For example, if the alarm is informational (e.g., to inform the user that more insulin has been ordered), acknowledging the alarm may be a sufficient resolution action.

In some cases, whether the alarm condition is resolved may depend on an identity of the user. For example, if a child interacts with an alarm related to reordering of insulin, the alarm may remain until a parent or guardian acknowledges the alarm. However, the child may be able to snooze the alarm. In some cases, a user interface that displays alarms may differ based on who is viewing the alarm. For example, a child may view the alarms, but may not be able to interact with the alarms. However, a parent or guardian may be able to snooze or dismiss an alarm. Further, a child may be instructed to bring the device to a parent or adult to address an alarm. In some cases, the child may be informed of how urgently to contact the parent (e.g., contact a parent immediately, within a day, within a week, etc.). Moreover, a designated adult may separately be alarmed (e.g., via a text or email alarm). The parent or guardian may receive additional information not provided to the child or subject (e.g., a link to repair instructions or a workflow to address the alarm condition).

In some cases, certain conditions may self-resolve over time. For example, a low battery alarm may resolve as the battery is charged. In such cases, the alarm may be cancelled automatically as the battery charge level exceeds a particular threshold. Further, in some cases, one or more alarms and/or the alarm list can be viewed and/or accessed on a home screen, a main screen, or other non-alarm based user interface screen in addition to a user-interface screen designated for display alarms. The alarm list may be accessed from the ambulatory medicament device and/or a computing system in communication with the ambulatory medicament device.

However, in some cases, the alarm condition may or may not be resolvable when the ambulatory medicament device is locked.

A user may interact with the alarms generated based on the alarm condition. In some cases, the user can only interact with the alarms when the AMD and/or the user interface is unlocked. In some cases, the user can interact with the alarms to snooze them or to obtain further information, when the AMD is locked. However, the user may not be able to dismiss the alarm without unlocking the ambulatory medicament device. Interacting with the alarms may include providing information associated with the alarm to a user in response to the user interacting with the alarm, or an indicator representative of the alarm.

Example AMD with Alarm Management System

Figure 33A:
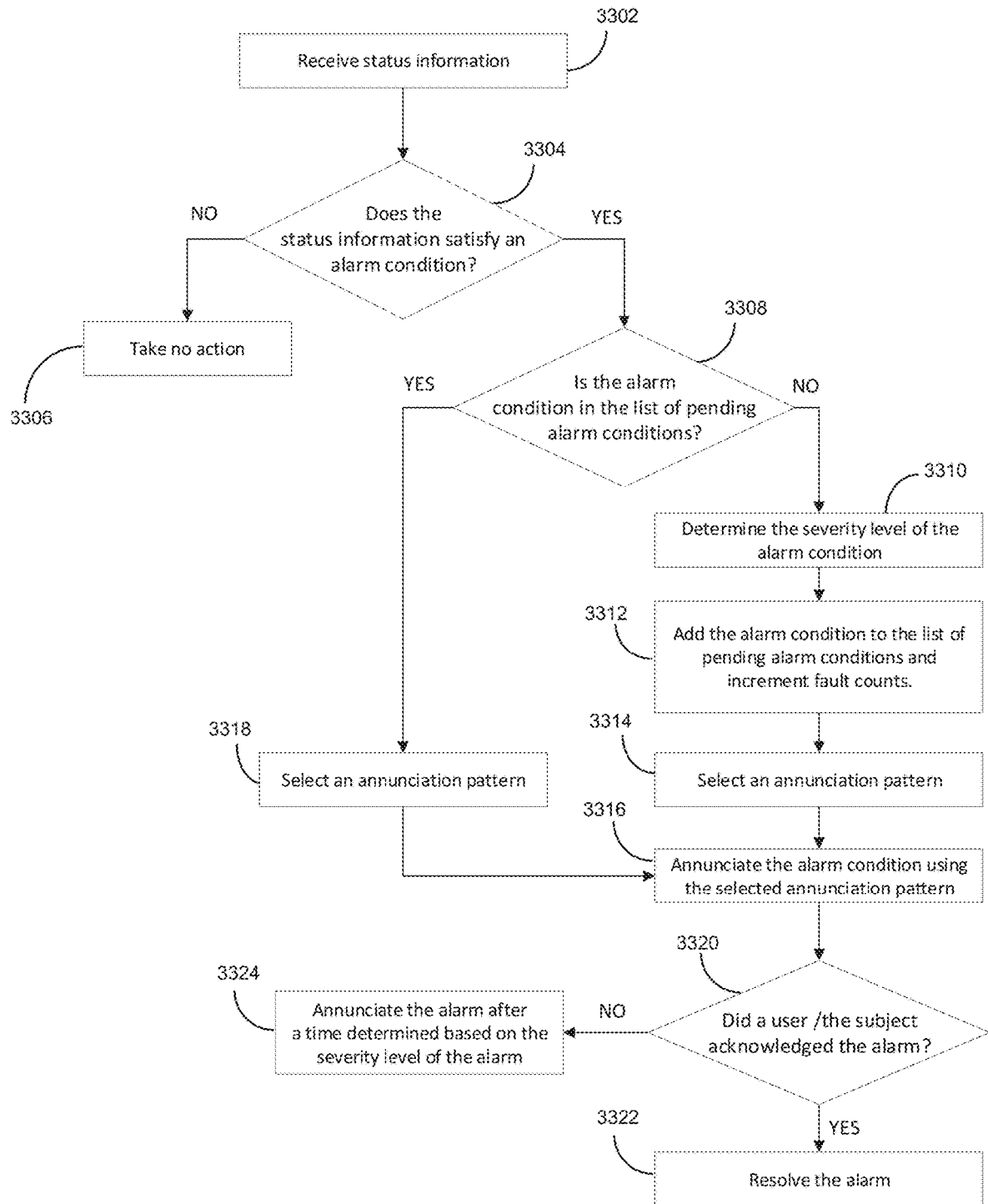
FIG. 33A is a flow diagram illustrating an example procedure that may be used by the alarm system of an AMD to annunciate an alarm condition upon receiving a status information that satisfies an alarm condition.

FIG. 33A shows a flow diagram illustrating an example procedure that may be used by the alarm system of an AMD to annunciate an alarm condition upon receiving a status information that satisfies an alarm condition. In some examples, the alarm annunciation and control system 3228 implements an annunciation process by execution of instructions by a processor in CCM of the AMD, where the instructions can be stored in the main memory, storage of the AMD, or in a memory of a connected electronic device or computing system.

The alarm system may receive status information at block 3302 from one or more device sensors 3224 and/or one or more subject sensors 3220 via the monitoring system interface 3226. The one or more device sensors 3224 may include any type of sensor that can determine a condition of the AMD. For example, the one or more device sensors 3224 may include a battery charge sensor that determines a charge of a battery, a battery condition sensor that determines a condition of a battery, a medicament sensor that determines a quantity of medicament remaining, or any other type of sensor that can determine a condition of one or more electronic or mechanical components of the AMD. The one or more device sensors may determine if a quantity of medicament is below a threshold or if a battery charge is below a threshold.

The one or more subject sensors 3220 can include any type of sensor that can determine a health-related characteristic or physiological parameter of the subject. For example, the one or more subject sensors 3220 can determine a blood glucose measurement, a blood pressure measurement, a respiratory rate, a blood oxygenation level, a pulse rate, or any other physiological characteristics of a subject. In particular, although not limited as such, the one or more subject sensors 3220 may measure any physiological parameter of the subject that may relate to monitoring, managing, or treating a subject's diabetes.

In some examples, the alarm annunciation and control system 3228 determines whether the received status information satisfies an alarm condition at decision block 3304. In some examples, the alarm condition may be an alarm condition in an alarm profile. If the received status information does not satisfy an alarm condition, no action may be taken at block 3306. If the received status information satisfies an alarm condition 3304, the alarm system may determine whether the alarm condition is already present in the list of pending alarm conditions at decision block 3308. If the alarm condition is not present in the list of pending alarm conditions, the alarm system may determine the severity level of the alarm condition at block 3310, add the alarm condition to the list of pending alarm conditions at block 3312, and increment an alarm count that tracks a number of occurrences of an alarm or a fault count that tracks a number of faults occurring in the AMD. In some examples, the placement of the alarm condition in the list of pending alarm conditions may depend on the determined severity level of the alarm condition. In some such examples, the alarm conditions may be categorized numerically in descending order with the highest priority fault displayed at the top.

Next, based on the determined level of severity, the alarm annunciation and control system 3228 may select an annunciation pattern at block 3314 and annunciate the alarm condition using the selected annunciation pattern at block 3316. If the alarm condition is present in the list of pending alarm conditions, the alarm system may select an annunciation pattern at block 3318 and annunciate the alarm condition using the selected annunciation pattern at the block 3316. In some examples, the annunciation pattern selected at block 3318, may be an annunciation pattern that is different than the previously used annunciation patterns for the alarm condition. In some such examples, the annunciation pattern selected at block 3318, may be selected based at least in part on a number of times that the same alarm condition is satisfied by a received status information. The process of the alarm detection and control function may repeat periodically, intermittently, according to a particular schedule, or while the ambulatory medical device is in use. The frequency with which the process is repeated may depend on the particular alarm condition detected from the status information. In some examples, after an alarm is annunciated, the alarm system may wait for user acknowledgment of the alarm at block 3320. If the user acknowledges the alarm, the system proceeds to resolve the alarm 3322. In some cases, resolving the alarm may include providing instructions to a user or indicating where a user can locate instructions to resolve the alarm condition. For example, the user may be provided with repair instructions for repairing the AMD. Further, in some cases, resolving the alarm may include automatically ordering or requesting that the user confirm an order is to be placed to replenish a medicament. If the user fails to acknowledge the alarm, the annunciation may be repeated after a certain time period at block 3324 determined based on the severity level of the alarm. In some examples, if the user fails to acknowledge the alarm, the annunciation continues and may escalate depending on the severity level of the alarm.

Figure 33B:
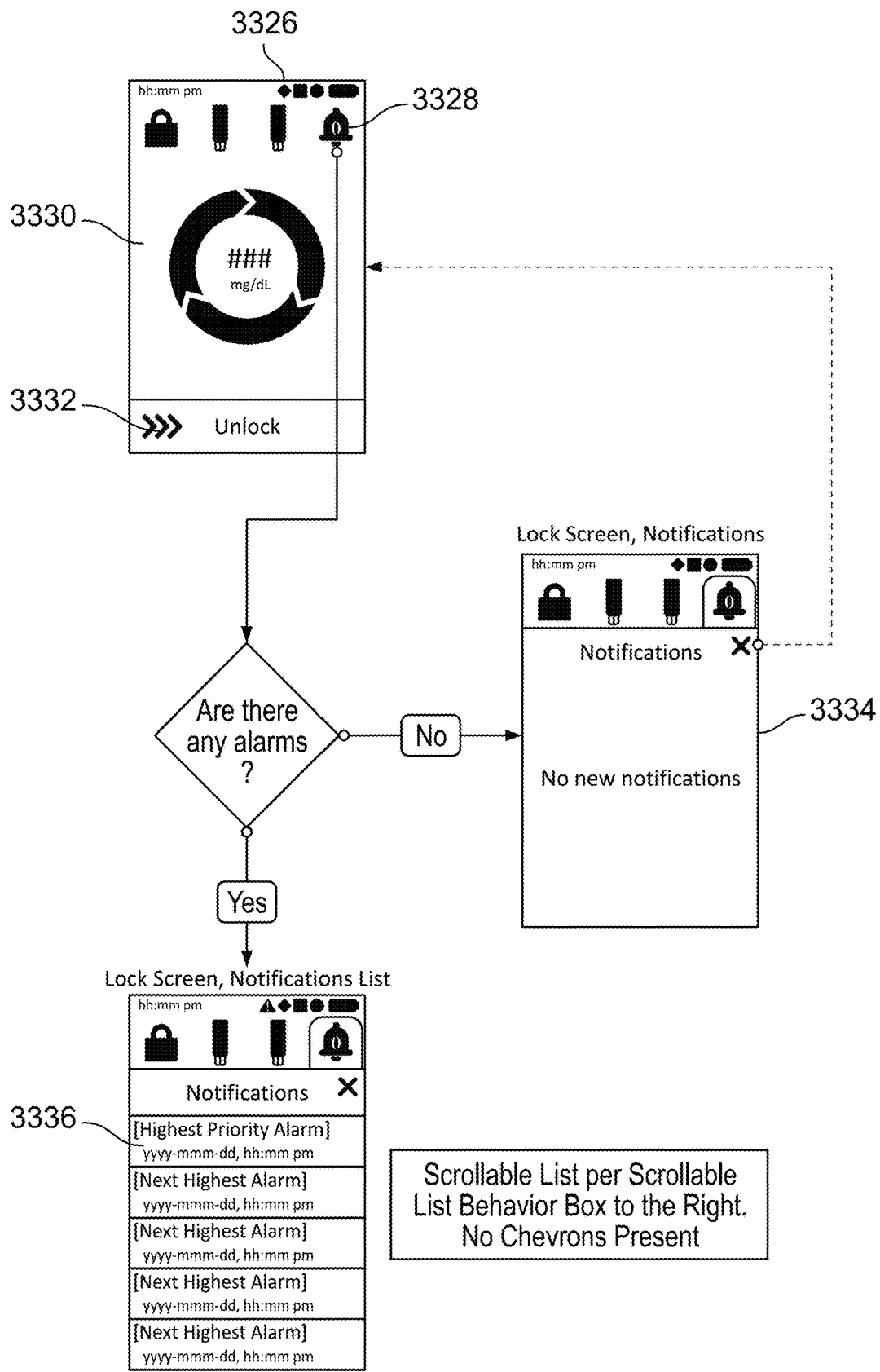
FIG. 33B is an illustration of a user interface provided on a touch screen display for accessing the alarm notifications screen when the touch screen display is locked.

As described above, in some examples, a user or the subject may view an alarm using a user interface provided on a touchscreen display both when the display is locked and when the display is unlocked. FIG. 33B is an illustration of such user interface 3326 for accessing the alarm notifications screen when the display is locked. As illustrated, the user interface 3326 includes an alarm icon 3328; a pump operation field 3330; and an unlock button (or a first gesture field) 3332. The alarm icon 3328, in this exemplary embodiment, is shaped as an alarm bell with a counter in the middle indicating the number of annunciated alarms (e.g., "0" in the examples shown).

In some examples, the unlock field is configured such that the user may unlock the display by sliding in the direction of the chevrons, for example. However, the user may still view the alarms without unlocking the interface. Thus, for example, if the user selects the alarm icon, the display illustrated in 3334 will appear if there is no alarm in the system. If there are existing alarms in the system, the display of 3336 appears wherein a list of alarms is displayed however the user cannot select the alarms (e.g., to see more information or acknowledge the alarms). The inability to select the alarms is exemplified by the absence of chevrons by each alarm. The number of alarms displayed may be limited by the size of the screen.

Figure 33C:
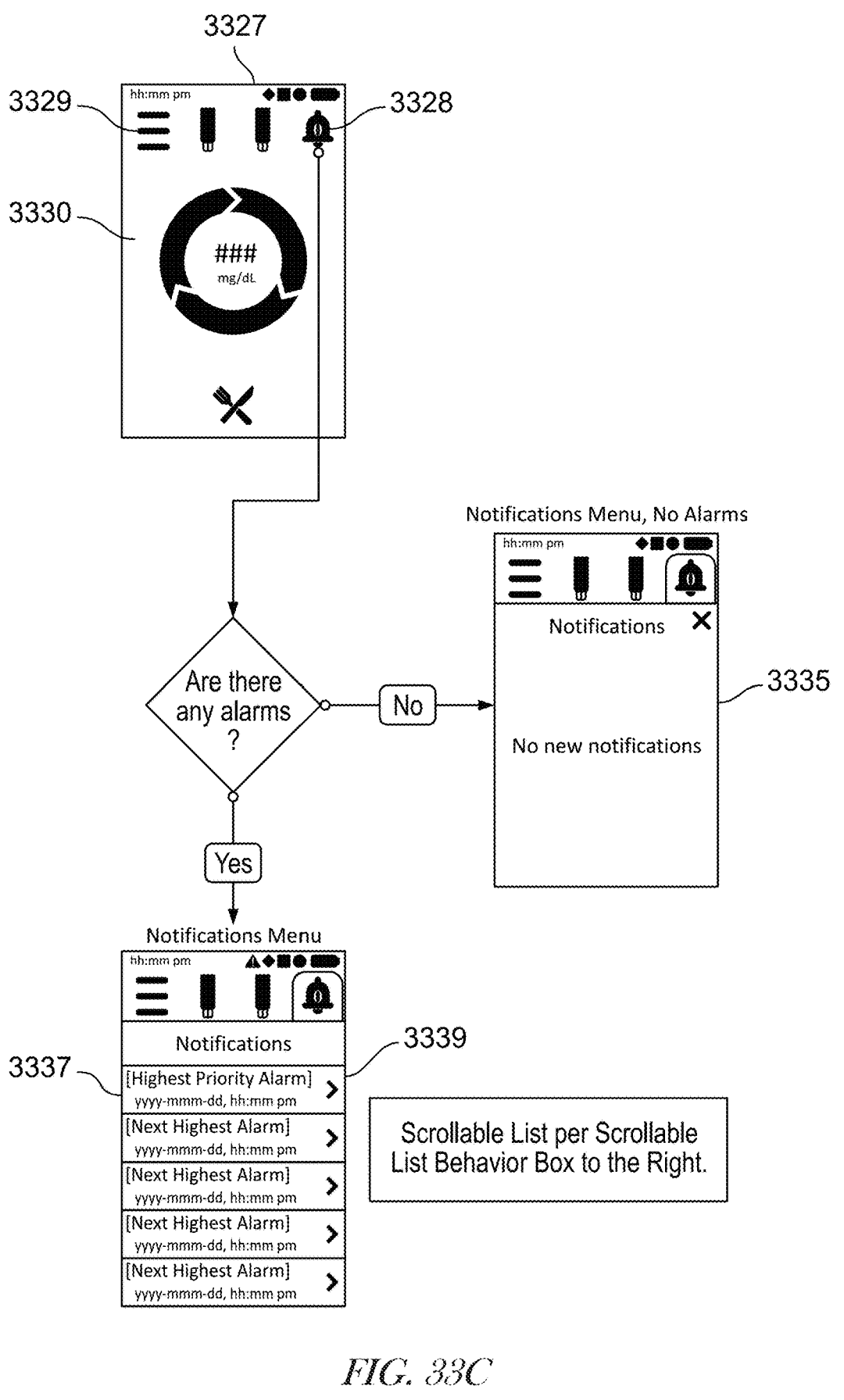

In some such examples, if the user unlocks the screen by sliding the unlock button 3332, the user interface 3327 illustrated in FIG. 33C may be displayed. As illustrated, the user interface 3327 includes the alarm icon 3328; a menu icon 3329; and the pump operation field 3330. In some cases, the menu icon 3329 may allow the user to control operation of the AMD 600 and the alarm icon 3328 may provide the user with access to the alarm control functions. Thus, for example, if the user selects the alarm icon 3328, the display illustrated in 3335 may appear on the screen if there is no alarm in the system. If there are existing alarms in the system, the display of 3337 may appear wherein a list of alarms is displayed with each alarm having a chevron 3339 that enables selecting the alarm to access further control functions for the selected alarm.

As mentioned above, the alarm conditions may be categorized based and annunciated based on their severity level. In some examples, the alarms are categorized numerically in descending order with the highest priority fault displayed at the top of the list. In some examples, a level 0 severity, may be for a trivial fault that does not require any action by the user thus not warranting an alarm notification. In some examples, a level 1 severity may be an informational type notification that repeats at a certain frequency (e.g. every 30 minutes) until acknowledged by the user which results in it being reset. The annunciation may include a brief vibration and a beep, for example. In some examples, a level 2 severity, may be one relating to an imminent loss of system function. Thus, such an annunciation may include two brief vibrations and two beeps, for example, and repeating at a certain frequency (e.g. every 30 minutes). Thus, the user would still need to address the situation creating the fault to completely stop the annunciation. In some examples, a level 3 fault may be for when the system is no longer fully functional thus requiring user intervention to correct the issue. The annunciation may begin with a base level intensity with three brief vibrations and three audio beeps, for example, and repeating at a certain frequency (e.g. every 5 minutes). The annunciation escalates at a second frequency, e.g. every 30 minutes, up to a maximum intensity level. The escalation may be a change in vibration intensity and/or audio level, for example. The escalation may be cleared to a base level when the user acknowledges the fault; however, the base alarm may remain if the underlying condition persists. Thus, the user would still need to address the situation creating the fault to completely stop the annunciation. In some examples, a level 4 severity, may be for when the system is no longer functional and not correctable by the user. The annunciation may begin with a base level intensity with three audio beeps, for example, and repeating at a certain frequency (e.g. every 5 minutes). The annunciation escalates at a second frequency, e.g. every 30 minutes, up to a maximum intensity level. The escalation may be a change in audio level, for example. The escalation may be cleared when the user acknowledges the fault; however, the base alarm remains because the underlying condition persists. In some examples, a level 5 severity, may be for high priority alarms per IEC 60601-1-8. The annunciation when activated may be cleared only when the underlying issue is resolved, e.g. glucose level is raised.

Additional embodiments relating to determining a severity of an alarm condition and annunciating the alarm based at least in part on the severity of the alarm condition that can be combined with one or more embodiments of the present disclosure are described in U.S. Provisional Application No. 62/911,017, which was filed on Oct. 4, 2019 and is titled "ALARM SYSTEM AND METHOD IN A DRUG INFUSION DEVICE," the disclosure of which is hereby incorporated by reference in its entirety herein for all purposes.

Non-Critical AMD Condition Management

In some cases, a condition may occur that impacts the operation of the ambulatory medical device (AMD) that provides therapy to a subject. In some examples, an AMD can be an ambulatory medicament device. This condition may be associated with the ability of the AMD to operate as intended by the manufacturer, a subject receiving therapy from the AMD, and/or user (e.g., healthcare provider, parent, or guardian of the subject). In some cases, the condition or malfunction of the AMD may prevent the AMD from providing therapy to the subject. In some cases, the condition or malfunction may permit, at least for a period of time, the AMD to continue providing at least partial therapy to the subject. It is generally desirable to generate an alert to inform the subject and/or one or more users of the condition of the AMD and/or the subject to provide and facilitate non-critical malfunction management in an ambulatory medical device. Moreover, it is desirable to track the alert until the condition that caused the alert is resolved. Further, it is desirable to issue different types of alerts for different conditions to enable a subject or user to easily distinguish the severity of the condition that triggered the alert.

In many cases, if the nature of the alert is non-critical, it may be safer to continue the underlying therapy and notify the user of the condition than to cease therapy. In some such cases, the best response to a problem with the device for a subject is to notify the device manufacturer, or other user that can address the problem, while the subject continues to receive therapy until a replacement device can be obtained or a repair can be made.

Additionally, alert fatigue can be an issue with medical devices due to excessive alerts which do not necessarily require user interaction. Alert fatigue can be dangerous because it can lead users to ignore serious alerts or alerts that require action in the short term.

The method described herein may be performed by an AMD (e.g., by one or more processor of the AMD) to detect device malfunctions for the AMD and that can generate alerts corresponding to the AMD and prioritize the alerts to enable the subject or user to quickly and easily determine whether the device malfunction will impact therapy, should be addressed in the short-term (e.g., immediately, in 1-2 hours, within the day, etc.), and/or can be addressed at the subject's convenience (e.g., within a month, or more). In some cases, the method of device malfunction alert prioritization may be used by other systems.

In certain embodiments, the system disclosed herein can detect a condition in which the AMD does not meet a manufacturer's specification (e.g. a failure of a haptic annunciator, a Bluetooth® radio malfunction, glucagon or insulin runs out, there is a medicament delivery malfunction, a touchscreen failure, etc.). In some cases, there can be several tiers of critical and/or non-critical faults. If it is determined that the underlying condition is not sufficient to stop therapy (e.g., stop delivery of insulin), the fault may be deemed non-critical. In some cases, the fault may not be a fault of the device, but may be indicative of required maintenance (e.g., recharge battery indicator, order more medicament indicator, etc.). The condition may be annunciated to the user with appropriate instructions (e.g., call manufacturer for replacement medicament or parts) for addressing the fault or issue.

After the annunciation is acknowledged, the alert may be re-annunciated, or annunciated again, as a reminder at some later period in time (e.g. the alert may be re-annunciated daily at 4:00 PM or on Saturdays at noon providing, for example, for a fixed static time period or periodically between alerts). The length of time between annunciations may depend on the severity of the fault. In some cases, the re-annunciation cannot be stopped by the user, but may only cease if the underlying condition is resolved. In some cases, the re-annunciation time period may be a variable time period and may gradually increase to minimize fatigue alert. In some cases, the re-annunciation time period may be a variable time period and may gradually decrease if the alert becomes more urgent or increase in urgency. In some cases, the re-annunciation time period may change during the day based on time of day. For example, alerts may be provided during the day, but silenced or reduced during the night.

The method may include detecting a condition of the AMD. In some examples, the condition of the AMD may comprise a set of operating parameters of the AMD. In some such examples, the condition of the AMD may be determined using one or more sensors of the AMD. Further, the condition of the AMD may be determined by the presence or absence of one or more errors when performing one or more functions of the AMD. For example, if the AMD fails to establish a communication connection with a control system or a data storage system, it may be determined that there is a possible malfunction with the AMD. As another example, if the AMD fails to deliver medicament or detects an error when attempting to deliver medicament, there may be a malfunction with the medicament pump. In some cases, the condition of the AMD may be determined based on one or more configuration values being outside a normal operating range. For example, if the speed of delivery of medicament is faster or slower than a configured operating range, then it may be determined that there is a malfunction with the medicament pump or a connection with a medicament delivery tube (e.g., a catheter). In some examples, the condition of the AMD may be determined based on the performance of the AMD over period.

The method may include comparing the detected condition of the AMD to a set of normal operating parameters. In some examples, the set of normal operating parameters may be the specifications set by the manufacturer for when the AMD is operating as intended by the manufacturer. In some examples, at least some of the normal operating parameters may be provided by a healthcare provider. In some examples, at least some of the normal operating parameters may be provided by the subject or an authorized user. In some cases, the normal operating parameters may be associated with a range of values. For example, the operating parameter for a speed of medicament delivery may be associated with a range of speeds, which may vary based on user settings, medicament type, site location of medicament delivery, or manufacturing tolerances, among other parameters. Comparing the detected condition of the AMD to the set of normal operating parameters may include comparing each operating parameter in the specification to a corresponding detected operating parameter of the AMD. The AMD may generate a user alert or non-critical malfunction alert based on the determined condition of the AMD. For example, the AMD may generate an alert when the detected condition of the AMD does not satisfy a set of normal operating parameters.

The method may further include determining whether the detected condition satisfies a minimum set of operating parameters. In some cases, the minimum set of operating parameters may match the normal operating parameters. However, typically the minimum set of operating parameters differ from the normal operating parameters. The minimum operating parameters may include the minimum specifications, minimum parameters, or minimum condition required by the AMD to maintain or continue providing therapy to the subject. In other words, the minimum operating parameters are the operating parameters sufficient to provide therapy. However, the minimum operating parameters may not be sufficient to enable all features of the AMD. For example, the minimum operating parameters may permit the AMD to deliver insulin to the subject, but may not be sufficient to deliver the insulin at a normal delivery speed for the particular AMD. As another example, the minimum operating parameters may permit the delivery of therapy, but may not be sufficient to track a log of therapy or to transmit a therapy log to another computing system. In some cases, the normal operating parameters and/or minimum operating parameters may be specified by be specified by the manufacturer at the time of manufacturing. In some some cases the normal operating parameters and/or minimum operating parameters may be specified by a subject or healthcare provider (e.g., the minimum amount of medicament that is to be provided in each bolus may be specified by a healthcare provider). In some cases, the normal or minimum operating parameters may be modified.

When it is determined that the condition of the AMD satisfies at least the minimum operating parameters, the AMD may be configured to maintain delivery of therapy to the subject. Maintaining delivery of therapy may include maintaining therapy at the same rate, at a reduced rate (e.g., providing only basal therapy and therapy responsive to a meal announcement), or at a minimum rate or minimum maintenance rate (e.g., providing only basal insulin). Advantageously, the ability of the AMD to distinguish between a minimum set of operating parameters and a normal set of operating parameters enables an AMD with a malfunction to continue providing therapy, which sometimes includes life-saving treatment, to a subject until the AMD can be repaired or until the condition of the device worsens to a point where the minimum operating parameters cannot be maintained. In some cases, the AMD may temporarily maintain delivery of therapy. Temporarily maintaining therapy may provide a subject time to address the issue that caused the AMD to not satisfy the normal operating parameters before the subject loses access to therapy. In some cases, the AMD temporarily maintains therapy until the device condition makes it no longer possible to maintain therapy.

Figure 34:
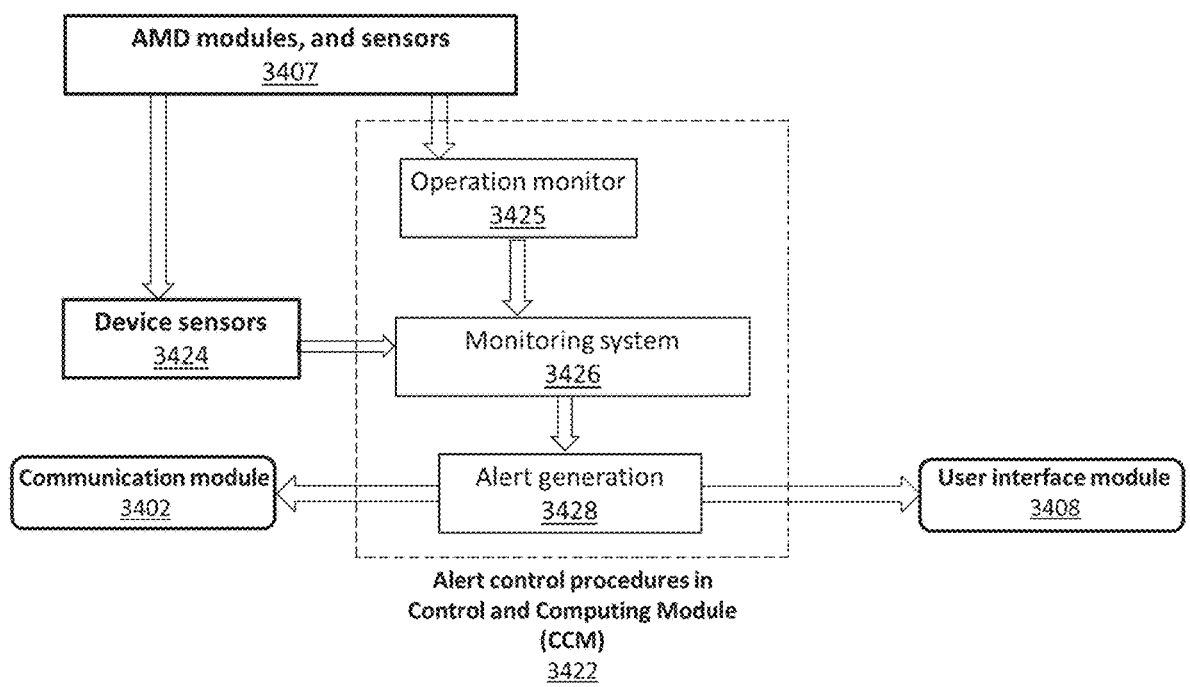
FIG. 34 is a block diagram illustrating the interconnection among modules and procedures in AMD involved in monitoring the condition of the AMD and generating alerts when a device malfunction is detected.

FIG. 34 is a block diagram illustrating an example of the interconnection among modules and procedures in AMD that may be involved in monitoring the condition of the AMD and generating an alert when a device malfunction is detected. In some examples, the condition of AMD may include the status of the modules and components of the AMD and/or operation of modules and procedures of the AMD. In some embodiments, the alert system may be implemented as a set of alert control procedures 3422 in the control and computing module 610 (CCM) of the AMD. The alert control procedures 3422, may be implemented as instructions stored in a memory of AMD (e.g., a memory in CCM 610) and executed by a hardware processor 614 of the AMD (e.g., a processor in CCM 610) to generate an alert upon detection of a malfunction of the AMD. In some cases, the hardware processor may be a hardware processor of the AMD that controls medicament delivery. In some cases, the hardware processor of the monitoring system may be a separate hardware processor.

In some examples, the alert control procedures 3422 may include a monitoring system 3426, a set of operation monitoring procedures 3425 and a set of alert generation procedures 3428. In some examples, a set of device sensors 3424 may be configured to track the status of the components of the AMD. A set of operation monitoring procedures 3425 may be configured to monitor the operation of the components, modules and other procedures (e.g., temporal behavior of the signals provided by the components, communication between different devices and modules, performance of the procedures implemented in the CCM 610 and the like). For example, a device sensor may determine that a component is properly connected and it is functional, while the operation monitoring procedures 3425 may provide data related to signals generated by the component over a period. The monitoring system 3426 may monitor and evaluate a set of operating parameters of the AMD at least partially based on the information received from the operation monitoring procedures 3425 and device sensors 3424.

In some embodiments, the alert generation procedures 3428 may compare the determined operating parameters of the AMD, received from the monitoring system 3426, with a set of normal operating parameters. In some examples, the alert generation procedures 3428 may also determine whether the operating parameters of the AMD satisfies a minimum set of operating parameters. In some examples, if it is determined that one or more operating parameters of the AMD do not satisfy the normal operating parameters, the alert generation procedures 3428 may generate an alert. In some examples, the alert may be transmitted to the user interface module 3408 and displayed on a display of the AMD (e.g., a touchscreen display). In some examples, once an alert is generated the AMD may establish a connection (e.g., a wireless connection) with another device using the communication module 3402. This other device may include a local device (e.g., a laptop, smartphone or smartwatch of the user) or a computing system of a cloud-based service. In some such examples, the alert may be transmitted by the communication module 3402 to the local device and/or the computing systems where it may be displayed on user interface associated with the local device or the computing system. In some cases, the local devices and/or the computing system may receive data from the AMD device enabling the user to monitor the operating parameters of the AMD.

The type of the alert, and the frequency at which the alert is repeated, or whether an alert is dismissible or not, may be determined by the alert generation procedure based on the detected condition of the AMD and the alert information stored in a memory of the AMD. In some examples, the alert information may be provided by the subject, an authorized user or a healthcare provider. In some examples, the alert information may be stored in the AMD at time of manufacturing.

In some examples, upon determination that the detected AMD condition (e.g., comprising a set of operating parameters) does not satisfy a normal condition (e.g., a set of normal operating parameters), the alert generation procedures 3428 may cause the medicament delivery interface 606 to stop therapy delivery or modify one or more delivery parameters (e.g., therapy delivery rate). In some examples, upon determination that the detected or determined that the operational parameters of AMD do not satisfy a set of normal operating parameters, but satisfy a set of minimum operating parameters, the therapy delivery may be maintained at a normal rate.

The alert may include any type of alert. For example, the alert may be a visual alert (e.g., a light or changing light), an audible alert (e.g., a beep or series of beeps), a haptic or vibration alert, an email alert, a text alert, or any other type of alert. In some examples, different AMD conditions or different operational parameters of the AMD may be associated with or may trigger different types of alerts. Thus, the alert may enable the user to determine the device condition of the AMD based on the type of alert. For example, an indication that the AMD failed to deliver a medicament may trigger one type of alert while an indication that the level of a medicament in the AMD has dropped below a particular level may trigger a different type of alert. In some cases, the user alert or non-critical malfunction alert is dismissible and/or may be snoozed by the user. In some cases, such as when the AMD fails to satisfy a set of minimum operating parameters, the user alert or non-critical malfunction alert may not be dismissible or cannot be snoozed.

A dismissible alert may be scheduled to repeat on a particular schedule until an alert modification condition occurs. The frequency with which the dismissible alert repeats may depend on the severity of the condition or the particular operating parameters that do not satisfy normal or minimum operating parameters. More urgent device conditions may result in alerts that repeat more frequently. Further, alerts may vary based on when the condition was detected, the time of day, or the detected activity of a subject (e.g., sleep, abnormal activity, or elevated activity, such as exercise). Similarly, the snooze options may vary for different alerts or any of the aforementioned conditions. In some cases, the AMD may escalate or prioritize an alert if it detects that the condition of the AMD has become more critical. In some cases, the re-annunciation time period or variable time period may gradually increase to minimize fatigue alert, or the condition of the AMD has become less critical. In some cases, the re-annunciation time period or variable time period may gradually decrease if the condition of the AMD has become more critical.

The alert frequency may be for a static time period (e.g., every 5 hours) or may ramp towards more frequency (e.g., every 5 hours for 1 to 3 reminders, every 4 hours for 3 to 6 reminders, etc.), or may change based on time of day (e.g., snooze alerts during sleeping hours for non-urgent alerts), etc.

In some examples, the alert modification condition may include any action that causes the operating parameters of the AMD to return to normal operating parameters. For example, the alert modification condition may be a repair or replacement of a faulty component. In some cases, the alert modification condition may be an acknowledgement of the alert. In some examples, the alert modification condition may include a worsening of the AMD condition. In such cases, the modification to the alert may include the substitution or prioritization of the alert to a different alert that indicates a different or more serious condition of the AMD. For example, an urgent condition may become critical if the detected malfunction is not addressed after generating certain number of alerts. When an urgent condition becomes critical, it may be prioritized, trigger a different alert types or different user/non-critical malfunction alert types (e.g., a louder sound, different sound, different frequency, brighter image or the like), and/or escalation in the alert frequency. For example, the audible alert may become louder and may be combined with a vibration alert from a haptic annunciator. Moreover, if the condition reaches a critical state, the AMD may cease providing therapy to the subject.

In some cases, generating the alert may further include contacting a manufacturer and/or healthcare provider (e.g., clinician). Further, generating the alert may include ordering replacement parts. In some cases, the alert may instruct a subject or user on how to repair the ambulatory medical device.

Once the malfunction is addressed, the AMD is repaired, or the condition that caused the alert is resolved, a user may permanently (or until the next time a device condition triggers the alert) dismiss the alert. Alternatively, or in addition, the AMD may automatically dismiss the alert when it determines that the device condition that caused the alert has been resolved (e.g., using the alert control procedures 3422). In some cases, the AMD may periodically recheck the device condition to determine whether the alert condition has been resolved.

In some cases, the manufacturer or healthcare provider may remotely clear or stop an alert using, for example, using a device or computing systems that is connected to the AMD (e.g., via a wireless connection such as an NB-LTE connection). In some cases, only the manufacturer and/or healthcare provider can clear or stop the alert. Further, in some cases, a manufacturer and/or a healthcare provider may notify a user (e.g., a subject, or parent or guardian) of an issue or impending issue with the AMD. The notification may be received by the AMD device via a wireless connection (e.g., NB-LTE connection). Alternatively, or in addition, the notification may be received via a computing device, such as a smartphone or laptop.

Figure 35:
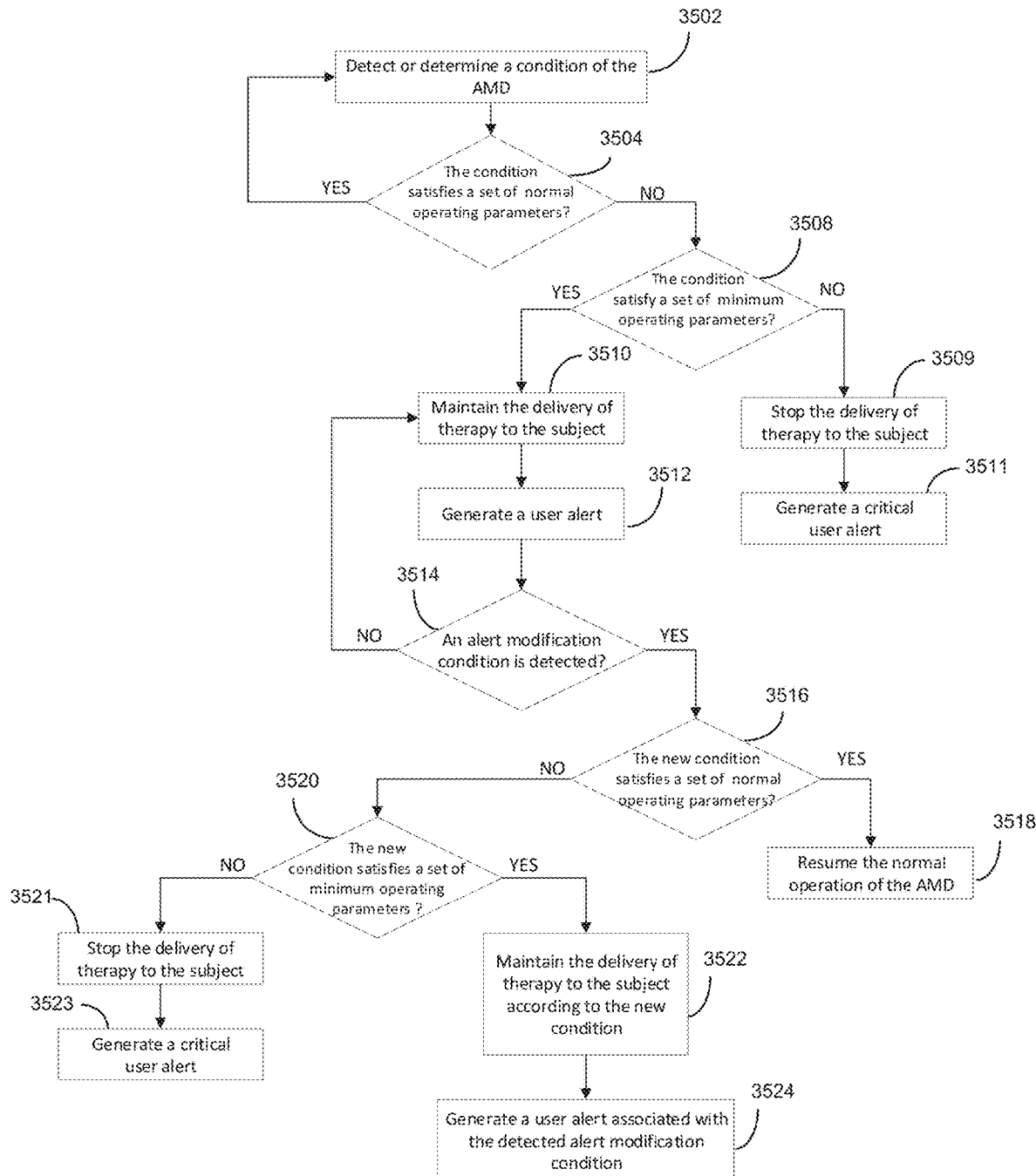
FIG. 35 is a flow diagram illustrating an example procedure that may be used by the alert system of an AMD to monitor the operation of an AMD and generate alerts when a device malfunction is detected.

FIG. 35 is a flow diagram illustrating an example procedure that may be used by the alert system of an AMD to monitor the operation of an AMD and generate alerts when a device malfunction is detected. In some examples, the alert system continuously monitors the status of all modules and components associated with AMD as well as the operation of all modules and procedures of the AMD. When a condition of the AMD is detected 3502, the alert system may determine whether the detected device condition satisfies a set of normal operating parameters 3504. If it is determined that the detected device condition satisfies a set of normal operating parameters, the alert system takes no action and continuous monitoring the AMD 3502.

If it is determined that the device condition does not satisfy a set of normal operating parameters, the alert system determines whether the detected device condition satisfies a set of minimum operating parameters 3508. If, at block 3508, it is determined that the device condition does not satisfy a set of minimum operating parameters, the alert system may send a signal to the therapy delivery module 606 or medicament delivery interface 1806 (e.g., using medicament dose control procedures 1830) to stop delivery of therapy to the subject 3509, and to generate a critical user alert or critical alert 3511 that is prioritized by indicating that immediate or urgent action is required. In some examples, upon generation of a critical alert the alarm system of the AMD, may contact a healthcare provider or certified user (e.g., parent or guardian of the subject) and also send the critical alert to one or more computing devices (e.g., laptop, cell phone, personal computer, and the like) of the healthcare provider or certified user.

If, at block 3508, it is determined that the device condition satisfies a set of minimum operating parameters, the alert system may maintain the delivery of therapy to the subject 3510 and generate a user alert or non-critical malfunction alert 3512. In some such examples, the alert system may maintain the delivery of the therapy at rate associated with the detected condition of the AMD (e.g., normal rate or minimum maintenance rate) until an alert modification condition is detected 3514.

Upon detection of an alert modification condition 3514, the alert system may determine whether the new device condition satisfies a normal set of parameters 3516. If, at block 3516, it is determined that the new device condition satisfies a set of normal operating parameters, the alert system may resume the normal operation of the AMD 3518

(e.g., deliver the therapy at a normal rate). If at block 3516, it is determined that the new device condition does not satisfy a set of normal operating parameters, the alert system may determine whether the new device condition satisfies a minimum set of parameters 3520. If, at block 3520, it is determined that the new device condition satisfies a set of minimum operating parameters. The alert system may maintain or modify the rate of therapy delivery according to the new device condition 3522 and generate a user alert or non-critical malfunction alert 3524 according to the new device condition. If, at block 3520, it is determined that the new device condition does not satisfy a set of minimum operating parameters, the alert system may send a signal to the therapy delivery module to stop delivery of therapy to the subject 3521, and generate a critical user alert 3523 indicating that immediate or urgent action is required. The critical user alert 3523 may be prioritized over other types of alerts and alarms. In some examples, upon generation of a critical alert the alarm system of the AMD, may contact a healthcare provider or certified user (e.g., parent or guardian of the subject) and also send the critical alert to one or more computing devices (e.g., laptop, cell phone, personal computer, and the like) of the healthcare provider or certified user.

Managing Doses of Glucose Control Agents

Ambulatory medical devices allow subjects the freedom to treat themselves while being mobile. Self-managed medical treatment comes with inherent risks to the subject.

An automated blood glucose control system may automatically provide insulin and/or a counter-regulatory agent (e.g., Glucagon) to a subject to help control the blood glucose level of the subject. Generally, a control algorithm is implemented by an automated blood glucose control system (BGCS) to determine when to deliver one or more glucose control agents and how much agent to provide to the subject. Further, the control algorithm may control both an ongoing or periodic delivery of insulin (e.g., a basal dose), and a correction bolus that may be provided to adjust a subject's blood glucose level to within a desired range. The control algorithm may use blood glucose level readings obtained from a sensor, such as a continuous glucose monitoring (CGM) sensor, that obtained automated blood glucose measurements from the subject. Moreover, in some cases, the control algorithm may deliver a bolus of insulin in response to an indication of a meal to be consumed or being consumed by the subject.

Insulin may be administered subcutaneously into blood of a subject. There is often a delay between when the insulin is provided and when the amount of insulin in the subject's blood plasma reaches maximum concentration. This amount of time may vary based on the type of insulin and on the physiology of the particular subject. For example, with a fast-acting insulin, it may take approximately 65 minutes for a bolus of insulin to reach maximum concentration in the blood plasma of the subject. For some other types of insulin, it may take anywhere from 3-5 hours to reach maximum concentration in the blood plasma of the subject. Accordingly, the blood glucose control system may implement a predictive algorithm that implements a bi-exponential pharmacokinetic (PK) model that models the accumulation of insulin doses in the blood plasma of the subject. The blood glucose control system may modify its predictions based on the type of insulin, one or more blood glucose readings, and/or characteristics of the subject.

In some cases, a subject may receive a manual bolus of insulin or medicament. For example, a user (e.g., healthcare provider, parent, or guardian) or subject may inject a dose of insulin into the subject. As another example, the user or subject may manually direct the automated blood glucose control system to provide a bolus of insulin to the subject.

It is generally undesirable to have too much insulin. An excess of insulin can lead to Hypoglycemia. As described above, it may take time for insulin to reach maximum concentration in the blood plasma of the subject. Thus, a blood glucose level reading from a sensor may not immediately, or even after a particular period of time, reflect the amount of insulin within a subject. Thus, a manual bolus of insulin may not be detected by the automated blood glucose control system. As a result, if the automated blood glucose control system is operating during delivery of a manual bolus, or is configured to operate on the subject prior to blood glucose level readings reflecting the effect of the manual bolus on the subject, the automated blood glucose control system may unnecessarily administer additional insulin to the subject potentially leading to hypoglycemia.

The present disclosure relates to an automated blood glucose control system configured to provide automatic delivery of glucose control therapy to a subject and receive information about manual glucose control therapy provided to the subject. Using the received information about the manual glucose control therapy, the automated blood glucose control system can adjust the blood glucose control algorithm to account for the manual dosing of insulin (or counter-therapy agents). The manual glucose control therapy may be provided by injection therapy, or it may be provided by an insulin pump.

In some cases, the automated blood glucose control system may receive an indication of insulin or medicament to administer to a subject in place of an automatically calculated dose of insulin. For example, the automated blood glucose control system may receive an indication that a subject is consuming or will consume a meal. The indication may include a type of meal to be consumed (e.g., breakfast, lunch, or dinner) and an estimate of the quantity of food or carbohydrates to be consumed (e.g., less than usual, a usual amount, more than usual, 30-40 grams of carbohydrates, 45-60 grams of carbohydrates, etc.). Based on the indication, or meal announcement, the automated blood glucose control system may calculate an amount of insulin to administer to the subject. The calculation may be based on an insulin to carbohydrate ratio provided by a clinician and/or determined by the automated blood glucose control system. Moreover, the calculation may be based at least in part on a history of blood glucose level measurements for the subject when consuming particular meals.

The calculated amount of insulin for the meal announced by the user may be presented to the user. The user (e.g., the subject) may modify the amount of insulin to administer. For example, the user may determine that for the size meal the subject is consuming or planning to consume, more or less insulin should be administered. In such cases, the user may modify the calculated insulin dosage to match the user's determination of the amount of insulin to administer. In some cases, the automated blood glucose control system may modify its control algorithm based on the user's input. Thus, future meal announcements may result in a calculation of insulin that satisfies the subject's insulin needs and/or preferences.

For example, automated blood glucose control system can receive a meal announcement from a user responsive to the user interaction with the user interface. The meal announcement can correspond to an indication of a size of a meal consumed or to be consumed by the subject as discussed herein. The automated blood glucose control system can determine a meal bolus of insulin to administer to the subject based at least in part on the meal announcement. The meal bolus of insulin can correspond to an amount of insulin to administer to the subject to compensate for a change in blood glucose attributable to the meal. The automated blood glucose control system can output for display an indication of the meal bolus of insulin. The automated blood glucose control system can receive an indication of a requested modification to the meal bolus of insulin from the user. The automated blood glucose control system operate a control algorithm for automatic generation of an insulin dosing signal configured to operate the medicament pump to control blood glucose level in the subject based at least in part on a glucose level of the subject and the modification to the meal bolus of insulin.

In some cases, the indication of an amount of a manual bolus may be received by a user entering a numerical value (e.g., an amount of insulin, a number of carbohydrates, or another calculation) associated with administering insulin, which may be considered a specified gesture interaction required for entry of the manual bolus of medicament. In some cases, a specified gesture interaction required for entry of the manual bolus of medicament may be a sliding action or other movement on a touchscreen to confirm or initiate desired functions as discussed herein. As described above, the automated blood glucose control system may automatically-calculate a meal dose of insulin and present it to a user via a user interface where a user may enter the manual bolus information. At the time of making the meal announcement, the user may have an option to enter the manual bolus. The meal controller of the blood glucose pump can provide a recommendation against the manual entry if there is a prior history of online operation or a basis for making the recommendation.

The information may be received from a user via a user interface. This user interface may be provided by the automated blood glucose control system. Alternatively, or in addition, the user interface may be generated by another device, such as a laptop or desktop, a smartphone, a smartwatch, or any other computing device that can communicate via wired or wireless communication with the automated blood glucose control system. The information may include one or more of: an indication of delivery of a manual bolus (e.g., via injection therapy), an amount of the manual bolus, a type of the insulin (or other medicament), a time when the manual bolus was delivered, a general location that the manual bolus was administered to the subject (e.g., back, stomach, arm, leg, etc.), a reason for the manual bolus (e.g., a meal, a maintenance dose, a blood glucose level reading, in advance of exercise, etc.), and any other information that may be useable by the blood glucose control system in controlling the blood glucose level of the subject.

Advantageously, in certain embodiments, providing manual dosing information to the automated blood glucose control system can help the blood glucose control system maintain the blood glucose level of the subject within a desired range when the automated features of the blood glucose control system are active or operational. For example, if the automated blood glucose control system determines from a CGM sensor reading that a subject's blood glucose level is high, the automated blood glucose control system might normally administer a bolus of insulin. However, if the automated blood glucose control system receives an indication that a manual bolus of insulin was administered recently (e.g., within the past thirty minutes), the automated blood glucose control system may reduce or not administer a bolus of insulin, thereby preventing a hypoglycemic event and providing glycemic control. In some such cases, the automated blood glucose control system may continue monitoring the blood glucose level of the subject and may administer additional insulin at a later time if the blood glucose level readings do not reflect an expected blood glucose level based on the reported manual bolus of insulin.

In some cases, it may be unnecessary to receive an indication of the manual bolus because, for example, a user may cause the automated blood glucose control system to provide the manual bolus. In such cases, the automated blood glucose control system may track the amount of insulin delivered and the timing of the administering of the bolus. To track the manual bolus, the automated blood glucose control system may store the information associated with the manual bolus in a therapy log. Accordingly, when the automated blood glucose control system is operating in an automatic mode, the automated blood glucose control system can access the therapy log to determine whether any manual bolus were administered and, if so, the timing and amount of the manual bolus.

In some cases, the automated blood glucose control system may model the diminishing of insulin, or other medicament, in the blood plasma over time based on the information associated with the manual bolus. Modeling the diminishing of medicament over time may be used to estimate a future effect of the medicament previously administered. In some cases, the model may account for previously administered medicament by the automated blood glucose control system. Further, in some cases, the model may account for physiological characteristics of the subject, such as the subject's weight or an input parameter related to the subject's weight (e.g., body mass value, body mass index value). Moreover, the model may account for perfusion over time of the medicament bolus from a subcutaneous infusion site into the blood plasma of the subject. Further, the automated blood glucose control system may model an accumulation of insulin, model time course of activity of insulin, or model a finite rate of utilization of insulin.

Based on the model, the automated blood glucose control system may adjust the automated administering of insulin, or other medicament, when operating in an automatic mode to automatically generate an insulin dosing signal configured to operate the medicament pump to control blood glucose level. Further, the automated blood glucose control system may operate the administering of medicament (e.g., by controlling a medicament pump) based on a glucose level of the subject and the modeled concentration of medicament in the subject, which can include a time course of activity of the medicament in the subject due to a finite rate of utilization of the medicament as discussed herein.

In some cases, the automated blood glucose control system may confirm that the manual bolus was delivered to the subject. The confirmation may be determined based at least in part on whether blood glucose level readings by the CGM sensor match or are within a threshold level anticipated by the automated blood glucose control system based on the manual dosing information. Alternatively, or in addition, the automated blood glucose control system may request, via a user interface, that a user confirm that the manual bolus was delivered. In cases where the manual bolus in delivered by the automated blood glucose control system, a user may be requested to confirm the administering of the manual bolus by using a particular gesture or sequence of interactions with a user interface (e.g., a touchscreen) of the automated blood glucose control system or of a device (e.g., laptop or smartphone, etc.) that communicates with the automated blood glucose control system.

As previously described, in some cases, the information relating to the manual bolus may include an amount of insulin and a reason the manual bolus was administered (e.g., for a meal of a particular size). In some such cases, the automated blood glucose control system may determine an amount of insulin the automated blood glucose control system would administer in an automatic operating mode based on the manual dosing information if the manual bolus had not been supplied. If the automated blood glucose control system determines it would have supplied a different quantity of the medicament, and if the difference exceeds a threshold, the automated blood glucose control system may adjust a blood glucose control algorithm to account for the difference. For example, the automated blood glucose control system may change the operating setpoint or range of insulin the automated blood glucose control system attempts to maintain in the subject. As another example, the automated blood glucose control system may supplement the manual bolus with additional insulin to account for an under-administering of insulin or may reduce a subsequent dosage of insulin to account for an over-administering of insulin.

As previously indicated, the automated blood glucose control system may maintain a therapy log of manual insulin therapy. This therapy log may be maintained based on the use of the automated blood glucose control system to provide a manual bolus or based on information provided by the user based on manual administering of insulin (e.g., via injection). The manual boluses may be supplied when the automated blood glucose control system is not operating, is not operating in an automatic mode, or is not connected to the subject. Once the automated blood glucose control system is connected to the subject and is configured in automatic mode, the automated blood glucose control system may determine therapy, if any, to provide to the subject based on a combination of the therapy log and the glucose control algorithm implemented by the automated blood glucose control system.

The automated blood glucose control system may generate a dose control signal based on the determined therapy. This dose control signal may be supplied to a medicament pump, which may control delivery of the medicament (e.g., insulin) to the subject.

In some cases, a user may control whether the automated blood glucose control system is operating in a manual mode or an automatic mode by interacting with a user interface of the automated blood glucose control system or of a device that communicate with the automated blood glucose control system. The user interaction may include any type of user interaction with a user interface. For example, the user interaction may include interaction why physical buttons or interactions with a touchscreen including gestures or taps on the touchscreen.

Additional embodiments relating to managing meal medicament doses and manual dosing that can be combined with one or more embodiments of the present disclosure are described in U.S. Provisional Application No. 62/911,143, which was filed on Oct. 4, 2019 and is titled "SYSTEM AND METHOD OF MANAGING MEAL DOSES IN AN AMBULATORY MEDICAL DEVICE," the disclosure of which is hereby incorporated by reference in its entirety herein for all purposes.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method including: providing an option to a user to select between receiving medicament using a manual delivery component or an automated delivery system. The method also includes receiving, by the automated delivery system, subjective information regarding the activity or action that may alter the blood-glucose level. The method also includes receiving, by the manual delivery component, an amount of the medicament to be infused. The method also includes storing a time and the amount of medicament that is infused into the automated delivery system that controls blood glucose level. Other embodiments of this aspect include corresponding computer systems, apparatus, and computer programs recorded on one or more computer storage devices, each configured to perform the actions of the methods.

Implementations may include one or more of the following features. The method where the automated delivery system modifies medicament delivery based on the time and the amount of medicament that was received from either the manual delivery component or the automated delivery system. The method where the manual delivery component includes a keypad which allows the user to type in the dosage amount of the desired medicament. The method where providing the option to select is provided prior to a user performing the activity that may alter the blood-glucose level. The method where the activity that may alter the blood-glucose level includes of consuming food or exercising. The method where the subjective information regarding the activity of consuming food includes the approximate relative size of the food that is to be digested. The method where the approximate relative size of the food is compared to the recommended meal doses for the user, and depending on whether the approximate relative size is the same, larger, or smaller than the recommended doses, the model predictive control component is able to determine the actions that is required to regulate the glucose level of the blood. The method where the subjective information regarding the activity of exercising includes the intensity and the duration of the exercise. The method where the intensity and the duration of the exercise is compared to the recommended intensity and duration, and depending on whether it is the same, larger, or smaller than the recommended intensity and duration, the automated delivery system is able to determine the actions that are required to regulate the glucose level of the blood. Implementations of the described techniques may include hardware, a method or process, or computer software on a computer-accessible medium.

One general aspect includes a system having a medical device configured to provide an option to a user to select between receiving medicament using a manual delivery component or an automated delivery system. The system also includes automated delivery system configured to receive subjective information regarding the activity that may alter the blood-glucose level. The system also includes a manual delivery component configured to receive an amount of the medicament to be infused. The system also includes where the medical device storing a time and the amount of medicament that is infused into an automated delivery system that controls blood glucose levels. Other embodiments of this aspect include corresponding computer systems, apparatus, and computer programs recorded on one or more computer storage devices, each configured to perform the actions of the methods.

Upon utilizing an ambulatory medical device to request for a therapy change, users may have different preferences. Therefore, it is desirable for modern technology, especially ambulatory medical devices to be equipped with optionality features. These optionality features may fulfill the different preferences of the users and subjects. The optionality features may allow users to control the therapy changes more closely and may allow them to be more engaged with the medical assistance of the ambulatory medical device.

In order to fulfill the variety of preferences, an ambulatory medical device needs to provide options which allows the user to either manually request the amount of the desired medicament or choose an automated delivery system that automatically delivers the right amount of the medicament at the right time without further assistance. For the manual component, the user may personally input the desired amount on a keypad that is provided by the medical device. The medical device further confirms and delivers the requested medicament. After the medicament is infused through a manual delivery component, the data is stored into a model predicative control component which is further used to control and regulate the blood glucose level. However, if the user decides to use the automated delivery system, the user must provide subjective information regarding the activity or the action that may alter the blood-glucose level. For example, if the blood-glucose level changing activity is consuming food, the user must provide the time and the dosage amount of the food that is going to be digested. This information is tied to the automated delivery system, and the subjective information is further stored into a model predicative control component.

Embodiments described herein include an ambulatory medical device that has a keypad which allows a user to type in a dose of insulin or glucagon to be administered to a user. A user may wish to receive a single dose of insulin prior to consuming food and decide how much insulin need to be administered. In other embodiments, the user may choose to receive a burst of glucagon due to low blood sugar because of physical activities. Embodiments may include the options for manual inputs of medicament and automated delivery system of medicament. In various implementations, the automated delivery system of medicament is driven by the blood glucose level or related trends. Embodiments herein address a problem that may arise when the user has just received a manual dose and has switched on the automated delivery system. In such cases, the automated delivery system may be made aware of all manual medicament infusion amounts and the timing of such infusions. Accordingly, the manual delivery component may inform the automated delivery system upon delivering any medicament the type of medicament delivered, the amount of medicament and the timing of the medicament delivered. By having the above information, the automated delivery system may determine the amount of medicament that is the user's blood stream and adjust the automated delivery of medicament and the timing of the automated delivery. Accordingly, embodiments are directed to allows for a risk free or minimized transition from the manual delivery component and the automated delivery system.

Differences from other system may include that the manual delivery may be tied to an automated delivery system, the dose input from the user is then stored into the MPC algorithm (Model Predictive Control) instead of the meal delivery algorithm and is handled by the MPC algorithm. Other embodiments may include selection being able to have a relativistic algorithmically tuned value. Other embodiments may include a learning algorithm that includes a usual size meal or larger size meal or small size meal. Embodiments may include correlating the manual inputs to asking the user what the size of the meal was and learning how the insulin affects the user. Embodiments may include correlating the manual inputs to asking the user what activity the user performed and learning how the glucagon affects the user for a particular activity.

BGCS with Manual Dose Management

Figure 36:
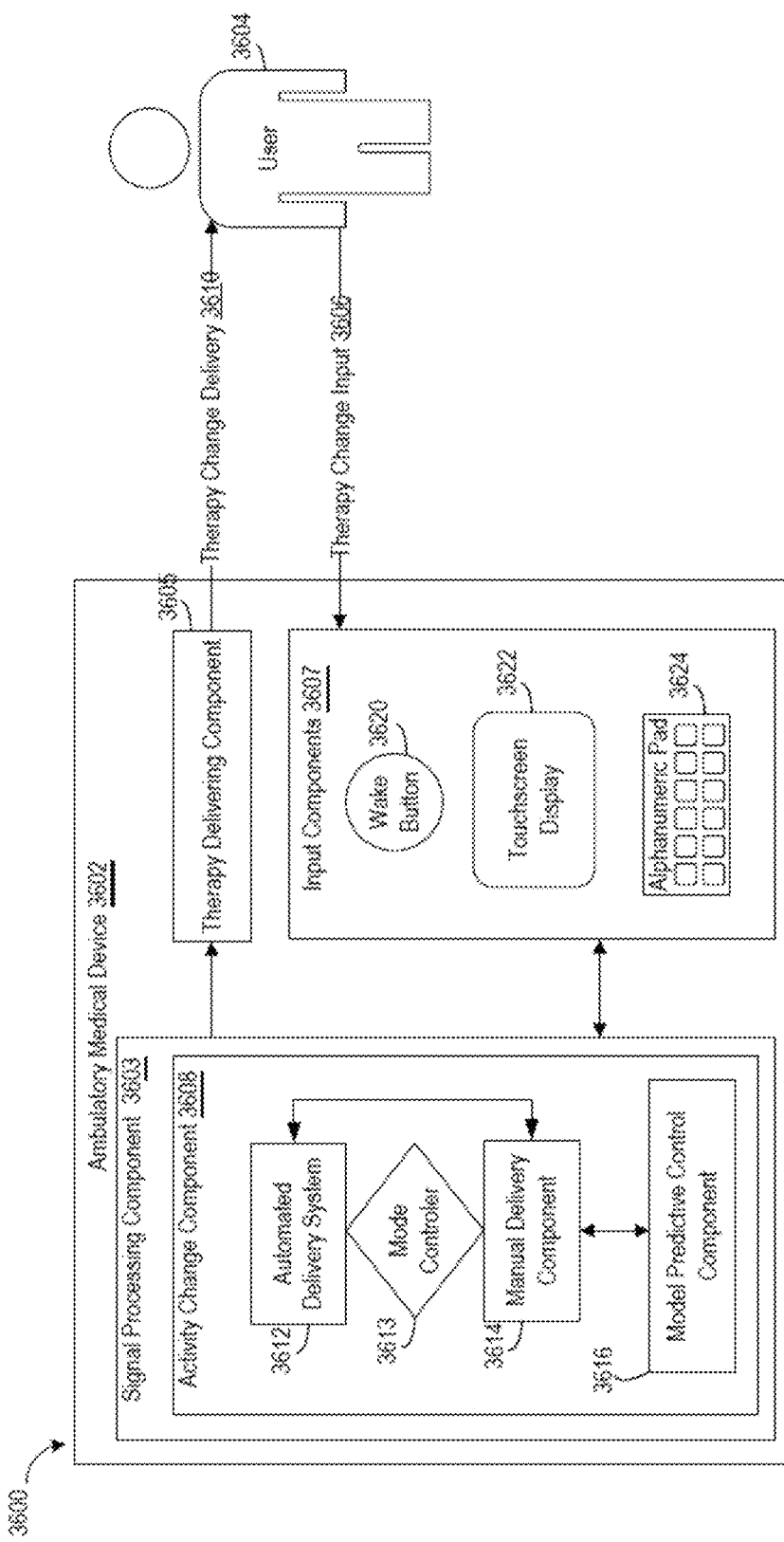
FIG. 36 is a schematic diagram illustrating an ambulatory medical device that provides the user with various options for providing medicament.

FIG. 36 illustrates a schematic of the therapy change delivery system 3600 in an ambulatory medical device 3602 that allows the user the choice of receiving manual delivery of medicament or automated delivery of medicament. Moreover, the therapy change delivery system 3600 allow the user to transition between the manual mode and the automated mode with ease. The therapy change delivery system 3600 includes the ambulatory medical device 3602, a signal processing component 3603, a user 3604, a therapy delivery component 3605, a therapy change input 3606, input components 3607, activity change component 3608, and a therapy change delivery 3610. When the user intends to receive a therapy from an ambulatory medical device 3602, the user 3604 may initiate a therapy change input 3606 to request the manual or automated medicament.

The ambulatory medical device 3602 is any medical device that a user 3604 may carry around and use with the approval of a medical professional. There are many different types of ambulatory medical devices 3602. In one embodiment, the ambulatory medical device 3602 is an insulin and/or glucagon infusion device for user 3604 that have type I diabetes. Ambulatory medical devices 3602 allow users 3604 the freedom to receive medical care in any setting at their convenience. However, the drawback of using an ambulatory medical device 3602 could be the user 3604 making mistakes when the user is away from the medical professionals. One possible issue may be caused when the user 3604 switches from a manual delivery mode to an automated delivery mode when the automated delivery mode is unable to determine the amount of medicament in the user's blood stream. Embodiments are directed to the manual medicament delivery information being provided to the automated medicament delivery system so that it can adjust its operations based on the current and future medicament in the user's blood stream. In some cases, such as the embodiment where the ambulatory medical device 3602 is an insulin and/or glucagon infusion device, doing automated delivery of medicament can be problematic.

The ambulatory medical device 3602 includes a signal processing component 3603, a therapy delivery component 3605, and input components 3607. The signal processing component 3603, therapy delivery component 3605, and input components 3607 may be physically connected, wirelessly connected, connected via a cloud-based computer system, or connected in any other way.

The signal processing component 3603 is a computing system that performs the computing functions for the ambulatory medical device 3602. The signal processing component 3603 includes a processor, memory, and storage. The signal processing component 3603 may be a single computing system or may be made up of several computing systems. The signal processing component 3603 may perform the computing functions for a single ambulatory medical device 3602 or many ambulatory medical devices 3602. The signal processing component 3603 receives signals from the therapy delivery component 3605 and from the input components 3607. The signal processing component 3603 also transmits signals to the therapy delivery component 3605 and the input components 3607. Signals of the therapy change input 3606, the therapy change delivery 3610, and all steps of the 3608 may be received or transmitted by the signal processing component 3603.

The user 3604 is any individual that uses the ambulatory medical device 3602. In one embodiment the user 3604 is an individual with diabetes that requires a periodic infusion of insulin or glucagon to maintain healthy blood sugar levels. In various embodiments, the ambulatory medical device 3602 infuses insulin or glucagon into the user 3604. The user 3604 may transport the ambulatory medical device 3602. Thus, as the user 3604 moves around, there is a danger that the user 3604 will inadvertently activate input in the ambulatory medical device 3602 that initiates a therapy change input 3606.

The therapy delivery component 3605 provides medicaments to the user 3604. Signals received from the signal processing component 3603 are executed by the therapy delivery component 3605 to change therapy such as starting, modifying, or stopping a therapy. The therapy delivery component 3605 may have a computing component for interpreting and executing instructions from the signal processing component 3603. Thus, the therapy delivery component 3605 can follow a program that is controlled by the signal processing component 3603. In one embodiment, the therapy delivery component 3605 is one or more infusion pumps. An infusion pump is capable of delivering fluids at varying rates to a user 3604. The infusion pump may deliver any fluid, including medicaments. The infusion pump may be connected to a user 3604 through any means. In one example, the infusion pump is connected to the body through a cannula. In an exemplary embodiment, the therapy delivery component 3605 is an insulin infusion pump. Also, in an exemplary embodiment, the therapy delivery component 3605 is an insulin and glucagon infusion pump. Signals received from the signal processing component 3603 may be interpreted by an insulin and glucagon pump to start, stop, or change the rate of insulin and glucagon being delivered into a user 3604.

In an exemplary embodiment, the therapy delivery component 3605 is an electrical stimulation device. An example of an electrical stimulation device is a cardiac pacemaker. A cardiac pacemaker stimulates the cardiac muscle to control heart rhythms. Instructions received from the signal processing component 3603 may be interpreted by a cardiac pacemaker to start stimulating a cardiac muscle, stop stimulating a cardiac muscle, or change the rate of stimulation of a cardiac muscle. Another example of an electrical stimulation device is a deep brain stimulator to treat Parkinson's disease or movement disorders. Instructions received from the signal processing component 3603 may be interpreted by the deep brain stimulator to start, stop, or modify the stimulation of the brain.

The therapy change input 3606 is an input provided by the user 3604 to change a therapy that is currently being delivered to the user 3604. The change of therapy may be to start a therapy, modify a therapy, or cancel a therapy. There are many types of possible therapy changes, and the types of therapy changes are dependent on the type of ambulatory medical device 3602. In one embodiment, the ambulatory medical device 3602 is an insulin or glucagon infusion device. However, there are many possible embodiments of ambulatory medical devices 3602 for the disclosed subject matter. The therapy change input 3606 in an insulin or glucagon infusion device may be an instruction that when executed, causes the insulin or glucagon infusion device to start infusing an amount of insulin or glucagon into the user 3604. Alternatively, the therapy change input 3606 may be an instruction to modify the rate of insulin or glucagon infusion into the user 3604. The therapy change input 3606 may also be an instruction to cancel insulin or glucagon infusion into the user 3604 from the insulin or glucagon infusion device. In an exemplary embodiment, the ambulatory medical device 3602 is an electrical implant, that when operated, stimulates a part of the body. An example is an electrical brain implant for users 3604 with Parkinson's disease or for pain management. The implementation of the therapy change can be to modify the rate of electrical stimulation to the body.

Figure 43:
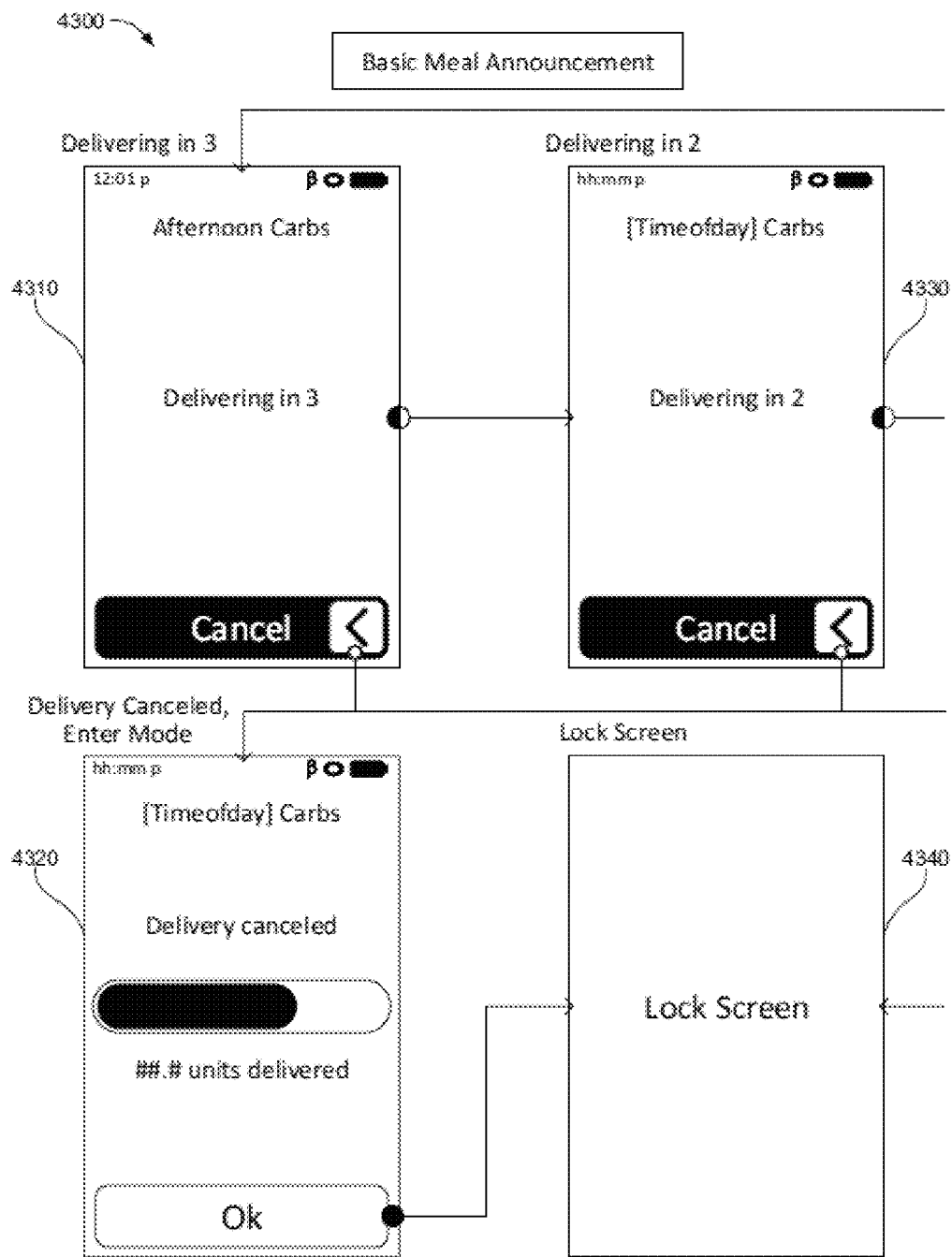
FIG. 43 is a series of screen displays showing an ambulatory medical device delivering the units and cancelling the delivery of the units.

The therapy change delivery 3610 is the performance, by the ambulatory medical device 3602, of the therapy change input 3606 that was verified by the 3608. The therapy change that is delivered by the therapy change delivery 3610 corresponds to the therapy change selection made by the user 3604. In one embodiment, the ambulatory medical device 3602 alerts the user 3604 that it is performing a therapy change delivery 3610. In an example of various embodiments, the ambulatory medical device 3602 displays the therapy change during the therapy change delivery 3610. Any number of details of the therapy change may be displayed during the therapy change delivery 3610. As shown in FIGS. 23 and 43, a simple message of "Delivering" may be displayed during the therapy change delivery 3610. Alternatively, more exact details, such as "Delivering 2 units of insulin" or "Delivering insulin at 2 units per minute" may be displayed. In another example, the ambulatory medical device 3602 plays a sound effect during the therapy change delivery 3610. In an exemplary embodiment that is shown in FIG. 43, the therapy change delivery 3610 may be canceled by an input by the user 3604. The input to cancel a therapy change delivery 3610 may be any input such as a wake signal input or a series of touch inputs such as a gesture.

The input components 3607 allow the user 3604 to interact with and control the ambulatory medical device 3602. The amount of control that a user 3604 has may vary based on the type of ambulatory medical device 3602 and the user 3604. For example, an ambulatory medical device 3602 that delivers pain medication may allow the user more control than an ambulatory medical device 3602 that controls heart rhythms. In another example. a user 3604 that is a young child (less than about 10, 11 or 12 years) may be allowed less control over an ambulatory medical device 3602 than a user 3604 that is a teen or an adult. The input components 3607 include a wake button 3620, a touchscreen display 3622, and an alphanumeric pad 3624.

The wake button 3620 is activated by a user 3604 to create a wake signal input to unlock an ambulatory medical device 3602. The wake button 3620 may be any input button. In one embodiment, the wake button 3620 is a capacitive button that detects a change in capacitance. The wake button 3620 may have a computing component for interpreting and executing instructions from the signal processing component 3603. Thus, the wake button 3620 can follow a program that is dictated by the signal processing component 3603.

The touchscreen display 3622 may display a therapy change user interface for the user 3604 and receive user 3604 inputs on the touchscreen display 3622 input surface. Inputs on the touchscreen display 3622 may be registered by any touch technology including, but not limited to capacitive and resistive sensing. The touchscreen display 3622 may be a part of a mobile computing device, such as a cellular phone, tablet, laptop, computer or the like. The touchscreen display 3622 may have a computing component for interpreting and executing instructions from the signal processing component 3603. Thus, the touchscreen display 3622 can follow instructions that are directed by the signal processing component 3603. To receive input, the touchscreen display 3622 may display buttons, alphanumeric characters, symbols, graphical images, animations, or videos. The touchscreen display 3622 may display an image to indicate when the ambulatory medical device 3602 is locked or inaccessible via the touchscreen display 3622. The touchscreen display may receive the series of inputs that make up the first gesture and the second gesture.

The alphanumeric pad 3624 registers numerical inputs, alphabetical inputs, and symbol inputs. The alphanumeric pad 3624 includes a multitude of keys corresponding to numerical, alphabetical, and symbol inputs. The alphanumeric pad 3624 may have a computing component for interpreting and executing instructions from the signal processing component 3603. Thus, the alphanumeric pad 3624 can follow instructions that are dictated by the signal processing component 3603. The alphanumeric pad 3624 may be configured to provide haptic feedback from its keys. The alphanumeric pad or pads 3624 may have any number of keys and any number of characters and may span multiple screens that the user 3604 can toggle between in order to find all of their sought-after characters. In one embodiment, the wake button 3620 is incorporated into the alphanumeric pad 3624. In various embodiments, the wake button 3620 may be any one or more keys of the alphanumeric pad 3624. In an exemplary embodiment, the alphanumeric pad 3624 is displayed as part of the touchscreen display 3622. Characters from the alphanumeric pad 3624 may be used as input for the wake signal input, first gesture, therapy change selection, and second gesture. In an exemplary embodiment, the first gesture and/or second gesture are created by entering predetermined characters on the alphanumeric pad 3624.

The activity change component 3608 may be part of a specialized software that is executed on an ambulatory medical device or include a specialized hardware that performs the various functions described here. The activity change component 3608 may receive inputs from the user regarding whether the user is about to conduct activities that will change the blood glucose of the user. For example, the user may provide input using the input components 3607 that the user is about to perform exercise that may lower their blood sugar or eat a meal that will increase their blood sugar. Upon receiving the activity change from the input components 3607, the activity change component 3608 offers the user the option via the mode controller 3613 to select between the automated delivery system 3612 or the manual delivery component 3614. As shown in FIG. 36, the manual delivery system may inform the automated delivery system 3612 and the model predictive control component 3616 regarding any manual medicament deliveries of insulin or glucagon as discussed herein, including via therapy logs.

In various embodiments, the user may choose the dosage amount, the drug type (insulin or glucagon; fast or slow acting) and the time of the delivery and the manual delivery component 3614 may receive such information and deliver the medicament(s) accordingly. In one embodiment, the manual delivery component 3614 may inform the automated delivery system 3612 and the model predictive control component 3616 regarding the drug type (insulin or glucagon; fast or slow acting) and the time of the delivery.

When the user activates the automated delivery system 3612, the data from previous manual medicament infusions can be readily available so that the automated delivery system 3612 may be able to determine how much medicament is still in the user's blood stream. The automated delivery system 3612 may make that determination by tracking the finite rate of utilization of infused insulin by the subject based on the time and amount of any manual medicament infusions reported to the automated delivery system 3612, for example, by determining a time course of activity of the medicament in the subject.

Figure 37:
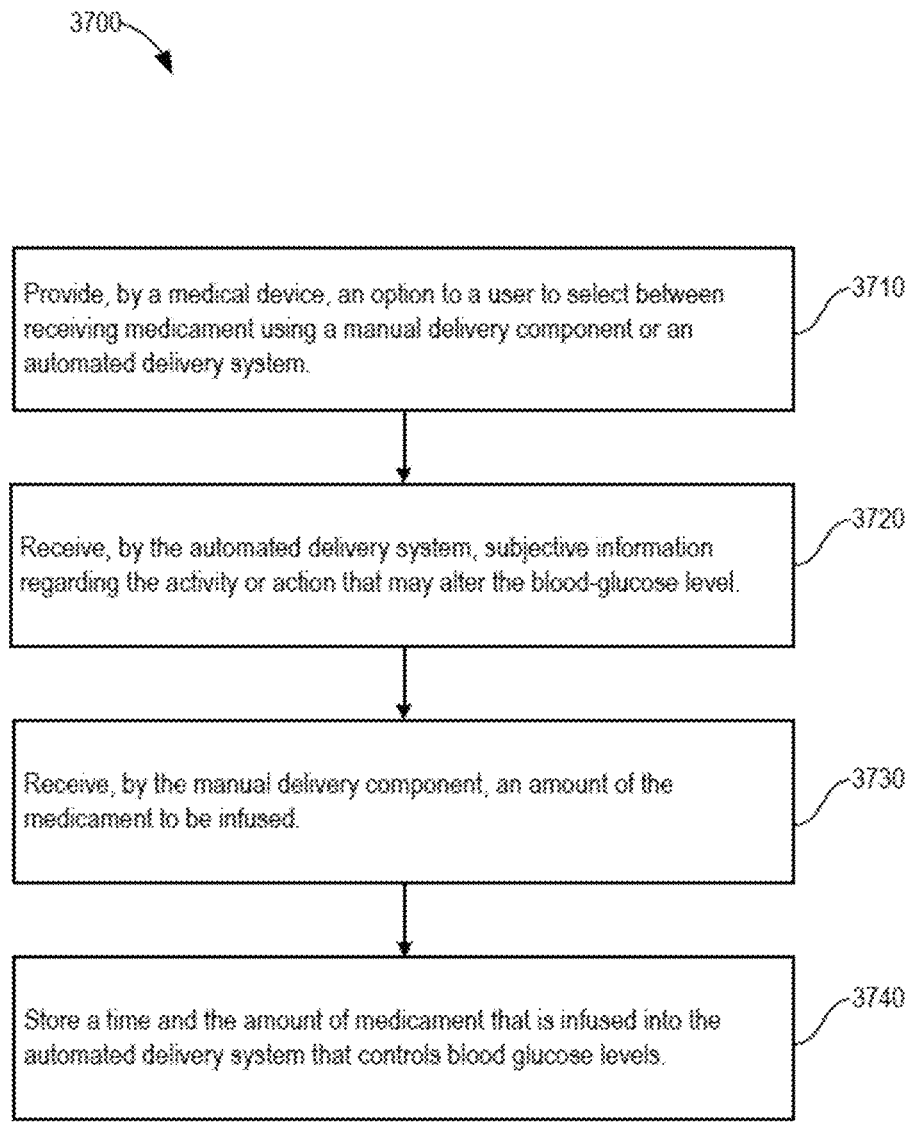
FIG. 37 is a flow diagram of a process for providing options for meal dosage selection on an ambulatory device.

FIG. 37 is a flow chart of a process 3700 detailing a medicament selection process, according to an exemplary embodiment. In step 3710, the medical device provides an option to a user to select between receiving medicament using a manual delivery component or an automated delivery system. By using the mode controller 3613, the user can select the method for the therapy change request between manual delivery component and the automated delivery system.

In step 3720, the medical device may receive subjective information regarding the activity or action that may alter the blood-glucose level. Subjective information may include the size of the meal and/or the type of physical activity. In step 3730, the manual delivery component may receive an amount of the medicament to be infused. The medicament may be a plurality of hormones, including but not limited to, glucagon or insulin. At step 3740, the medical device may store a time and the amount of medicament that was infused into the automated delivery component that controls the blood glucose level. The systems that are disclosed in FIG. 36 will be utilized to accomplish each and every step from steps 3710, 3720, 3730 and 3740.

Figure 38:
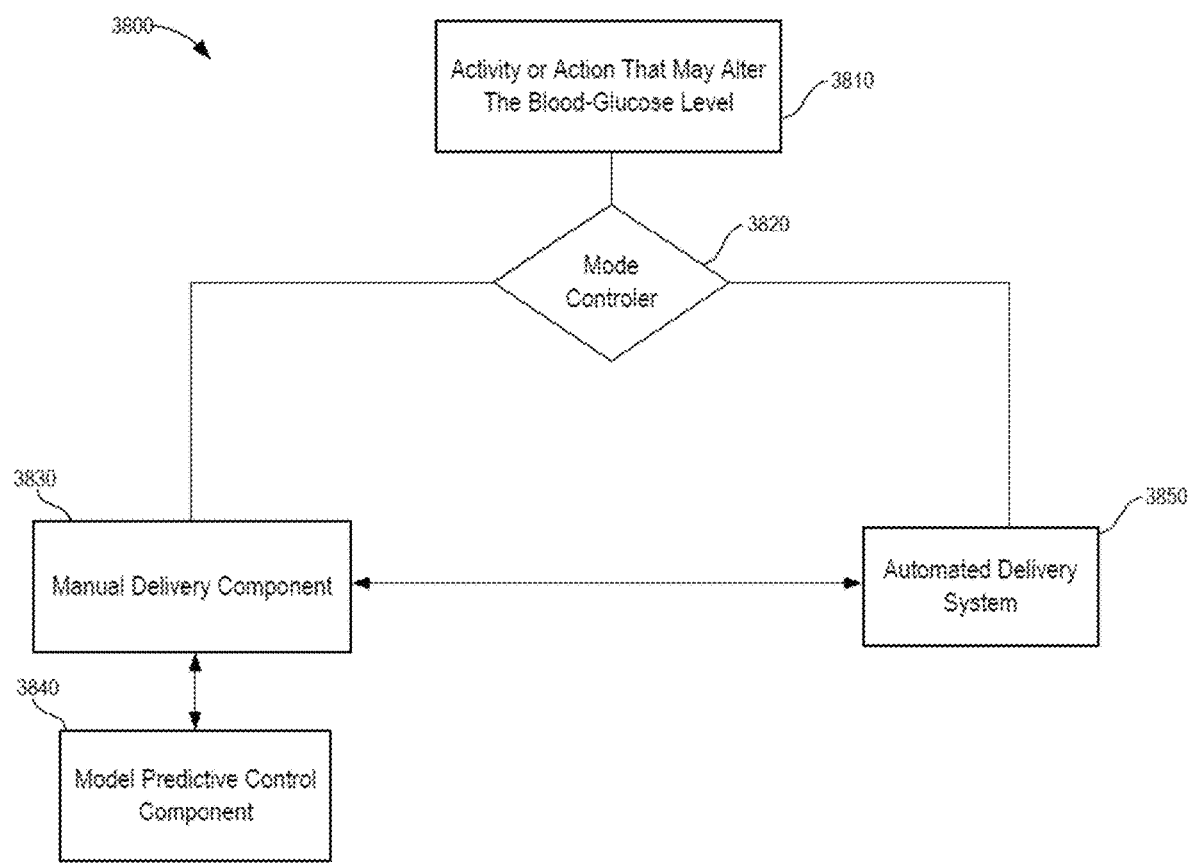
FIG. 38 is another flow diagram of a process for providing options for meal dosage selection on an ambulatory device.

FIG. 38 is another flow diagram of a process 3800 for providing options for meal dosage selection or physical activity of the user on an ambulatory device. Embodiments described herein include an ambulatory medical device that has a keypad which allows a user to type in a dose of insulin or glucagon to be administered to a user. A user may wish to receive a single dose of insulin prior to consuming food and decide how much insulin needs to be administered. In some cases, the user may choose to receive a burst of glucagon due to low blood sugar because of physical activities. Embodiments may include the options for manual inputs of medicament and automated delivery system of medicament. In various implementations, the automated delivery system of medicament is driven by the blood glucose level or related trends. Embodiments herein address a problem that may arise when the user has just received a manual dose and has switched on the automated delivery system. In such cases, the automated delivery system may be made aware of all manual medicament infusion amounts and the timing of such infusions, for example, in a therapy log as discussed herein. Accordingly, the manual delivery component may inform the automated delivery system upon delivering any medicament the type of medicament delivered, the amount of medicament and the timing of the medicament delivered. By having the above information, the automated delivery system may determine the amount of medicament that is the user's blood stream and adjust the automated delivery of medicament and the timing of the automated delivery. Accordingly, embodiments are directed to allowing for a risk free or minimized risk transition from the manual delivery component and the automated delivery system.

At block 3810, the user may inform the activity change component 3608 that the user is about to engage in activities that may alter the blood-glucose level of the user. The mode controller 3613 may be activated at decision block 3820 and ask whether the user wants to use the manual delivery component 3614 to proceed to block 3830 or the automated system 3612 to proceed to block 3850. The mode controller 3613 may include a display of a manual bolus screen comprising a manual bolus control element and a bolus recommendation comprising the indication of the amount of the bolus of medicament generated by the control algorithm as discussed herein.

If the user chooses to use the manual delivery component 3614 at block 3830 and the user provides an input to infuse medicament (e.g., an indication of an amount of a manual bolus of medicament), the ambulatory device 3602 may deliver the medicament to the user. The activity change component 3608 may automatically adjust the insulin dose control signal based on the amount of the manual bolus of insulin. The activity change component 3608 may generate a glucagon dose control signal based at least in part on the indication of the amount of the manual bolus of insulin. Upon the manual delivery process completion, the manual delivery component 3614 at block 3830 may inform at least one of the model predictive control component 3616 at block 3840 and the automated delivery system 3612 at block 3850 regarding the type of medicament, amount of medicament and the time when the medicament was delivery. The predictive control component 3616 at block 3840 and automated delivery system 3612 at block 3850 may track these manual infusions of medicament and determine that based on the rate of decay or the half-life of the medicament the total amount of medicament that remains in the user's blood stream at a particular time or a period of time, for example, in a therapy log as discussed herein. Accordingly, when the automated delivery system 3850 is activated by the user, the automated delivery system 3850 may change its medicament infusion based on the medicament that remains in the user's blood stream after a manual infusion by the user. The predictive control component 3616 may store the indication of the amount of the manual bolus of medicament supplied to the subject and an indication of a time when the manual bolus of medicament was supplied to the subject. The predictive control component 3616 may model a diminishment of the medicament in the subject over time based at least in part on the manual bolus of medicament. The predictive control component 3616 may model an accumulation of the manual bolus of the medicament in blood of the subject following subcutaneous infusion of the medicament.

Differences from other systems may include that the manual delivery may be tied to an automated delivery system, the dose input from the user is then stored into the MPC algorithm (Model Predictive Control) instead of the meal delivery algorithm and is handled by the MPC algorithm. Other embodiments may include selection being able to have a relativistic algorithmically tuned value. Other embodiments may include a learning algorithm that includes a usual size meal or larger size meal or small size mean. Embodiments may include correlating the manual inputs to asking the user what the size of the meal was and learning how the insulin affects the user. Embodiments may include correlating the manual inputs to asking the user what activity the user performed, learning how the glucagon affects the user for a particular activity, and/or storing the information in a therapy log to model a diminishment of the medicament in the subject over time based at least in part on the manual bolus of medicament.

Figure 39:
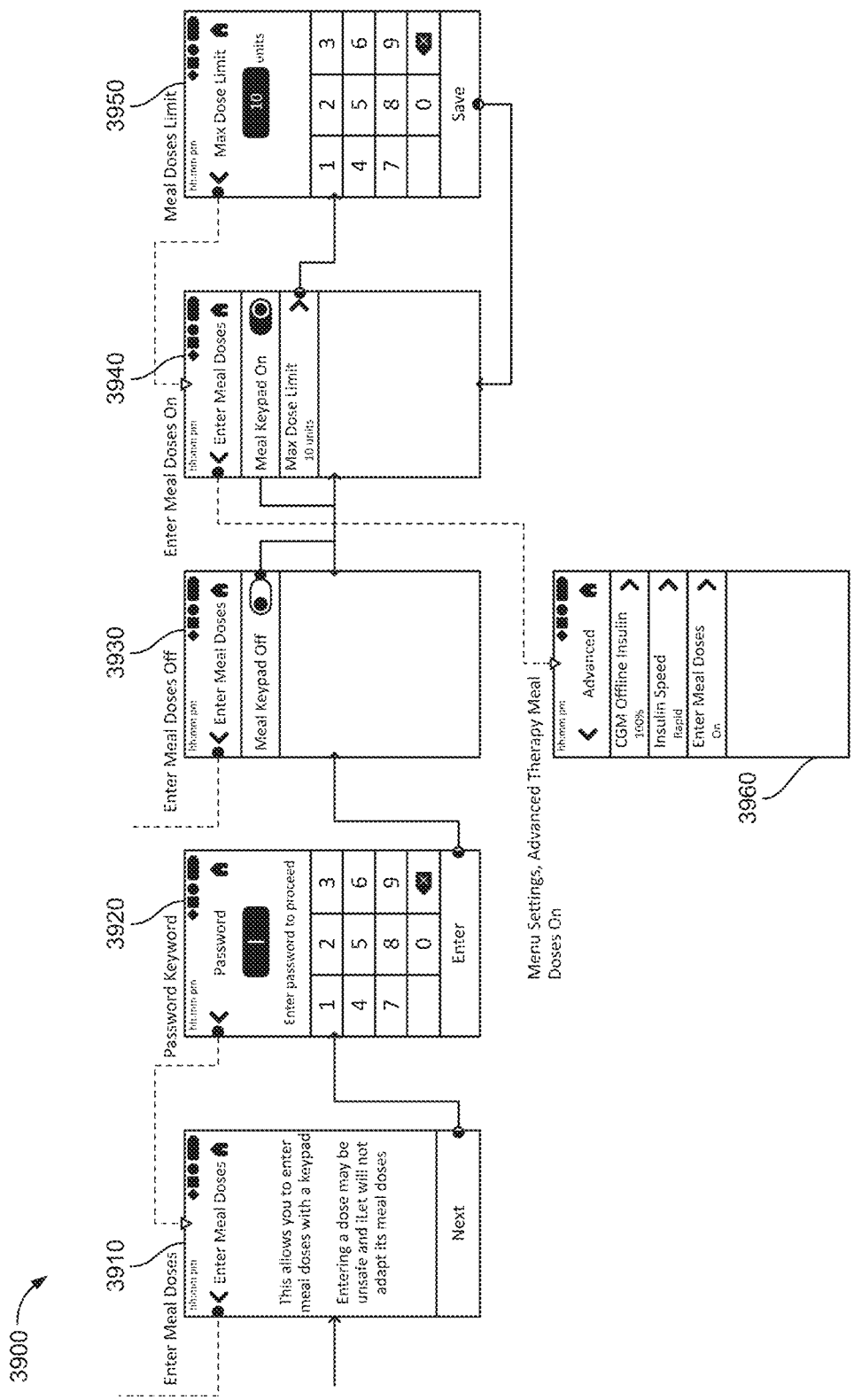
FIG. 39 is a series of screen displays showing a user initiating the activation of meal dosage on an ambulatory device.

FIG. 39 illustrates a plurality of screens 3900 that may be produced by the ambulatory medical device 100. The plurality of screens 3900 demonstrates a process that a user may take in order to enter meal doses. When the mode controller 3608 is activated, the enter meal doses screen 3910 may be displayed. Once the screen 3910 is displayed, a warning text may be displayed for the user to ensure safety. The warning text states that entering a dose may be unsafe and the device will not adapt its meal doses. This warning text cautions the user of the risks that may be involved in the process of using the ambulatory medical device 3602. After a user acknowledges the warning sign and chooses to proceed, a password screen 3920 may be displayed. Once the password screen 3920 is displayed, a keypad is provided for the user to enter a predetermined sequence of numbers to ensure that the user is the actual registered user of the ambulatory medical device 3602. When the ambulatory medical device 3602 receives the correct predetermined password from the user, the enter meal doses official screen 3930 and meal doses official screen 3940 may be displayed. The user may decide to access the advanced screen 3960, and upon doing so, the advanced screen 3960 will allow the user to double check the CGM Insulin levels and change the speed of the insulin pump. In screen 3930 and screen 3940, the user is provided the option to have the meal keypad on or off. If the user selects to have the keypad on, then an option may be provided for the user to choose the max dose limit. If the user decides to choose the max dose limit, the official max dose limit screen 3950 is displayed, where the user may enter up to 10 units of the dose. The provided number of units is then stored in the model predictive control component 116 for further regulation of the blood glucose level.

Figure 40:
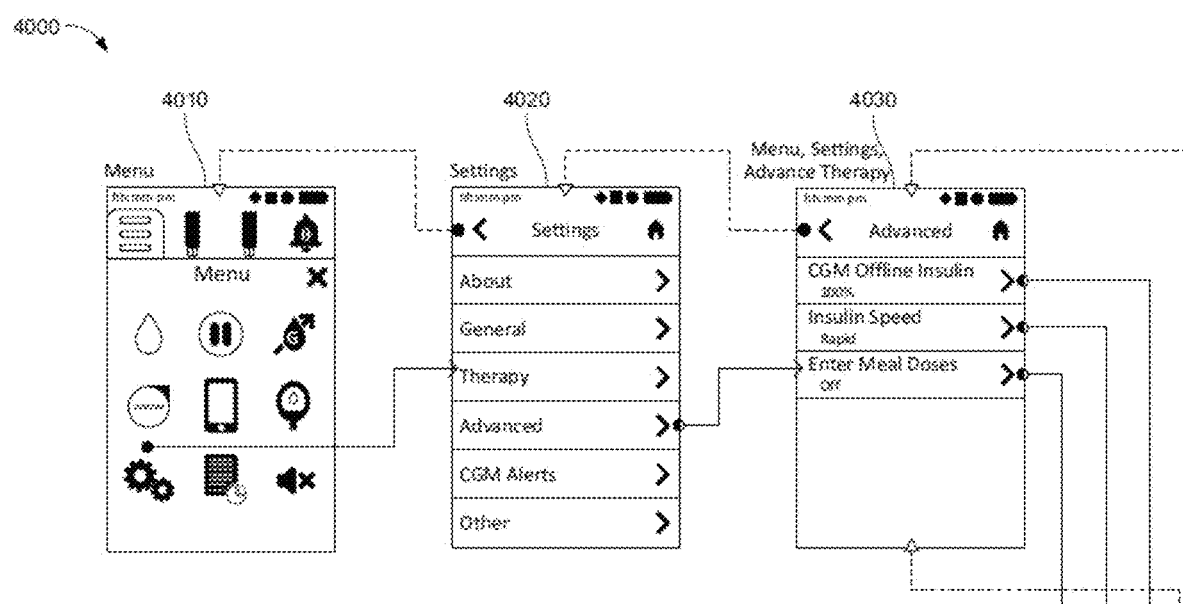
FIG. 40 is a series of screen displays showing a user activating meal dosage on an ambulatory device.

FIG. 40 illustrates a plurality of screens 4000 that may be produced by the ambulatory medical device 3602. Upon activating the ambulatory medical device 3602, the initial menu screen 4010 may be displayed. In the menu screen 4010, options regarding functionalities of the ambulatory medical device 3602 is provided. The list of functionalities may cover all the aspects of the ambulatory medical device 3602. The user may access and control many aspects of the device by choosing the setting option. The setting option will allow the user to further assess and regulate the adjustable functionalities of the ambulatory medical device 3602. Upon selecting the setting option, the setting screen 4020 may be displayed and the user may select the advanced setting option. Upon selecting the advanced option, the advanced setting screen 4030 is displayed, and the user is provided the option to double check the CGM insulin levels and change the speed of the insulin pump. The user may speed up the process or slow down the process depending on the regulation stats that are provided by the model predictive control component 3616. The advanced setting screen or state 4030 may be passcode protected as discussed herein.

Figure 41:
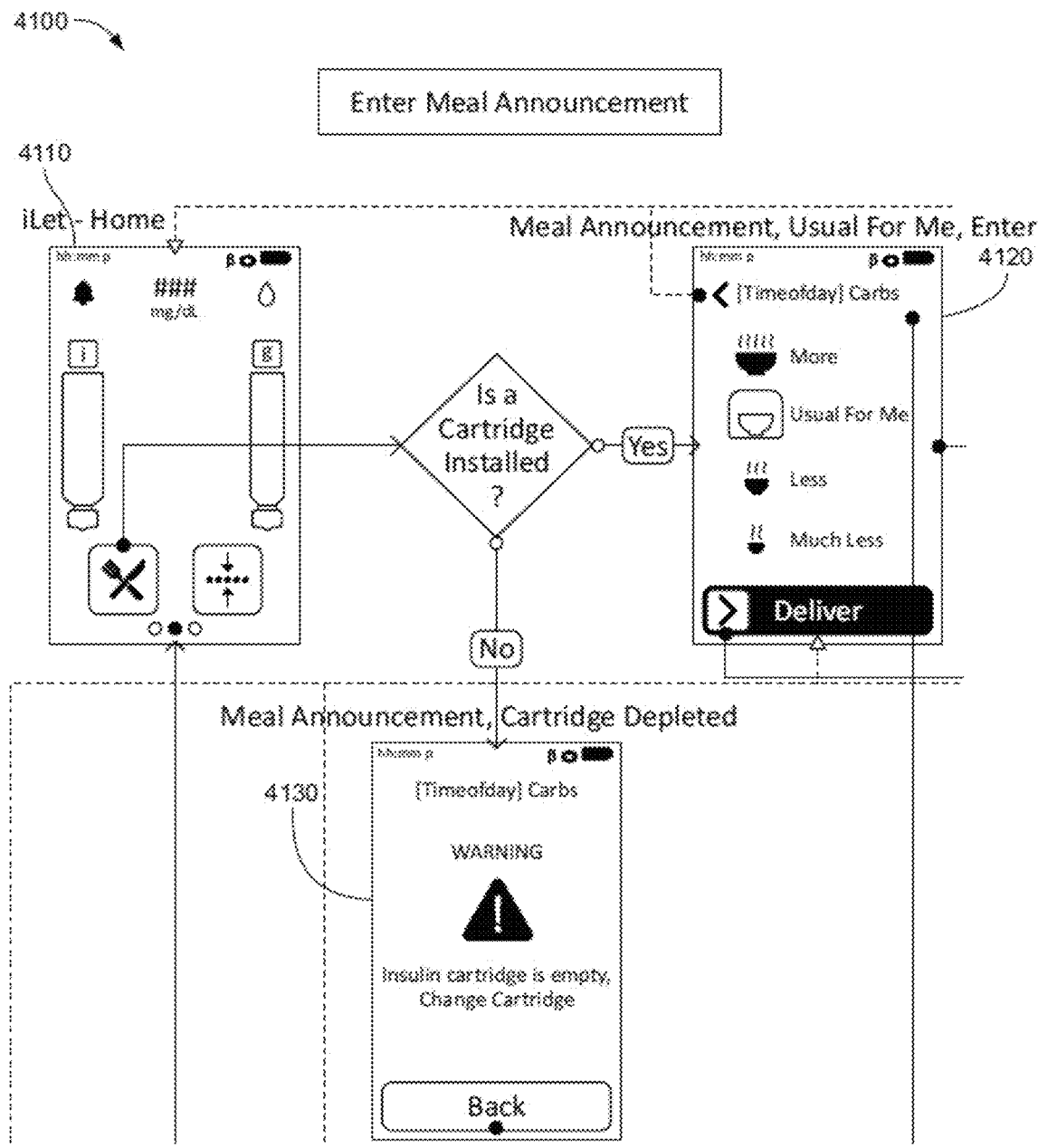
FIG. 41 is a series of screen displays showing a user activating meal announcement on an ambulatory device.

FIG. 41 illustrates a plurality of screens 4100 that may be produced by the ambulatory medical device 3602. The plurality of screens 4100 is the process that a user may take in order to enter meal announcements. The home screen 4110 provides information and stats regarding the cartridge of the ambulatory medical device 3602. The user may select the meal button with or without an installation of a new cartridge. If a user selects the meal button without installing a new cartridge, the ambulatory device 3602 will display the warning screen 4130, where the user is warned that the insulin cartridge is empty, and the device further advises the user to change the cartridge. However, if a new cartridge is already installed and the food button is pressed, the ambulatory medical device 3602 will display the carbs screen 4120, where the user is provided the option to choose a meal dose option, which can correspond to an indication of a size of a meal consumed or to be consumed by the subject. The carbs screen 4120 allows the user to provide subjective information regarding the food that is to be digested. This subjective data provided by the user is further stored in the model predictive control component 3616 for further regulation of the blood glucose level.

Figure 42:
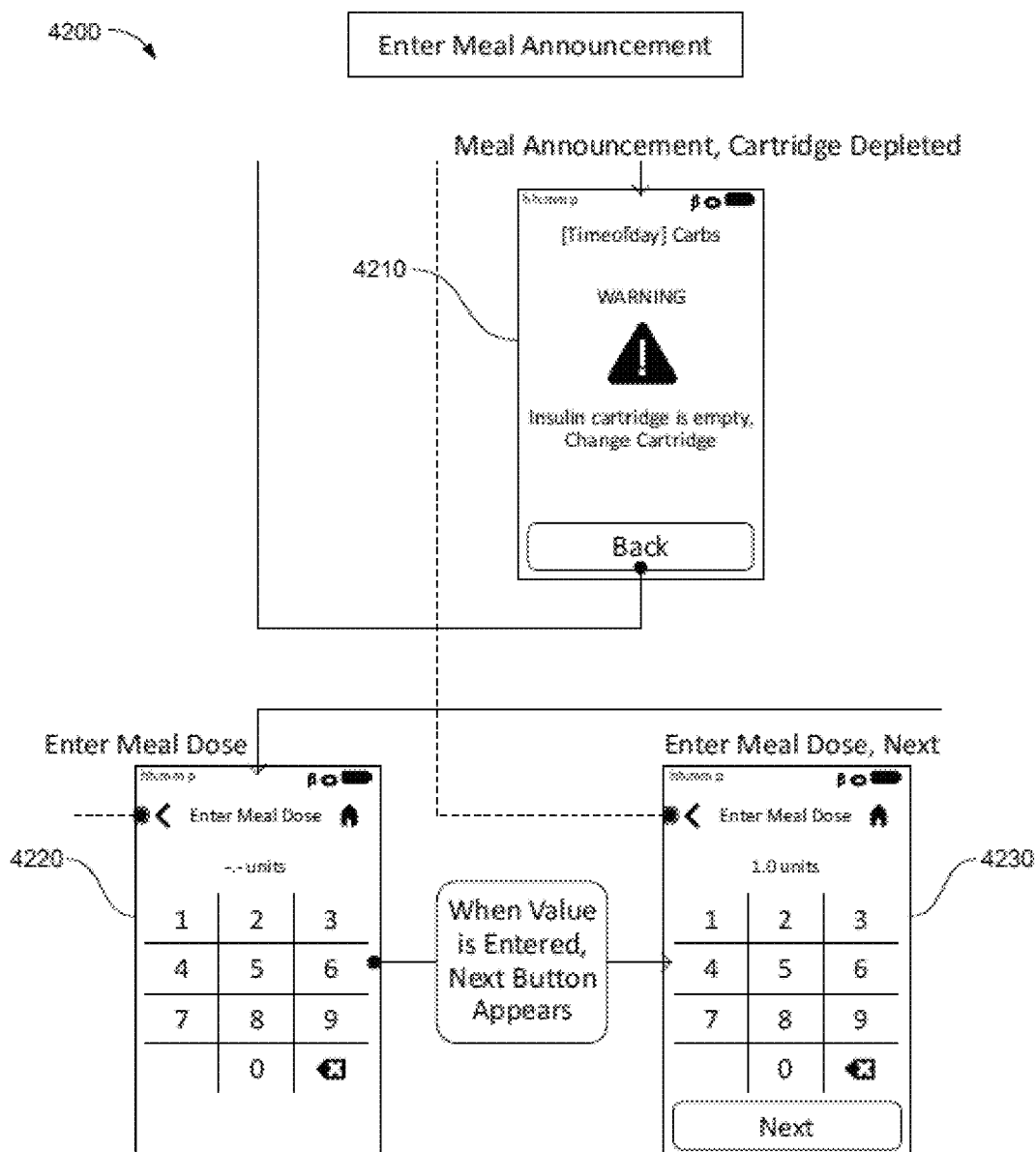
FIG. 42 is a series of screen displays showing a user inputting the total number of units on an ambulatory device.

FIG. 42 illustrates a plurality of screens 4200 that may be produced by the ambulatory medical device 3602. The plurality of screens 4200 demonstrates the process of the user being alerted about the empty cartridge and having the option to replace the cartridge and further enter the meal doses. Warning screen 4210 alerts the user that the insulin cartridge is empty and the fact that it needs to be replaced. Upon replacing the cartridge, screens 4220 and 4230 will be displayed. Screen 4220 is initially displayed, and a user may enter a specified dose for each meal on a numerical pad, which can correspond to an indication of a size of a meal consumed or to be consumed by the subject. Upon inserting a numerical specified dose, screen 4230 is displayed where a next button is provided for the user to further complete the therapy change. The numerical specified dose is further stored in the model predictive control component 3616 for further regulation of the blood glucose level. For example, the AMD can proceed to determine a meal bolus of insulin to administer to the subject based at least in part on the meal announcement as discussed herein. The meal bolus of insulin can correspond to an amount of insulin to administer to the subject to compensate for a change in blood glucose attributable to the meal.

FIG. 43 illustrates a plurality of screens 4300 that may be produced by the ambulatory medical device 3602. Upon selecting the delivery request, a user may cancel the delivery of the medicaments prior to the completion of the delivery. The ambulatory medical device 3602 displays a countdown prior to delivery. The initial countdown screen 4310 is proceeded by the secondary countdown screen 4330. During these countdown screens, a cancel button is provided for the user to cancel the therapy change. During the initial countdown screen 4310 or the secondary countdown screen 4330, the user may cancel the delivery at any time. By swiping the cancel button, the user may officially stop the delivery of the therapy change. If the user does not cancel, the therapy change may be delivered successfully. Furthermore, the time and the amount of the therapy change delivery is stored in the model predictive control component 3616 for further regulation of the blood glucose level. However, if the user decides to cancel the delivery, the delivery will be canceled and the screen 4320 will be provided. Once the delivery cancelation is requested and the screen 4320 is displayed, upon pressing the ok button, the ambulatory medical device 3602 will display a lock screen 4340 and take the time to officially cancel the therapy change request.

Figure 45:
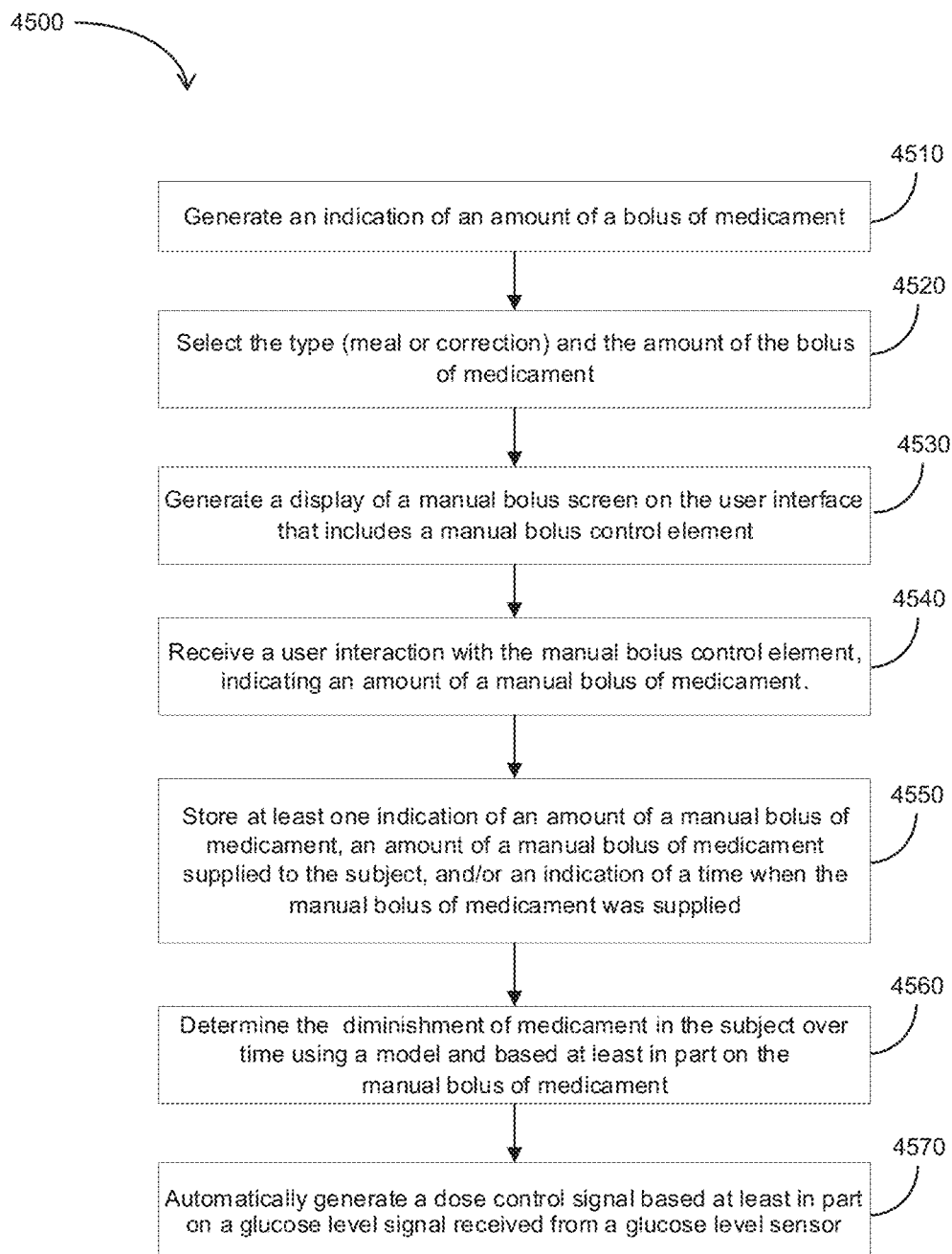
FIG. 45 is a flow diagram of a process for receiving manual entry of a medicament dose on an ambulatory device.

FIG. 45 illustrates an example process 4500 for receiving input, via user interaction with a user interface, for manual glucose control therapy provided by a glucose control system. An automated blood glucose control system can be configured to provide automatic delivery of glucose control therapy to a subject and to also provide manual glucose control therapy when requested by a user. At block 4510, a control algorithm generates an indication of an amount of a bolus of medicament. The control algorithm is configured to provide automatic control of blood glucose level in the subject and can automatically generate bolus amounts for correction doses and for meal doses based on at least one of an indicated glucose level of the subject, a meal announcement, an indicated meal size, control parameters selected manually or automatically by the control system, or any combination of the preceding values. In block 4520, the bolus of medicament can correspond to a meal bolus of medicament or a correction bolus of medicament, and the amount of the bolus of medicament can be selected by the control algorithm based at least in part on preceding periods of glycemic control in the subject.

At block 4530, the glucose control system generates a display of a manual bolus screen that can include a manual bolus control element that can facilitate manual entry of an indication of a medicament bolus amount. The indication of the medicament bolus amount can include a volume of medicament, an amount of carbohydrates in a meal, and/or other manual therapy instructions. The manual bolus screen can include a bolus recommendation, which can include an indication of the amount of the bolus of medicament generated by the control algorithm. The bolus recommendation can be for a correction dose or a meal dose, and can be in the form of a volume of medicament and/or, in the case of a meal dose, an estimated amount of carbohydrates consumed in a typical meal or a meal of the size selected by the user. The meal dose can account for the time of the meal and the typical meal composition as indicated by preceding periods of glycemic response in prandial and post-prandial periods.

At block 4540, the glucose control system can receive, via user interaction with the manual bolus control element, the indication of an amount of a manual bolus of medicament. The indication can include one or more than one indication entered manually via user interaction with one or more user interface control elements.

At block 4550, the glucose control system can store one or more of the following in a therapy log or another suitable location: at least one indication of an amount of a manual bolus of medicament, an amount of a manual bolus of medicament actually supplied to the subject, and/or an indication of a time when the manual bolus of medicament was supplied to the subject.

At block 4560, the glucose control system may use a model to determine the diminishment of medicament in the subject over time based at least in part on the manual bolus of medicament. Modeling the diminishment of medicament can account for a finite rate of utilization of the manual bolus of medicament and can use one of more models as described herein and in the Controller Disclosures.

At block 4570, the glucose control system can operate the control algorithm for automatic generation of an insulin dosing signal configured to operate a medicament pump to control blood glucose level in the subject based at least in part on a glucose level signal received from a glucose level sensor operatively connected to the subject and a time course of activity of the medicament in the subject due to a finite rate of utilization of the medicament. The medicament in the subject can include the manual bolus of medicament and/or one or more automatically generated boluses of medicament.

Figure 44:
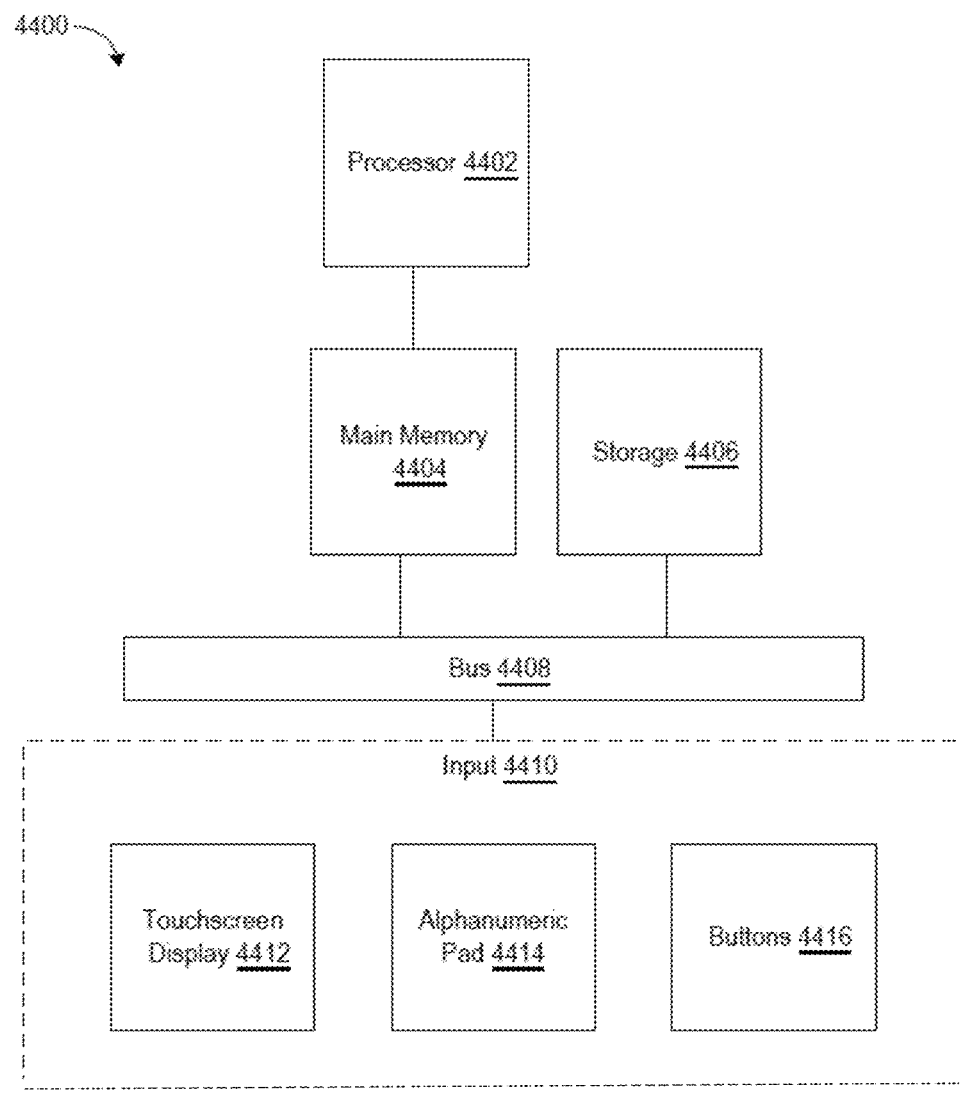
FIG. 44 is a schematic illustrating a computer system that can be implemented in various embodiments of the described subject matter.

FIG. 44 is a block diagram illustrating a computer system 4400 that may be implemented in the various embodiments in the described subject matter. The computer system 4400 includes a processor 4402, main memory 4404, storage 4406, a bus 4408, and input 4410. The processor 4402 may be one or more processors. The processor 4402 executes instructions that are communicated to the processor through the main memory 4404. The main memory 4404 feeds instructions to the processor 4402. The main memory 4404 is also connected to the bus 4408. The main memory 4404 may communicate with the other components of the computer system through the bus 4408. Instructions for the computer system 4400 are transmitted to the main memory 4404 through the bus 4408. Those instructions may be executed by the processor 4402. Executed instructions may be passed back to the main memory 4404 to be disseminated to other components of the computer system 4400. The storage 4406 may hold large amounts of data and retain that data while the computer system 4400 is unpowered. The storage 4406 is connected to the bus 4408 and can communicate data that the storage holds to the main memory 4404 through the bus 4408.

The processor 4402 may be any type of general purpose processor including, but not limited to a central processing unit ("CPU"), a graphics processing unit ("GPU"), a complex programmable logic device ("CPLD"), a field programmable gate array ("FPGA"), or an application-specific integrated circuit ("ASIC"). One embodiment of the computer system 4400 in the ambulatory medical device 100 features a CPU as the processor 4402. However, embodiments may be envisioned for the computer system of the ambulatory medical device 100 that incorporate other types of processors 4402.

The main memory 4404 can be any type of main memory that can communicate instructions to the processor 4402 and receive executed instructions from the processor 4402. Types of main memory 4404 include but are not limited to random access memory ("RAM") and read only memory ("ROM"). In one embodiment, the computer system 4400 incorporates RAM as the form of main memory 4404 to communicate instructions to the processor 4402 and receive executed instructions from the processor 4402. Other embodiments may be envisioned that incorporate other types of main memory 4404 in the computer system 4400.

The storage 4406 can be any type of computer storage that can receive data, store data, and transmit data to the main memory 4404 via the bus 4408. Types of storage 4406 that can be used in the computer system 4400 include, but are not limited to, magnetic disk memory, optical disk memory, and flash memory. In one embodiment, flash memory is used as the storage 4406 in the computer system 4400 of the ambulatory medical device 100. Other embodiments that use other types of storage 4406 for the computer system 4400 may be envisioned.

The bus 4408 connects the internal components of the computer system 4400. The bus 4408 may include a multitude of wires that are connected to the components of the computers system 4400. The wires of the bus 4408 may differ based on the components of the computer system 4400 to which the bus 4408 connects. In various embodiments, the bus 4408 connects the processor 4402 to the main memory 4404. In various embodiments, the processor 4402 is directly connected to the main memory 4404.

The input 4410 of the computer system 4400 includes a touchscreen display 4412, an alphanumeric pad 4414, and buttons 4416. The touchscreen display 4412 both produces output and accepts input. The bus 4408 may be coupled to the touchscreen display 4412 to produce visual output. The touchscreen display 4412 may also accept input via capacitive touch, resistive touch, or other touch technology. The input surface of the touchscreen display 4412 can register the position of touches on the surface. Some types of touchscreen display 4412 can register multiple touches at once. The alphanumeric pad 4414 includes a multitude of keys with numerical, alphabetical, and symbol characters. Signals from the alphanumeric pad 4414 are communicated by the bus 4408 to the main memory 4404. Keys of the alphanumeric pad 4414 may be capacitive or mechanical. In some embodiments, the alphanumeric pad 4414 is displayed on the touchscreen display 4412. Buttons 4416, such as the wake button 120, may be capacitive, mechanical, or other types of input buttons.

Terminology

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware. Further, the computing system may include, be implemented as part of, or communicate with an automated blood glucose system, an ambulatory medicament system, or an ambulatory medical device.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Many variations and modifications may be made to the above-described embodiments, the elements of which are to be understood as being among other acceptable examples. All such modifications and variations are intended to be included herein within the scope of this disclosure.

What is claimed is:

1. An automated glucose control system configured to provide automatic delivery of glucose control therapy to a subject and receive information about manual glucose control therapy provided to the subject, the automated glucose control system comprising:
    a medicament delivery interface configured to operatively connect to a medicament pump configured to infuse medicament into the subject;
    a user interface controller configured to receive input signals corresponding to user interaction with a user interface;
    a memory configured to store specific computer-executable instructions and a therapy log; and
    a hardware processor in communication with the memory and configured to execute the specific computer-executable instructions to at least:
        generate an indication of an amount of a bolus of medicament via a control algorithm configured to control glucose level in the subject, wherein the bolus of medicament corresponds to a meal bolus of medicament or a correction bolus of medicament, and wherein the amount of the bolus of medicament is selected by the control algorithm based at least in part on preceding periods of glycemic control in the subject;
        generate a display of a manual bolus screen comprising a manual bolus control element and a bolus recommendation comprising the indication of the amount of the bolus of medicament generated by the control algorithm;
        receive, via user interaction with the manual bolus control element, an indication of an amount of a manual bolus of medicament;
        store, in the therapy log, the indication of the amount of the manual bolus of medicament supplied to the subject and an indication of a time when the manual bolus of medicament was supplied to the subject;
        model a diminishment of the medicament in the subject over time based at least in part on the manual bolus of medicament; and
        operate the control algorithm for automatic generation of an insulin dosing signal configured to operate the medicament pump to control glucose level in the subject based at least in part on a glucose level signal received from a glucose level sensor operatively connected to the subject and a time course of activity of the medicament in the subject due to a finite rate of utilization of the medicament, wherein operating the control algorithm for automatic generation of the insulin dosing signal comprises modifying administration of a bolus of insulin in response to a time interval between the time of the manual bolus and a time of the automatic generation of the insulin dosing signal being less than or equal to a threshold time interval.

2. An ambulatory medical device comprising the automated glucose control system of claim 1 and the medicament pump.

3. The ambulatory medical device of claim 2, wherein the medicament pump comprises at least one of an insulin pump or a counter-regulatory agent pump.

4. The automated glucose control system of claim 1, wherein the hardware processor is further configured to execute the specific computer-executable instructions to at least model an accumulation of the manual bolus of the medicament in the subject following subcutaneous infusion of the medicament.

5. The automated glucose control system of claim 1, further comprising a wireless electronic communications interface configured to receive the indication of the amount of the manual bolus of medicament from an electronic device remote from the automated glucose control system.

6. The automated glucose control system of claim 1, wherein receiving the indication of the amount of the manual bolus of medicament comprises detecting a gesture interaction made by a user.

7. The automated glucose control system of claim 6, wherein detecting the gesture interaction made by the user comprises confirming that the gesture interaction matches a specified gesture interaction required for entry of the manual bolus of medicament.

8. The automated glucose control system of claim 1, wherein receiving the indication of the amount of the manual bolus of medicament comprises receiving an estimate of a meal size or an estimate of a number of carbohydrates consumed by the subject.

9. The automated glucose control system of claim 1, wherein receiving the indication of the amount of the manual bolus of medicament comprises receiving an estimate of an intensity of exercise engaged in by the subject.

10. The automated glucose control system of claim 1, wherein the hardware processor is further configured to execute the specific computer-executable instructions to at least generate a dose control signal based at least in part on the indication of the amount of the manual bolus of medicament.

11. The automated glucose control system of claim 10, wherein the hardware processor is further configured to execute the specific computer-executable instructions to at least provide the dose control signal to the medicament pump.

12. The automated glucose control system of claim 10, wherein the manual bolus of medicament is infused through injection therapy or pump therapy.

13. The automated glucose control system of claim 10, wherein modeling the diminishment of the medicament in the subject over time enables an estimate of a future effect of medicament previously infused into the subject.

14. The automated glucose control system of claim 1, wherein the hardware processor is further configured to execute the specific computer-executable instructions to at least determine the time interval based at least in part on the therapy log.

15. The automated glucose control system of claim 1, wherein modifying the administration of the bolus of insulin comprises omitting administration of the bolus of insulin or reducing the bolus of insulin administered.

16. The automated glucose control system of claim 1, wherein the hardware processor is further configured to execute the specific computer-executable instructions to at least:
determine an expected glucose level of the subject based at least in part on the manual bolus of medicament; and
administer additional medicament in response to determining that a measured glucose level does not satisfy the expected glucose level.

17. The automated glucose control system of claim 1, wherein the hardware processor is further configured to execute the specific computer-executable instructions to at least confirm delivery of the manual bolus of medicament based at least in part on the glucose level signal.

18. The automated glucose control system of claim 1, wherein the hardware processor is further configured to execute the specific computer-executable instructions to at least modify the administration of the bolus of insulin based on the model of the diminishment of the medicament in the subject over time based at least in part on the manual bolus of medicament.

19. An automated glucose control system configured to provide automatic delivery of glucose control therapy to a subject and receive information about manual glucose control therapy provided to the subject, the automated glucose control system comprising:
a glucose sensor interface operative to receive a glucose level signal from a sensor operative to determine a glucose level of the subject at periodic measurement intervals;
a delivery device interface configured to transmit an insulin dose control signal to a medicament pump operative to deliver doses of insulin to the subject;
a memory configured to store specific computer-executable instructions; and
a hardware processor in communication with the memory and configured to execute the specific computer-executable instructions to at least:
receive an indication of an amount of a manual bolus of insulin from a user interface; and
automatically generate the insulin dose control signal based at least in part on the glucose level signal, an accumulation of insulin in the subject due to finite rate of utilization of the insulin, an input parameter corresponding to a weight of the subject, the indication of the amount of the manual bolus of insulin, and an indication of a time when the manual bolus of insulin was supplied to the subject, wherein automatically generating the insulin dose control signal further comprises modifying administration of a bolus of insulin in response to a time interval between the time when the bolus of insulin was supplied to the subject and a time of the automatic generation of the insulin dose control signal being less than or equal to a threshold time interval.

20. The automated glucose control system of claim 19, wherein the input parameter comprises a measure of weight, a body mass value, or a body mass index value.

21. The automated glucose control system of claim 19, wherein the insulin dose control signal is automatically adjusted based on the amount of the manual bolus of insulin.

22. The automated glucose control system of claim 19, wherein the hardware processor is further configured to execute the specific computer-executable instructions to at least generate a glucagon dose control signal based at least in part on the indication of the amount of the manual bolus of insulin.

23. An automated glucose control system configured to provide automatic delivery of glucose control therapy to a subject and receive information about manual glucose control therapy provided to the subject, the automated glucose control system comprising:
a medicament delivery interface configured to operatively connect to a medicament pump configured to infuse medicament into the subject;
a user interface controller configured to receive input signals corresponding to user interaction with a user interface;
a memory configured to store specific computer-executable instructions; and
a hardware processor in communication with the memory and configured to execute the specific computer-executable instructions to at least:
receive a meal announcement from a user responsive to the user interaction with the user interface, wherein the meal announcement comprises an indication of a size of a meal consumed or to be consumed by the subject;
determine a meal bolus of insulin to administer to the subject based at least in part on the meal announcement, the meal bolus of insulin comprising an amount of insulin to administer to the subject to compensate for a change in glucose attributable to the meal;
output for display an indication of the meal bolus of insulin;
receive an indication of a requested modification to the meal bolus of insulin from the user; and
operate a control algorithm for automatic generation of an insulin dosing signal configured to operate the medicament pump to control glucose level in the subject based at least in part on a glucose level of the subject and the modification to the meal bolus of insulin, wherein operating the control algorithm for automatic generation of the insulin dosing signal further comprises modifying administration of a bolus of insulin in response to a time interval between the time of the modification to the meal bolus and a time of the automatic generation of the insulin dosing signal being less than or equal to a threshold time interval.

24. The automated glucose control system of claim 23, wherein the user is the subject or a caregiver of the subject.

25. The automated glucose control system of claim 23, wherein the meal announcement is received via a wireless electronic communications interface configured to connect to a remote electronic device.

* * * * *